US012788789B2

(12) United States Patent
Buss et al.

(10) Patent No.: US 12,788,789 B2
(45) Date of Patent: Nov. 10, 2026

(54) ACOUSTIC REPORTER GENES FOR NONDESTRUCTIVE IN VIVO IMAGING

(71) Applicant: California Institute of Technology, Pasadena, CA (US)

(72) Inventors: Marjorie T. Buss, Pasadena, CA (US); Robert C. Hurt, Pasadena, CA (US); Katie K. Wong, San Ramon, CA (US); Mikhail G. Shapiro, Pasadena, CA (US); Mengtong Duan, Pasadena, CA (US); Arash Farhadi, Pasadena, CA (US); Mei Yi You, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 889 days.

(21) Appl. No.: 18/066,814

(22) Filed: Dec. 15, 2022

(65) Prior Publication Data

US 2023/0210926 A1 Jul. 6, 2023

Related U.S. Application Data

(60) Provisional application No. 63/420,147, filed on Oct. 28, 2022, provisional application No. 63/290,425, filed on Dec. 16, 2021, provisional application No. 63/290,402, filed on Dec. 16, 2021.

(51) Int. Cl.

| | |
|---|---|
| ***A61K 35/748*** | (2015.01) |
| ***A61K 35/00*** | (2006.01) |
| ***A61K 48/00*** | (2006.01) |
| ***A61K 49/22*** | (2006.01) |
| ***A61P 35/00*** | (2006.01) |
| ***C07K 14/195*** | (2006.01) |

(52) U.S. Cl.

CPC ............ *A61K 35/748* (2013.01); *A61K 49/22* (2013.01); *A61P 35/00* (2018.01); *C07K 14/195* (2013.01); *A61K 2035/115* (2013.01); *A61K 48/00* (2013.01)

(58) Field of Classification Search

CPC ...... C12N 2740/16043; C12N 2800/90; C12N 15/85; A61K 49/223

See application file for complete search history.

(56) References Cited

U.S. PATENT DOCUMENTS

| | | | |
|---|---|---|---|
| 6,326,193 | B1 | 12/2001 | Liu |
| 2014/0288411 | A1 | 9/2014 | Shapiro |
| 2014/0288421 | A1 | 9/2014 | Shapiro |
| 2018/0028693 | A1 | 2/2018 | Lakshmanan |
| 2018/0030501 | A1 | 2/2018 | Bourdeau |
| 2018/0038922 | A1 | 2/2018 | Lu |
| 2019/0175763 | A1 | 6/2019 | Shapiro |
| 2019/0314001 | A1 | 10/2019 | Maresca |
| 2020/0164095 | A1 | 5/2020 | Lakshmanan |
| 2020/0237346 | A1 | 7/2020 | Sawyer |
| 2021/0060185 | A1 | 3/2021 | Lakshmanan |
| 2023/0016245 | A1 | 1/2023 | Duan |
| 2023/0047753 | A1 | 2/2023 | Szablowski |
| 2023/0094152 | A1 | 3/2023 | Shivaei |
| 2023/0109152 | A1 | 4/2023 | Jin |
| 2023/0173489 | A1 | 6/2023 | Wu |

FOREIGN PATENT DOCUMENTS

| | | |
|---|---|---|
| WO | WO2001/029058 | 4/2001 |
| WO | WO2001/096584 | 12/2001 |
| WO | WO2016/210373 | 12/2016 |
| WO | WO2020/146379 | 7/2020 |

OTHER PUBLICATIONS

Whisstock et al. Quaterly Reviews of Biophysics, 2003, "Prediction of protein function from protein sequence and structure", 36(3):307-340. (Year: 2003).*

Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*

Kisselev L., Polypeptide release factors in prokaryotes and eukaryotes: same function, different structure. Structure, 2002, vol. 10:8-9. (Year: 2002).*

Abedi et al., "Ultrasound-controllable engineered bacteria for cancer immunotherapy," Nature Communications 2022, 13(1), in 11 pages.

Abel et al., "Systems-informed genome mining for electroautotrophic microbial production," bioRxiv 2020, in 24 pages.

Allouche-Arnon et al., "Computationally designed dual-color MRI reporters for noninvasive imaging of transgene expression," Nature Biotechnology 2022, 40(7), 1143-1149.

Alnahhas et al., "Majority sensing in synthetic microbial consortia," Nature Communications 2020, 11(1), in 10 pages.

Ammar et al., "Regulation of metabolism in *Escherichia coli* during growth on mixtures of the non-glucose sugars: arabinose, lactose, and xylose," Scientific Reports 2018, 8(1), in 11 pages.

Bar-Zion et al., "Acoustically triggered mechanotherapy using genetically encoded gas vesicles," Nature Nanotechnology 2021, 16(12), 1403-1412.

Birnbaum & Bailey, "Plasmid presence changes the relative levels of many host cell proteins and ribosome components in recombinant *Escherichia coli*," Biotechnology and Bioengineering 1991, 37(8), 736-745.

Borkowski et al., "Overloaded and stressed: whole-cell considerations for bacterial synthetic biology," Current Opinion in Microbiology 2016, 33, 123-130.

(Continued)

*Primary Examiner* — Iqbal H Chowdhury

(74) *Attorney, Agent, or Firm* — Dickinson Wright PLLC

(57) ABSTRACT

Disclosed herein include methods, compositions, and kits suitable for use in dynamic non-destructive imaging. The non-destructive imaging can be nonlinear ultrasound imaging. There are provided, in some embodiments, nucleic acid compositions encoding gas vesicles (GVs) capable of producing nonlinear ultrasound contrast upon expression in a prokaryotic cell (e.g., a probiotic bacterial cell) or a eukaryotic cell (e.g., a therapeutic mammalian cell).

9 Claims, 77 Drawing Sheets

Specification includes a Sequence Listing.

(56) References Cited

OTHER PUBLICATIONS

Bourdeau et al., "Acoustic reporter genes for noninvasive imaging of microorganisms in mammalian hosts," Nature 2018, 553(7686), 86-90.
Broadway & Scharf, "*Salmonella typhimurium* as an anticancer therapy: recent advances and perspectives," Current Clinical Microbiology Reports 2019, 6, 225-239.
Burstein et al., "New CRISPR-Cas systems from uncultivated microbes," Nature 2017, 542(7640), 237-241.
Ceroni et al., "Burden-driven feedback control of gene expression," Nature Methods 2018, 15(5), 387-393.
Charbonneau et al., "Developing a new class of engineered live bacterial therapeutics to treat human diseases," Nature Communications 2020, 11(1), in 11 pages.
Chien et al., "Advances in bacterial cancer therapies using synthetic biology," Current Opinion in Systems Biology 2017, 5, in 15 pages.
Chow et al., "High-performance genetically targetable optical neural silencing by light-driven proton pumps," Nature 2010, 463(7277), 98-102.
Christensen-Jeffries et al., "Super-resolution ultrasound imaging," Ultrasound in Medicine & Biology 2020, 46(4), 865-891.
Chu et al., "A bright cyan-excitable orange fluorescent protein facilitates dual-emission microscopy and enhances bioluminescence imaging in vivo," Nature Biotechnology 2016, 34(7), 760-767.
Dang et al., "Combination bacteriolytic therapy for the treatment of experimental tumors," Proceedings of the National Academy of Sciences 2001, 98(26), 15155-15160.
Din et al., "Synchronized cycles of bacterial lysis for in vivo delivery," Nature 2016, 536(7614), 81-85.
Donello et al., "Woodchuck hepatitis virus contains a tripartite posttranscriptional regulatory element," Journal of Virology 1998, 72(6), 5085-5092.
Drepper et al., "Reporter proteins for in vivo fluorescence without oxygen," Nature Biotechnology 2007, 25(4), 443-445.
Duong et al., "Bacteria-cancer interactions: bacteria-based cancer therapy," Experimental & Molecular Medicine 2019, 51(12), in 15 pages.
Durrant et al., "Large-scale discovery of recombinases for integrating DNA into the human genome," BioRxiv 2021, in 49 pages.
Errico et al., "Ultrafast ultrasound localization microscopy for deep super-resolution vascular imaging," Nature 2015, 527(7579), 499-502.
Farhadi et al., "Genetically encoded phase contrast agents for digital holographic microscopy," Nano Letters 2020, 20(11), 8127-8134.
Farhadi et al., "Ultrasound imaging of gene expression in mammalian cells," Science 2019, 365(6460), 1469-1475.
Fonfara et al., "Phylogeny of Cas9 determines functional exchangeability of dual-RNA and Cas9 among orthologous type II CRISPR-Cas systems," Nucleic Acids Research 2014, 42(4), 2577-2590.
Gao et al., "Diverse enzymatic activities mediate antiviral immunity in prokaryotes," Science 2020, 369(6507), 1077-1084.
Gasiunas et al., "A catalogue of biochemically diverse CRISPR-Cas9 orthologs," Nature Communications 2020, 11(1), in 10 pages.
Genove et al., "A new transgene reporter for in vivo magnetic resonance imaging," Nature Medicine 2005, 11(4), 450-454.
Gilad et al., "Artificial reporter gene providing MRI contrast based on proton exchange," Nature Biotechnology 2007, 25(2), 217-219.
Govorunova et al., "RubyACRs, nonalgal anion channelrhodopsins with highly red-shifted absorption," Proceedings of the National Academy of Sciences 2020, 117(37) 22833-22840.
Grady & Hayes, "Axe-Txe, a broad-spectrum proteic toxin-antitoxin system specified by a multidrug-resistant, clinical isolate of Enterococcus faecium," Molecular Microbiology 2003, 47(5), 1419-1432.
Gurbatri et al., "Engineered probiotics for local tumor delivery of checkpoint blockade nanobodies," Science Translational Medicine 2020, 12(530), in 12 pages.
Harrington et al., "A thermostable Cas9 with increased lifetime in human plasma," Nature Communications 2017, 8(1), in 8 pages.
Hays et al., "Better together: engineering and application of microbial symbioses," Current Opinion in Biotechnology 2015, 36, 40-49.
Hecht et al., "When wavelengths collide: bias in cell abundance measurements due to expressed fluorescent proteins," ACS Synthetic Biology 2016, 5(9), 1024-1027.
Hui et al., "Rapid monitoring of the target protein expression with a fluorescent signal based on a dicistronic construct in *Escherichia coli*," AMB Express 2018, 8(1), in 10 pages.
Hurt et al., "Genomically mined acoustic reporter genes enable real-time in vivo monitoring of tumors and tumor-homing probiotics," bioRxiv 2022, in 52 pages.
Hurt et al., "Genomically mined acoustic reporter genes enable real-time in vivo monitoring of tumors and tumor-homing probiotics," bioRxiv 2021, in 41 pages.
Jimenez et al., "Microbial therapeutics: new opportunities for drug delivery," Journal of Experimental Medicine 2019, 216(5), 1005-1009.
Johns et al., "Metagenomic mining of regulatory elements enables programmable species-selective gene expression," Nature Methods 2018, 15(5), 323-329.
Karim et al., "Characterization of plasmid burden and copy number in *Saccharomyces cerevisiae* for optimization of metabolic engineering applications," FEMS Yeast Research 2013, 13(1), 107-116.
Klapoetke et al., "Independent optical excitation of distinct neural populations," Nature Methods 2014, 11(3), 338-346.
Komárek et al., "Polyphasic evaluation of *Limnoraphis robusta*, a water-bloom forming cyanobacterium from Lake Atitlán, Guatemala, with a description of *Limnoraphis* gen. nov," Fottea 2013, 13(1), 39-52.
Komárek, "Planktic oscillatorialean cyanoprokaryotes (short review according to combined phenotype and molecular aspects)," Phytoplankton and Equilibrium Concept: The Ecology of Steady-State Assemblages: Proceedings of the 13th Workshop of the International Association of Phytoplankton Taxonomy and Ecology (IAP) 2003, 367-382.
Lakshmanan et al., "Acoustic biosensors for ultrasound imaging of enzyme activity," Nature Chemical Biology 2020, 16(9), 988-996.
Lakshmanan et al., "Molecular engineering of acoustic protein nanostructures," ACS Nano 2016, 10(8), 7314-7322.
Lambert et al., "Aequorea's secrets revealed: New fluorescent proteins with unique properties for bioimaging and biosensing," PLoS Biology 2020, 18(11), in 22 pages.
Larkin et al., "Clustal W and Clustal X version 2.0," Bioinformatics 2007, 23(21), 2947-2948.
Lee et al., "The Lacl-family transcription factor, RbsR, is a pleiotropic regulator of motility, virulence, siderophore and antibiotic production, gas vesicle morphogenesis and flotation in Serratia," Frontiers in Microbiology 2017, 8, in 14 pages.
Leventhal et al., "Immunotherapy with engineered bacteria by targeting the STING pathway for anti-tumor immunity," Nature Communications 2020, 11(1), in 15 pages.
Li & Cannon, "Gas vesicle genes identified in Bacillus megaterium and functional expression in *Escherichia coli*," Journal of Bacteriology 1998, 180(9), 2450-2458.
Li & Rinas, "Recombinant protein production associated growth inhibition results mainly from transcription and not from translation," Microbial Cell Factories 2020, 19(1), 1-11.
Loew et al., "Improved Tet-responsive promoters with minimized background expression," BMC Biotechnology 2010, 10(81), in 13 pages.
Lu et al., "Genetically encodable contrast agents for optical coherence tomography," ACS Nano 2020, 14(7), 7823-7831.
Mak et al., "Integrative genomic mining for enzyme function to enable engineering of a non-natural biosynthetic pathway," Nature Communications 2015, 6(1), in 10 pages.
Maresca et al., "Biomolecular ultrasound and sonogenetics," Annual Review of Chemical and Biomolecular Engineering 2018, 9, 229-252.
Maresca et al., "Nonlinear ultrasound imaging of nanoscale acoustic biomolecules," Applied Physics Letters 2017, 110(7), in 5 pages.
Maresca et al., "Nonlinear X-wave ultrasound imaging of acoustic biomolecules," Physical Review X 2018, 8(4), in 12 pages.

(56) References Cited

OTHER PUBLICATIONS

Matz et al., "Fluorescent proteins from nonbioluminescent *Anthozoa* species," Nature Biotechnology 1999, 17(10), 969-973.
Oren et al., "Gas vesicles isolated from Halobacterium cells by lysis in hypotonic solution are structurally weakened," FEMS Microbiology Letters 2005, 252(2), 337-341.
Pfeifer, "Distribution, formation and regulation of gas vesicles," Nature Reviews Microbiology 2012, 10(10), 705-715.
Piraner et al., "Going deeper: biomolecular tools for acoustic and magnetic imaging and control of cellular function," Biochemistry 2017, 56(39), 5202-5209.
Piraner et al., "Tunable thermal bioswitches for in vivo control of microbial therapeutics," Nature Chemical Biology 2017, 13(1), 75-80.
Raman et al., "The motility regulator flhDC drives intracellular accumulation and tumor colonization of *Salmonella*," Journal for ImmunoTherapy of Cancer 2019, 7 (44), in 16 pages.
Ramsay et al., "A quorum-sensing molecule acts as a morphogen controlling gas vesicle organelle biogenesis and adaptive flotation in an enterobacterium," Proceedings of the National Academy of Sciences 2011, 108(36), 14932-14937.
Ran et al., "In vivo genome editing using *Staphylococcus aureus* Cas9," Nature 2015, 520(7546), 186-191.
Rodriguez et al., "The growing and glowing toolbox of fluorescent and photoactive proteins," Trends in Biochemical Sciences 2017, 42(2), 111-129.
Sawyer et al., "Ultrasensitive ultrasound imaging of gene expression with signal unmixing," Nature Methods 2021, 18(8), 945-952.
Schilling et al., "MRI measurements of reporter-mediated increases in transmembrane water exchange enable detection of a gene reporter," Nature Biotechnology 2017, 35(1), 75-80.
Schultz, "Clinical use of *E. coli* Nissle 1917 in inflammatory bowel disease," Inflammatory Bowel Diseases 2008, 14(7), 1012-1018.
Seo & Bailey, "Effects of recombinant plasmid content on growth properties and cloned gene product formation in *Escherichia coli,*" Biotechnology and Bioengineering 1985, 27(12), 1668-1674.
Shapiro et al., "Biogenic gas nanostructures as ultrasonic molecular reporters," Nature Nanotechnology 2014, 9(4), 311-316.
Sievers et al., "Fast, scalable generation of high-quality protein multiple sequence alignments using Clustal Omega," Molecular Systems Biology 2011, 7(1), in 6 pages.
Sleight & Sauro, "Visualization of evolutionary stability dynamics and competitive fitness of *Escherichia coli* engineered with randomized multigene circuits," ACS Synthetic Biology 2013, 2(9), 519-528.
Sonnenborn & Schulze, "The non-pathogenic *Escherichia coli* strain Nissle 1917-features of a versatile probiotic," Microbial Ecology in Health and Disease 2009, 21(3-4), 122-158.
Stanton et al., "Genomic mining of prokaryotic repressors for orthogonal logic gates," Nature Chemical Biology 2014, 10(2), 99-105.
Stritzker et al., "Tumor-specific colonization, tissue distribution, and gene induction by probiotic *Escherichia coli* Nissle 1917 in live mice," International Journal of Medical Microbiology 2007, 297(3), 151-162.
Subramanian & Srienc, "Quantitative analysis of transient gene expression in mammalian cells using the green fluorescent protein," Journal of Biotechnology 1996, 49(1-3), 137-151.
Subramanian et al., "Evolview v3: a webserver for visualization, annotation, and management of phylogenetic trees," Nucleic Acids Research 2019, 47(W1), W270-W275.
Tashiro et al., "Molecular genetic and physical analysis of gas vesicles in buoyant enterobacteria," Environmental Microbiology 2016, 18(4), 1264-1276.
Toley & Forbes, "Motility is critical for effective distribution and accumulation of bacteria in tumor tissue," Integrative Biology 2012, 4(2), 165-176.
Wacklin et al., "Nomenclatural validation of the genetically revised cyanobacterial genus *Dolichospermum* (Ralfs ex Bornet et Flahault) comb. nova," Fottea 2009, 9(1), 59-64.
Walsby, "Gas vesicles, " Microbiological Reviews 1994, 58(1), 94-144.
Weinberger & Helmstetter, "Chromosome replication and cell division in plasmid-containing *Escherichia coli* B/r," Journal of Bacteriology 1979, 137(3), 1151-1157.
Westphal et al., "Containment of tumor-colonizing bacteria by host neutrophils," Cancer Research 2008, 68(8), 2952-2960.
Zhang et al., "*E. coli* Nissle 1917-derived minicells for targeted delivery of chemotherapeutic drug to hypoxic regions for cancer therapy," Theranostics 2018, 8(6), 1690-1705.
Zhou et al., "Optimization of the Tet-On system for regulated gene expression through viral evolution," Gene Therapy 2006, 13(19), 1382-1390.
Ziesack et al., "Engineered interspecies amino acid cross-feeding increases population evenness in a synthetic bacterial consortium," Msystems 2019, 4(4), in 15 pages.

* cited by examiner

FIG. 3A
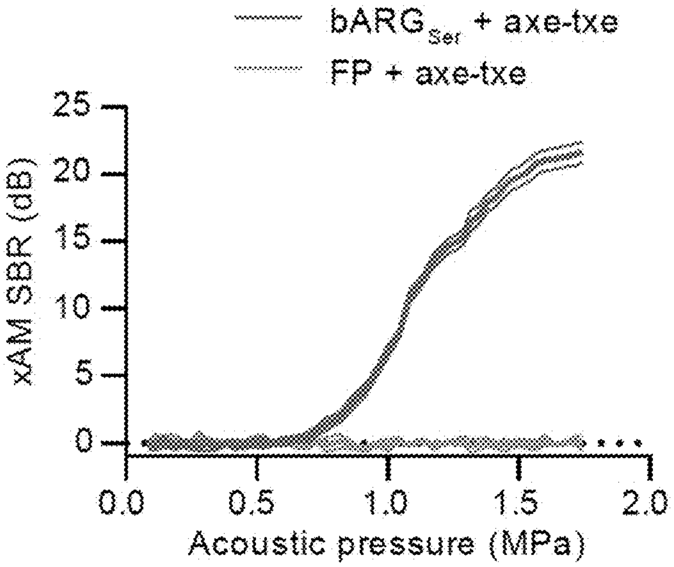
FIG. 3B
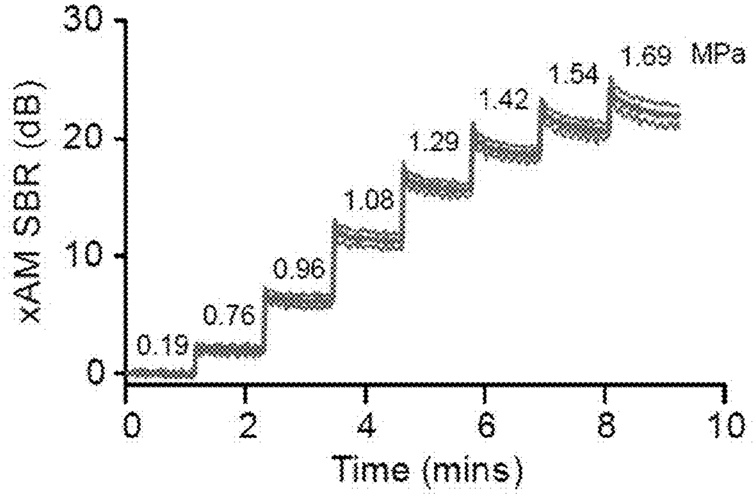
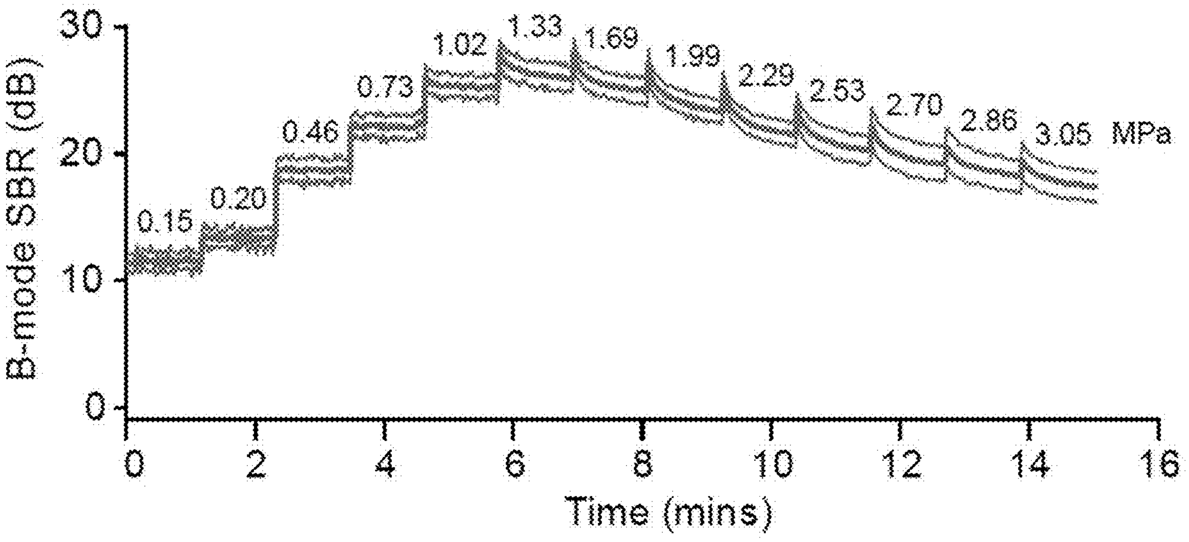
FIG. 3C 1 day post-induction (Day 18)

Re-expressed (Day 19)

Uninduced (Day 18)

FP (control) (Day 18)
B-mode
pAM
BURST
dB
50
40
30
20
10
40
30
20
10
60
50
40
30
20

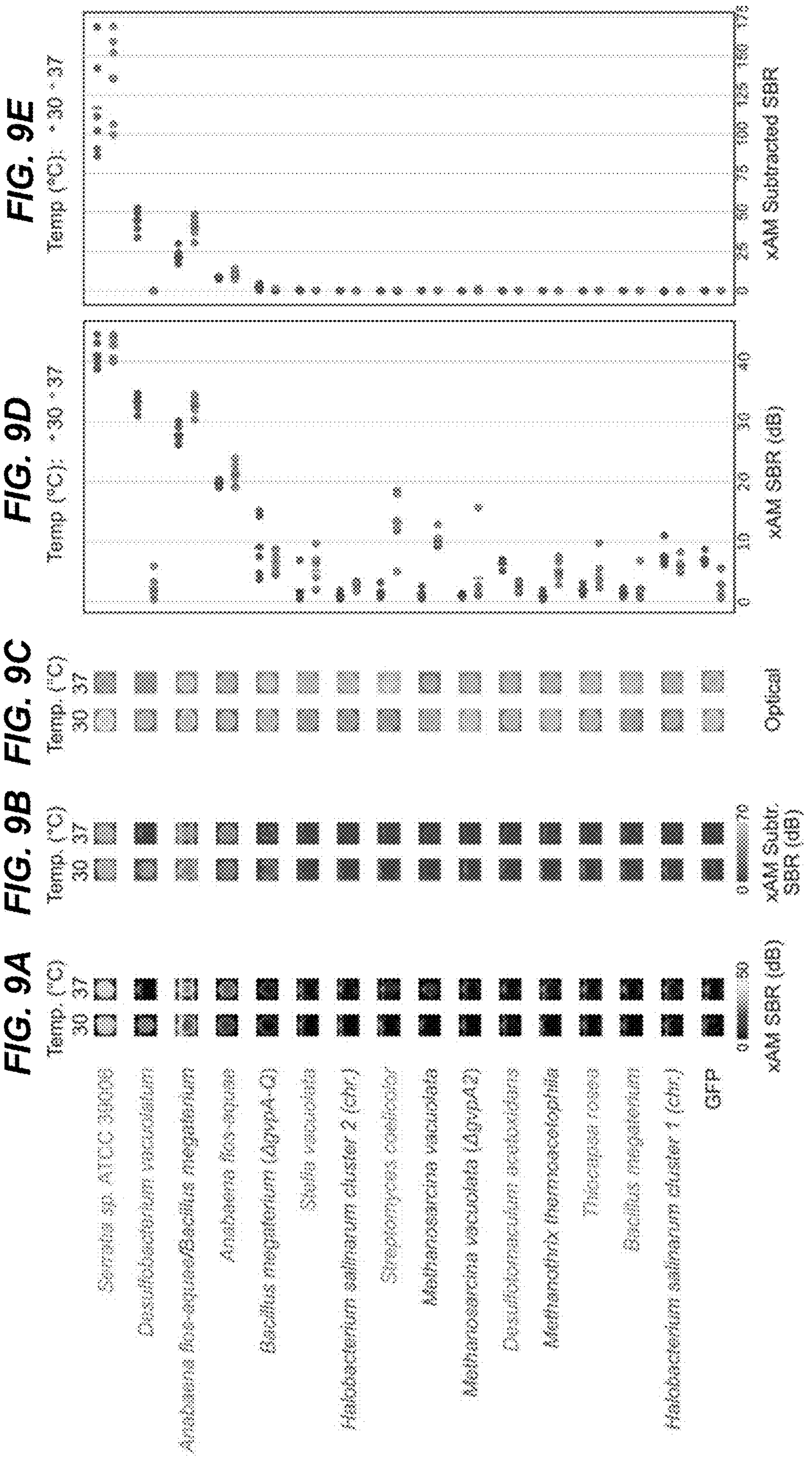
FIG. 9A
FIG. 9B
FIG. 9C
FIG. 9D
FIG. 9E
Temp. (°C)
30 37
Temp (°C): • 30 • 37
Serratia sp. ATCC 39006
Desulfobacterium vacuolatum
Anabaena flos-aquae/Bacillus megaterium
Anabaena flos-aquae
Bacillus megaterium (ΔgvpA-Q)
Stella vacuolata
Halobacterium salinarum cluster 2 (chr.)
Streptomyces coelicolor
Methanosarcina vacuolata
Methanosarcina vacuolata (ΔgvpA2)
Desulfobacterium acetoxidans
Methanothrix thermoacetophila
Thiocapsa rosea
Bacillus megaterium
Halobacterium salinarum cluster 1 (chr.)
GFP
xAM SBR (dB)
xAM Subtr. SBR (dB)
Optical
xAM Subtracted SBR

| | | | Non-white mutants / total colonies screened | | | |
|---|---|---|---|---|---|---|
| Condition | Replicate | Starter | Day 1 | Day 2 | Day 3 | Day 5 |
| +chlor | #1 | 0/226 | 0/68 | 0/69 | 0/60 | 0/40 |
| +chlor | #2 | | 0/55 | 0/47 | 0/355 | 0/54 |
| +chlor | #3 | | 0/48 | 0/39 | 0/98 | 0/42 |
| +chlor | #4 | | 0/56 | 0/21 | 0/49 | 0/233 |
| -chlor | #1 | | 0/39 | 0/54 | 0/70 | 0/64 |
| -chlor | #2 | | 0/28 | 0/46 | 0/65 | 0/46 |
| -chlor | #3 | | 0/47 | 0/57 | 0/75 | 0/52 |
| -chlor | #4 | | 0/36 | 0/57 | 0/57 | 0/38 |
| -chlor +ara | #1 | | 0/2 | 0/68 | 0/53 | 0/44 |
| -chlor +ara | #2 | | 0/2 | 0/62 | 2/86 | 0/68 |
| -chlor +ara | #3 | | ND* | 0/67 | 3/102 | 6/70 |
| -chlor +ara | #4 | | 0/1 | 0/76 | 0/34 | 0/56 |

*ND: no data because there were no colonies

FIG. 21A
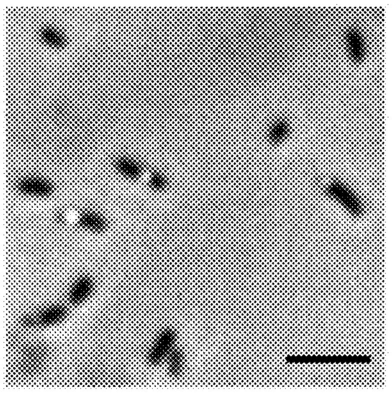
FIG. 21B
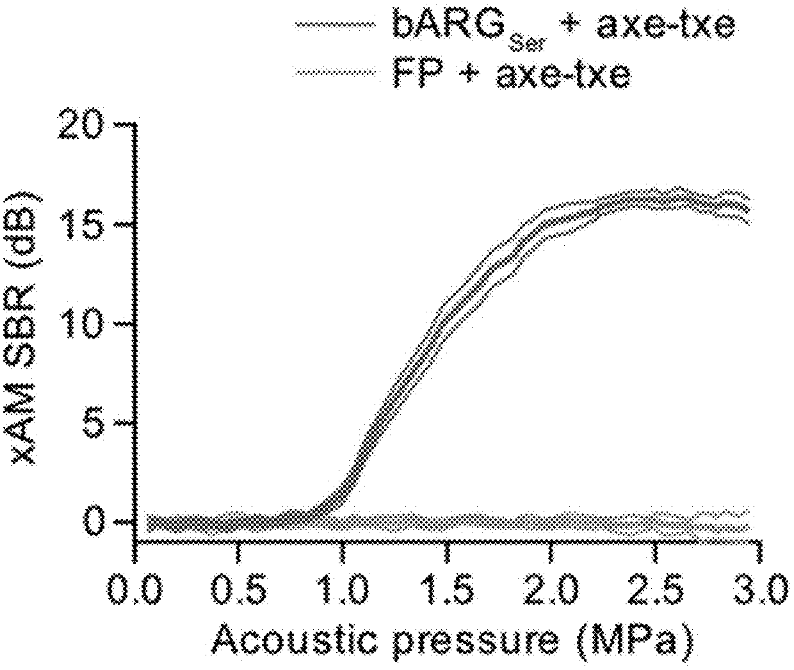
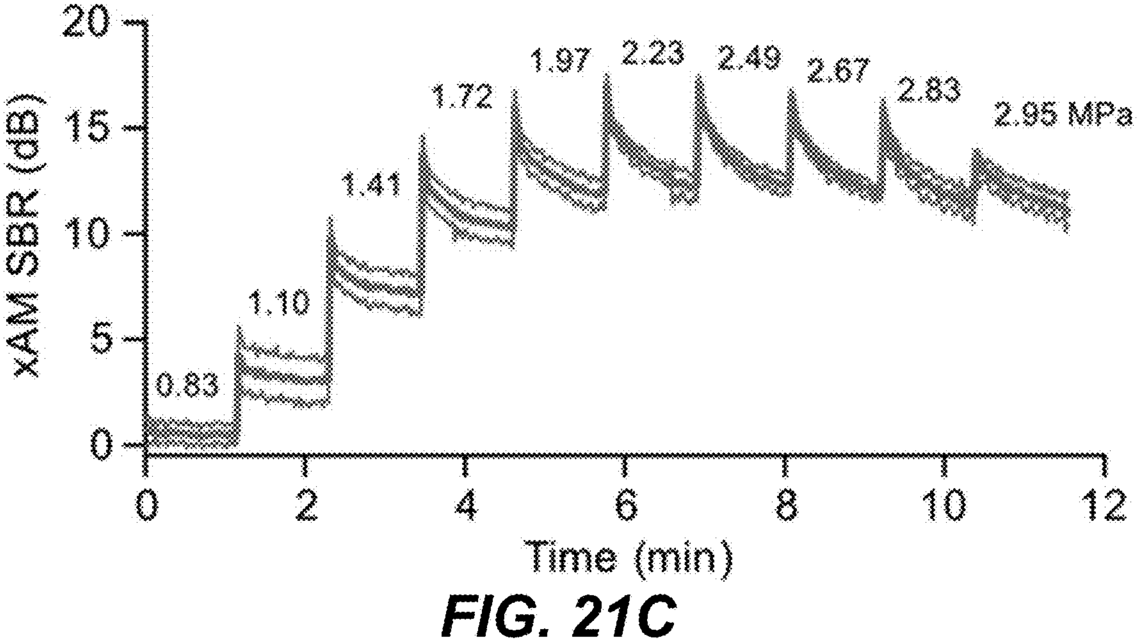
FIG. 21C

FIG. 21D
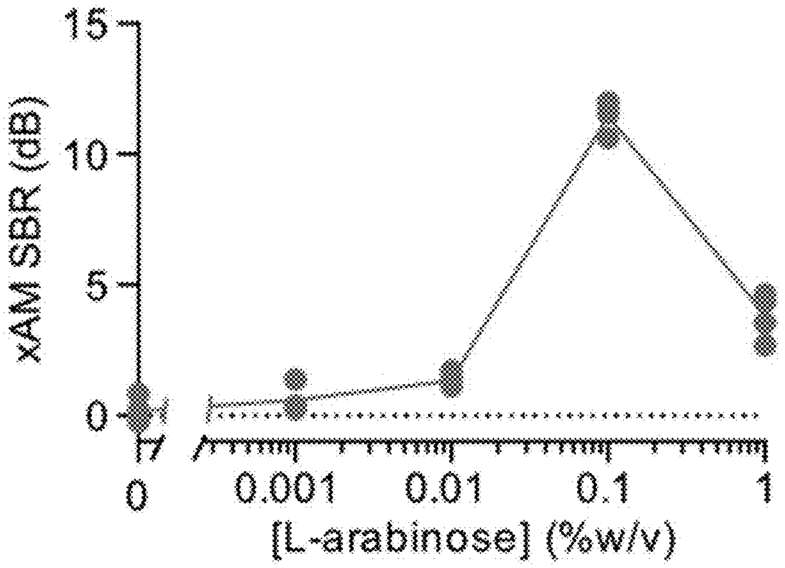
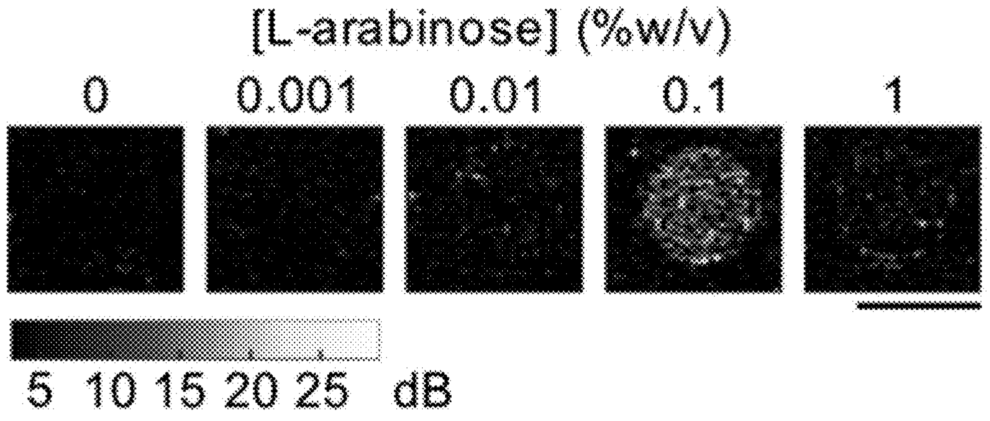
FIG. 21E
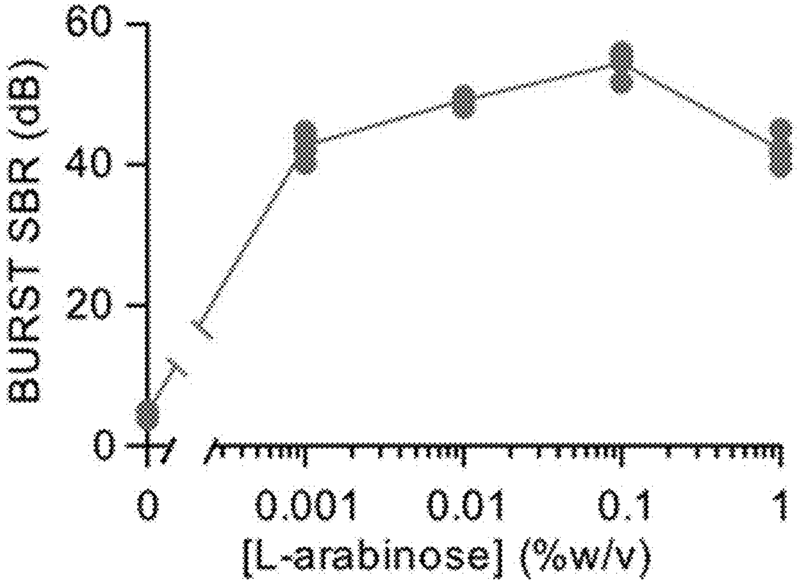
FIG. 21F

| Mouse | Condition | Non-white mutants / total colonies screened |
|---|---|---|
| #1 | Induced | 0/687 |
| #2 | Induced | 2/807 |
| #3 | Induced | 0/341 |
| #4 | Induced | 0/478 |
| #5 | Induced | 5/585 |
| #6 | Uninduced | 0/660 |
| #7 | Uninduced | 0/567 |
| #8 | Uninduced | 0/553 |
| #9 | Uninduced | 0/556 |
| #10 | Uninduced | 0/863 |
| Total | | 7/6097 ~ 0.1% |

pBAD-bARGSer-AxeTxe
23,202 bp
*(SEQ ID NO: 1)*

Assembled NV PiggyBac Cassette
12,217 bp (SEQ ID NO: 2)

Assembled A-IRES-eBFP2 PiggyBac Cassette
8143 bp
*(SEQ ID NO: 3)*

SEQUENCE LISTING

```
Sequence total quantity: 15
SEQ ID NO: 1            moltype = DNA  length = 23202
FEATURE                 Location/Qualifiers
source                  1..23202
                        mol_type = other DNA
                        organism = synthetic construct
SEQUENCE: 1
gaagatcatc ttattaatca gataaaatag ggttatttcg atgaaaggag agagtactaa  60
tgccaattgc aataggaaat aaacggttac ccgttacgtt ggatgaaaag agacaaaaag  120
aattgcagca actaaagcag aagtacggca aaagtgaatc caggattatg tgtattgcgt  180
tagatttatt gattgcccaa gaaaaagcag gatttgaggt accagcactc aaaaagtgac  240
gtcacttttt atcctaaaaa ctaaaagtga tagcactttt aattataaga agttagaata  300
ttaatcattt gcttaattgt acaatataat gtacaattgt tttatagaaa taaataaggg  360
gtgaaaggaa tggaagcagt agcttattca aatttccgcc aaaatttacg tagttatatg  420
aaacaagtta atgaggatgc tgaaacactt attgtaacaa gtaaagatgt agaagataca  480
gttgttgtat tatcaaaaag agattatgat tctatgcaag aaacgttgag aacactttct  540
aataattacg tcatggaaaa aattcgtcga ggagatgaac aattctccaa aggtgcattt  600
aaaacacatg acttaatcga ggttgaatct gatgattaag gcttggtctg atgatgcttg  660
ggatgattat ctttattggc atgagcaagg aaacaaaagc aatataaaaa agattaacaa  720
gttaataaaa gatatcgatc gttcccccttt tgctggatta ggaaaacctg agccattaaa  780
gcatgattta tctggaaaat ggtccagaag aattacagat gaacatagac tgatatatag  840
agttgaaaat gaaacgatat ttatttattc tgcaaaagat cactattaac caatcggaag  900
taaggaaagg gtcagaaact taaaagtttt tgatccttat tttatttacc ctagtcattt  960
aaaaagctaa tatagcttag tgttgattgt tattaatgaa tgtgtttgtt acgcgtatta  1020
cggatataag gttagtaaaa tcatttctaa agttgaggaa aagtaaatat aaatggctta  1080
aatttcaaca atttgaagtt gaatagatat gttataatac tattgtagtg tgggatgtta  1140
gttactaaag gatgacgctt atatatatga ctgaatagaa taagcaatag gtttaataat  1200
ctattttaaa tttttgtac tagttttagt taattagcgg atttgctcat gagcccgaag  1260
tggcgagccc gatcttcccc atcggtgatg tcggcgatat aggcgccagc aaccgcacct  1320
gtggcgccgg tgatgccggc cacgatgcgt ccggcgtaga tgatctgctc atgtttgaca  1380
gcttatcatc gatgcataat gtgcctgtca aatggacgaa gcagggattc tgcaaaccct  1440
atgctactcc gtcaagccgt caattgtctg attcgttacc aattatgaca acttgacggc  1500
tacatcattc acttttctt cacaaccggc acggaactcg ctcgggctgg ccccggtgca  1560
tttttaaat acccgcgaga aatagagttg atcgtcaaaa ccaacattgc gaccgacggt  1620
ggcgataggc atccgggtgg tgctcaaaag cagcttcgcc tggctgatac gttggtcctc  1680
gcgccagctt aagacgctaa tccctaactg ctggcggaaa agatgtgaca gacgcgacgg  1740
cgacaagcaa acatgctgtg cgacgctggc gatatcaaaa ttgctgtctg ccaggtgatc  1800
gctgatgtac tgacaagcct cgcgtacccg attatccatc ggtggatgga gcgactcgtt  1860
aatcgcttcc atgcgccgca gtaacaattg ctcaagcaga tttatcgcca gcagctccga  1920
atagcgccct tccccttgcc cggcgttaat gatttgccca aacaggtcgc tgaaatgcgg  1980
ctggtgcgct tcatccgggc gaaagaaccc cgtattggca aatattgacg gccagttaag  2040
ccattcatgc cagtaggcgc gcggacgaaa gtaaacccac tggtgatacc attcgcgagc  2100
```

```
ctccggatga cgaccgtagt gatgaatctc tccttgcggg aacagcaaaa tatcacccgg  2160
tcggcaaaca aattctcgtc cctgattttt caccaccccc tgaccgcgaa tggtgagatt  2220
gagaatataa cctttcattc ccagcggtcg gtcgataaaa aaatcgagat aaccgttggc  2280
ctcaatcggc gttaaacccg ccaccagatg ggcattaaac gagtatcccg gcagcagggg  2340
atcattttgc gcttcagcca tacttttcat actcccgcca ttcagagaag aaaccaattg  2400
tccatattgc atcagacatt gccgtcactg cgtcttttac tggctcttct cgctaaccaa  2460
accggtaacc ccgcttatta aaagcattct gtaacaaagc gggaccaaag ccatgacaaa  2520
aacgcgtaac aaaagtgtct ataatcacgg cagaaaagtc cacattgatt atttgcacgg  2580
cgtcacactt tgctatgcca tagcattttt atccataaga ttagcggatc ctacctgacg  2640
ctttttatcg caactctcta ctgtttctcc atacccgttt ttttgggcta acaggaggaa  2700
ttaaccttca ttgtggtgga tttattaaca ttaatagagc gctgatgcct ataggttggc  2760
gcatgagttg cattctacat gggcgtgcag taacaagtct gtacgtagaa cctaattaca  2820
tatgtaattt attaacattt tctaggagac gccatcatgg ctaaagtaca aaaatcaaca  2880
gactcttcca gcttggctga agtagtagac cgtattctgg acaaaggcat tgtgattgac  2940
gcttgggtca aagtctcatt ggttggtatt gaactgttat ccatcgaagc acgtgttgtt  3000
attgcttctg ttgaaactta tttgaaatac gcagaagcga ttggccttac agccagtgca  3060
gcgactccag cgtaattaag taagcagaat aaaagtgccc aagtggctga gtcattcagc  3120
tgcttgagta cttttcaacg cttcaagagt gctctatcac ataaggagaa tcctatggga  3180
tgcttaacag acggtatggc gcagctgcgt aagaatattg atgacagtca tgaatctcgc  3240
atagcacagc aaaatgcgcg ggtttccagt gtgagtgcgc agattgccgg tttttctaca  3300
actcgggcta gaaacgcggc tcaagacgca cgcgcacgcg cgacattcgt tgccgataat  3360
gtcagaggcg ttaatcggat gttgagtgac ttctgtcata cccgcgaggt aatgagtcgt  3420
caacagagtg aagaacgtgc caccttcgtg acggatatgt cgaagaaaac gctagcttta  3480
ttagacggtt ttaatgctga gcgtaaaagt atggctgaac gctgtgctaa agaacgagct  3540
gatttcattg ccaacgtggc aaacgatgtc gctgcttttc ttagtgcttc tgagaaggac  3600
agaatggctg cccatgctgt atttttcggc atgaccctgg ctaaaaaaaa aacgagcctc  3660
gcagtctagc cactcgtcct cttgataata ctctggcggt aagtagtgaa gatgaaaaaa  3720
ggtaagtagc ggtattagcc tctgtcgtcc atggagggtg aggtggatga acagtctgct  3780
cacaaacacg gagtgacatt attgggcata cagtttcgat taatcgctaa gttaaatcga  3840
aatataagaa tccgctaaaa tcgaccgatt ctagcggcta agacgatcac tgatttggcc  3900
atttcgtaga actggtgttg gctagggcgt acacggtttg gcacaggagt atttccatga  3960
ttaagcaaaa taccgtttcg cagtataccg tagacgatga tcttgtcgtt ccggaagcga  4020
gtgaacattt tgtagcgact tcttatgtga acgacattat agaacgcgca ttggtttatt  4080
tacgcgctgg ctatcccgtg cattttgccg gcccatctgg gatagggaaa acaaccctgg  4140
catttcatct cgcagcacta tggggtcgtc ccgttaccat gttgcaaggt aacgaagaat  4200
ttgtgagctc cgatttgacg gggaaagaca tcggctatcg taaaagcagc ctggtggata  4260
actacattca ttcagtgctt aaaactgaag aacagatgaa ccgcatgtgg gtggataacc  4320
gtttgaccac cgcgtgtcgt aacggcgaca tgctgatcta tgatgagttc aatcgttcca  4380
aagcagaaac caataatgtg ctgttatccg tattatccga agggatttta aaccttcctg  4440
gtttacgtgg tgtaggggaa gggtatctcg atgtacaccc agaatttcgc gctattttta  4500
cctccaatcc agaagagtat gccggtacgc ataagaccca ggacgctctg atggatcgta  4560
tgattactat caacattggt cttgtcgatc gggatactga actacagata ctgcatgcgc  4620
gctctgaatt ggaattaaaa gaagcggcat atatcgttga tataatcaga gagttgcgtg  4680
gtaacgaaca cgaaaccaaa catgggttac gtgcaggaat tgccatcgcc cacatcctac  4740
accagcaagg aataaaacca cgttatggtg acaaattatt ccatgctatc tgctacgacg  4800
tcttgagtat ggacgctgcc aaaatacaac acgctggacg ttctatatac cgtgaaatgg  4860
tcgatggcgt tattcgtaaa atctgtccac caataggttc agacacggtt aaagcatcca  4920
cacaaaaaat aaaagcagtg gagtaattat catggctata agtactcgtc ctctcagaac  4980
actgtcagac ataaaaactc attcaggtcg agtgagtggt gagcatcaaa cctatcgtga  5040
ttattttcag ataggtgcgc tggaattaga gcgttggcgg cgaacacgag aacgtgaggc  5100
tgcctcatcg cgtattgcca gtattgatga gcgtatcgcg gatattgata aagaaaaagc  5160
agcgctgctt gcagacgcga cagcggcgag tgctgtggct gaaaataatg ataaatcaga  5220
agcggccgag aagaagaaaa agtcttctgg tttgcgaatc aagtattgag gttgtcatta  5280
tgaacaaaat tcgcaccctc gctcatatcc gtacaccgcg tatggtgaag agctttcgca  5340
catgcgtcaa catgacgggg aagtcacaaa ttctcgctga ttttggacgt atttatttag  5400
aagaatatcg acgattgaac cgtgtgcaat gcgccaaaag taaacgtatt tcattgagga  5460
gtgcatgatg agtattgata aatccagaaa tcatcgtgcc aaggtgcttt atgcgctctg  5520
tgtttccgat gactcaacgc ctaactataa aatacgcgga ttggaagcag caccggttta  5580
ttctattgat caagatggct taagagctgt ggtcagcgat acgctcagta cccggttacg  5640
tccagaaaga cgtaatatca cggcgcatca ggctgtatta cataagttga ctgaagaagg  5700
taccgtattg ccgatgcgct ttgggggttat tgcccgtaat gctgaagcag taaagaattt  5760
gctggtcgct aatcaggata cgatcagaga acattttgaa cgcttggatg gctgtgtgga  5820
aatggggcta cgtgtttcct gggatgttac taatatttat gaatattttg ttgctacata  5880
tccagtctta agtgaaacgc gcgatgaaat ctggaatgga aattccaatg ccaataatca  5940
ccgtgaagag aagattcggc tgggtaattt gtacgagtca ttgcgtagtg gagacagaaa  6000
agaatcgacg gaaaaagtaa aagaagttct gttggattat tgcgaagaga ttattgaaaa  6060
cccggttaaa aaagaaaaag acgtaatgaa tctagcctgt ttggtagcaa gagaacggat  6120
ggatgaattt gccaaaggcg tttttgaggc atcaaagtta ttcgataacg tttatctgtt  6180
cgattatacc ggcccatggg caccgcataa tttcgttact ctggatttac atgctcctac  6240
agcgaagaag aaaacgttga cccgcgctgg tactctctct gactgaggct aagccatgct  6300
gctgatcgat gacatcctgt tttctcctgt caaaggcgtc atgtggattt ttcggcaaat  6360
tcacgaactg gcggaagatg aattggctgg tgaggcggat cgtattcgtg aaagtttgac  6420
tgatctttat atgttactgg agactggcca gattaccgaa gatgaatttg aacaacagga  6480
agctgtactg ctggatagat tagacgcact ggatgaagaa gatgacatgc taggcgacga  6540
gcctggggat gacgaagacg acgaatacga agaggacgac gacgaagagg acgacgacga  6600
agaggatgac gacgacgagg atgacgacga cgaggatgac gacgacgaag aggatgacga  6660
cgacgacgag gatgacgacg acgaggatga gccagagggt acgacgaaat gaaacctgct  6720
atttatccca agttcttact ggagtcgccg ctgaaactgg ttttcttcgg cggtaaggga  6780
ggagtaggta aaagtacctg tgcgacgtcg acggcgttaa ggctggcgca ggaacagccg  6840
```

-continued

```
cagcaccatt ttttgctggt ttctaccgat ccagcacatt ccctgcaaaa tattctctcc  6900
gatctggtat tgccaaaaaa tctggacgta cgtgaattaa atgccgcagc ctccttgcat  6960
gaatttaaat cgcagcatga aggtgttctg aaagagatag cgtatcgcgg cactgttctc  7020
gatcaaaacg acgtacaagg attgatggat accgcgcttc ccggcatgga tgaattggcc  7080
gcttatcttg aaatagctga atggattcaa aaagatactt actatcgtat tattattgat  7140
actgctccta caggtcatac attgcggctt ttggaaatgc cggatttgat ttatcggtgg  7200
ttgaccgctc tggataccct gcttgccaaa cagcgttata tccggaaacg ttttgccggt  7260
gataatcgat tggatcatct ggatcatttt ctgctggaca tgaatgattc acttaaagct  7320
atgcacgagc tggtgacgga ttccacgcgt tgttgttttg tgttagtgat gctggcggaa  7380
gcgatgagtg tggaagaaag cattgatctt gctggcgcgt tgaatcagca acgggtgttt  7440
ctgtccgatt tagtggtcaa tcgactattt cctgaaaatg actgtccaac ctgttgtgtt  7500
gagcgtaaca gacaaatgct tgcgctccag aacggatacc aacgtttgcc tgggcacgta  7560
ttctggacgt tgcctttgct tgccatcgaa ccgcgtggtg cgttgcttca cgaattttgg  7620
tccggggtcc gtttacttga tgaaaacgaa gtcatggcta cgacgtgtca tcatcaactg  7680
cctttacgtg tagagagttc catttcgctg cctgccagca cattccgact gctgattttt  7740
gcaggtaaag gtggggtagg taaaacgacg ctggcctgtg ctacggcatt gcgtctgaac  7800
agtgaatatc cagaattgcg tattctgttg ttctcagccg atcctgctca ctcgctgagt  7860
gattgtctgg gtgtaaccct acagcagcag cctatatcgg tgttggttaa cattgatgcc  7920
caggaaatta atgcacaagc tgattttgac aaaatccggc agggatatcg tgcggaatta  7980
gaagctttct tgctggatac gttacccaat ctggatatta cttttgatcg tgaagtgttg  8040
gagcatttgc tcgatctcgc gccccccgga ttagatgaaa tcatggcatt gactgcgatc  8100
atggatcatc tagacagcgg tcgttatgac atggtcatcg tggatggcgc acctagcgga  8160
catttgctac gtttattaga gttgcctgaa ttgattcggg attggctaaa acagtttttc  8220
tcgttattgc tgaaatatcg caaagtcatg cgtttcccgc atttatcgga acgtttggta  8280
cagctttcac gcgaattaaa aaatctacgc gctctactgc aggataccaa acaaacgggg  8340
ttgtatgcag ttactgttcc gacgcatttg gcacttgaga agacctatga aatgacatgc  8400
gcattgcagc gattaggctt aacggcaaac gcgttgttta tcaaccagat tacacctccc  8460
agcgattgca cactgtgcca ggcaatcacg agtcgagagt cgttggagct gaagtgcgca  8520
gatgagatgt tccacagcca accacacgcg cagattttcc ggcaaacaga acctacggga  8580
ttgagcaagc taaagacatt gggttcggca ttgtttttat aaactgtgag cgtacacatt  8640
atgccagtga acaaacagta tcaggatgaa cagcaacagg tctctctgtg tgaggccttg  8700
gaccgcgttc tgaacaaagg tgtggtgatt gtcgctgata tcaccatttc agtcgctaat  8760
attgatttga tttatttaag cctacaggct ttggtttctt ctgtagaagc gaaaaaccgt  8820
ttacccggta gggagtaaca ctatgacaac caatcagtta tcgcaccata gtcctgtgtt  8880
cggcccgaca tcgccagcaa tacaacggcc aattactgaa gctaatcgac ataaaataga  8940
catcgatgga gaacgcgtcc gtgatggttt ggcgcaactc gtcctgaccc tggtcaaact  9000
gctgcacgaa ctactggagc gtcaagccat aaggcggatg gattcgggtt cgcttagtga  9060
tgaagaagtc gagcgtttgg gtttggcgct aatgcgccaa gccgaggagt tgacacattt  9120
gtgcgacgtt tttggcttca aggatgatga tttgaacttg gatttaggcc cgctaggccg  9180
attgctgtaa ggaaattgta tgatgaacaa caacatacga ttatttttta gttcccatat  9240
aaatgttatc agtctgtttt cggcagaggg tgtgtaccat ggttaatact accaatgaca  9300
taaatgcggc tacgcgtggt cttctactgc gtatgggtaa tgcatggttt gaacaagatg  9360
aactgcgaca agcagtggat atctatctga aaataatcga gcaatatcct gacagcaagg  9420
agagtaaaac cgcgcaaacg gcgctgttga ccatttcaca acgttatgaa cgagatggtt  9480
tgttccggct gtcacttgat atccttgaac gcgttgggga aataacaccg acatccatat  9540
aagtttcagg atattaacgt ggcctattta tcaggtttga atcctatatt aagtcgcaag  9600
cgatatcgcc agcagtgttt tctacgcagt gagatccatg ttcaggatac cctggatcca  9660
agaattaaga gcatcagtac ggtatagatc atctttcaag ttgcaggtgc gttgtctgcc  9720
cacgctaacc ccagtcactt actggagtaa gccttgggga tttactcgat tgtcgccttc  9780
ctgtgtgttg aaatttattg ggtatatatg cttttgattt tagagagaag gggatgagga  9840
tttgaggtct ttaggttgtt taccctataa ggatttgcac catgagcggc aacaaaaaac  9900
taacccattc aaccgattcg accaccgtag cggatttgtt agagcgatta ctggacaaag  9960
gggttgtcat cagcggtgac attcgcatca gactggttga agtcgaattg ctgacactgg  10020
aaattcgcct gcttatctgt tccgtagata aagcggtaga aatggggctg gattggtgga  10080
gtggcaatcc ggcgtttgat tccagagcca gagtgtcatc atcagcgcct gctccagagt  10140
tggaagaacg tctgcagcgg ctagaggctc gtttggaagc ggcaccgtcc gtcatagaag  10200
aaactcattt ataaggatta tctttttat gcgagcgctg attcattttc ccattattca  10260
tagccctaaa gatttaggga cattgagcga agcggcaagt catttgcgaa ccgaaactca  10320
aacgcgtgcg tatcttgctg ccgtcgaggg gttctggaca atgattacca ctacgattga  10380
gggtttagat ctggactata cacatctgaa actttatcag gatggtctgc cggtttgtgg  10440
aaaagaaaat gaaatagtga ccgatgttgc taacgctggt agccagaatt acaagctctt  10500
gcttacgttg caacataaag gcgcaattct gatgggaaca gagtcccctg aactattgtt  10560
gcaagagcgc gatctgatga cgcagttgtt acaatctacg gagcaaaccg aagcgtcctt  10620
ggaaacagca aaaacattat tgaaccggcg ggatgattat attgcccagc gcattgatga  10680
aacgctgcaa gatggcgaga tggcgatact tttcctgggg cttatgcaca atattgaagc  10740
gaagctgccc gcagatattg tttttattca accgttaggt aaacccccag gaggggaaag  10800
tatttagtga ctacattcct tgttctgcat tatcgttggc attagaagtg gatttattca  10860
ccgagaatat tagaggtagt ataaatataa tttatatgtc attttaatag actacataat  10920
aatgggactt tgttgctttt tttatatttt tatgcgtttt tttgactgat gaaaaacgta  10980
ataataacca actatgtttg tttgtaaaag tatcggcata gcagcaatat agtgcgtata  11040
cggtgataaa taaatattat ggaacccgtg gtcggaattt ccatcacggg atgattttgt  11100
taatactacc cttcctgttt gtctgtttca gccttcattt ttgtgtaaag aaatcgaaat  11160
caatattcat tattttgtta gataatatat ggtgcttcta gtggaattga tgccagatgt  11220
gacataggca aacgtttttt ggcggtggtt tattagctat ttatgtgatg tatgtctctt  11280
agttattacc agttttatcg atagccctat gatcttttga tactaaaaat gtgacctaat  11340
cggctaaaaa gggagtgtcg cccttgatat ggctgatagc catcagtaga cagatgatgg  11400
gatgatgttt atcatgtcca gaataaagtc tctcgcttat ttgaccgggt agttaaaata  11460
ttcgttaata aatagaaata cttgcctaaa ttattgtcac aaaatcgaaa agaaaattgt  11520
gttatcttaa atttgtacta taagtattaa ggatgctatt cattaaaatt aggcaccgtc  11580
```

```
taggcgatga ttaggcggtt gtgttaaaaa aataactaga gtgttaataa ttctttttt  11640
gcgtcaaata tatacgtgat agaagggaga tttatcctct tcttccccgt atcttttaac  11700
tattattaaa aatgaaataa ccaattggat gtagtcgatg aaaagtattg atcctggcta  11760
tgttttaata attgatgacg acaaagatat ttgtgacctg ctatcacact tgctggaaaa  11820
ggctggttgt gaaactcagc aaggttacga tggcgacatg gcaataaagt tgttgtctca  11880
gcgtgaaccg gatgtactgt tacttgatag tattctccct aaacacagtg gcatggaggt  11940
gttagccaat gcccatgctc tgtatccgca actccccgtt atcattatta ctggcaatgt  12000
cggcattctt agcgcggttg gtgctatcaa agctggtgca tgggattaca ttcccaagcc  12060
gtttgataac aaacgagtat tagatctggt gaatcgtgca atgcaaatgc gttggggtaa  12120
ctacgattca aactgcaaag ccagcaagga tactaaaacg cgtatcgctg ccatgatggg  12180
gaatagccgc gagattcagt cggtgatcag agatgtcgtt aacgtggctc atacggattt  12240
ttctgtcgtt attcagggtg aaacgggaac tggcaaagaa ttggttgcga aaaacatcca  12300
tttagccagt cagcatgcca caggggtttt tgttcccatt gattgtggct ccatacccga  12360
ctcgttgatc gaaaatgaac tatttggtca tgaaaaaggc tcgtacaccg ggctgatca  12420
ggttcatgcg ggtaagtttg aagcggctga cggcggtacg ttattcctgg atgaaatcgc  12480
caacatgtct ttatccgcac aggccaagct actgcgtgtg ctacaagagc acgttgtcta  12540
tcgtattggc gcgactaaac ccattcctgt caatgtgcga gtcctggctg ccagcaatga  12600
tgatctactg gacgcggtag ttaaagggaa atttcgcgag gatctctatt atcgattgaa  12660
tgagtatgtc attcggattc cgccgttacg caatcggcac gaggatattc tgtttttgtc  12720
caatcggttt atcgccgaaa ccagcgtcga attgaacaaa acaccgcctg atttgtccgt  12780
tgcggctaaa gaaacactgt tacgttatcc atggccgggt aacgtgcgag agttacgcgc  12840
tgtcatccgc cgtgctgttt tggtatccga caaaagagta ggggttgatg atttaggcct  12900
ggtcatcaaa gaagatcact ttccgcaatc aacgaaaaat ccgtatctga gaacgataca  12960
gaatttctgt ctggaaggtt cgtctcttaa agagatcact caactcaata ttgatcaaat  13020
agagcgaatt atcattcaag acacattaga gaaaacaggc aataacaagg cagaagcagc  13080
gcggcgtttg aatattgact ataaaacgct gcactctaaa ctcaaaaaga tcaatgcagc  13140
cgaggtaaac aatcatgagt agtaaaaaaa aaatgatgtg acagggaatg ttgaaggaat  13200
tttgcgcggt ttgggcgatc tggtggaaaa attggttgaa accggcgaac agataaagcg  13260
tagcggtgcg ttcgatattg acacgaacga cggtaagaat gccaaagccg tgtatggttt  13320
ctccatcaag atgggtttgg atggaaacca ggaaaatcgg gtagaacctt ttggcaacat  13380
acgccgggat gagcaaaccg gggaagctac agtgcaggaa gtgtctgaac cgttggttga  13440
tgttatcgaa gaaagtgatc atgtgctggt actggcagaa atgccggggg tcgctgatga  13500
agatgtgcaa gtcgaattga atggcgacat tctgacgtta cactcggaaa gaggcagtaa  13560
aaaatatcat aaagaaatcg tgttgccgtg ctcattcgat gacaaggcga tggaacggtc  13620
ttgccgtaat ggcattttgg aagtcaaatt aggaaaatga ggcagtcatg tctgaagaac  13680
tcaagctcaa ggtcgccgag gctctgccaa aggatgctgg gcgcggttat gctcgcttag  13740
atccggccga tatggccagg ttaaatctgg ctgtcggtga catagtgcag ttaaccagta  13800
aaaaaggcac cgggattgct aaattgatgc cgacttatcc cgatatgcgg aataaaggca  13860
tcgtacaact ggatggtttg acgcggcgta ataccagcct gagtttagat gaaaaagtgc  13920
agattgaacc cgcttcctgc aaacacgcca cacagatcgt cctcattccc accacgatta  13980
cgcccaacca acgtgacctg tattatatcg gtagcctgct cgatgggttg cccgtacaga  14040
aaggcgatct gctgcgcgcg cacctgtttg gcagtcgttc tgctgatttt aaagtcgaaa  14100
gcaccatacc tgatggtgcg gtactgattg atccgaccac gacactggtg attggcaaat  14160
caaatgctgt cgggaattcg agtcatagca cacaacgttt gtcgtatgag gatgttggcg  14220
gccttaaaaa ccaggtcgcg cgtattcgag aaatgatcga attaccatta cgctatcctg  14280
aggtctttga acgtttaggt atagatgccc ccaaaggtgt actgctctct ggtcccccgg  14340
gatgtggtaa aaccctcatc gcccgcatta ttgcgcaaga aaccgatgcg caatttttta  14400
ccatcagcgg cccggaaatt gtgcataagt tttatggtga aagtgaagcc cacttacgca  14460
aaatttttga ggaagccgga cgcaaagggc caagtatcat ttttctggat gaaattgact  14520
ctattgcacc acaccgcgac aaggtcgtcg gtgatgtaga aaaacgtatc gttgcgcaac  14580
tgctcgcatt aatggatggt ctcaagaatc gaggcaaagt cattgtcatt gccgcgacca  14640
atctacctaa tgcgattgat cccgcgttgc gccgtccggg acgctttgac cgtgaaatca  14700
gcattcctat tccagaccgt gaaggtcgcc gcgagattat cgaaattcat agcacgggaa  14760
tgccgctgaa tgctgatgtc gatctgaacg tgcttgccga tatcactcac ggttttgtcg  14820
gtgccgatct ggaagcgtta tgccgtgaag ccgcgatgag tgcgttacgc cgtttactgc  14880
ctgagatcga tttcagttcg gcggagctac cttatgatcg tctggccgaa ttaacggtga  14940
tgatggatga ttttcgtgcc gccttgtgtg aagtatcacc gtcagcgatt cgtgagctgt  15000
tcgtcgatat tcccgatgtg cgttgggaag atgtcggcgg tttggatgac gtacgccgtc  15060
gattgatcga atccgtcgag tggcctatca agtaccctga gctctatgaa caagcgggtg  15120
ttaagccgcc taaaggtctg ctgttagctg ggcctcccgg cgttgggaaa acgctgatcg  15180
ccaaagccgt tgctaatgaa agtggcgtta atgtcatttc agttaaaggt ccggcgctga  15240
tgtcgcgtta tgtcggtgat tcggaaaaag gtgtccgaga gctgtttctc aaagctcgtc  15300
aggctgcgcc ctgcattatt ttccttgatg aagtcgattc tgtgattcct gcccgtaacg  15360
agggcgctat cgactcacat gtcgcagaac gggtgttgag ccaattctta tctgaaatgg  15420
atgggctgga agaactcaaa ggtgttttcg ttatgggggc gaccaatcgt gcggacttga  15480
tcgatcccgc gatgctgcga ccaggacgtt ttgatgaaat aatcgaattg ggcctgcccg  15540
acgaggacgc ccgtcggcag attctggcgg tgcatttacg taataaaccg ctgggtgaca  15600
atattcatgc tgacgatttg gcagaacgtt gtgatggtgc cagcggtgca gaattggccg  15660
cggtgtgtaa tcgtgccgca ttagcggcat tgcgtcgtgc aatccagcag tctgaagagg  15720
ctgttctgag cccgtcaacg gtaggagaaa cccctgtggc gctgacggta cgcattgaac  15780
agcatgattt tgctgaagtg attgccgaaa tgtttggcga tgatgcatga cgatgaacac  15840
agaagcacag actgagcagg ccatttatct gtatggcctg acgttgcccg atttagccgc  15900
accgccaatt ttgggcgttg ataatcagca tccgattaat acacatcaat gtgccggatt  15960
gaatgcggtg attagcccag tggcactctc cgatttcacg ggtgaaaagg gtgaagacaa  16020
tgtacagaat gtcacttggc taacgccgcg tatttgtcgg catgcgcaga ttattgacag  16080
cctgatggcc caaggtccgg tctatccttt gcccttcggc acgctgtttt ccagtcagaa  16140
cgcgttggaa caggaaatga aaagccgcgc tactgacgta tttgtgtcgc tacgtcgcat  16200
aaccggctgt caggaatggg cactggaagc gacactggat cgtaaacagg ccgttgacgt  16260
tttattcacc gaaggtctgg actccggtcg cttttgccta cccgaagcca taggccgccg  16320
```

ccatttggaa gagcagaaat tacgccgcag gttaaccact gagttgagtg actggttggc 16380
acatgctttg actgccatgc agaacgaatt acatcctttg gtacgtgatt tccgttcacg 16440
tcggttgttg gacgataaaa ttttgcattg ggcgtattta ctcccggtgg aggacgttgc 16500
cgcgtttcaa cagcaggttg ctgacattgt tgaacgctat gaagcttacg gttttagttt 16560
tcgcgtgaca ggcccgtggg cagcctacag tttttgccaa cctgacgaat catgagctta 16620
ctactgtacg gcattgttgc cgaggatact caactggcgc ttgaaccaga cggttcgccg 16680
cacgccggtg aagagccgat gcagcttgtt aaagcggcaa cgttggcggc gctggtcaag 16740
ccttgtgaag cagacgtcag tcgcgagccc gcggcagcgt tggcttttgg ccaacagata 16800
atgcatgttc atcaacagac cacgattatt ccgattcgtt atggttgtgt gttggcagat 16860
gaagatgcgg taacacagca tttactcaac catgaggcac attatcaaac gcaattggtt 16920
gagctggaaa attgtgacga aatgggtatt cggttatccc tggcgtcggc tgaggataat 16980
gccgttacta cgccgcaagc gagtggtctg gactatttgc ggagtcgaaa actcgcttat 17040
gccgtacctg aacacgctga acggcaggct gcactactga ataatgcgtt tacggggttg 17100
tatcgccgac actgcgcgga aatcagtatg tttaatggtc agcggactta cctgttgagc 17160
tatctggtgc cacgaaccgg gttacaggcg tttcgcgacc aatttaatac tctggccaac 17220
aacatgacgg atataggggt tatcagtggg ccttggcctc cctataactt cgccagctaa 17280
tttgttaacg acaggctacc atgtcagata atcctttgga acagcagtca gaaaaccact 17340
ttgaacttct ttacaacatg ctattggatg caattccttc ttccgtgtta atggtggatg 17400
agaaactgca tgtggtttca gtcaatcaga atttttaat caagggtcat cgcggcaacc 17460
cggatacaat tggtcgcccg ttatcggacg tctttccgag cgtcattttg gaaaatacgg 17520
gtcttgaagc acatatccgg gatgtattcc gtagcggatt acccgttaat ggtcagaaaa 17580
tgacctaccg tgcgccaggc gtaccgattc ggatttatta ctattctatt ctacccatcc 17640
ccattaacca gattatgctg ttcatggagg atgtcaccga gcaggttcgc ctgtctgaag 17700
aagtccatcg agtagaacgg cacctcgctt cagttgtaga aaacgccagc gacattgttc 17760
tttcgaccga tattgaagga tgcatattga cgtggaattc agcggcggaa aagctgtcag 17820
gtttacccac gcatgaagtc tatgggcgat actttttga gttctgcgat accaaccaaa 17880
aggaggcggt gcgtctgatt ttcatgcgta tgaagaacag caatgaatca catacgactg 17940
aatttcattt attaacgcct aacaatggtg gcagcatatt gatttcctgg gtattttcac 18000
caatgaagga tgactatggg caaacggtgg gcaccgtagt tgtcggtcgt gatttggctg 18060
aacgtcggaa attggaactg caattacgtc aatcacagaa gttgaccgcg ttgggcgtca 18120
tggcgggcgg tatcgctcat gaaattcgta atcctcttgc tgtttgttct tcagcggcgc 18180
aatttttgct ggaagacgag attacggctg aatttcataa agagtgttca agaaaaatac 18240
agactaacat tcaaaaagcc tcggccatca ttgagaattt actccgtttt gcccgttctt 18300
ccctcgatac cgaaatggta gaggtcaatc tgatcacggt gctgaaagaa actatcgacc 18360
tgatcgccaa ccaggccaaa gtgcagaaaa ttcagatcct gttgccgttg caaaaaggaa 18420
atatattggt gtcaggtgtg tcgggcttac tgcaacaggt gttcatgaat atttttctta 18480
atgccattaa tgcgatgccg gaaggcggtg tgttaagtat tgcggtagag acctttgaag 18540
accgggttat tgtgcgtatt tctgatactg gcgtaggcat tcccgccggc gagttggata 18600
aaattttcga tccgttccac acgtcttcac ccgtaggcca aggtactggt ttgggtttgt 18660
ccatttgtta cagcattatc caacagcacc ttggttccat acaggcagag agttgtctgg 18720
gtgaaggttc cactattatt gttaccttac ctatactcta aaatgatgaa cgcacccatt 18780
ctgatagttg atgatgaacc tgacatgtgt tgggccattt cccatattat tcaatcacaa 18840
ggcatgagtg tcattaccgc ttacagtggg gaagatgctt gcgttaagct gatgaccggc 18900
aatttttcct ttgtgttttt agatgccaag ttaccggata tggacggtct ggaagtggcg 18960
cgtcgagcca gtaccttgct agagcgaaga ccgcgtgtag tgctggtttc cggttatcac 19020
tattacgatg atccggttat tcgccatgct atcgttgaag gcattatctg cggttttctg 19080
gcgaagcctt ttaccaataa agagctgctg aaaacattac agacactatc acagccgagc 19140
gagtagttgc gtcgctagct taatcaacgc tctgcttctt cggggggaat tactgacacg 19200
ctgcacctta aaacgggcat tatgacgata gtgctcgttt taaggtgcaa atggtgtttt 19260
atcgttagcg tgatgtgatg agatgtgcag cttcttttt cgatacatga gcggagtcat 19320
cttcatttct tttcgaaact gattaataaa atagcttgta ctattaaacc ctacttgata 19380
ggcgacttcc gtcacattga gagaagattt tcagcctgat acagattaaa tcagaacgca 19440
gaagcggtct gataaaacag aatttgcctg gcggcagtag cgcggtggtc ccacctgacc 19500
ccatgccgaa ctcagaagtg aaacgccgta gcgccgatgg tagtgtgggg tctccccatg 19560
cgagagtagg gaactgccag gcatcaaata aaacgaaagg ctcagtcgaa agactgggcc 19620
tttcgtttta tctgttgttt gtcggtgaac gctctcctga gtaggacaaa tccgccggga 19680
gcggatttga acgttgcgaa gcaacggccc ggagggtggc gggcaggacg cccgccataa 19740
actgccaggc atcaaattaa gcagaaggcc atcctgacgg atggcctttt tgcgtttcta 19800
caaactcttt tgtttatttt tctaaataca ttcaaatatg tatccgctca tgagacaata 19860
accctgataa atgcttcaat aatattgaaa aaggaagagt atgagtattc aacatttccg 19920
tgtcgccctt attccctttt ttgcggcatt ttgccttcct gtttttgctc acccagaaac 19980
gctggtgaaa gtaaaagatg ctgaagatca gttgggtgca gcaaactatt aactggcgaa 20040
ctacttactc tagcttcccg gcaacaatta atagactgga tggaggcgga taaagttgca 20100
ggaccacttc tgcgctcggc ccttccggct ggctggttta ttgctgataa atctggagcc 20160
ggtgagcgtg ggtctcgcgg tatcattgca gcactggggc cagatggtaa gccctcccgt 20220
atcgtagtta tctacacgac ggggagtcag gcaactatgg atgaacgaaa tagacagatc 20280
gctgagatag gtgcctcact gattaagcat tggtaactgt cagaccaagt ttactcatat 20340
atactttaga ttgatttacg cgccctgtag cggcgcatta agcgcggcgg gtgtggtggt 20400
tacgcgcagc gtgaccgcta cacttgccag cgccctagcg cccgctcctt tcgctttctt 20460
cccttccttt ctcgccacgt tcgccggctt tccccgtcaa gctctaaatc gggggctccc 20520
tttagggttc cgatttagtg ctttacggca cctcgacccc aaaaaacttg atttgggtga 20580
tggttcacgt agtgggccat cgccctgata gacggttttt cgccctttga cgttggagtc 20640
cacgttcttt aatagtggac tcttgttcca aactggaaca acactcaacc ctatctcggg 20700
ctattctttt gatttataag ggattttgcc gatttcggcc tattggttaa aaaatgagct 20760
gatttaacaa aaatttaacg cgaattttaa caaaatatta acgtttacaa tttaaaagga 20820
tctaggtgaa gatccttttt gataatctca tgaccaaaat cccttaacgt gagttttcgt 20880
tccactgagc gtcagacccc gtagaaaaga tcaaaggatc ttcttgagat cctttttttc 20940
tgcgcgtaat ctgctgcttg caaacaaaaa aaccaccgct accagcggtg gtttgtttgc 21000
cggatcaaga gctaccaact ctttttccga aggtaactgg cttcagcaga gcgcagatac 21060

```
caaatactgt ccttctagtg tagccgtagt taggccacca cttcaagaac tctgtagcac  21120
cgcctacata cctcgctctg ctaatcctgt taccagtcag gcatttgaga agcacacggt  21180
cacactgctt ccggtagtca ataaaccggt aaaccagcaa tagacataag cggctattta  21240
acgaccctgc cctgaaccga cgaccgggtc gaatttgctt tcgaatttct gccattcatc  21300
cgcttattat cacttattca ggcgtagcaa ccaggcgttt aagggcacca ataactgcct  21360
taaaaaaatt acgccccgcc ctgccactca tcgcagtact gttgtaattc attaagcatt  21420
ctgccgacat ggaagccatc acaaacggca tgatgaacct gaatcgccag cggcatcagc  21480
accttgtcgc cttgcgtata atatttgccc atggtgaaaa cgggggcgaa gaagttgtcc  21540
atattggcca cgtttaaatc aaaactggtg aaactcaccc agggattggc tgagacgaaa  21600
aacatattct caataaaccc tttagggaaa taggccaggt tttcaccgta acacgccaca  21660
tcttgcgaat atatgtgtag aaactgccgg aaatcgtcgt ggtattcaca ccagagcgat  21720
gaaaacgttt cagtttgctc atggaaaacg gtgtaacaag ggtgaacact atcccatatc  21780
accagctcac cgtctttcat tgccatacgg aattccggat gagcattcat caggcgggca  21840
agaatgtgaa taaaggccgg ataaaacttg tgcttatttt tctttacggt ctttaaaaag  21900
gccgtaatat ccagctgaac ggtctggtta taggtacatt gagcaactga ctgaaatgcc  21960
tcaaaatgtt ctttacgatg ccattgggat atatcaacgg tggtatatcc agtgattttt  22020
ttctccattt tagcttcctt agctcctgaa aatctcgata actcaaaaaa tacgcccggt  22080
agtgatctta tttcattatg gtgaaagttg gaacctctta cgtgccgatc aacgtctcat  22140
tttcgccaaa agttggccca gggcttcccg gtatcaacag ggacaccagg atttatttat  22200
tctgcgaagt gatcttccgt cacaggtatt tattcggcgc aaagtgcgtc gggtgatgct  22260
gccaacttac tgatttagtg tatgatggtg tttttgaggt gctccagtgg cttctgtttc  22320
tatcagctgt ccctcctgtt cagctactga cggggtggtg cgtaacggca aaagcaccgc  22380
cggacatcag cgctagcgga gtgtatactg gcttactatg ttggcactga tgagggtgtc  22440
agtgaagtgc ttcatgtggc aggagaaaaa aggctgcacc ggtgcgtcag cagaatatgt  22500
gatacaggat atattccgct tcctcgctca ctgactcgct acgctcggtc gttcgactgc  22560
ggcgagcgga aatggcttac gaacggggcg gagatttcct ggaagatgcc aggaagatac  22620
ttaacaggga agtgagaggg ccgcggcaaa gccgtttttc cataggctcc gcccccctga  22680
caagcatcac gaaatctgac gctcaaatca gtggtggcga aacccgacag gactataaag  22740
ataccaggcg tttccccctg gcggctccct cgtgcgctct cctgttcctg cctttcggtt  22800
taccggtgtc attccgctgt tatggccgcg tttgtctcat tccacgcctg acactcagtt  22860
ccgggtaggc agttcgctcc aagctggact gtatgcacga accccccgtt cagtccgacc  22920
gctgcgcctt atccggtaac tatcgtcttg agtccaaccc ggaaagacat gcaaaagcac  22980
cactggcagc agccactggt aattgattta gaggagttag tcttgaagtc atgcgccggt  23040
taaggctaaa ctgaaaggac aagttttggt gactgcgctc ctccaagcca gttacctcgg  23100
ttcaaagagt tggtagctca gagaaccttc gaaaaaccgc cctgcaaggc ggtttttttcg  23160
ttttcagagc aagagattac gcgcagacca aaacgatctc aa                     23202

SEQ ID NO: 2            moltype = DNA  length = 12217
FEATURE                 Location/Qualifiers
source                  1..12217
                        mol_type = other DNA
                        organism = synthetic construct
SEQUENCE: 2
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgt gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaac aaaaactcaa  1080
aatttcttct ataaagtaac aaaactttta tgagggacag cccccccccca aagcccccag  1140
ggatgtaatt acgtccctcc cccgctaggg ggcagcagcg agccgcccgg ggctccgctc  1200
cggtccggcg ctccccccgc atccccgagc cggcagcgtg cggggacagc ccgggcacgg  1260
ggaaggtggc acgggatcgc tttcctctga acgcttctcg ctgctctttg agcctgcaga  1320
cacctggggg gatacgggga aaaggcctcc acggccacta gtttcactcg agtttactcc  1380
ctatcagtga tagagaacgt atgaagagtt tactccctat cagtgataga gaacgtatgc  1440
agactttact ccctatcagt gatagagaac gtataaggag tttactccct atcagtgata  1500
gagaacgtat gaccagttta ctccctatca gtgatagaga acgtatctac agtttactcc  1560
ctatcagtga tagagaacgt atatccagtt tactccctat cagtgataga gaacgtatgt  1620
cgaggtaggc gtgtacggtg ggcgcctata aaagcagagc tcgtttagtg aaccgtcaga  1680
tcgcctggag caattccaca acacttttgt cttatacttg gtacctatgt ccgccaccat  1740
ggtgaccacc accaaagtga accacaagcg ggccgtgctg agactgaggc ctggccagtt  1800
tgtcgtgacc cccgccattg agcgggtggc cattagagcc ctgagatacc tgaagtccgg  1860
cttccccgtg cacctgagag gacctgccgg aaccggcaag accacactgg ccatgcacct  1920
ggccaactgc ctggacagac ccgtgatgct gctgttcggc gacgaccagt tcaagagcag  1980
cgacctgatc ggcagcgaga gcggctacac ccacaagaag gtgctggaca actacatcca  2040
cagcgtcgtg aagctggaag atgagttcaa gcagaactgg gtggacagca gactgaccct  2100
ggcctgccgg gaaggcttca ccctggtgta cgacgagttc aaccggtcca gacccgaagt  2160
```

```
gaacaacgtg ctgctgagcg ccctggaaga gaagatcctg agcctgcccc ccagcagcaa  2220
ccagccagag tacctgagcg tgaaccccca gttcagagtg atcttcacca gcaaccccga  2280
ggaatatgcc ggcgtgcaca gcacccagga cgccctgatg gaccggctcg tgaccatctc  2340
catgcccgag cccgatgaga tcacccagac cgagatcctg atccagaaaa caaacatcga  2400
ccgcgagagc gccaacttca tcgtgcggct cgtgaagtcc ttcagactgg ccacaggcgc  2460
cgagaaaacc agcggcctga gaagctgcct gatgatcgcc aaagtgtgcg ccgacaacaa  2520
catccccgtg accaccgaga gcctggactt ccccgatatc gccatcgaca tcctgttcaa  2580
ccgcagccac ctgagcatga gcgagtccac caacatcttt ctggaactgc tggataagtt  2640
cagcgccgag gaactggaaa tcctgaacaa cagagtgacc ggcgacaacg acttcctgat  2700
cgacaacagc cagttcgtgt cccagcagct ggccggacag cccaacggag cgccaggttc  2760
cggggctact aacttcagcc tccttaaaca ggctggcgat gtggaagaaa atcccggacc  2820
agtgctgccc accagacccc agaccaacag cagccggacc atcaacacca gcacccaggg  2880
cagcaccctg gccgacatcc tggaaaagagt gctggacaag ggcatcgtga tcgccgggga  2940
catcagcatc tctatcgcca gcaccgagct ggtgcacatc cggatcagac tgctgatctc  3000
cagcgtggac aaggccaaag agatgggcat caactggtgg gagagcgacc cctacctgag  3060
caccaaggcc cagagactgg tggaagagaa ccagcagctc cagcacagac tggaaagcct  3120
ggaagccaag ctgaacagcc tgaccagcag cagcgtgaaa gaggaaatcc ccctggccgc  3180
cgacgtgaag gacgacctgt atcagaccag cgccaagatc cccagccccg tggataccccc  3240
tatcgaggtg ctggacttcc aggcccagtc tagcggcggc acaccccctt acgtgaacac  3300
ctctatggaa atactggatt ttcaggctca gacctccgcc gagagcagca gccctgtggg  3360
ctctaccgtg gaaatactgg acttccaggc acagacaagc gaggaatcca gctcccccgt  3420
ggtgtccaca gtggaaatac tggatttcca ggcccagact tctgaagagt ccagctctcc  3480
agtgggaagc actgtggaaa tactggactt tcaggcccag accagtgaag agatccccag  3540
ctctgtggac cccgccatcg atgtgggtgc cccgggatct ggcgcaacaa attttagtct  3600
cctcaagcag gcaggagatg tcgaggaaaa ccctggaccc gtggtgtgca cccctgccga  3660
gaacttcaac aacagcctga caatcgccag caagcccaag aacgaggccg gactggctcc  3720
tctgctgctg accgtgctgg aactcgtgcg gcagctgatg gaagcccaag tgatccggcg  3780
gatggaagag gacctgctga gcgagcccga cctggaaaga gccgccgata gcctccagaa  3840
gctggaagaa cagatcctgc acctgtgcga gatgttcgag gtggaccccg ccgacctgaa  3900
catcaacctg ggcgagatcg gcaccctgct gcctagcagc ggcagctact atcctggcca  3960
gccaagcagc agaccctctg tgctggaact gctggaccgg ctgctgaaca ccggcatcgt  4020
ggtggacggc gagattgacc tgggaatcgc ccagatcgac ctgatccacg ccaagctgag  4080
actggtgctg acctccaagc ccatcggggc acctggctca ggagcgacca acttctcatt  4140
gctcaaacaa gccggagatg ttgaggagaa tccaggccct gtgagcatcc ccctgtacct  4200
gtacggcatc ttccccaaca ccatccccga gacactggaa ctggaaggcc tggacaagca  4260
gcccgtgcac agccaggtgg tggacgagtt ctgcttcctg tacagcgagg cccggcagga  4320
aaagtacctg gccagcagac ggaacctgct gacccacgag aaggtgctgg aacagaccat  4380
gcacgccggc ttcagagtgc tgctgcccct gagatttggc ctggtcgtga aggactggga  4440
gacaatcatg agccagctga tcaaccccca caaggaccag ctgaaccagc tgttccagaa  4500
gctggccggc aagcgggaag tgtccatcaa gattttctgg gacgccaagg ccgagcttca  4560
gaccatgatg gaaagccacc aggacctgaa gcagcagcgg gacaacatgg aaggcaagaa  4620
actgagcatg gaagaagtga tccagatcgg gcagctgatc gagatcaacc tgctggcccg  4680
gaagcaggcc gtgatcgagg tgttcagcca ggaactgaac cccttcgccc aggaaatcgt  4740
ggtgtccgac cccatgaccg aggaaatgat ctacaacgcc gccttcctga tcccctggga  4800
gagcgagagc gagttcagcg agcgggtgga agtgatcgac cagaagttcg gcgaccggct  4860
gcggatcaga tacaacaact tcaccgcccc ctacaccttt gcccagctgg actctggcgc  4920
tcccgggtca ggtgccacta atttttcatt gttgaagcaa gctggggatg ttgaagagaa  4980
cccagggcct gtgctgacca aactcctgct gctgcccatc atgggacccc tgaatggcgt  5040
cgtgtggatc gccgagcaga tccaggaacg gaccaacacc gagttcgacg cccaggaaaa  5100
cctgcacaaa cagctgctga gcctccagct gagcttcgac atcggcgaga tcggagagga  5160
agagttcgag attcaggaag aggaaatcct gctgaagatc caggccctgg aagaagaggc  5220
ccggctggaa ctggaagccg agcaggaaga agccagactg gaactggaag ctgaacagga  5280
agatttcgag tacccaccac agttcaccgc cgaagtgaac aaggatcagc atctggtgct  5340
gctgcccggt gccccgggat ctggcgctac taacttcagc ctccttaaac aggctggcga  5400
tgtggaagaa aatcccggac cagtggaact ggaaaacctg tacacctacg cctttctgga  5460
aatccccagc agcccccctga tcctgcctca gggcgctgct aatcaggtgg tgctgatcaa  5520
cggcaccgag ctggccgcca tcgtggaacc tggcatcttc ctggaatcct tccagaacaa  5580
cgacgagaag atcatccaga tggccctgag ccacgacaga gtgatctgcg agctgttcca  5640
gcagatcacc gtgctgcccc tgagattcgg cacctacttc accagcacca acaacctgct  5700
gaaccacctg aagtcccacg agaaagagta ccagaacaag ctggaaaaga tcaacgggaa  5760
gaacgagttc accctgaagc tgatcccccg gatgatcgag gaaatcgtgc cctctgaggg  5820
cggaggcaag gactacttcc tggccaagaa gcagcgctac cagaatcaga acaacttctc  5880
tatcgcccag gccgccgaga agcagaacct gatcgacctg atcaccaaag tgaaccagct  5940
gcccgtggtg gtgcaggaac aggaagaaca gatccaaatc tacctgctgg tgtcctgcca  6000
ggataagacc ctgctgctgg aacagttcct gacctggcag aaagcctgcc ccaagtggga  6060
tctgctgctg ggcgactgcc tgcccccta ccactttatc ggagcgccag gttccggggc  6120
aacaaatttt agtctcctca agcaggcagg agatgtcgag gaaaaccctg gacccgtgat  6180
caagaacatc caggtgttct ttatgaaaac catcagcaac cggtccatca gccgggccaa  6240
gatcagcacc atgcccagac ctaagagcga cgccagcagc cagctggacc tgtacaagat  6300
ggtcaccgag aagcagagaa tccagcggga tatgtacagc atcaaagaac ggatgggcct  6360
gctccagcag cggctggaca tcctgaacca gcagatcgag gccaccgaga aaaccatcca  6420
caagctgcgg cagccccaca gcaacaccgc ccagaatatc gtgcggagca acatcttcgt  6480
ggaaagcaac aactaccaga ccttcgaggt ggaatacggg gcacctggct caggagccac  6540
taatttttca ttgttgaagc aagctgggga tgttgaagag aacccagggc ctgtggtgtc  6600
caagggcgag gaactgttca ccggcgtggt gcccatcctg gtggaactgg atggcgacgt  6660
gaacggccac aagttcagcg tgtccggcga gggcgaaggc gacgccacat acggaaagct  6720
gaccctgaag ttcatctgca ccaccggcaa gctgcccgtg ccttggccta ccctcgtgac  6780
cacactgacc tacggcgtgc agtgcttcgc cagatacccc gaccacatga agcagcacga  6840
tttcttcaag agcgccatgc ccgagggcta cgtgcaggaa cggaccatct tcttcaagga  6900
```

-continued

```
cgacggcaac tacaagacaa gagccgaagt gaagttcgag ggcgacaccc tcgtgaaccg  6960
gatcgagctg aagggcatcg acttcaaaga ggatggcaac atcctgggcc acaagctgga  7020
gtacaactac aacagccaca aggtgtacat caccgccgac aagcagaaaa acggcatcaa  7080
agtgaacttc aagacccggc acaacatcga ggacggcagc gtgcagctgg ccgaccacta  7140
ccagcagaac acccccatcg gagatggccc cgtgctgctg cccgacaacc actacctgag  7200
cacacaaagc gccctgagca aggaccccaa cgagaagcgg gaccacatgg tgctgctgga  7260
atttgtgacc gccgctggca tcaccctggg catggacgag ctgtacaagt gactcgagtc  7320
tagagggccc cgtggctgta atctagagga tccctcgagg ggcccaagct tacgcgtgca  7380
tgcgacgtca tagctctctc cctatagtga gtcgtattat aagctagctt gggatctttg  7440
tgaaggaacc ttacttctgt ggtgtgacat aattggacaa actacctaca gagatttaaa  7500
gctctaaggt aaatataaaa tttttaagtg tataatgtgt taaactagct gcatatgctt  7560
gctgcttgag agttttgctt actgagtatg atttatgaaa atattataca caggagctag  7620
tgattctaat tgtttgtgta ttttagattc acagtcccaa ggctcatttc aggcccctca  7680
gtcctcacag tctgttcatg atcataatca gccataccac atttgtagag gttttacttg  7740
ctttaaaaaa cctcccacac ctccccctga acctgaaaca taaaatgaat gcaattgttg  7800
ttgttcgtgg ctgaatcaac ctctggatta caaaatttgt gaaagattga ctggtattct  7860
taactatgtt gctcctttta cgctatgtgg atacgctgct ttaatgcctt tgtatcatgc  7920
tattgcttcc cgtatggctt tcattttctc ctccttgtat aaatcctggt tgctgtctct  7980
ttatgaggag ttgtggcccg ttgtcaggca acgtggcgtg gtgtgcactg tgtttgctga  8040
cgcaaccccc actggttggg gcattgccac cacctgtcag ctcctttccg ggactttcgc  8100
tttccccctc cctattgcca cggcggaact catcgccgcc tgccttgccc gctgctggac  8160
aggggctcgg ctgttgggca ctgacaattc cgtggtgttg tcggggaaat catcgtcctt  8220
tccttggctg ctcgcctgtg ttgccacctg gattctgcgc gggacgtcct tctgctacgt  8280
cccttcggcc ctcaatccag cggaccttcc ttcccgcggc ctgctgccgg ctctgcggcc  8340
tcttccgcgt cttcgccttc gccctcagac gagtcggatc tccctttggg ccgcctcccc  8400
gccagagaca attaacttcg cgggtggcat ccctgtgacc cctccccagt gcctctcctg  8460
gccctggaag ttgccactcc agtgcccacc agccttgtcc taataaaatt aagttgcatc  8520
attttgtctg actaggtgtc cttctataat attatggggt ggaggggggt ggtatggagc  8580
aaggggcaag ttgggaagac aacctgtagg gcctgcgggg tctattggga accaagctgg  8640
agtgcagtgg cacaatcttg gctcactgca atctccgcct cctgggttca agcgattctc  8700
ctgcctcagc ctcccgagtt gttgggattc caggcatgca tgaccaggct cagctaattt  8760
ttgttttttt ggtagagacg gggtttcacc atattggcca ggctggtctc caactcctaa  8820
tctcaggtga tctacccacc ttggcctccc aaattgctgg gattacaggc gtgaaccact  8880
gctcccttcc ctgtccttga agttctcatc atgtctggaa ttgactcaaa tgatgtcaat  8940
tagtctatca gaagctcatc tggtctccct tccgggggac aagacatccc tgtttaatat  9000
ttaaacagca gtgttcccaa actgggttct tatatccctt gctctggtca accaggttgc  9060
agggtttcct gtcctcacag gaacgaagtc cctaaagaaa cagtggcagc caggtttagc  9120
cccggaattg actggattcc ttttttaggg cccattggta tggctttttc cccgtatccc  9180
cccaggtgtc tgcaggctca aagagcagcg agaagcgttc agaggaaagc gatcccgtgc  9240
caccttcccc gtgcccggc tgtccccgca cgctgccggc tcggggatgc ggggggagcg  9300
ccggaccgga gcggagcccc gggcggctcg ctgctgcccc ctagcggggg agggacgtaa  9360
ttacatccct gggggctttg gggggggggct gtccctgata tctataacaa gaaaatatat  9420
atataataag ttatcacgta agtagaacat gaaataacaa tataattatc gtatgagtta  9480
aatcttaaaa gtcacgtaaa agataatcat gcgtcatttt gactcacgcg gtcgttatag  9540
ttcaaaatca gtgacactta ccgcattgac aagcacgcct cacgggagct ccaagcggcg  9600
actgagatgt cctaaatgca cagcgacgga ttcgcgctat ttagaaagag agagcaatat  9660
ttcaagaatg catgcgtcaa ttttacgcag actatctttc tagggttaat ctagctgcat  9720
caggatcata tcgtcgggtc tttttccgg ctcagtcatc gcccaagctg gcgctatctg  9780
ggcatcgggg aggaagaagc ccgtgccttt tcccgcgagg ttgaagcggc atggaaagag  9840
tttgccgagg atgactgctg ctgcattgac gttgagcgaa aacgcacgtt taccatgatg  9900
attcgggaag gtgtggccat gcacgccttt aacggtgaac tgttcgttca ggccacctgg  9960
gataccagtt cgtcgcggct tttccggaca cagttccgga tggtcagccc gaagcgcatc  10020
agcaacccga acaataccgg cgacagccgg aactgccgtg ccggtgtgca gattaatgac  10080
agcggtgcgg cgctgggata ttacgtcagc gaggacgggt atcctggctg gatgccgcag  10140
aaatggacat ggataccccg tgagttaccc ggcgggcgcg cttggcgtaa tcatggtcat  10200
agctgtttcc tgtgtgaaat tgttatccgc tcacaattcc acacaacata cgagccggaa  10260
gcataaagtg taaagcctgg ggtgcctaat gagtgagcta actcacatta attgcgttgc  10320
gctcactgcc cgctttccag tcgggaaacc tgtcgtgcca gctgcattaa tgaatcggcc  10380
aacgcgcggg gagaggcggt ttgcgtattg ggcgctcttc cgcttcctcg ctcactgact  10440
cgctgcgctc ggtcgttcgg ctgcggcgag cggtatcagc tcactcaaag gcggtaatac  10500
ggttatccac agaatcaggg gataacgcag gaaagaacat gtgagcaaaa ggccagcaaa  10560
aggccaggaa ccgtaaaaag gccgcgttgc tggcgttttt ccataggctc cgcccccctg  10620
acgagcatca caaaaatcga cgctcaagtc agaggtggcg aaacccgaca ggactataaa  10680
gataccaggc gtttccccct ggaagctccc tcgtgcgctc tcctgttccg accctgccgc  10740
ttaccggata cctgtccgcc tttctccctt cgggaagcgt ggcgctttct catagctcac  10800
gctgtaggta tctcagttcg gtgtaggtcg ttcgctccaa gctgggctgt gtgcacgaac  10860
cccccgttca gcccgaccgc tgcgccttat ccggtaacta tcgtcttgag tccaacccgg  10920
taagacacga cttatcgcca ctggcagcag ccactggtaa caggattagc agagcgaggt  10980
atgtaggcgg tgctacagag ttcttgaagt ggtggcctaa ctacggctac actagaagga  11040
cagtatttgg tatctgcgct ctgctgaagc cagttacctt cggaaaaaga gttggtagct  11100
cttgatccgg caaacaaacc accgctggta gcggtggttt ttttgtttgc aagcagcaga  11160
ttacgcgcag aaaaaaagga tctcaagaag atcctttgat cttttctacg gggtctgacg  11220
ctcagtggaa cgaaaactca cgttaaggga ttttggtcat gagattatca aaaaggatct  11280
tcacctagat ccttttaaat taaaaatgaa gttttaaatc aatctaaagt atatatgagt  11340
aaacttggtc tgacagttac caatgcttaa tcagtgaggc acctatctca gcgatctgtc  11400
tatttcgttc atccatagtt gcctgactcc ccgtcgtgta gataactacg atacgggagg  11460
gcttaccatc tggccccagt gctgcaatga taccgcgaga cccacgctca ccggctccag  11520
atttatcagc aataaaccag ccagccggaa gggccgagcg cagaagtggt cctgcaactt  11580
tatccgcctc catccagtct attaattgtt gccgggaagc tagagtaagt agttcgccag  11640
```

```
ttaatagttt gcgcaacgtt gttgccattg ctacaggcat cgtggtgtca cgctcgtcgt  11700
ttggtatggc ttcattcagc tccggttccc aacgatcaag gcgagttaca tgatccccca  11760
tgttgtgcaa aaaagcggtt agctccttcg gtcctccgat cgttgtcaga agtaagttgg  11820
ccgcagtgtt atcactcatg gttatggcag cactgcataa ttctcttact gtcatgccat  11880
ccgtaagatg cttttctgtg actggtgagt actcaaccaa gtcattctga gaatagtgta  11940
tgcggcgacc gagttgctct tgcccggcgt caatacggga taataccgcg ccacatagca  12000
gaactttaaa agtgctcatc attggaaaac gttcttcggg gcgaaaactc tcaaggatct  12060
taccgctgtt gagatccagt tcgatgtaac ccactcgtgc acccaactga tcttcagcat  12120
cttttacttt caccagcgtt tctgggtgag caaaaacagg aaggcaaaat gccgcaaaaa  12180
agggaataag ggcgacacgg aaatgttgaa tactcat                           12217

SEQ ID NO: 3           moltype = DNA  length = 8142
FEATURE                Location/Qualifiers
source                 1..8142
                       mol_type = other DNA
                       organism = synthetic construct
SEQUENCE: 3
actcttcctt tttcaatatt attgaagcat ttatcagggt tattgtctca tgagcggata  60
catatttgaa tgtatttaga aaaataaaca aataggggtt ccgcgcacat ttccccgaaa  120
agtgccacct aaattgtaag cgttaatatt ttgttaaaat tcgcgttaaa tttttgttaa  180
atcagctcat tttttaacca ataggccgaa atcggcaaaa tcccttataa atcaaaagaa  240
tagaccgaga tagggttgag tgttgttcca gtttggaaca agagtccact attaaagaac  300
gtggactcca acgtcaaagg gcgaaaaacc gtctatcagg gcgatggccc actacgtgaa  360
ccatcaccct aatcaagttt tttggggtcg aggtgccgta aagcactaaa tcggaaccct  420
aaagggagcc cccgatttag agcttgacgg ggaaagccgg cgaacgtggc gagaaaggaa  480
gggaagaaag cgaaaggagc gggcgctagg gcgctggcaa gtgtagcggt cacgctgcgc  540
gtaaccacca cacccgccgc gcttaatgcg ccgctacagg gcgcgtccca ttcgccattc  600
aggctgcgca actgttggga agggcgatcg gtgcgggcct cttcgctatt acgccagctg  660
gcgaaagggg gatgtgctgc aaggcgatta agttgggtaa cgccagggtt ttcccagtca  720
cgacgttgta aaacgacggc cagtgagcgc gcctcgttca ttcacgtttt tgaacccgtg  780
gaggacgggc agactcgcgg tgcaaatgtg ttttacagcg tgatggagca gatgaagatg  840
ctcgacacgc tgcagaacac gcagctagat taaccctaga aagataatca tattgtgacg  900
tacgttaaag ataatcatgt gtaaaattga cgcatgtgtt ttatcggtct gtatatcgag  960
gtttatttat taatttgaat agatattaag ttttattata tttacactta catactaata  1020
ataaattcaa caaacaattt atttatgttt atttatttat taaaaaaaac aaaaactcaa  1080
aatttcttct ataaagtaac aaaacttta tgagggacag cccccccccca aagcccccag  1140
ggatgtaatt acgtccctcc cccgctaggg ggcagcagcg agccgcccgg ggctccgctc  1200
cggtccggcg ctcccccccgc atccccgagc cggcagcgtg cggggacagc ccgggcacgg  1260
ggaaggtggc acgggatcgc tttcctctga acgcttctcg ctgctctttg agcctgcaga  1320
cacctggggg gatacgggga aaaggcctcc acggccacta gtttcactcg agtttactcc  1380
ctatcagtga tagagaacgt atgaagagtt tactccctat cagtgataga gaacgtatgc  1440
agactttact ccctatcagt gatagagaac gtataaggag tttactccct atcagtgata  1500
gagaacgtat gaccagttta ctccctatca gtgatagaga acgtatctac agtttactcc  1560
ctatcagtga tagagaacgt atatccagtt tactccctat cagtgataga gaacgtatgt  1620
cgaggtaggc gtgtacggtg ggcgcctata aaagcagagc tcgtttagtg aaccgtcaga  1680
tcgcctggag caattccaca acacttttgt cttatacttg gtacctatgt ccgccaccat  1740
ggccgtggaa aagaccaaca gcagcagctc cctggccgaa gtgatcgaca gaatcctgga  1800
caagggcatc gtgatcgacg cctgggtgcg cgtgtccctc gtgggaattg agctgctggc  1860
catcgaggcc cggatcgtga ttgccagcgt ggaaacctac ctgaagtacg ccgaggccgt  1920
gggcctgaca cagagtgctg ctgtgcctgc ttgataatac taaatcgcac tgtcggcgtc  1980
ccccccctaac gttactggcc gaagccgctt ggaataaggc cggtgtgcgt ttgtctatat  2040
gttattttcc accatattgc cgtcttttgg caatgtgagg gcccggaaac ctggccctgt  2100
cttcttgacg agcattccta ggggtctttc ccctctcgcc aaaggaatgc aaggtctgtt  2160
gaatgtcgtg aaggaagcag ttcctctgga agcttcttga agacaaacaa cgtctgtagc  2220
gacccttttgc aggcagcgga acccccccacc tggcgacagg tgcctctgcg gccaaaagcc  2280
acgtgtataa gatacacctg caaaggcggc acaaccccag tgccacgttg tgagttggat  2340
agttgtggaa agagtcaaat ggctctcctc aagcgtattc aacaaggggc tgaaggatgc  2400
ccagaaggta ccccattgta tgggatctga tctggggcct cggtgcacat gctttacatg  2460
tgtttagtcg aggttaaaaa acgtctaggc cccccgaacc acggggacgt ggttttcctt  2520
tgaaaaacac gatgataata tggccacaac catggtgtcc aagggcgagg aactgttcac  2580
cggcgtggtg cccatcctgg tggaactgga tggcgacgtg aacggccaca agttctctgt  2640
gcggggagag ggcgaaggcg acgccacaaa tggcaagctg accctgaagt tcatctgcac  2700
caccggcaag ctgcccgtgc cttggcctac cctcgtgacc acactgtctc acggcgtgca  2760
gtgcttcgcc agatacccg accacatgaa gcagcacgat ttcttcaaga gcgccatgcc  2820
cgagggctac gtgcaggaac ggaccatctt cttcaaggac gacggcacct acaagaccag  2880
agccgaagtg aagttcgagg gcgacaccct cgtgaaccgg atcgagctga agggcgtgga  2940
cttcaaagag gacggcaaca tcctgggcca caagctggag tacaacttca acagccacaa  3000
catctacatc atggccgtga agcagaaaaa cggcatcaaa gtgaacttca agatccggca  3060
caacgtggaa gatggcagcg tgcagctggc cgaccactac cagcagaaca cccccatcgg  3120
agatggcccc gtgctgctgc ctgatagcca ctacctgagc acccagagcg tgctgagcaa  3180
ggaccccaac gagaagcggg accacatggt gctgctggaa tttcggaccg ccgctggcat  3240
caccctgggc atggatgagc tgtacaagtg aaggatccct cgaggggccc aagcttacgc  3300
gtgcatgcga cgtcatagct ctctccctat agtgagtcgt attataagct agcttgggat  3360
ctttgtgaag gaaccttact tctgtggtgt gacataattg gacaaactac ctacagagat  3420
ttaaagctct aaggtaaata taaaattttt aagtgtataa tgtgttaaac tagctgcata  3480
tgcttgctgc ttgagagttt tgcttactga gtatgattta tgaaaatatt atacacagga  3540
gctagtgatt ctaattgttt gtgtatttta gattcacagt cccaaggctc atttcaggcc  3600
cctcagtcct cacagtctgt tcatgatcat aatcagccat accacatttg tagaggtttt  3660
acttgcttta aaaaacctcc cacacctccc cctgaacctg aaacataaaa tgaatgcaat  3720
```

```
tgttgttgtt cgtggctgaa tcaacctctg gattacaaaa tttgtgaaag attgactggt  3780
attcttaact atgttgctcc ttttacgcta tgtggatacg ctgctttaat gcctttgtat  3840
catgctattg cttcccgtat ggctttcatt ttctcctcct tgtataaatc ctggttgctg  3900
tctctttatg aggagttgtg gcccgttgtc aggcaacgtg gcgtggtgtg cactgtgttt  3960
gctgacgcaa cccccactgg ttggggcatt gccaccacct gtcagctcct ttccgggact  4020
ttcgctttcc ccctccctat tgccacggcg gaactcatcg ccgcctgcct tgcccgctgc  4080
tggacagggg ctcggctgtt gggcactgac aattccgtgg tgttgtcggg gaaatcatcg  4140
tcctttcctt ggctgctcgc ctgtgttgcc acctggattc tgcgcgggac gtccttctgc  4200
tacgtccctt cggccctcaa tccagcggac cttccttccc gcggcctgct gccggctctg  4260
cggcctcttc cgcgtcttcg ccttcgccct cagacgagtc ggatctccct ttgggccgcc  4320
tccccgccag agacaattaa cttcgcgggt ggcatccctg tgacccctcc ccagtgcctc  4380
tcctggccct ggaagttgcc actccagtgc ccaccagcct tgtcctaata aaattaagtt  4440
gcatcatttt gtctgactag gtgtccttct ataatattat ggggtggagg ggggtggtat  4500
ggagcaaggg gcaagttggg aagacaacct gtagggcctg cggggtctat tgggaaccaa  4560
gctggagtgc agtggcacaa tcttggctca ctgcaatctc cgcctcctgg gttcaagcga  4620
ttctcctgcc tcagcctccc gagttgttgg gattccaggc atgcatgacc aggctcagct  4680
aatttttgtt tttttggtag agacggggtt tcaccatatt ggccaggctg gtctccaact  4740
cctaatctca ggtgatctac ccaccttggc ctcccaaatt gctgggatta caggcgtgaa  4800
ccactgctcc cttccctgtc cttgaagttc tcatcatgtc tggaattgac tcaaatgatg  4860
tcaattagtc tatcagaagc tcatctggtc tcccttccgg gggacaagac atccctgttt  4920
aatatttaaa cagcagtgtt cccaaactgg gttcttatat cccttgctct ggtcaaccag  4980
gttgcagggt ttcctgtcct cacaggaacg aagtccctaa agaaacagtg gcagccaggt  5040
ttagccccgg aattgactgg attccttttt tagggcccat tggtatggct ttttccccgt  5100
atccccccag gtgtctgcag gctcaaagag cagcgagaag cgttcagagg aaagcgatcc  5160
cgtgccacct tccccgtgcc cgggctgtcc ccgcacgctg ccggctcggg gatgcggggg  5220
gagcgccgga ccggagcgga gccccgggcg gctcgctgct gcccccctagc gggggaggga  5280
cgtaattaca tccctggggg ctttgggggg gggctgtccc tgatatctat aacaagaaaa  5340
tatatatata ataagttatc acgtaagtag aacatgaaat aacaatataa ttatcgtatg  5400
agttaaatct taaaagtcac gtaaaagata atcatgcgtc attttgactc acgcggtcgt  5460
tatagttcaa aatcagtgac acttaccgca ttgacaagca cgcctcacgg gagctccaag  5520
cggcgactga gatgtcctaa atgcacagcg acggattcgc gctatttaga aagagagagc  5580
aatatttcaa gaatgcatgc gtcaatttta cgcagactat ctttctaggg ttaatctagc  5640
tgcatcagga tcatatcgtc gggtcttttt tccggctcag tcatcgccca agctggcgct  5700
atctgggcat cggggaggaa gaagcccgtg ccttttcccg cgaggttgaa gcggcatgga  5760
aagagtttgc cgaggatgac tgctgctgca ttgacgttga gcgaaaacgc acgtttacca  5820
tgatgattcg ggaaggtgtg gccatgcacg cctttaacgg tgaactgttc gttcaggcca  5880
cctgggatac cagttcgtcg cggcttttcc ggacacagtt ccggatggtc agcccgaagc  5940
gcatcagcaa cccgaacaat accggcgaca gccggaactg ccgtgccggt gtgcagatta  6000
atgacagcgg tgcggcgctg ggatattacg tcagcgagga cgggtatcct ggctggatgc  6060
cgcagaaatg gacatggata ccccgtgagt tacccggcgg gcgcgcttgg cgtaatcatg  6120
gtcatagctg tttcctgtgt gaaattgtta tccgctcaca attccacaca acatacgagc  6180
cggaagcata aagtgtaaag cctggggtgc ctaatgagtg agctaactca cattaattgc  6240
gttgcgctca ctgcccgctt tccagtcggg aaacctgtcg tgccagctgc attaatgaat  6300
cggccaacgc gcggggagag gcggtttgcg tattgggcgc tcttccgctt cctcgctcac  6360
tgactcgctg cgctcggtcg ttcggctgcg gcgagcggta tcagctcact caaaggcggt  6420
aatacggtta tccacagaat caggggataa cgcaggaaag aacatgtgag caaaaggcca  6480
gcaaaaggcc aggaaccgta aaaaggccgc gttgctggcg tttttccata ggctccgccc  6540
ccctgacgag catcacaaaa atcgacgctc aagtcagagg tggcgaaacc cgacaggact  6600
ataaagatac caggcgtttc cccctggaag ctccctcgtg cgctctcctg ttccgaccct  6660
gccgcttacc ggatacctgt ccgcctttct cccttcggga agcgtggcgc tttctcatag  6720
ctcacgctgt aggtatctca gttcggtgta ggtcgttcgc tccaagctgg gctgtgtgca  6780
cgaacccccc gttcagcccg accgctgcgc cttatccggt aactatcgtc ttgagtccaa  6840
cccggtaaga cacgacttat cgccactggc agcagccact ggtaacagga ttagcagagc  6900
gaggtatgta ggcggtgcta cagagttctt gaagtggtgg cctaactacg gctacactag  6960
aaggacagta tttggtatct gcgctctgct gaagccagtt accttcggaa aaagagttgg  7020
tagctcttga tccggcaaac aaaccaccgc tggtagcggt ggtttttttg tttgcaagca  7080
gcagattacg cgcagaaaaa aaggatctca agaagatcct ttgatctttt ctacggggtc  7140
tgacgctcag tggaacgaaa actcacgtta agggattttg gtcatgagat tatcaaaaag  7200
gatcttcacc tagatccttt taaattaaaa atgaagtttt aaatcaatct aaagtatata  7260
tgagtaaact tggtctgaca gttaccaatg cttaatcagt gaggcaccta tctcagcgat  7320
ctgtctattt cgttcatcca tagttgcctg actccccgtc gtgtagataa ctacgatacg  7380
ggagggctta ccatctggcc ccagtgctgc aatgataccg cgagacccac gctcaccggc  7440
tccagattta tcagcaataa accagccagc cggaagggcc gagcgcagaa gtggtcctgc  7500
aactttatcc gcctccatcc agtctattaa ttgttgccgg gaagctagag taagtagttc  7560
gccagttaat agtttgcgca acgttgttgc cattgctaca ggcatcgtgg tgtcacgctc  7620
gtcgtttggt atggcttcat tcagctccgg ttcccaacga tcaaggcgag ttacatgatc  7680
ccccatgttg tgcaaaaaag cggttagctc cttcggtcct ccgatcgttg tcagaagtaa  7740
gttggccgca gtgttatcac tcatggttat ggcagcactg cataattctc ttactgtcat  7800
gccatccgta agatgctttt ctgtgactgg tgagtactca accaagtcat tctgagaata  7860
gtgtatgcgg cgaccgagtt gctcttgccc ggcgtcaata cgggataata ccgcgccaca  7920
tagcagaact ttaaaagtgc tcatcattgg aaaacgttct tcggggcgaa aactctcaag  7980
gatcttaccg ctgttgagat ccagttcgat gtaacccact cgtgcaccca actgatcttc  8040
agcatctttt actttcacca gcgtttctgg gtgagcaaaa acaggaaggc aaaatgccgc  8100
aaaaaaggga ataagggcga cacggaaatg ttgaatactc at                     8142
```

```
SEQ ID NO: 4            moltype = DNA  length = 55
FEATURE                 Location/Qualifiers
source                  1..55
                        mol_type = other DNA
```

```
                       organism = synthetic construct
SEQUENCE: 4
gtgagcggat aacaattccc atgactcata tttatagtta ttctcctcat ttccc       55

SEQ ID NO: 5           moltype = DNA  length = 55
FEATURE                Location/Qualifiers
source                 1..55
                       mol_type = other DNA
                       organism = synthetic construct
SEQUENCE: 5
gaggccccaa ggggttatgc tagctaaata aagtggtaag gaggaagaca atctc       55

SEQ ID NO: 6           moltype = DNA  length = 56
FEATURE                Location/Qualifiers
source                 1..56
                       mol_type = other DNA
                       organism = synthetic construct
SEQUENCE: 6
ggggaattgt gagcggataa caattccgtt aagcaggttc attagtagca tcattc      56

SEQ ID NO: 7           moltype = DNA  length = 53
FEATURE                Location/Qualifiers
source                 1..53
                       mol_type = other DNA
                       organism = synthetic construct
SEQUENCE: 7
cccgtttaga ggccccaagg ggttatgcta ggctgcacat ctcatcacat cac         53

SEQ ID NO: 8           moltype = DNA  length = 54
FEATURE                Location/Qualifiers
source                 1..54
                       mol_type = other DNA
                       organism = synthetic construct
SEQUENCE: 8
tcactatagg ggaattgtga gcggataaca attccgccat gggccagaag tttc        54

SEQ ID NO: 9           moltype = DNA  length = 23
FEATURE                Location/Qualifiers
source                 1..23
                       mol_type = other DNA
                       organism = synthetic construct
SEQUENCE: 9
caatccctct tcaagggctt ttc                                          23

SEQ ID NO: 10          moltype = DNA  length = 26
FEATURE                Location/Qualifiers
source                 1..26
                       mol_type = other DNA
                       organism = synthetic construct
SEQUENCE: 10
cagagatgat cctgcaatca gaaaag                                       26

SEQ ID NO: 11          moltype = DNA  length = 61
FEATURE                Location/Qualifiers
source                 1..61
                       mol_type = other DNA
                       organism = synthetic construct
SEQUENCE: 11
gacccgttta gaggccccaa ggggttatgc tagggtatta gatgccatga taaattcctc  60
c                                                                  61

SEQ ID NO: 12          moltype = DNA  length = 60
FEATURE                Location/Qualifiers
source                 1..60
                       mol_type = other DNA
                       organism = synthetic construct
SEQUENCE: 12
gggaattgtg agcggataac aattccttca ttgtggtgga tttattaaca ttaatagagc  60

SEQ ID NO: 13          moltype = DNA  length = 23
FEATURE                Location/Qualifiers
source                 1..23
                       mol_type = other DNA
                       organism = synthetic construct
SEQUENCE: 13
ctaaatactt tcccctcctg ggg                                          23

SEQ ID NO: 14          moltype = DNA  length = 21
FEATURE                Location/Qualifiers
```

-continued

```
source                  1..21
                        mol_type = other DNA
                        organism = synthetic construct
SEQUENCE: 14
tcaaccgtta ggtaaacccc c                                       21

SEQ ID NO: 15           moltype = DNA  length = 58
FEATURE                 Location/Qualifiers
source                  1..58
                        mol_type = other DNA
                        organism = synthetic construct
SEQUENCE: 15
gacccgttta gaggccccaa ggggttatgc tagacgctaa cgataaaaca ccatttgc    58
```

ACOUSTIC REPORTER GENES FOR NONDESTRUCTIVE IN VIVO IMAGING

RELATED APPLICATIONS

The present application claims priority to U.S. Provisional Application No. 63/290,402, filed Dec. 16, 2021; U.S. Provisional Application No. 63/290,425, filed Dec. 16, 2021; and U.S. Provisional Application No. 63/420,147, filed Oct. 28, 2022. The entire contents of these applications are hereby expressly incorporated by reference in their entireties.

STATEMENT REGARDING FEDERALLY SPONSORED R&D

This invention was made with government support under Grant No. EB018975 awarded by the National Institutes of Health. The government has certain rights in the invention.

REFERENCE TO SEQUENCE LISTING

The present application is being filed along with a Sequence Listing in electronic format. The Sequence Listing is provided as a file entitled 30KJ-365852-US, created Dec. 14, 2022, which is 60.0 kilobytes in size. The information in the electronic format of the Sequence Listing is incorporated herein by reference in its entirety.

BACKGROUND

Field

The present disclosure relates generally to the field of in vivo ultrasound imaging.

Description of the Related Art

Basic biological research, in vivo synthetic biology and the development of cell-based medicine require methods to visualize the functions of specific cells deep inside intact organisms. In this context, widely used optical techniques based on fluorescent and luminescent proteins have limited utility due to the scattering and absorption of light by tissue. In contrast, ultrasound is a widely used technique for deep-tissue imaging, providing sub-100 μm spatial resolution and penetrating several cm into tissue. The relative simplicity and low cost of ultrasound make it widely accessible for both research and clinical medicine, while recently developed super-resolution methods push its spatial resolution below 10 μm. Recently, the first genetically encodable reporters for ultrasound were introduced based on gas vesicles (GVs): air-filled protein nanostructures encoded by clusters of 8-20+ genes, which evolved as flotation devices in a wide range of mostly aquatic bacteria and archaea. The low density and high compressibility of their air-filled interiors compared to surrounding tissues allow GVs to scatter sound waves and thereby produce ultrasound contrast when heterologously expressed as acoustic reporter genes (ARGs) in genetically engineered bacteria or mammalian cells.

Despite the conceptual promise of first-generation ARGs, several limitations prevent their widespread use for monitoring bacterial or mammalian gene expression in vivo. First-generation bacterial ARGs cannot scatter ultrasound nonlinearly (making them difficult to distinguish from background tissues), express poorly at 37° C., and are too metabolically burdensome for in situ expression in vivo. Likewise, first-generation mammalian ARGs also produced only linear contrast, and cell-to-cell variability in their expression and burden meant that they could only be imaged robustly with ultrasound in clonally selected cell lines stimulated with potent epigenetic reagents. In both cases, the lack of nonlinear signal had to be circumvented by destructive ultrasound pulse sequences, which destroyed the GVs and limited dynamic imaging. Just as the widespread use of fluorescent proteins did not take off until the development of enhanced versions of GFP, an analogous breakthrough is required for acoustic proteins to become widely useful in in vivo biological research and potential clinical applications.

There is a need for next-generation ARGs that, when expressed heterologously in either probiotic bacterial strains or mammalian cancer cell lines, can produce GVs with strong nonlinear ultrasound contrast and enable robust, sustained expression under physiological conditions. These qualities would enable long-term noninvasive imaging of gene expression in a broad range of in vivo applications.

SUMMARY

Disclosed herein include compositions (e.g, nucleic acid compositions, delivery compositions, mammalian cells, probiotic bacterial cells). In some embodiments, the composition comprises: a nucleic acid composition comprising one or more promoters operably connected to one or more gas vesicle (GV) polynucleotides comprising: one or more gas vesicle assembly (GVA) gene(s) encoding one or more GVA protein(s); and one or more gas vesicle structural (GVS) gene(s) encoding one or more GVS protein(s), wherein the one or more GVA protein(s) and the one or more GVS protein(s) are capable of forming gas vesicles (GVs) upon expression in a mammalian cell, and wherein said GVs are capable of producing nonlinear ultrasound contrast. In some embodiments, the composition comprises: a mammalian cell comprising one or more promoters operably connected to one or more gas vesicle (GV) polynucleotides comprising: one or more gas vesicle assembly (GVA) gene(s) encoding one or more GVA protein(s); and one or more gas vesicle structural (GVS) gene(s) encoding one or more GVS protein (s), wherein the one or more GVA protein(s) and the one or more GVS protein(s) are capable of forming gas vesicles (GVs) upon expression in the mammalian cell, and wherein said GVs are capable of producing nonlinear ultrasound contrast. In some embodiments, the composition comprises: a nucleic acid composition comprising one or more promoters operably connected to one or more gas vesicle (GV) polynucleotides comprising: one or more gas vesicle assembly (GVA) gene(s) encoding one or more GVA protein(s); and one or more gas vesicle structural (GVS) gene(s) encoding one or more GVS protein(s), wherein the one or more GVA protein(s) and the one or more GVS protein(s) are capable of forming gas vesicles (GVs) upon expression in a probiotic bacterial cell, and wherein said GVs are capable of producing nonlinear ultrasound contrast. In some embodiments, the composition comprises: a probiotic bacterial cell comprising one or more promoters operably connected to one or more gas vesicle (GV) polynucleotides comprising: one or more gas vesicle assembly (GVA) gene (s) encoding one or more GVA protein(s); and one or more gas vesicle structural (GVS) gene(s) encoding one or more GVS protein(s), wherein the one or more GVA protein(s) and the one or more GVS protein(s) are capable of forming gas vesicles (GVs) upon expression in a probiotic bacterial cell, and wherein said GVs are capable of producing nonlinear ultrasound contrast. In some embodiments, the composition comprises: a delivery composition comprising a nucleic acid composition disclosed herein, wherein the delivery composition is or comprises one or more vectors, a ribonucleoprotein (RNP) complex, a liposome, a nanoparticle, an exosome, a microvesicle, or any combination thereof.

In some embodiments, the probiotic bacterial cell comprises *Salmonella enterica* serovar *typhimurium* and/or *E. coli* Nissle 1917 (EcN). In some embodiments, the probiotic bacterial cell comprises tumor-homing bacteria. In some embodiments, the tumor-homing bacteria comprises *Bifidobacterium, Caulobacter, Clostridium, Escherichia coli, Listeria, Mycobacterium, Salmonella, Streptococcus*, and *Vibrio*, e.g., *Bifidobacterium adolescentis, Bifidobacterium bifidum, Bifidobacterium breve* UCC2003, *Bifidobacterium infantis, Bifidobacterium longum, Clostridium acetobutylicum, Clostridium butyricum, Clostridium butyricum* M-55, *Clostridium butyricum miyairi, Clostridium cochlearum, Clostridium felsineum, Clostridium histolyticum, Clostridium multifermentans, Clostridium novyi*-NT, *Clostridium paraputrificum, Clostridium pasteureanum, Clostridium pectinovorum, Clostridium perfringens, Clostridium roseum, Clostridium sporogenes, Clostridium tertium, Clostridium tetani, Clostridium tyrobutyricum, Corynebacterium parvum, Escherichia coli* MG1655, *Escherichia coli* Nissle 1917, *Listeria monocytogenes, Mycobacterium bovis, Salmonella choleraesuis, Salmonella typhimurium*, and *Vibrio cholera*, variants thereof, derivatives thereof, or any combination thereof. In some embodiments, the probiotic bacterial cell is an obligate anaerobic, facultative anaerobic, aerobic, Gram-positive, Gram-negative, commensal, or any combination thereof. In some embodiments, the probiotic bacterial cell comprises naturally pathogenic bacteria that are modified or mutated to reduce or eliminate pathogenicity. In some embodiments, the mammalian cell comprises a cancer cell, an immortalized cell line, an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, a zymogenic cell, or any combination thereof. In some embodiments, the stem cell comprises an embryonic stem cell, an induced pluripotent stem cell (iPSC), a hematopoietic stem/progenitor cell (HSPC), or any combination thereof. In some embodiments, the mammalian cell is a reporting therapeutic cell configured to treat a disease or disorder of a subject upon administration. In some embodiments, the presence and/or functionality of the reporting therapeutic cell is capable of being monitored in vivo by application of ultrasound (US). In some embodiments, the reporting therapeutic cell is a replacement for a cell that is absent, diseased, infected, and/or involved in maintaining, promoting, or causing a disease or condition in a subject in need. In some embodiments, the disease is a metabolic disease, e.g., selected from the group consisting of T1D (type-1 diabetes), T2D (type-2 diabetes), diabetic ketoacidosis, obesity, cardiovascular disease, the metabolic syndrome and cancer. In some embodiments, the reporting therapeutic cell is autologous, allogenic, or xenogenic.

In some embodiments, the expression of the GVs within the probiotic bacterial cell and/or mammalian cell is capable of being detected via dynamic non-destructive imaging, such as, for example, (i) nonlinear ultrasound imaging, optionally cross-propagating amplitude modulation pulse sequence (xAM) imaging and/or parabolic AM (pAM) imaging, (ii) at an acoustic pressure of about 0.3 MPa, to about 1.75 MPa, (iii) nonlinear ultrasound signal is proportional to cell concentration, further optionally between about $10^2$ cells/mL and $10^9$ cells/mL, and/or (iv) about 3 hours upon induction of expression. In some embodiments, the GVs are capable of producing at least about 1.1-fold greater non-linear ultrasound signals as compared to GVs expressed from first generation acoustic reporter genes (ARGs) in the probiotic bacterial cell and/or a mammalian cell, optionally said first generation ARGs comprise bARG1 or $mARG_{Mega}$. In some embodiments, the probiotic bacterial cell and/or mammalian cell is capable of exhibiting an about 5 dB to about 50 dB enhancement in nonlinear ultrasound contrast as compared to a probiotic bacterial cell and/or a mammalian cell comprising first generation acoustic reporter genes (ARGs), optionally said first generation ARGs comprise bARG1 or $mARG_{Mega}$.

In some embodiments, the probiotic bacterial cell and/or mammalian cell is capable of exhibiting an at least about 1.1-fold increase in contrast to noise ratio (CNR) as compared to a probiotic bacterial cell and/or a mammalian cell comprising first generation acoustic reporter genes (ARGs), optionally said first generation ARGs comprise bARG1 or $mARG_{Mega}$. In some embodiments, the probiotic bacterial cell and/or mammalian cell exhibits a growth rate within about 20 percent of the growth rate of a probiotic bacterial cell and/or a mammalian cell (i) comprising first generation acoustic reporter genes (ARGs) or (ii) not comprising GVA genes and GVS genes, optionally said first generation ARGs comprise bARG1 or $mARG_{Mega}$, further optionally in vitro growth rate and/or in vivo growth rate. In some embodiments, the mammalian cell is capable of expressing an at least about 1.1-fold greater amount of GVs as compared to a mammalian cell comprising first generation acoustic reporter genes (ARGs), optionally $mARG_{Mega}$. In some embodiments, the probiotic bacterial cell is capable of expressing an at least about 1.1-fold greater amount of GVs as compared to a probiotic bacterial cell comprising first generation acoustic reporter genes (ARGs), optionally bARG1. In some embodiments, less than about 10 percent of cells of a population the probiotic bacterial cells and/or mammalian cells express less than a threshold amount of the GVs, optionally the threshold amount of the GVs is the threshold amount of the GVs detectable via nonlinear ultrasound imaging.

In some embodiments, the one or more GVS gene(s) and/or the one or more GVA gene(s) are derived from *Serratia* sp. ATAC 39006, optionally gvpA, gvpC, gvpN, gvpV, gvpF1, gvpG, gvpW, gvpJ1, gvpK, gvpX, gvpJ2, gvpY, gvrA, gvpH, gvpZ, gvpF2, gvpF3, gvrB, gvrC, or any combination thereof. In some embodiments, the one or more GVS gene(s) and/or the one or more GVA gene(s) are derived from *Desulfobacterium vacuolatum*, optionally gvrA, gvpH, gvpZ, gvpF2, gvpF3, gvrB, gvrC, gvpA, gvpC, gvpN, gvpV, gvpF1, gvpG, gvpW, gvpJ1, gvpK, gvpJ2, or any combination thereof. In some embodiments, the one or more GVS gene(s) comprise gvpA and/or gvpC of *Anabaena flos-aquae* and the one or more GVA gene(s) are derived from *Bacillus megaterium*, optionally gvpR, gvpN, gvpF, gvpG, gvpL, gvpS, gvpK, gvpJ, gvpT, gvpU, or any combination thereof. In some embodiments, the one or more GVA gene(s) and/or the one or more GVA gene(s) are derived from *Anabaena flos-aquae*, optionally gvpA, gvpC, gvpN, gvpJ, gvpK, gvpF, gvpG, gvpV, gvpW, or any combination thereof. In some embodiments, the one or more GVA gene(s) and/or the one or more GVA gene(s) are derived from *Bacillus megaterium*, optionally gvpB, gvpR, gvpN, gvpF, gvpG, gvpL, gvpS, gvpK, gvpJ, gvpT, gvpU, or any combination thereof.

In some embodiments, the nucleic acid composition and/or mammalian cell comprises: a first GV polynucleotide encoding GvpA, a second GV polynucleotide encoding GvpN, a third GV polynucleotide encoding GvpJ, a fourth GV polynucleotide encoding GvpK, a fifth GV polynucleotide encoding GvpF, a sixth GV polynucleotide encoding GvpG, a seventh GV polynucleotide encoding GvpW, and an eighth GV polynucleotide encoding GvpV, optionally two or more of the GV polynucleotides are operably connected to a tandem gene expression element. In some embodiments, the one or more GV polynucleotides do not comprise Ser39006_001280. In some embodiments, the nucleic acid composition and/or probiotic bacterial cell comprises a DNA sequence that is at least 80%, 85%, 90%, 95%, 98%, 99%, or 100% identical to SEQ ID NO: 1, or a portion thereof. In some embodiments, the nucleic acid composition and/or mammalian cell comprises a DNA sequence that is at least 80%, 85%, 90%, 95%, 98%, 99%, or 100% identical to SEQ ID NO: 2 and/or SEQ ID NO: 3, or a portion thereof.

The composition can comprise: one or more gene(s) encoding one or more detectable protein(s), optionally a detectable protein selected from the group comprising green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mScarlet, mApple, mCitrine, mCherry, mruby3, rsCherry, rsCherryRev, derivatives thereof, or any combination thereof, further optionally said one or more detectable protein(s) are co-expressed with the one or more GVS gene(s) and/or the one or more GVA gene(s). In some embodiments, the nucleic acid composition is configured to express the GVS gene(s) at a higher stoichiometry relative to the GVA gene(s), optionally about 1.1-fold to about 9-fold higher stoichiometry. In some embodiments, the probiotic bacterial cell and/or mammalian cell is robust to mutations reducing or abrogating GV expression. In some embodiments, the probiotic bacterial cell and/or mammalian cell is robust to said mutations for at least about 5 days, about 10 days, about 20 days, about 40 days, about 80 days, about 80 days, or about 100 days, of continuous culture and/or presence in a subject. In some embodiments, the GVs do not comprise GvpC, and wherein the absence of the GvpC enhances the nonlinear signal in xAM imaging of said GVs. In some embodiments, the GVs comprise a GvpC variant. In some embodiments, the GvpC variant comprises: a protease-sensing GvpC protein comprising at least one protease recognition site inserted within the central portion and/or attached to at least one of the N-terminus and the C-terminus of the Gyp; and/or a $Ca^{2+}$-sensing GvpC protein comprising a $Ca^{2+}$-binding domain and an interaction domain.

The composition can comprise: one or more promoters operably connected to one or more secondary gas vesicle (sGV) polynucleotides comprising: one or more gas vesicle assembly (GVA) gene(s) encoding one or more GVA protein (s); and one or more gas vesicle structural (GVS) gene(s) encoding one or more GVS protein(s), wherein the one or more GVA protein(s) and the one or more GVS protein(s) are capable of forming secondary gas vesicles (sGVs) upon expression in a probiotic bacterial cell and/or a mammalian cell, wherein the GVs and the sGVs differ in composition with respect to at least one GVA protein and/or GVS protein, and wherein the sGVs comprise distinctive mechanical, acoustic, surface and/or magnetic properties as compared to the GVs. In some embodiments, the GVs and sGVs are configured to be expressed in different cell types and/or different cell states.

In some embodiments, the GVs have a first buckling pressure profile. In some embodiments, the first buckling pressure profile comprises a buckling function from which a GV buckling amount can be determined for a given pressure value. In some embodiments, the buckling amount comprises the amount of nonlinear contrast. In some embodiments, the first buckling pressure profile comprises a first buckling threshold pressure where a GV starts to buckle and produce nonlinear contrast, a first optimum buckling pressure where a GV exhibits maximum buckling and produces the highest level of nonlinear contrast, a first collapse pressure wherein a GV collapses, any pressure between the first buckling threshold pressure and the first optimum buckling pressure, and any pressure between the first optimum buckling pressure and the first collapse pressure. In some embodiments, the sGV has a second buckling pressure profile. In some embodiments, the second buckling pressure profile comprises a buckling function from which a sGV buckling amount can be determined for a given pressure value. In some embodiments, the buckling amount comprises the amount of nonlinear contrast. In some embodiments, the second buckling pressure profile comprises a second buckling threshold pressure where a sGV starts to buckle and produce nonlinear contrast, a second optimum buckling pressure where a sGV exhibits maximum buckling and produces the highest level of nonlinear contrast, a second collapse pressure wherein a sGV collapses, any pressure between the second buckling threshold pressure and the second optimum buckling pressure, and any pressure between the second optimum buckling pressure and the second collapse pressure. In some embodiments, the first buckling pressure profile and the second buckling pressure profile are different. In some embodiments, a selectable buckling pressure is the pressure value which produces the maximal difference in buckling between a GV and a sGV. In some embodiments, the selectable buckling pressure is: from about 40 kPa to about 1500 kPa; any collapse pressure within the first buckling pressure profile; any collapse pressure within the second buckling pressure profile; the first optimum buckling pressure; and/or the second optimum buckling pressure.

In some embodiments, the GV has a first collapse pressure profile. In some embodiments, the first collapse pressure profile comprises a collapse function from which a GV collapse amount can be determined for a given pressure value. In some embodiments, the first collapse pressure profile comprises a first initial collapse pressure where 5% or lower of a plurality of GVs are collapsed, a first midpoint collapse pressure where 50% of a plurality of GVs are collapsed, a first complete collapse pressure where at least 95% of a plurality of GVs are collapsed, any pressure between the first initial collapse pressure and the first midpoint collapse pressure, and any pressure between the first midpoint collapse pressure and the first complete collapse pressure. In some embodiments, a first selectable collapse pressure is: any collapse pressure within the first collapse pressure profile; selected from the first collapse pressure profile at a value between 0.05% collapse of a plurality of GVs and 95% collapse of a plurality of GVs; equal to or greater than the first initial collapse pressure; equal to or greater than the first midpoint collapse pressure; and/or equal to or greater than the first complete collapse pressure. In some embodiments, the sGV has a second collapse pressure profile. In some embodiments, the second collapse pressure profile comprises a collapse function from which a sGV collapse amount can be determined for a given pressure value. In some embodiments, the first collapse pressure profile and the second collapse pressure profile are different. In some embodiments, a midpoint of the second collapse profile has a higher pressure component than a midpoint of the first collapse profile. In some embodiments, the second collapse pressure profile comprises a second initial collapse pressure where 5% or lower of a plurality of sGVs are collapsed, a second midpoint collapse pressure where 50% of a plurality of sGVs are collapsed, a second complete collapse pressure where at least 95% of a plurality of sGVs are collapsed, any pressure between the second initial collapse pressure and the second midpoint collapse pressure, and any pressure between the second midpoint collapse pressure and the second complete collapse pressure. In some embodiments, a second selectable collapse pressure is: any collapse pressure within the second collapse pressure profile; selected from the second collapse pressure profile at a value between 0.05% collapse of a plurality of sGVs and 95% collapse of a plurality of sGVs; equal to or greater than the second initial collapse pressure; equal to or greater than the second midpoint collapse pressure; and/or equal to or greater than the second complete collapse pressure.

In some embodiments, the one or more promoters comprise one or more first promoters, one or more inducible promoters, and/or one or more context-dependent promoters, optionally: one or more inducible promoters is operably connected to one or more GV polynucleotides comprising GVS gene(s) and one or more first promoters is operably connected to one or more GV polynucleotides comprising GVA gene(s); or one or more context-dependent promoters is operably connected to one or more GV polynucleotides comprising GVS gene(s) and one or more first promoters is operably connected to one or more GV polynucleotides comprising GVA gene(s). In some embodiments, at least two of the GV polynucleotides is operably connected to a tandem gene expression element selected from the group comprising an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A), or any combination thereof. In some embodiments, at least one of the one or more promoters is an inducible promoter, such as, for example, an anhydrotetracycline-inducible promoter, an IPTG-inducible promoter, a rhamnose-inducible promoter, or an arabinose-inducible promoter. In some embodiments, the inducible promoter is induced by the cellular event. In some embodiments, the cellular event is marked by a stimulus received by the cell. In some embodiments, the stimulus is a small molecule, a protein, a peptide, an amino acid, a metabolite, an inorganic molecule, an organometallic molecule, an organic molecule, a drug or drug candidate, a sugar, a lipid, a metal, a nucleic acid, a molecule produced during the activation of an endogenous or an exogenous signaling cascade, light, heat, sound, pressure, mechanical stress, shear stress, or a virus or other microorganism, change in pH, or change in oxidation/reduction state.

In some embodiments, at least one of the one or more promoters comprises the TlpA operator/promoter, lambda phage pL, lambda phage pR, lambda phage pRM, or any combination thereof. In some embodiments, at least one of the one or more promoters is a promoter selected from the group comprising: a bacteriophage promoter, optionally Pls1con, T3, T7, SP6, or PL; a bacterial promoter, optionally Pbad, PmgrB, Ptrc2, Plac/ara, Ptac, or Pm; and/or a bacterial-bacteriophage hybrid promoter, optionally PLlacO or PLtetO. In some embodiments, at least one of the one or more promoters is a positively regulated *E. coli* promoter selected from the group comprising: a $\sigma^{70}$ promoter, optionally inducible pBad/araC promoter, Lux cassette right promoter, modified lamdba Prm promoter, plac Or2-62 (positive), pBad/AraC with extra REN sites, pBad, P(Las) TetO, P(Las) CIO, P(Rhl), Pu, FecA, pRE, cadC, hns, pLas, or pLux; a as promoter, optionally Pdps; a $\sigma^{32}$ promoter, optionally heat shock; and/or a $\sigma^{54}$ promoter, optionally glnAp2.

In some embodiments, at least one of the one or more promoters is a negatively regulated *E. coli* promoter selected from the group comprising: a $\sigma^{70}$ promoter, optionally Promoter (PRM+), modified lamdba Prm promoter, TetR-TetR-4C P(Las) TetO, P(Las) CIO, P(Lac) IQ, RecA_Dlex-O_DLacO1, dapAp, FecA, Pspac-hy, pcI, plux-cI, plux-lac, CinR, CinL, glucose controlled, modified Pr, modifed Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, or RcnR; a as promoter, optionally Lutz-Bujard LacO with alternative sigma factor $\sigma^{38}$; a $\sigma^{32}$ promoter, optionally Lutz-Bujard LacO with alternative sigma factor $\sigma^{32}$; and/or a $\sigma^{54}$ promoter, optionally glnAp2. In some embodiments, at least one of the one or more promoters is a P7 promoter. In some embodiments, at least one of the one or more promoters is a heat-shock promoter, optionally pTSR, pR-pL, GrpE, HtpG, Lon, RpoH, Clp, and/or DnaK. In some embodiments, at least one of the one or more promoters is a constitutive promoter, optionally selected from the group comprising: a constitutive *Escherichia coli* a $\sigma^S$ promoter, optionally osmY promoter (BBa_J45993); a constitutive *Escherichia coli* $\sigma^{32}$ promoter, optionally htpG heat shock promoter (BBa_J45504); a constitutive *Escherichia coli* a $\sigma^{70}$ promoter, optionally lacq promoter (BBa_J54200 or BBa_J56015), *E. coli* CreABCD phosphate sensing operon promoter (BBa_J64951), GlnRS promoter (BBa_K088007), lacZ promoter (BBa_K119000 or BBa_K119001), M13K07 gene I promoter (BBa_M13101), M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), or M13110 (BBa_M13110); a constitutive *Bacillus subtilis* $\sigma^A$ promoter, optionally promoter veg (BBa_K143013), promoter 43 (BBa_K143013), $P_{liaG}$(BBa_K823000), $P_{lepA}$ (BBa_K823002), or $P_{veg}$ (BBa_K823003); a constitutive *Bacillus subtilis* $\sigma_B$ promoter, optionally promoter ctc (BBa_K143010) or promoter gsiB (BBa_K143011)), a *Salmonella* promoter, optionally Pspv2 from *Salmonella* (BBa_K112706) or Pspv from *Salmonella* (BBa_K112707); a bacteriophage T7 promoter, optionally BBa_I712074, BBa_I719005, BBa_J34814, BBa_J64997, BBa_K113010, BBa_K113011, BBa_K113012, BBa_R0085, BBa_R0180, BBa_R0181, BBa_R0182, BBa_R0183, BBa_Z0251, BBa_Z0252, or BBa_Z0253; and/or a bacteriophage SP6 promoter, optionally SP6 promoter (BBa_J64998). In some embodiments, at least one of the one or more promoters comprises at least one −10 element and/or at least one −35 element.

In some embodiments, the one or more first promoters comprise: a minimal promoter, optionally TATA, miniCMV, and/or miniPromo; a tissue-specific promoter and/or a lineage-specific promoter; and/or a ubiquitous promoter, optionally a minEf1a promoter, a cytomegalovirus (CMV) immediate early promoter, a CMV promoter, a viral simian virus 40 (SV40) (e.g., early or late), a Moloney murine leukemia virus (MoMLV) LTR promoter, a Rous sarcoma virus (RSV) LTR, an RSV promoter, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus, a Ubiquitin C promoter (UBC), a phosphoglycerate kinase-1 (PGK) promoter, 3-phosphoglycerate kinase promoter, a cytomegalovirus enhancer, human 3-actin (HBA) promoter, chicken 3-actin (CBA) promoter, a CAG promoter, a CASI promoter, a CBH promoter, or any combination thereof. In some embodiments, the activity of the context-dependent promoter and/or the degree of expression of the GVs operably connected to a context-dependent promoter is associated with the presence and/or amount a unique cell type and/or a unique cell state.

In some embodiments, the composition comprises: a context-dependent promoter operably linked to a transactivator polynucleotide comprising a transactivator gene, wherein the context-dependent promoter is capable of inducing transcription of the transactivator gene to generate a transactivator transcript, wherein the transactivator transcript is capable of being translated to generate a transactivator, wherein the activity of the context-dependent promoter and/or the degree of expression of the transactivator is associated with the presence and/or amount a unique cell type and/or a unique cell state, wherein, in the presence of the transactivator and a transactivator-binding compound, the first promoter is capable of inducing transcription of the one or more GV polynucleotides to generate GV transcript (s), and wherein the GV transcript(s) are capable of being translated to generate GVA protein(s) and/or GVS protein (s). In some embodiments, the first promoter comprises one or more copies of a transactivator recognition sequence the transactivator is capable of binding to induce transcription, and wherein the transactivator is incapable of binding the transactivator recognition sequence in the absence of the transactivator-binding compound, optionally the one or more copies of a transactivator recognition sequence comprise one or more copies of a tet operator (TetO). In some embodiments, the one or more copies of a transactivator recognition sequence comprise one or more copies of a tet operator (TetO). In some embodiments, the first promoter comprises a tetracycline response element (TRE), and wherein the TRE comprises one or more copies of a tet operator (TetO). In some embodiments, the transactivator comprises reverse tetracycline-controlled transactivator (rtTA). In some embodiments, the transactivator comprises tetracycline-controlled transactivator (tTA). In some embodiments, the transactivator-binding compound comprises tetracycline, doxycycline or a derivative thereof. In some embodiments, the transactivator comprises a constitutive signal peptide for protein degradation, optionally PEST.

In some embodiments, one or more GV polynucleotides and/or transactivator polynucleotide comprise: a 5'UTR and/or a 3'UTR; a tandem gene expression element selected from the group comprising an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A), or any combination thereof; and/or a transcript stabilization element (e.g., woodchuck hepatitis post-translational regulatory element (WPRE), bovine growth hormone polyadenylation (bGH-polyA) signal sequence, human growth hormone polyadenylation (hGH-polyA) signal sequence, or any combination thereof).

In some embodiments, the unique cell state comprises activation of one or more cellular activities of interest. In some embodiments, a unique cell type and/or a unique cell state is caused by hereditable, environmental, and/or idiopathic factors. In some embodiments, a unique cell type and/or a unique cell state is caused by and/or associated with the expression of one or more endogenous proteins whose expression is regulated by the endogenous context-dependent promoter. In some embodiments, the unique cell state and/or unique cell type is characterized by signaling of one or more endogenous signal transducer(s), optionally signal transducer(s) regulated by the endogenous context-dependent promoter. In some embodiments, the unique cell type and/or the cell in the unique cell state (i) causes and/or aggravates a disease or disorder and/or (ii) is associated with the pathology of a disease or disorder.

In some embodiments, the unique cell state and/or unique cell type is characterized by aberrant signaling of one or more signal transducer(s). In some embodiments, the aberrant signaling involves: an overactive signal transducer; a constitutively active signal transducer over a period of time; an active signal transducer repressor and an active signal transducer; an inactive signal transducer activator and an active signal transducer; an inactive signal transducer; an underactive signal transducer; a constitutively inactive signal transducer over a period of time; an inactive signal transducer repressor and an inactive signal transducer; and/or an active signal transducer activator and an inactive signal transducer. In some embodiments, the aberrant signaling comprises an aberrant signal of at least one signal transduction pathway regulating cell survival, cell growth, cell proliferation, cell adhesion, cell migration, cell metabolism, cell morphology, cell differentiation, apoptosis, or any combination thereof. In some embodiments, the signal transduscer(s) is AKT, PI3K, MAPK, p44/42 MAP kinase, TYK2, p38 MAP kinase, PKC, PKA, SAPK, ELK, INK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof. In some embodiments, the disease or disorder is characterized by an aberrant signaling of the first transducer.

In some embodiments, the unique cell state comprises: a physiological state, optionally a cell cycle state, a differentiation state, a development state, a metabolic state, or a combination thereof; and/or a pathological state, optionally a disease state, a human disease state, a diabetic state, an immune disorder state, a neurodegenerative disorder state, an oncogenic state, or a combination thereof. In some embodiments, the unique cell state and/or unique cell type is characterized by one or more of cell proliferation, stress pathways, oxidative stress, stress kinase activation, DNA damage, lipid metabolism, carbohydrate regulation, metabolic activation including Phase I and Phase II reactions, Cytochrome P-450 induction or inhibition, ammonia detoxification, mitochondrial function, peroxisome proliferation, organelle function, cell cycle state, morphology, apoptosis, DNA damage, metabolism, signal transduction, cell differentiation, cell-cell interaction and cell to non-cellular compartment. In some embodiments, the unique cell state and/or unique cell type is characterized by one or more of acute phase stress, cell adhesion, AH-response, anti-apoptosis and apoptosis, antimetabolism, anti-proliferation, arachidonic acid release, ATP depletion, cell cycle disruption, cell matrix disruption, cell migration, cell proliferation, cell regeneration, cell-cell communication, cholestasis, differentiation, DNA damage, DNA replication, early response genes, endoplasmic reticulum stress, estogenicity, fatty liver, fibrosis, general cell stress, glucose deprivation, growth arrest, heat shock, hepatotoxicity, hypercholesterolemia, hypoxia, immunotox, inflammation, invasion, ion transport, liver regeneration, cell migration, mitochondrial function, mitogenesis, multidrug resistance, nephrotoxicity, oxidative stress, peroxisome damage, recombination, ribotoxic stress, sclerosis, steatosis, teratogenesis, transformation, disrupted translation, transport, and tumor suppression. In some embodiments, the unique cell state and/or unique cell type is characterized by one or more of nutrient deprivation, hypoxia, oxidative stress, hyperproliferative signals, oncogenic stress, DNA damage, ribonucleotide depletion, replicative stress, and telomere attrition, promotion of cell cycle arrest, promotion of DNA-repair, promotion of apoptosis, promotion of genomic stability, promotion of senescence, and promotion of autophagy, regulation of cell metabolic reprogramming, regulation of tumor microenvironment signaling, inhibition of cell stemness, survival, and invasion.

In some embodiments, the cell type is: an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, a zymogenic cell, or any combination thereof. In some embodiments, the stem cell comprises an embryonic stem cell, an induced pluripotent stem cell (iPSC), a hematopoietic stem/progenitor cell (HSPC), or any combination thereof.

In some embodiments, the context-dependent promoter comprises a tissue-specific promoter and/or a lineage-specific promoter. In some embodiments, the tissue specific promoter is a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a hSynapsin promoter, a α-myosin heavy chain (α-MHC) promoter, or a cardiac Troponin T (cTnT) promoter. In some embodiments, the tissue specific promoter is a neuronal activity-dependent promoter and/or a neuron-specific promoter, optionally a synapsin-1 (Syn) promoter, a CaMKIIa promoter, a calcium/calmodulin-dependent protein kinase II a promoter, a tubulin alpha I promoter, a neuron-specific enolase promoter, a platelet-derived growth factor beta chain promoter, TRPV1 promoter, a $Na_v1.7$ promoter, a $Na_v1.8$ promoter, a $Na_v1.9$ promoter, or an Advillin promoter. In some embodiments, the tissue specific promoter is a muscle-specific promoter, optionally the muscle-specific promoter comprises a creatine kinase (MCK) promoter. In some embodiments, the expression of a payload protein is linked to the expression of a GVS protein via a tandem gene expression element, optionally a tandem gene expression element selected from the group comprising an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A), or any combination thereof. In some embodiments, the GVA genes and GVS genes have sequences codon optimized for expression in a eukaryotic cell. In some embodiments, the GVs comprise a GVS variant engineered to present a tag enabling clustering in the cell.

In some embodiments, nucleic acid composition is complexed or associated with one or more lipids or lipid-based carriers, thereby forming liposomes, lipid nanoparticles (LNPs), lipoplexes, and/or nanoliposomes, optionally encapsulating the nucleic acid composition. In some embodiments, the nucleic acid composition is, comprises, or further comprises, one or more vectors. In some embodiments, at least one of the one or more vectors is a viral vector, a plasmid, a transposable element, a naked DNA vector, a lipid nanoparticle (LNP), or any combination thereof. In some embodiments, the viral vector is an AAV vector, a lentivirus vector, a retrovirus vector, an adenovirus vector, a herpesvirus vector, a herpes simplex virus vector, a cytomegalovirus vector, a vaccinia virus vector, a MVA vector, a baculovirus vector, a vesicular stomatitis virus vector, a human papillomavirus vector, an avipox virus vector, a Sindbis virus vector, a VEE vector, a Measles virus vector, an influenza virus vector, a hepatitis B virus vector, an integration-deficient lentivirus (IDLV) vector, or any combination thereof. In some embodiments, the transposable element is piggybac transposon or sleeping beauty transposon. In some embodiments, the one or more gas vesicle (GV) polynucleotides are situated on the same vector or two or more separate vectors.

In some embodiments, the plasmid comprises an origin of replication, optionally a low-copy, a medium-copy, or a high-copy origin of replication, further optionally the origin of replication is selected from the group comprising a low copy number modified pSC101 origin of replication, a RK2 origin of replication, a wildtype pSC101 origin of replication, a p15a origin of replication, and a pACYC origin of replication, derivatives thereof, or any combination thereof. In some embodiments, the vector is capable of being maintained within the probiotic bacterial cell in the absence of antibiotic selection for at least five days, optionally the probiotic bacterial cell comprises a toxin-antitoxin stability cassette, further optionally Axe-Txe. The composition can comprise: a polynucleotide encoding a toxin and/or an antitoxin, optionally one or more elements of the Axe-Txe type II toxin anti-toxin system, further optionally the nucleic acid composition is capable of being retained in a probiotic bacterial cell without antibiotic selection for at least about 10 days, about 20 days, about 40 days, about 80 days, about 80 days, or about 100 days. In some embodiments, the probiotic bacterial cell chromosome comprises a polynucleotide encoding a toxin and/or antitoxin, optionally one or more elements of the Axe-Txe type II toxin anti-toxin system. In some embodiments, the probiotic bacterial cell comprises a polynucleotide conferring resistance to an antibiotic, optionally the antibiotic is selected from the group comprising phleomycin D1 (ZEOCIN™), kanamycin, spectinomycin, streptomycin, ampicillin, carbenicillin, bleomycin, erythromycin, polymyxin B, tetracycline and chloramphenicol, further optionally the nucleic acid composition comprises said polynucleotide conferring resistance to an antibiotic.

Disclosed herein include methods of treating or preventing a disease or disorder in a subject. In some embodiments, the method comprises: administering to the subject an effective amount of a composition disclosed herein; and applying ultrasound (US) to a target site of the subject, thereby monitoring the treatment or prevention of the disease or disorder. In some embodiments, upon administration, the probiotic bacterial cells accumulate in one or more target sites of the subject, optionally hypoxic environments and/or immunosuppressive environments, further optionally the necrotic core of a solid tumor.

Disclosed herein include methods of monitoring a cell-based therapy. In some embodiments, the method comprises: administering to a subject an effective amount of the reporting therapeutic cell(s) disclosed herein; and applying ultrasound (US) to a target site of the subject, thereby monitoring the cell-based therapy. In some embodiments, monitoring the cell-based therapy comprises: monitoring the mass and/or function of the administered reporting therapeutic cells, and/or determining the ratio of functional reporting therapeutic cells post-administration. In some embodiments, the reporting therapeutic cells are administered to a target site of the subject. In some embodiments, the administering comprises transplantation of the reporting therapeutic cells, optionally transplantation at one or more target sites, optionally the target site comprises a site of disease or disorder or is proximate to a site of a disease or disorder. In some embodiments, the cell-based therapy is a transplant and/or tissue replacement. In some embodiments, the administering comprises implanting the reporting therapeutic cells into a target site of the subject.

Disclosed herein include methods of imaging a target site of a subject. In some embodiments, the method comprises: administering to the subject an effective amount of a composition disclosed herein; and applying ultrasound (US) to the target site of the subject to obtain a US image of the target site, optionally a nonlinear US image.

Disclosed herein include methods of imaging gene expression within a subject. In some embodiments, the method comprises: administering to the subject an effective amount of a composition disclosed herein; and applying ultrasound (US) to the target site of the subject to obtain a US image of gene expression at the target site, optionally a nonlinear US image.

Disclosed herein include methods of imaging gene expression within target cells. In some embodiments, the method comprises: administering to the subject an effective amount of a composition disclosed herein; and applying ultrasound (US) to said target cells to obtain a US image of gene expression of target cells at the target site, optionally a nonlinear US image.

Disclosed herein include methods of detecting a unique cell type and/or unique cell state within a subject. In some embodiments, the method comprises: administering to the subject an effective amount of a composition disclosed herein; and applying ultrasound (US) to the target site of the subject, thereby detecting the unique cell type and/or unique cell state within said subject.

In some embodiments, the administering step comprises: (i) isolating target cells from the subject; introducing a nucleic acid composition and/or a delivery composition disclosed herein into said target cells; and administering to the subject an effective amount of said target cells; (ii) administering to the subject an effective amount of the probiotic bacterial cells, the reporting therapeutic cell(s), and/or the mammalian cells of disclosed herein; and/or (iii) administering to the subject an effective amount of the delivery composition disclosed herein. In some embodiments, the target cells are situated within a target site of a subject, and wherein applying US comprises applying US to the target site to obtain a US image of the target site; the target cells are situated within a plurality of target sites of a subject, and wherein applying US comprises applying US to the plurality of target sites to obtain US images of the plurality of target sites, and/or applying US to the target site comprises applying US to a plurality of target sites of a subject, optionally the target cells comprise the probiotic bacterial cells, the reporting therapeutic cell(s), and/or the mammalian cells disclosed herein. In some embodiments, the target cells are situated within a target site of a subject, and wherein applying US comprises applying US to the target site to obtain a US image of the target site.

In some embodiments, the target cells in a unique cell type and/or a unique cell state express GVs, and wherein said GVs produce nonlinear ultrasound contrast. In some embodiments, applying US causes the production of unique cell type-dependent and/or unique cell state-dependent nonlinear ultrasound contrast. In some embodiments, detecting a unique cell type and/or unique cell state comprises detecting an at least about 1 dB enhancement in nonlinear ultrasound contrast.

In some embodiments, imaging gene expression comprises: detecting an at least about 1 dB enhancement in nonlinear ultrasound contrast; and/or quantified GV expression over time as a volumetric sum of xAM signal over all acquired image planes. In some embodiments, applying US comprises nonlinear US imaging. In some embodiments, applying US comprises applying one or more US pulse(s) over a duration of time. In some embodiments, the duration of time is about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, or about 5 minutes. In some embodiments, the one or more US pulse(s) each have a pulse duration of about 1 hour, about 30 minutes, about 15 minutes, about 10 minutes, about 5 minutes, about 1 minute, about 1 second, or about 1 millisecond. In some embodiments, applying one or more US pulse(s) comprises applying one or more focused US pulse(s). In some embodiments, applying one or more US pulse(s) comprises applying US at a frequency of 100 kHz to 100 MHz. In some embodiments, applying one or more US pulse(s) comprises applying ultrasound at a frequency of 0.2 to 1.5 mHz. In some embodiments, applying one or more US pulse(s) comprises applying ultrasound having a mechanical index in a range between 0.2 and 0.6. In some embodiments, the one or more US pulse(s) comprise a peak pressure of about 40 kPa to about 800 kPa. In some embodiments, the one or more US pulse(s) comprise a peak pressure of about 70 kPa to about 150 kPa, and/or about 440 kPa to about 605 kPa. In some embodiments, the one or more US pulse(s) comprise a pressure value that is: the selectable buckling pressure; the first optimum buckling pressure; and/or equal to or less than the first initial collapse pressure. In some embodiments, the one or more US pulse(s) induces collapse of GVs, and wherein the one or more US pulse(s) comprise a pressure value that is the first selectable collapse pressure. In some embodiments, the nonlinear ultrasound imaging comprises cross-amplitude modulation (x-AM) ultrasound imaging or parabolic amplitude modulation (pAM) ultrasound imaging. In some embodiments, the nonlinear ultrasound imaging comprises differential nonlinear ultrasound imaging. In some embodiments, differential nonlinear ultrasound imaging comprises imaging of the second and/or higher harmonics with the first harmonic signal subtracted out, further optionally cross-phase modulation imaging and/or harmonic imaging. In some embodiments, the nonlinear ultrasound imaging comprises providing amplitude modulation (AM) ultrasound pulse sequences.

In some embodiments, the nonlinear ultrasound imaging comprises: pairs of cross-propagating plane waves to elicit nonlinear scattering from buckling GVs at the wave intersection; subtracting the signal generated by transmitting each wave on its own; and quantifying the resulting contrast. In some embodiments, the signals generated by transmitting each wave on its own has linear characteristics and/or lower nonlinear characteristics than the combined transmission of both plane waves produced at their intersection. In some embodiments, the nonlinear ultrasound imaging comprises: a peak positive pressure of two single tilted plane waves exciting the GV in a linear scattering regime; a doubled X-wave intersection amplitude exciting the GV in a nonlinear scattering regime; summing the echoes from the two single tilted plane-wave transmissions to generate a sum; and subtracting the sum from the echoes of the X-wave transmissions to derive nonzero differential GV signals. In some embodiments, applying US comprises detecting scattering of the one or more US pulse(s) by gas vesicles, optionally nonlinear scattering of the US by buckling gas vesicles. In some embodiments, detecting scattering comprises: detecting backscattered echoes of two half-amplitude transmissions at applied pressures below the buckling threshold of the GV, optionally said two half-amplitude transmissions trigger largely linear scattering, detecting backscattered echoes of a third full-amplitude transmission at pressures above the buckling threshold of the gas vesicles, optionally said third full-amplitude transmission triggers harmonic and nonlinear scattering, optionally the method comprises subtracting the backscattered echoes of the two half-amplitude transmissions from the backscattered echoes of the third full-amplitude transmission.

In some embodiments, the GVs have an acoustic collapse pressure threshold, and wherein applying ultrasound comprises: applying ultrasound to the target site at a peak positive pressure less than the acoustic collapse pressure threshold; increasing peak positive pressure (PPP) to above the selective acoustic collapse pressure value as a step function; and imaging the target site in successive frames during the increasing; and extracting a time-series vector for each of at least one pixel of the successive frames. The method can comprise: performing a signal separation algorithm on the time-series vectors using at least one template vector. In some embodiments, the signal separation algorithm includes template projection and/or template unmixing. In some embodiments, the at least one template vector includes linear scatterers, noise, gas vesicles, or a combination thereof. In some embodiments, the successive frames comprise a frame prior to GVs collapse, a frame during GVs collapse, and a frame after GVs collapse. In some embodiments, the increasing includes increasing the PPP to a hiBURST regime, optionally the PPP in hiBURST regime is 4.3 MPa or higher. In some embodiments, the increasing includes increasing the PPP to a loBURST regime, optionally the PPP in loBURST regime is no higher than 3.7 MPa.

In some embodiments, the method comprises: single-cell imaging; and/or imaging a large volume in deep tissue. In some embodiments, the method comprises US imaging with a spatiotemporal resolution of less than about 100 μm and less than about 1 ms. In some embodiments, the target site comprises: a volume larger than about 1 mm3; a depth deeper than about 1 mm; a depth and/or a volume inaccessible via optical imaging and/or fiber photometry; and/or the entire brain or a portion thereof.

In some embodiments, the disease or disorder is associated with expression of a tumor antigen. In some embodiments, the disease associated with expression of a tumor antigen is selected from the group consisting of a proliferative disease, a precancerous condition, a cancer, and a non-cancer related indication associated with expression of the tumor antigen. In some embodiments, the disease or disorder is a blood disease, an immune disease, a neurological disease or disorder, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or any combination thereof, optionally a solid tumor. In some embodiments, the cancer is selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. In some embodiments, the cancer is a hematologic cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia.

In some embodiments, the method further comprises performing one or more biopsies guided on the basis of one or more US images, optionally said one or more biopsies and applying US are performed concurrently, further optionally biopsies targeting either the xAM-positive and/or the xAM-negative regions of a target site. In some embodiments, the subject has a disease of the GI tract. In some embodiments, the disease of the GI tract is an inflammatory bowel disease, optionally the inflammatory bowel disease comprises Crohn's disease, ulcerative colitis, irritable bowel syndrome, microscopic colitis, lymphocytic-plasmocytic enteritis, coeliac disease, collagenous colitis, lymphocytic colitis and eosinophilic enterocolitis, indeterminate colitis, infectious colitis, pseudomembranous colitis, ischemic inflammatory bowel disease or Behcet's disease. In some embodiments, the target site comprises a section or subsection of the GI tract. In some embodiments, the section or subsection of the GI tract is selected from the group consisting of the stomach, proximal duodenum, distal duodenum, proximal jejunum, distal jejunum, proximal ileum, distal ileum, proximal cecum, distal cecum, proximal ascending colon, distal ascending colon, proximal transverse colon, distal transverse colon, proximal descending colon and distal descending colon, or any combination thereof. In some embodiments, the target site comprises: (i) a site of disease or disorder or is proximate to a site of a disease or disorder, optionally the location of the one or more sites of a disease or disorder is predetermined, is determined during the method, or both, further optionally the target site is an immunosuppressive environment; (ii) target cell(s); and/or (iii) a tissue, optionally the tissue is inflamed tissue and/or infected tissue. In some embodiments, the tissue comprises adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue. In some embodiments, the tissue comprises: (i) grade I, grade II, grade III or grade IV cancerous tissue; (ii) metastatic cancerous tissue; (iii) mixed grade cancerous tissue; (iv) a sub-grade cancerous tissue; (v) healthy or normal tissue; and/or (vi) cancerous or abnormal tissue.

In some embodiments, the target cell comprises an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, a zymogenic cell, or any combination thereof, further optionally the stem cell comprises an embryonic stem cell, an induced pluripotent stem cell (iPSC), a hematopoietic stem/progenitor cell (HSPC), or any combination thereof.

The method can comprise: administering an effective amount of a transactivator-binding compound and/or chemical inducer to the subject. In some embodiments, the transactivator-binding compound comprises tetracycline, doxycycline or a derivative thereof, optionally the chemical inducer is L-arabinose or a derivative thereof. In some embodiments, the administering comprises systemic administration, optionally the systemic administration is intravenous, intramuscular, intraperitoneal, or intraarticular. In some embodiments, administering comprises intracranial delivery, intrathecal administration, intracranial injection, aerosol delivery, nasal delivery, vaginal delivery, direct injection to any tissue in the body, intraventricular delivery, intraocular delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, intradermal injection, or any combination thereof. In some embodiments, the period of time between the administering and applying is about 21 days, about 14 days, about 7 days, about 3 days, about 48 hours, about 44 hours, about 40 hours, about 35 hours, about 30 hours, about 25 hours, 20 hours, 15 hours, 10 hours, about 8 hours, about 7 hours, about 6 hours, about 5 hours, about 4 hours, about 3 hours, about 2 hours, about 1 hour, about 30 minutes, about 15 minutes, about 10 minutes, or about 5 minutes. In some embodiments, the subject is a mammal, optionally the subject is not anesthetized. In some embodiments, the method does not comprise pre-expression of GVs under ideal laboratory conditions prior to the administering and/or the use of a global epigenetic activator.

The method can comprise: administering one or more additional agents to the subject, optionally a prodrug or a pro-death agent. In some embodiments, the one or more additional agents comprise a protein phosphatase inhibitor, a kinase inhibitor, a cytokine, an inhibitor of an immune inhibitory molecule, and/or or an agent that decreases the level or activity of a TREG cell. In some embodiments, the one or more additional agents comprise an immune modulator, an anti-metastatic, a chemotherapeutic, a hormone or a growth factor antagonist, an alkylating agent, a TLR agonist, a cytokine antagonist, a cytokine antagonist, or any combination thereof. In some embodiments, the one or more additional agents comprise a therapeutic agent useful for treating a disease of the GI tract, such as, for example: one of the following classes of compounds: 5-aminosalicyclic acids, corticosteroids, thiopurines, tumor necrosis factor-alpha blockers and JAK inhibitors; and/or one or more of Prednisone, Humira, Lialda, Imuran, Sulfasalazine, Pentasa, Mercaptopurine, Azathioprine, Apriso, Simponi, Enbrel, Humira Crohn's Disease Starter Pack, Colazal, Budesonide, Azulfidine, Purinethol, Proctosol HC, Sulfazine EC, Delzicol, Balsalazide, Hydrocortisone acetate, Infliximab, Mesalamine, Proctozone-HC, Sulfazine, Orapred ODT, Mesalamine, Azasan, Asacol HD, Dipentum, Prednisone Intensol, Anusol-HC, Rowasa, Azulfidine EN-tabs, Veripred 20, Uceris, Adalimumab, Hydrocortisone, Colocort, Pediapred, Millipred, Azathioprine injection, Prednisolone sodium phosphate, Flo-Pred, Aminosalicylic acid, Procto-Cream-HC, 5-aminosalicylic acid, Millipred DP, Golimumab, Prednisolone acetate, Rayos, Proctocort, Paser, Olsalazine, Procto-Pak, Purixan, Cortenema, Giazo, Vedolizumab, Entyvio, Micheliolide, and Parthenolide. In some embodiments, the disease of the GI tract is an inflammatory bowel disease.

BRIEF DESCRIPTION OF THE DRAWINGS

(FIG. 1A) 16S phylogenic tree of known GV-producing organisms, with the species from which GV genes were cloned and tested in this study indicated by name. See FIG. 8 for the fully annotated phylogenic tree. *B. megaterium* and *S. coelicolor* were not reported to produce GVs, but their GV gene clusters were tested here based on previous experiments in *E. coli* and to broadly sample the phylogenetic space. (FIG. 1B) Workflow for testing GV clusters. Selected GV gene clusters were expressed in BL21 (DE3) *E. coli* by growing patches of cells on plates containing the inducer IPTG, and the patches were then imaged with nonlinear ultrasound (xAM). (FIGS. 1C-1E) Diagrams of the GV gene clusters tested in *E. coli* (FIG. 1C), differential xAM images of representative patches (FIG. 1D), and quantification of the differential xAM signal-to-background ratio (SBR) of the patches (n=6 biological replicates) (FIG. 1E). (FIGS. 1F-1G) Representative xAM images (FIG. 1F) and quantification of the xAM SBR (n=3 biological replicates, each with 2 technical replicates; lines represent the mean) (FIG. 1G) for the top 5 GV-producing clusters expressed in *E. coli* at 30° C. on solid media and normalized to $5\times10^9$ cells/mL in agarose phantoms, imaged at 1.74 MPa. See FIGS. 14A-14B for the ultrasound signal at varying acoustic pressures and FIG. 14C for the corresponding BURST data.

(FIG. 2A) Diagram of the arabinose-inducible construct used to express $bARG_{Ser}$ in EcN (top), and optical and xAM images of $bARG_{Ser}$-expressing or FP-expressing patches of EcN on solid media with varying L-arabinose concentrations at 37° C. (bottom). The scale bar is 1 cm. See FIGS. 16A-16D for the corresponding results with IPTG-inducible and aTc-inducible constructs. (FIG. 2B) Quantification of the xAM SBR of all patches from the experiment in FIG. 2A versus the L-arabinose concentration (n=8 biological replicates). (FIG. 2C) Diagram of the construct from (FIG. 2A) with the toxin-antitoxin stability cassette Axe-Txe added to enable plasmid maintenance in the absence of antibiotics (top), and verification of plasmid maintenance in vitro (bottom). The percentage of chloramphenicol-resistant colonies was measured during daily sub-culturing into LB media with 25 µg/mL chloramphenicol (+chlor), without chloramphenicol (−chlor), or without chloramphenicol and with 0.1% (w/v) L-arabinose (−chlor +L-ara) using pBAD-bARG$_{Ser}$-AxeTxe EcN (n=4 biological replicates). The percentage of chloramphenicol-resistant colonies was calculated by dividing the number of colonies on plates with chloramphenicol by the number of colonies on plates without chloramphenicol. (FIGS. 2D-2E) Colony forming units (CFUs) per mL of culture on chloramphenicol plates (FIG. 2D) and optical density at 600 nm (FIG. 2E) of pBAD-bARG$_{Ser}$-AxeTxe EcN and pBAD-FP-AxeTxe EcN cultures 24 hours after sub-culturing into LB media with the same conditions as in FIG. 2C. Asterisks indicate statistical significance by two-tailed, unpaired Student's t-tests (**=p<0.0001, *=p<0.001, ns=no significance); n=4 biological replicates. (FIG. 2F) $OD_{600}$ versus time after inducing pBAD-bARG$_{Ser}$-AxeTxe (bARG$_{Ser}$+axe-txe) and pBAD-FP-AxeTxe (FP+axe-txe) EcN strains with 0.1% (w/v) L-arabinose in liquid culture at 37° C. (n=4 biological replicates). Between 5 and 24 hours post-induction, when the $OD_{600}$ of all cultures decreased, the $OD_{600}$ of FP-expressing cultures was slightly higher than that of the bARG$_{Ser}$-expressing cultures, likely due to expression of red fluorescent protein which is known to absorb light at 600 nm. (FIG. 2G) Representative image of colonies from the experiment in FIG. 2C on chloramphenicol plates with (right) and without (left) 0.1% (w/v) L-arabinose. The opacity of the colonies on plates with L-arabinose indicates bARG$_{Ser}$ expression and was used to screen for mutants deficient in bARG$_{Ser}$ expression (see FIGS. 18A-18B). (FIGS. 2H-2I) Representative phase contrast microscopy (FIG. 2H) and transmission electron microscopy (FIG. 2I) images of pBAD-bARG$_{Ser}$-AxeTxe EcN cells grown on plates with 0.1% (w/v) L-arabinose at 37° C. Scale bars are 10 µm (FIG. 2H) and 500 nm (FIG. 2I). Curves and lines represent the mean for FIGS. 2B-2F.

FIGS. 3A-3I depict data related to acoustic characterization of bARG$_{Ser}$-expressing EcN in vitro. (FIG. 3A) xAM SBR as a function of transmitted acoustic pressure for bARG$_{Ser}$-expressing and FP-expressing EcN. (FIGS. 3B-3C) xAM (FIG. 3B) and parabolic B-mode (FIG. 3C) SBRs measured over time when the transmitted acoustic pressure was increased approximately every 70 sec as indicated by the numbers above the curve for bARG$_{Ser}$-expressing EcN. Ultrasound was applied at a pulse repetition rate of 86.8 Hz. For FIGS. 3A-3C, pBAD-bARG$_{Ser}$-AxeTxe EcN were induced with 0.1% (w/v) L-arabinose for 24 hours at 37° C. in liquid culture, and were then normalized to $10^9$ cells/mL in agarose phantoms for ultrasound imaging. Bold lines represent the mean and thin lines represent±standard deviation; n=3 biological replicates, each with 2 technical replicates. (FIGS. 3D-3E) xAM ultrasound SBR (FIG. 3D) and corresponding representative ultrasound images (FIG. 3E) at several time points after inducing pBAD-bARG$_{Ser}$-AxeTxe (bARG$_{Ser}$+axe-txe) and pBAD-FP-AxeTxe (FP+axe-txe) EcN strains with 0.1% (w/v) L-arabinose in liquid culture at 37° C. (FIGS. 3F-3G) xAM ultrasound SBR (FIG. 3F) and corresponding representative ultrasound images (FIG. 3G) using varying L-arabinose concentrations to induce pBAD-bARG$_{Ser}$-AxeTxe EcN in liquid culture at 37° C. for 24 hours. (FIGS. 3H-3I) xAM ultrasound SBR (FIG. 3H) and corresponding representative ultrasound images (FIG. 3I) of varying concentrations of pBAD-bARG$_{Ser}$-AxeTxe or pBAD-FP-AxeTxe EcN cells induced for 24 hours at 37° C. with 0.1% (w/v) L-arabinose in liquid culture. For FIG. 3E, FIG. 3G, and FIG. 3I scale bars are 2 mm. For FIGS. 3D-3G, cells were normalized to $10^9$ cells/mL in agarose phantoms for ultrasound imaging. For FIG. 3D, FIG. 3F, FIG. 3H, each point is a biological replicate (n=4 for FIG. 3D and FIG. 3F; n=3 for FIG. 3H) that is the average of at least 2 technical replicates, and curves represent the mean. Asterisks represent statistical significance by two-tailed, unpaired Student's t-tests (**=p<0.0001, *=p<0.001, **=p<0.01, ns=no significance).

(FIG. 4A) Diagram of the in vivo protocol for assessing in situ bARG$_{Ser}$ expression in tumors. Mice were injected subcutaneously (SQ) with MC26 cancer cells on day 1 and the tumors were allowed to grow for 14 days. Mice were then injected with *E. coli* Nissle (EcN) carrying either pBAD-bARG$_{Ser}$-AxeTxe or pBAD-FP-AxeTxe plasmids via the tail vein. After allowing 3 days for the EcN to colonize the tumors, bARG$_{Ser}$ or FP expression was induced by injecting L-arabinose intraperitoneally (IP) on day 17. The next day, at least 24 hours after induction, tumors were imaged with ultrasound. Subsequently, all the GVs in the tumors were collapsed by applying maximum acoustic pressure (3.0 MPa) throughout the tumor. L-arabinose was then injected again to re-induce bARG$_{Ser}$ expression, and tumors were again imaged with ultrasound at least 24 hours later. The next day (day 20), all mice were sacrificed, and their tumors were homogenized and plated on selective media to quantify the levels of EcN colonization. In separate experiments for histological analysis, mice were sacrificed on day 18 directly after ultrasound imaging. (FIGS. 4B-4D) Representative B-mode, parabolic AM (pAM), and BURST ultrasound images of tumors colonized by pBAD-bARG$_{Ser}$-AxeTxe EcN at least 24 hours after induction with L-arabinose on day 18 (FIG. 4B), at least 24 hours after collapse and re-induction (day 19) (FIG. 4C), or uninduced on day 18 (FIG. 4D). (FIG. 4E) Representative B-mode, pAM, and BURST ultrasound images of tumors colonized by pBAD-FP-AxeTxe EcN at least 24 hours after induction with L-arabinose on day 18. (FIGS. 4F-4G) Optical images of tissue sections stained with H&E (FIG. 4F) or anti-*E. coli* antibodies (FIG. 4G) from a tumor colonized by bARG$_{Ser}$-expressing EcN after ultrasound imaging on day 19. (FIGS. 4H-4I) BURST (FIG. 4H) and xAM (FIG. 4I) ultrasound images of the same tumor as in FIGS. 4F-4G, with the boxed region showing the approximate BURST imaging region in the tissue section. Scale bars in (FIGS. 4B-4I) represent 2 mm. (FIGS. 4J-4K) Quantification of the pAM (FIG. 4J) and BURST (FIG. 4K) SBR for the same conditions in FIGS. 4B-4E. (FIG. 4L) Colony forming units (CFUs) per gram of tissue from tumors homogenized and plated on day 20. For FIGS. 4J-4L, points represent each mouse (n=5), and lines represent the mean of each group. The dotted line indicates the limit of detection (LOD). Asterisks represent statistical significance by two-tailed, unpaired Student's t-tests (*=p<0.001, =p<0.01, *=p<0.05, ns=no significance).

See FIGS. 20A-20F for representative xAM ultrasound images for the conditions in FIGS. 4B-4D, and FIGS. 21A-21K for more histological images of tissue sections from tumors colonized with pBAD-bARG$_{Ser}$-AxeTxe EcN.

FIGS. 5A-5K depict non-limiting exemplary schematics and data related to heterologous expression of the *A. flos-aquae* GV gene cluster in mammalian cells. (FIG. 5A) Schematic of the codon-optimized monocistronic plasmid sets used in this study. (FIG. 5B) Representative BURST images (top) and SBR quantification (n=5, bottom) of transient GV expression in HEK293T cells 3 days after cotransfection of mixtures with varying gvpA B fold excess relative to their respective assembly factor plasmids. (FIG. 5C) Diagram of GV structure with GvpC highlighted in orange. (FIG. 5D) Representative xAM ultrasound images (top) and SBR quantification (n=6, bottom) of transient cotransfection experiments of *A. flos-aquae* GV plasmids (4-fold gvpA excess) with and without gvpC at varying acoustic pressures. *B. megaterium* GV (at 2-fold gvpB excess) and GFP expression is included for quantitative comparison. (FIG. 5E) Schematic of the mARG$_{Ana}$ plasmid set with fluorescent reporters. (FIG. 5F) Representative BURST images (top) and SBR quantification (n=4, bottom) of transient GV expression in HEK293T cells 3 days after cotransfection of mARG$_{Ana}$ mixtures with varying gvpA fold excess relative to the assembly factor plasmid. (FIG. 5G) Schematic of MDA-MB-231-mARG$_{Ana}$ engineering (created with BioRender.com and FlowJo). The final population was ~95% double positive for gvpA and gvpNJKFGWV expression. (FIG. 5H) Representative xAM images (top) and SBR quantification (n=5, bottom) of MDA-MB-231-mARG$_{Ana}$ cells at 0.54 MPa after 1, 2, 4 and 6 days of 1 μg/ml doxycycline induction. (FIG. 5I) Representative xAM images (top) and SBR quantification (n=4, bottom) of MDA-MB-231-mARG$_{Ana}$ cells at 0.42 MPa as a function of doxycycline concentration after 4 days of expression. (FIG. 5J) Representative xAM images (top) and SBR quantification (n=4, bottom) of induced and uninduced MDA-MB-231-mARG$_{Ana}$ cells as a function of time under varying acoustic pressures. For FIG. 5J, thick lines represent the mean of 4 replicates and thin lines represent±standard deviation. For FIG. 5B, FIG. 5D, FIG. 5F, FIG. 5H, and FIG. 5I, gray lines connect the means of the replicates. All ultrasound image scalebars represent 1 mm.

Figure 6A:
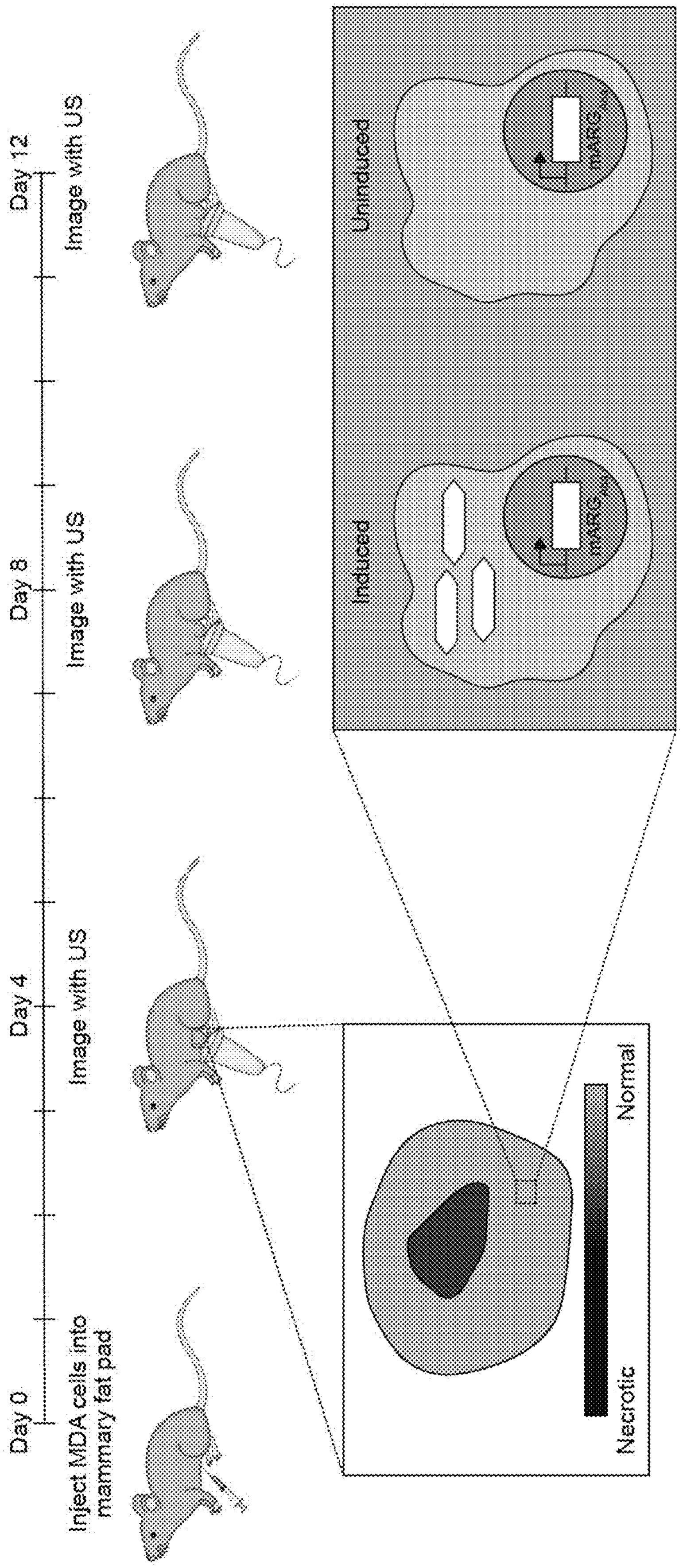
Figure 6B:
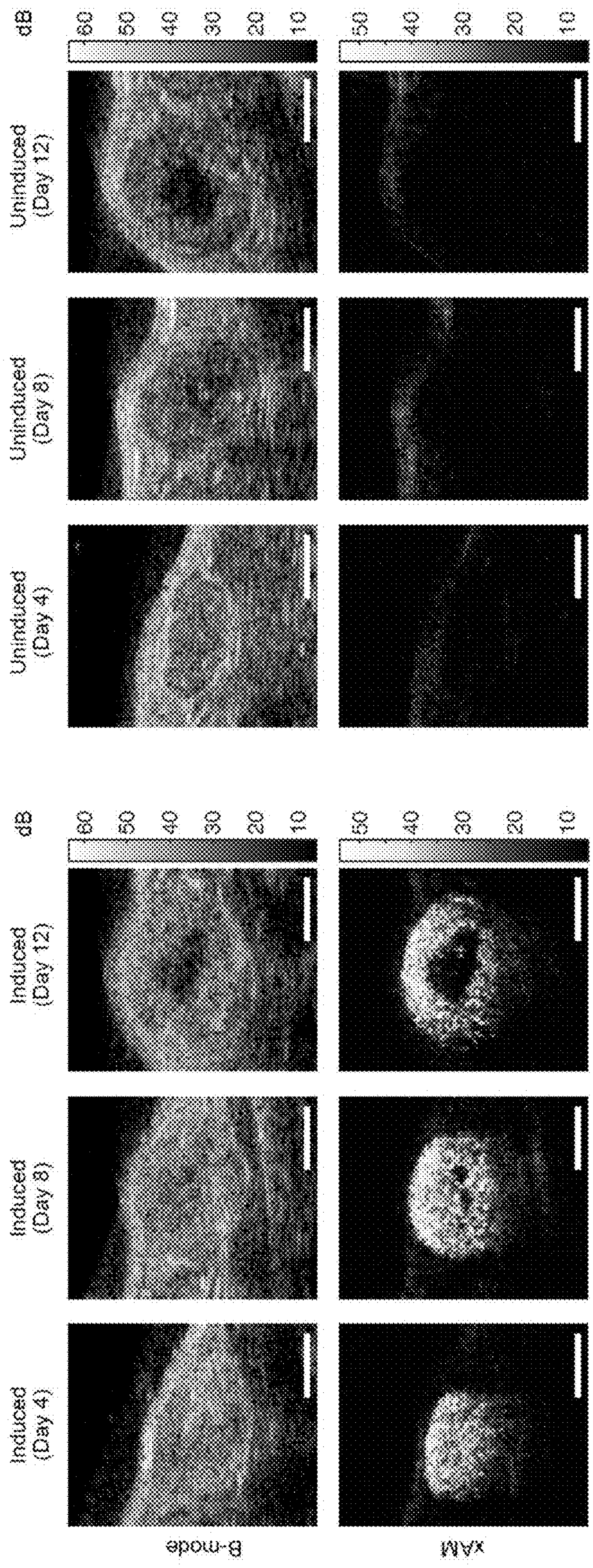

FIGS. 6A-6E depict non-limiting exemplary schematics and data related to in situ mARG$_{Ana}$ expression enabling nondestructive ultrasound imaging of orthotopic tumors. (FIG. 6A) Diagram of the in vivo protocol for assessing in situ mARG$_{Ana}$ expression in orthotopic tumors. Mice were injected bilaterally in 4$^{th}$ mammary fat pads with engineered MDA-MB-231-mARG$_{Ana}$ human breast adenocarcinoma cells on day 0. mARG$_{Ana}$ expression was induced by regular intraperitoneal (IP) doxycycline injections starting from the day of tumor injections. Tumors were imaged with ultrasound after 4, 8 and 12 days of expression. (FIG. 6B) Representative middle sections of B-mode and xAM ultrasound tomograms of MDA-MB-231 mARG$_{Ana}$ tumors induced with doxycycline (left) and uninduced control (right) imaged on day 4, 8 and 12. Scalebars represent 2 mm. Data now shown: video for the full ultrasound tomogram of the induced tumor at 12 days. (FIG. 6C) Fluorescence micrograph of a 100 nm thin tumor section. Green color shows GFP fluorescence, blue color shows BFP fluorescence, and red color shows TO-PRO-3 nuclear stain. See FIGS. 24A-24C for the uninduced control. Scalebars represent 2 mm. (FIG. 6D) Whole-animal fluorescence imaging of induced (left) and uninduced (right) mouse after 12-days of expression. All tumors are constitutively expressing CyOFP1 (Antares, red) whereas mARG$_{Ana}$ expression is linked to expression of GFP (green). The left (reader's right) tumors are shown in panel (FIG. 6B). Scalebars represent 5 mm. (FIG. 6E) Three-dimensional sum of xAM signal from ultrasound tomograms of induced (n=8) and uninduced (n=7 on day 4, n=5 on days 8 and 12) tumors from all three imaging sessions plotted on a linear scale in arbitrary units. Asterisks represent statistical significance by unpaired t tests between induced and uninduced conditions (*=p<0.001, =p<0.01, *=p<0.05, ns=no significance).

Figure 7A:
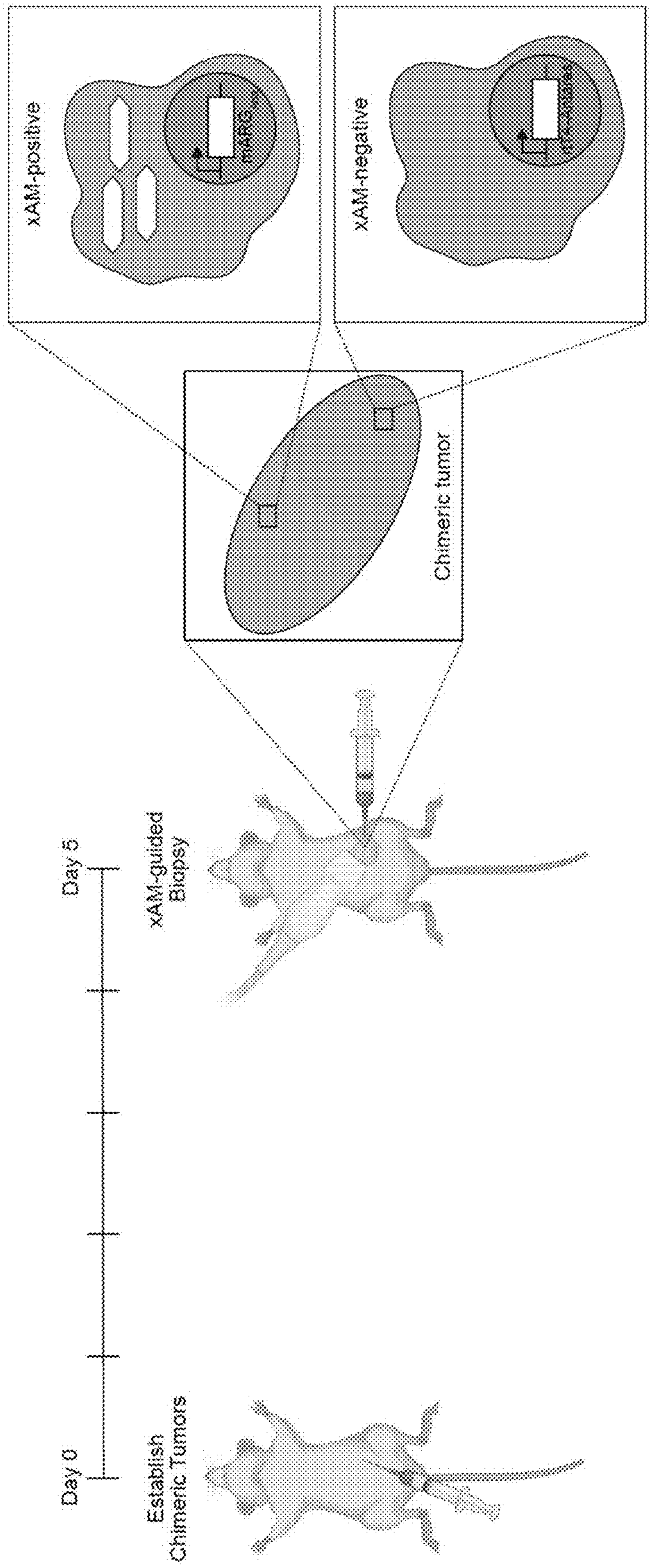
Figure 7C:
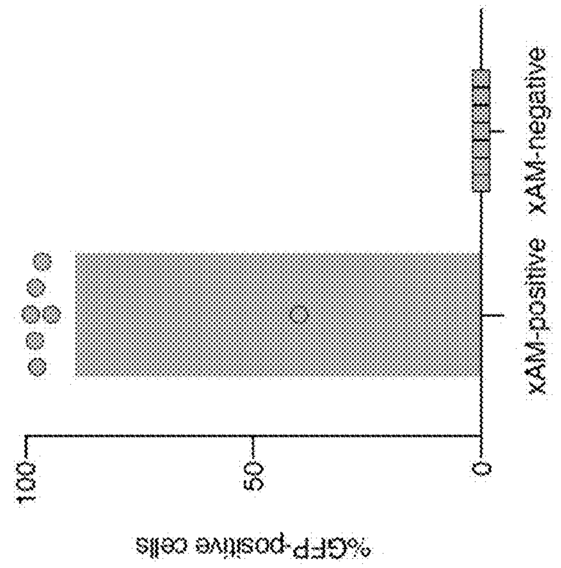
Figure 7B:
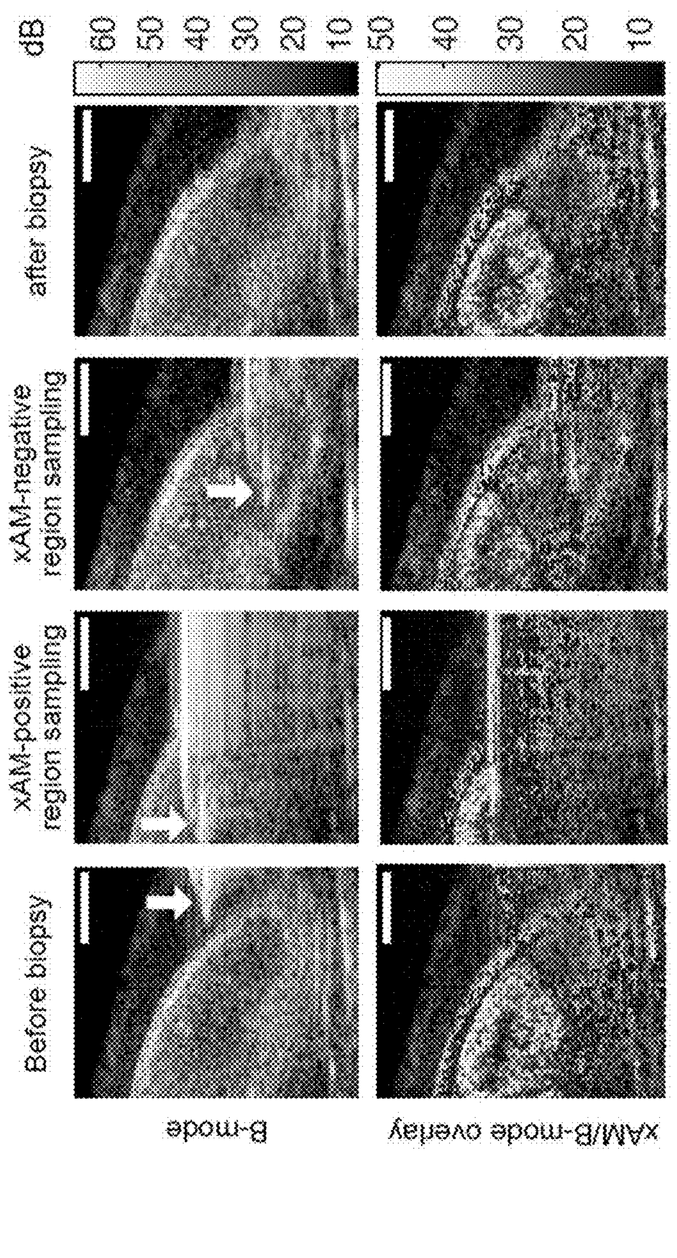

FIGS. 7A-7C depict non-limiting exemplary schematics and data related to xAM imaging of mARG$_{Ana}$ enabling ultrasound-guided genetically selective tumor biopsy. (FIG. 7A) Diagram of the in vivo protocol for establishing chimeric tumors, in situ expression of GVs and tumor biopsy. Chimeric tumors were established on day 0. mARG$_{Ana}$ expression was induced by regular intraperitoneal (IP) doxycycline injections starting from the day of tumor injections. Tumors were imaged with ultrasound and biopsied after 5 days of expression. (FIG. 7B) Representative B-mode and xAM an ultrasound-guided biopsy procedure. Scalebars represent 2 mm. Data not shown: videos for the full ultrasound tomogram of the induced chimeric tumor, 3D reconstruction of the chimeric tumor as well as the videos of the full procedure. (FIG. 7C) Results of flow cytometric analysis of biopsied samples from xAM-positive and xAM-negative regions of chimeric tumors (n=7 tumors). See FIG. 27 for flow cytometric gating strategy. Bar height represents the mean, circles represent individual data points.

Figure 1A:
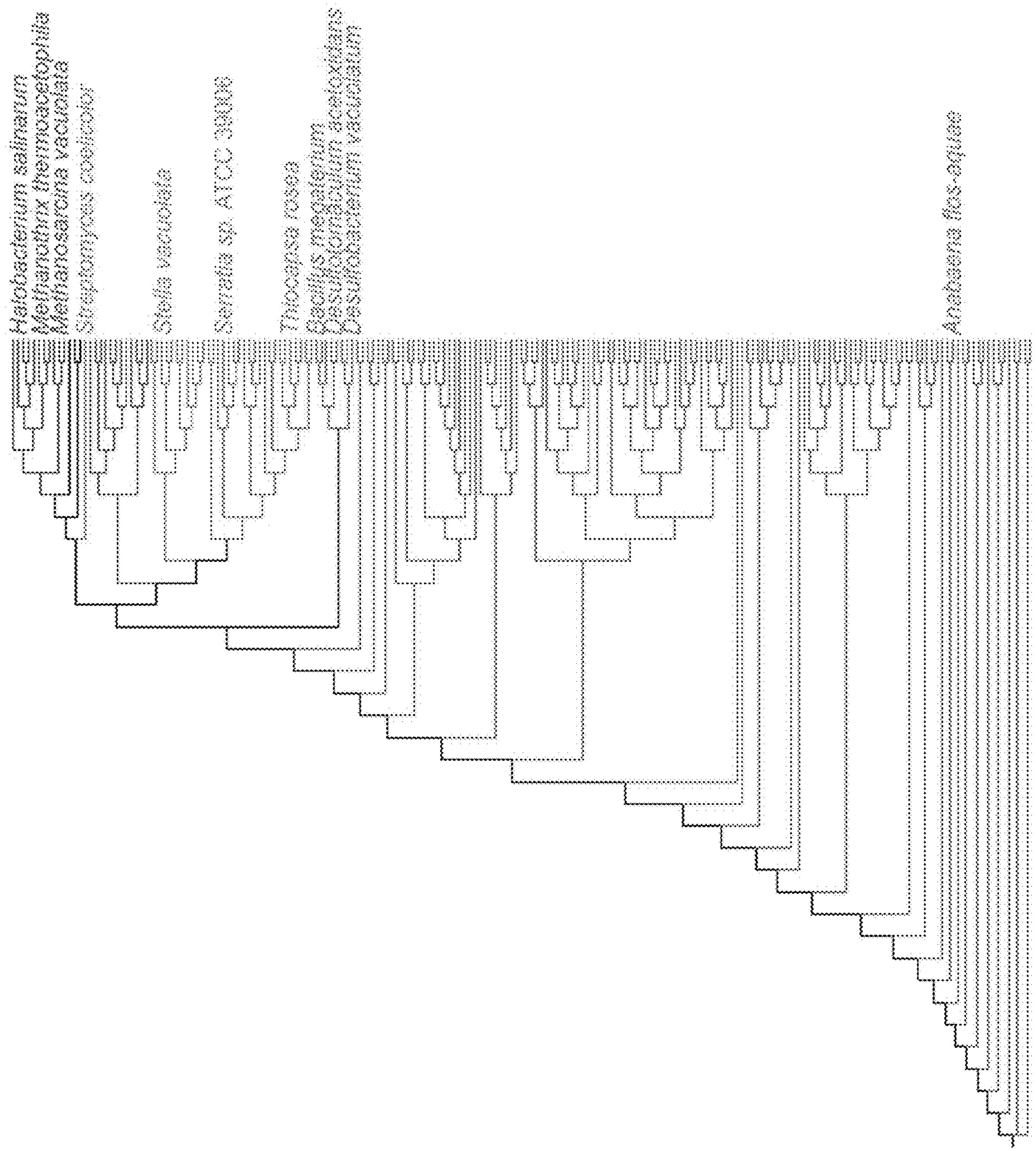
FIGS. 1A-1G depict non-limiting exemplary schematics and data related to genomic mining of gas vesicle gene clusters revealing homologs with nonlinear ultrasound contrast in *E. coli*.
Figure 1B:
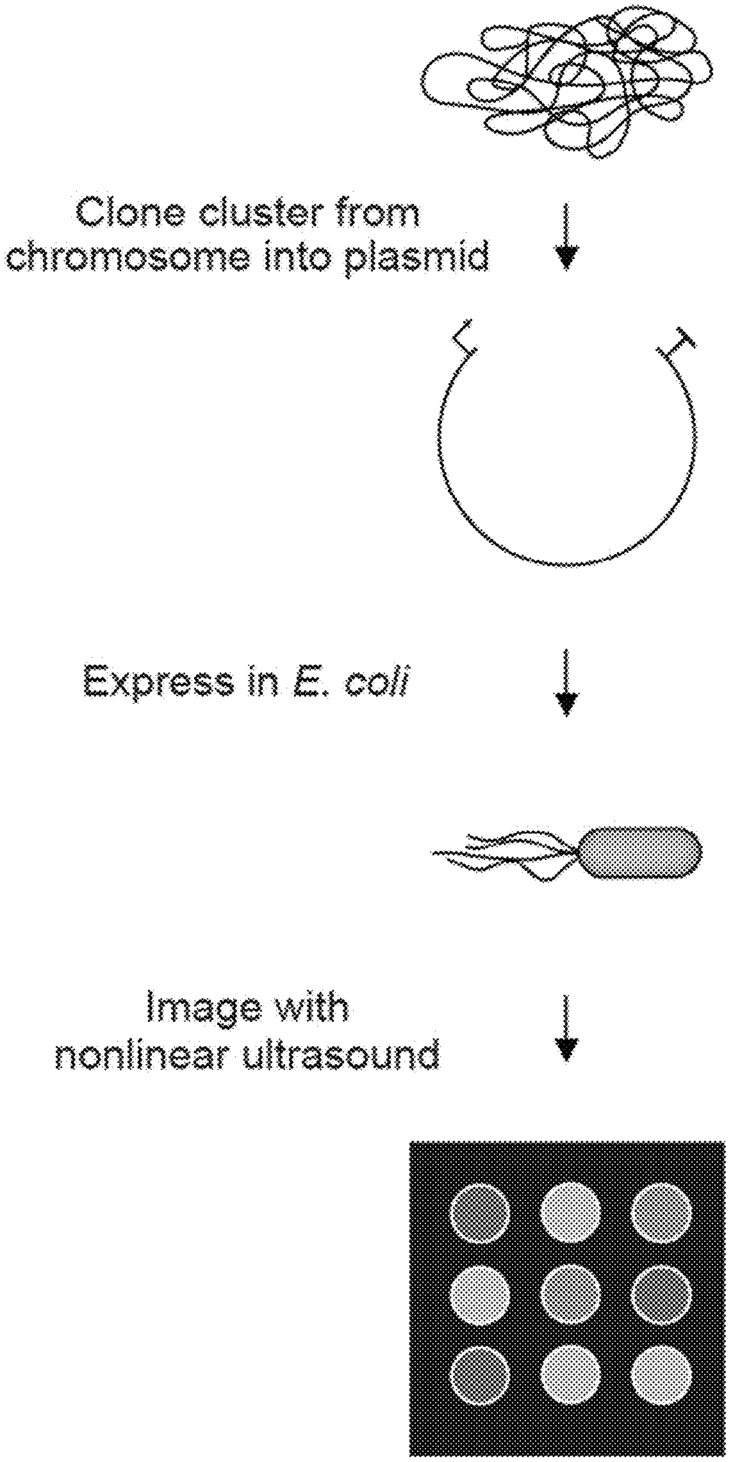
Figure 8:
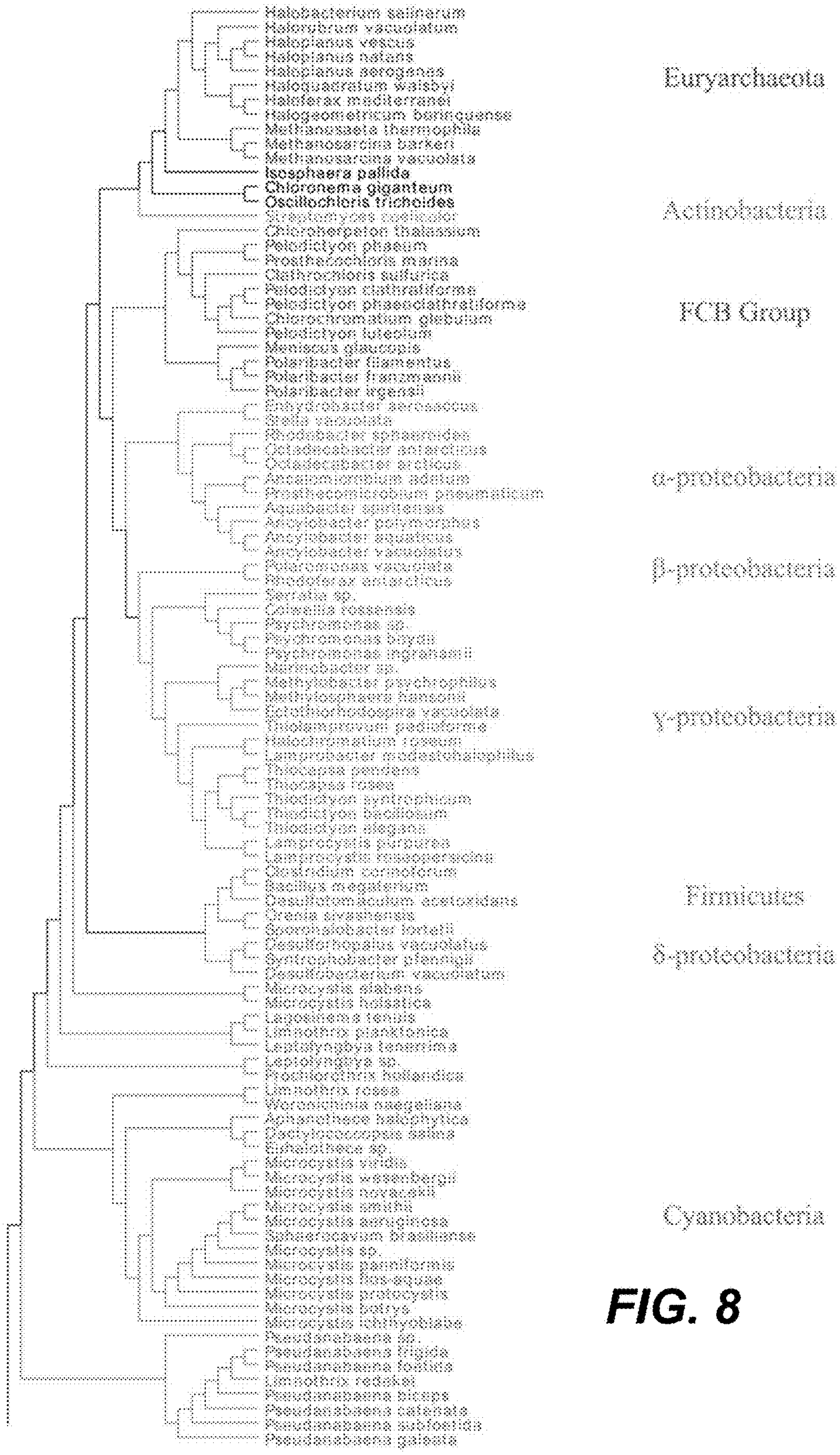
Figure 8:
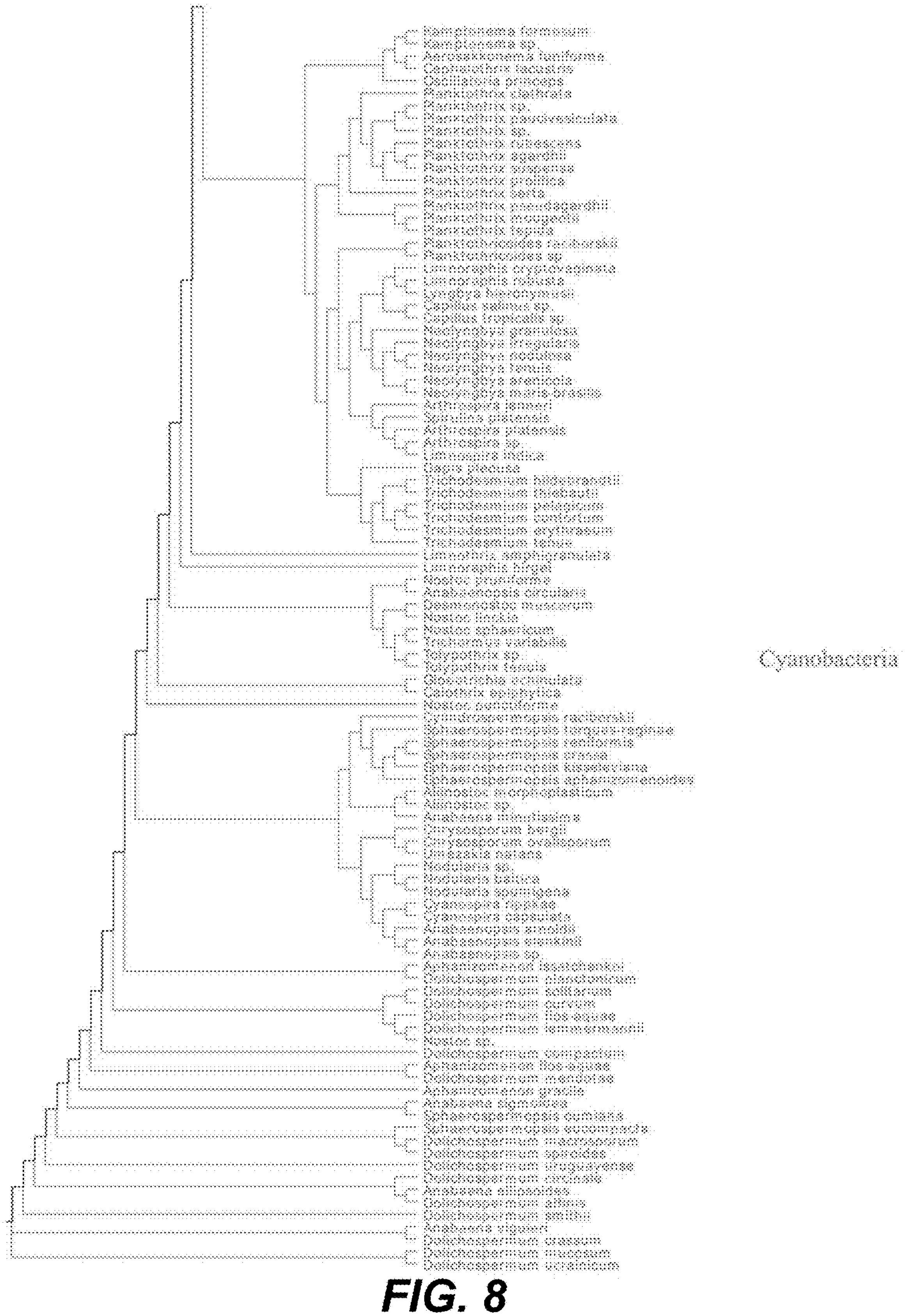

FIG. 8 depicts a non-limiting exemplary schematic related to 16S phylogenetic tree of all reported GV-producing organisms. Colors indicate groupings of phylogenetically similar organisms. Organisms from which GV genes were tested in *E. coli* are shown in FIG. 1A.

FIGS. 9A-9E depict data related to additional images and quantification of *E. coli* patches expressing select GV gene clusters. (FIGS. 9A-9C) xAM images (FIG. 9A), pre-minus-post-collapse xAM images (FIG. 9B), and optical images showing opacity (FIG. 9C) of patches of *E. coli* expressing various GV gene clusters from the organisms listed on the left. (FIGS. 9D-9E) Quantification of the xAM (FIG. 9D) and pre-minus-post-collapse xAM (FIG. 9E) signals from images in (a-b) (n=6). SBR, signal-to-background ratio.

Figure 12A:
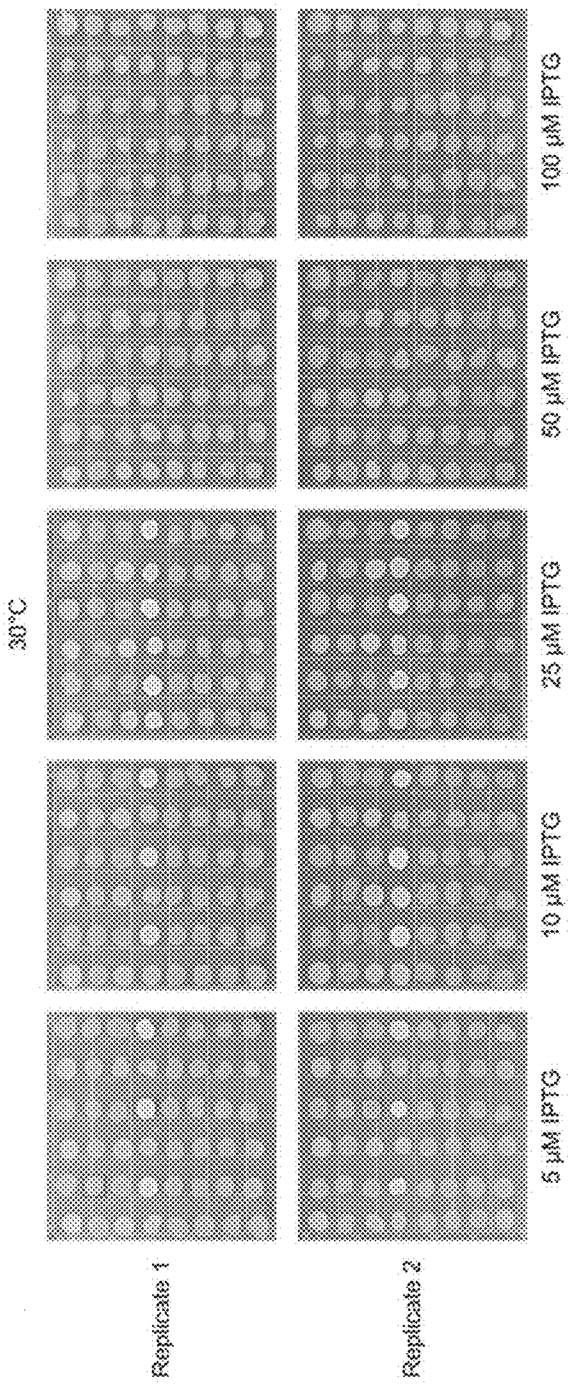
Figure 12B:
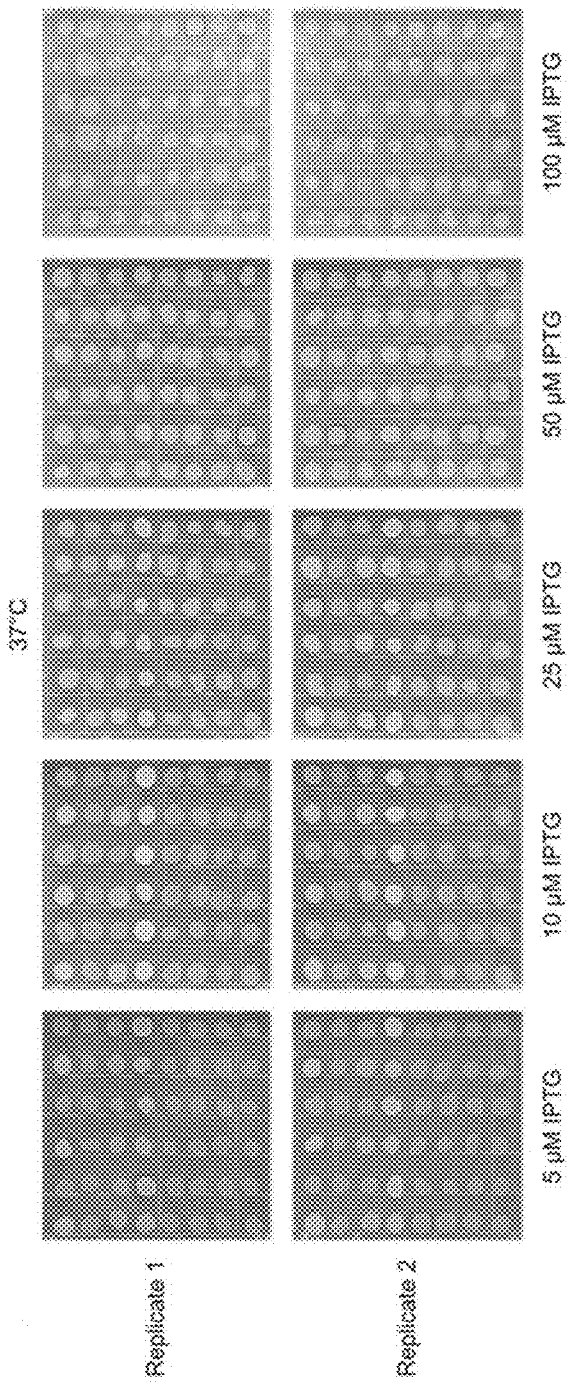
Figure 13A:
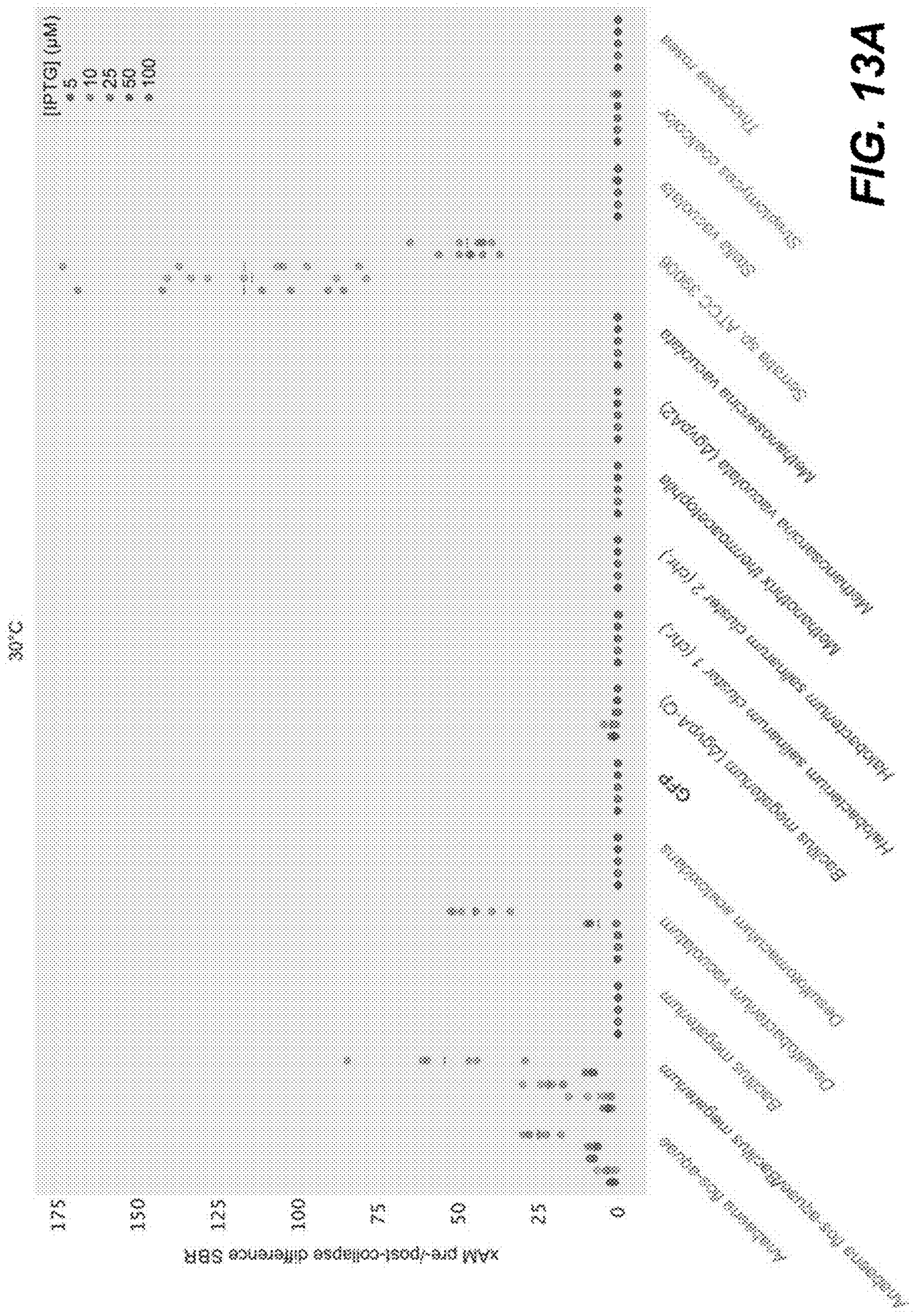
Figure 13B:
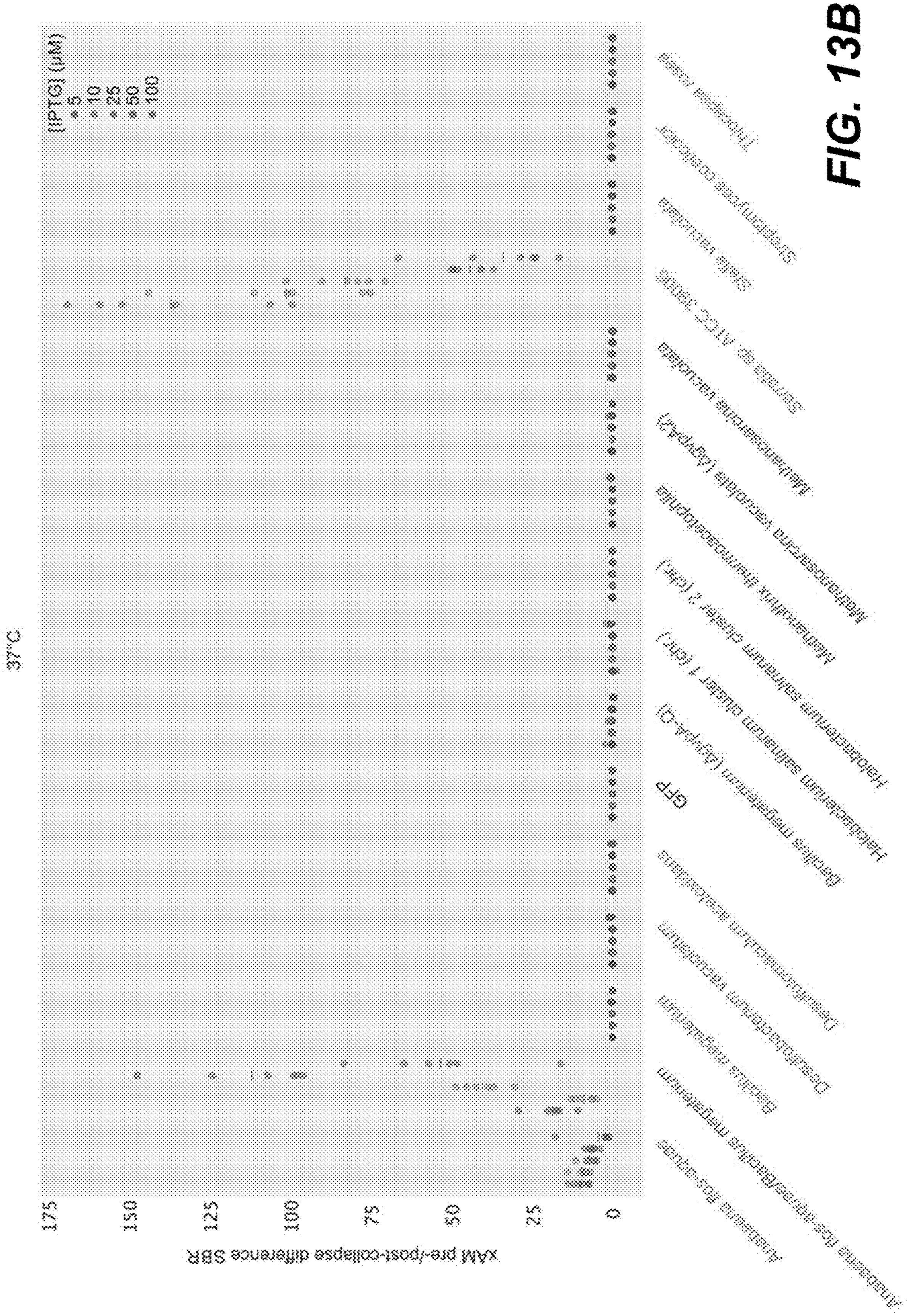

FIGS. 10A-10D depict data related to optimization of expression conditions for all tested clusters in BL21(DE3) *E. coli*. (FIGS. 10A-10B) xAM images of bacterial patches expressing each GV cluster at varying inducer concentrations and temperatures. Green boxes indicate the patches shown in FIG. 9A. The IPTG concentration selected was the one that resulted in the highest xAM pre-minus-post-collapse difference signal (FIGS. 13A-13B) while not creating toxicity, as determined by whether the patch was uniform or punctate (FIGS. 12A-12B). Some of the IPTG concentrations that led to toxicity also created significant xAM signal, but this signal did not originate from GVs, as indicated by the lack of xAM pre-minus-post-collapse signal difference (FIGS. 13A-13B). Further, there were some IPTG concentrations for certain genotypes that created significant xAM signal but no xAM pre-minus-post-collapse signal difference, and no visible toxicity (e.g., *Streptomyces coelicolor, Thiocapsa rosea*, and GFP at 37° C., 100 μM IPTG). This discrepancy was likely caused by subtle toxicity that is not apparent in optical images, but altered the texture of the patch enough to be detectable by US. (FIG. 10C) Key for genotypes tested in (FIGS. 10A-10B), with this pattern repeated in three pairs of columns replicated on each plate.

(FIG. 10D) Examples of the effects of toxic genotypes on bacterial patches, and of artifacts that can appear in bacterial patch scan images. Bacteria themselves can produce significant xAM signal (especially when present in extremely high concentrations, as they are in the confluent patches imaged here), which can be seen in the forms of rings around all patches, regardless of GV expression status. Further, expression of toxic proteins (or of large amounts of otherwise non-toxic proteins, such as GFP) can interfere with bacterial growth; in extreme cases this results in significant cell death and a punctate appearance, and in less extreme cases it simply reduces the optical density of patches. GV expression can increase the optical density of patches, but only at high levels of GV expression. Punctate patches produce considerably more xAM signal than uniform ones, even in the absence of GV expression. The xAM pre-minus-post-collapse difference can be used to qualitatively determine if a patch produces GVs, but because collapse is incomplete in some cases, it is not an ideal method for quantitatively comparing genotypes.

Figure 10A:
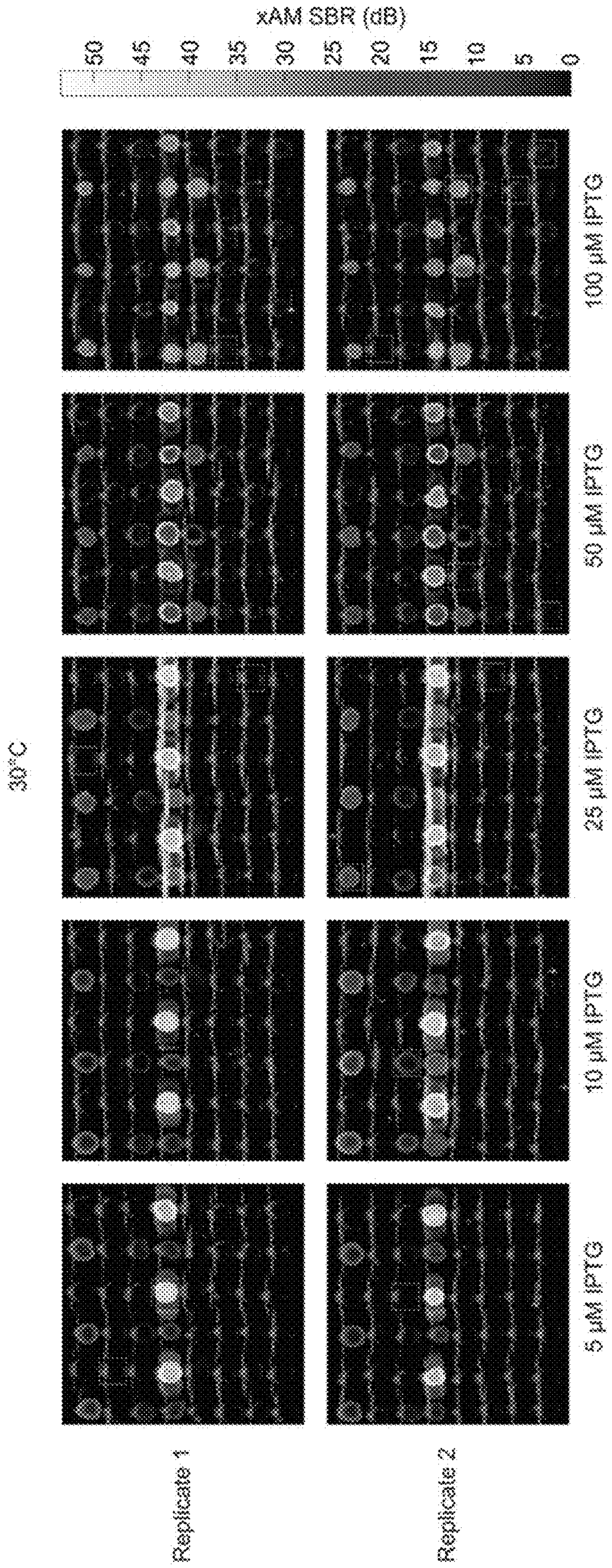
Figure 10B:
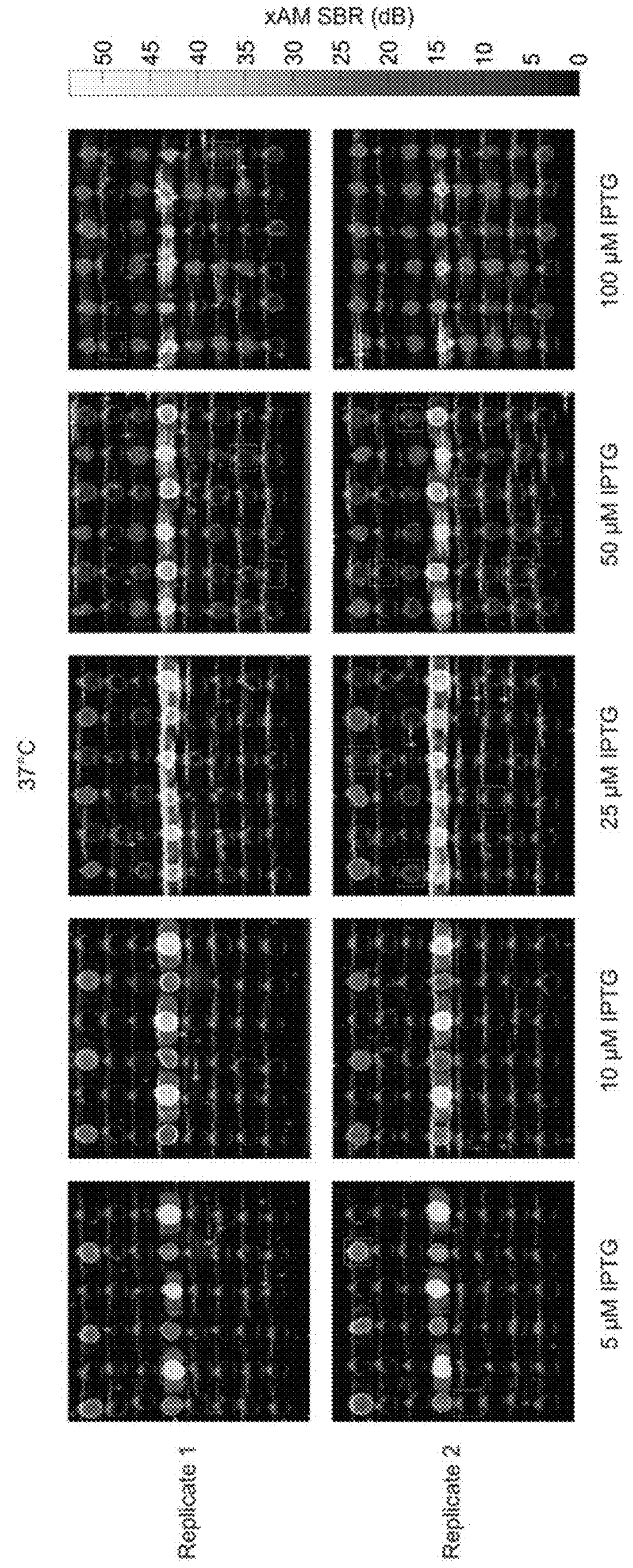
Figure 10C:
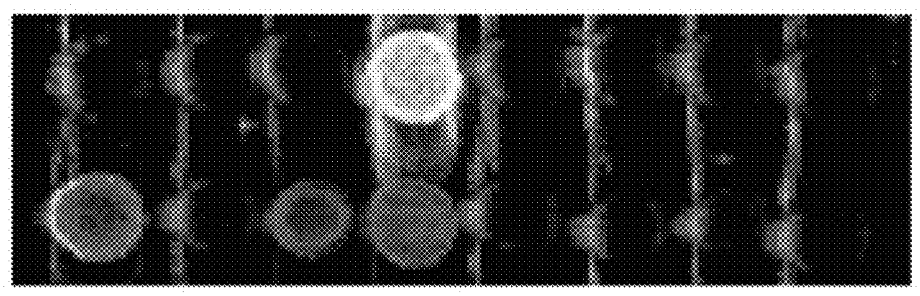
Figure 11A:
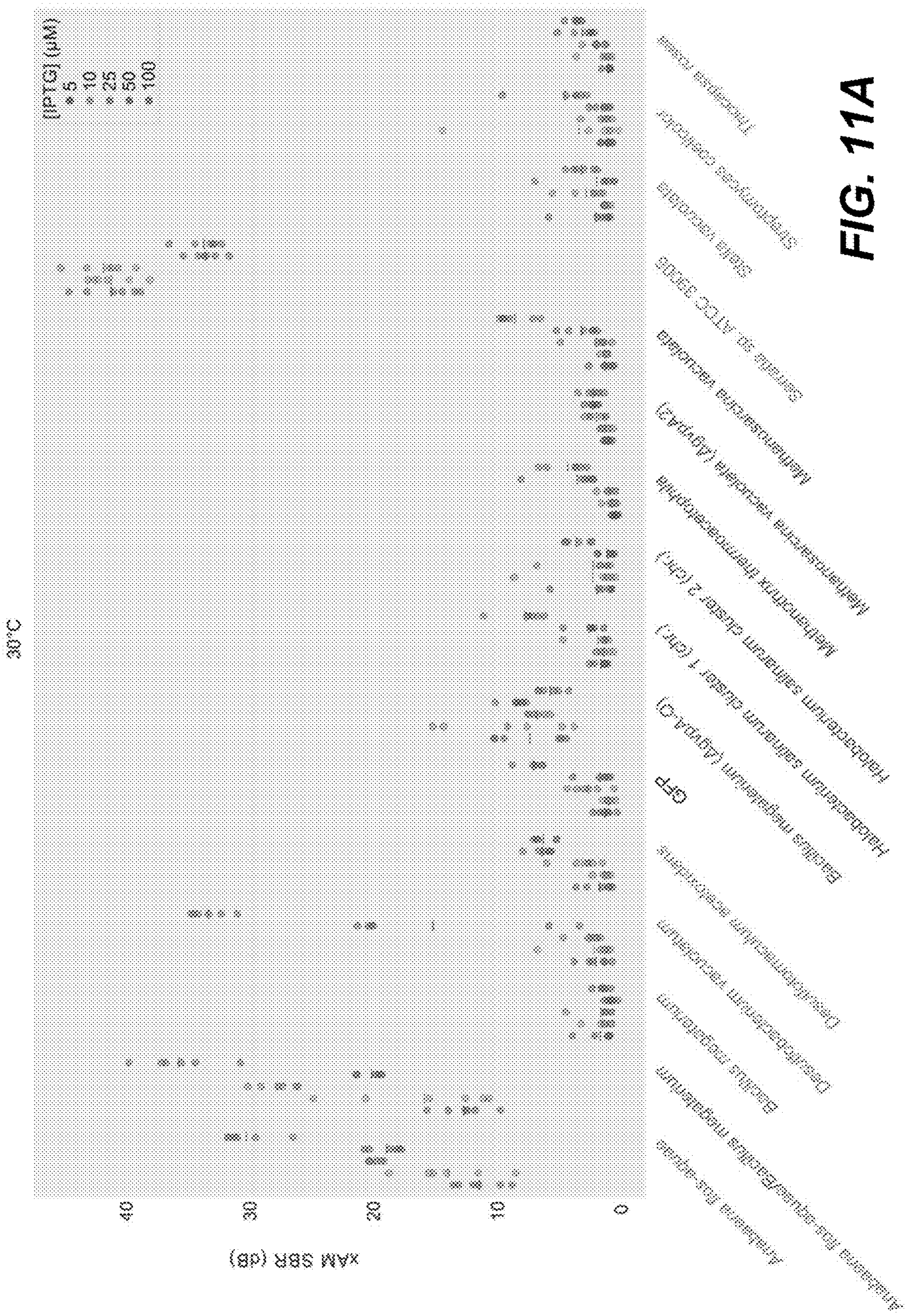
Figure 11B:
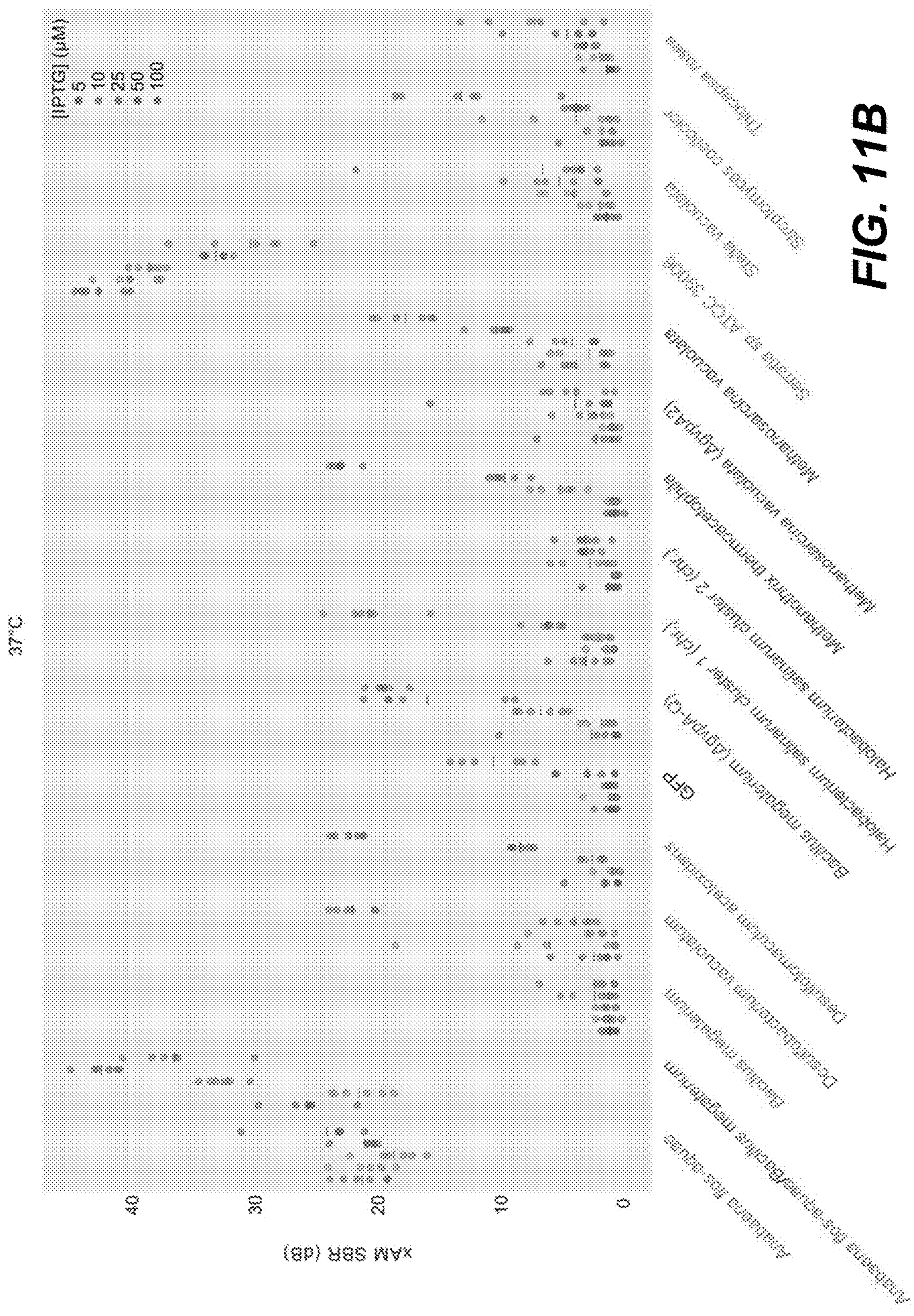

FIGS. 11A-11B depict data related to quantification of ultrasound signal for all samples shown in FIGS. 10A-10B. (FIGS. 11A-11B) xAM SBR of the patches at 30° C. (FIG. 11A) and 37° C. (FIG. 11B) shown in FIGS. 10A-10B (n=6; lines represent the mean).

FIGS. 12A-12D depict data related to optical and xAM pre-minus-post-collapse difference images of all samples shown in FIGS. 10A-10D. (FIGS. 12A-12B) Optical images of patches at 30° C. (FIG. 12A) and 37° C. (FIG. 12B) shown in FIGS. 10A-10B. (FIGS. 12C-12D) xAM pre-minus-post-collapse difference patches of samples at 30° C. (FIG. 12A) and 37° C. (FIG. 12B) shown in FIGS. 10A-10B. Red boxes indicate the patches shown in FIGS. 9B-9C.

Figure 12C:
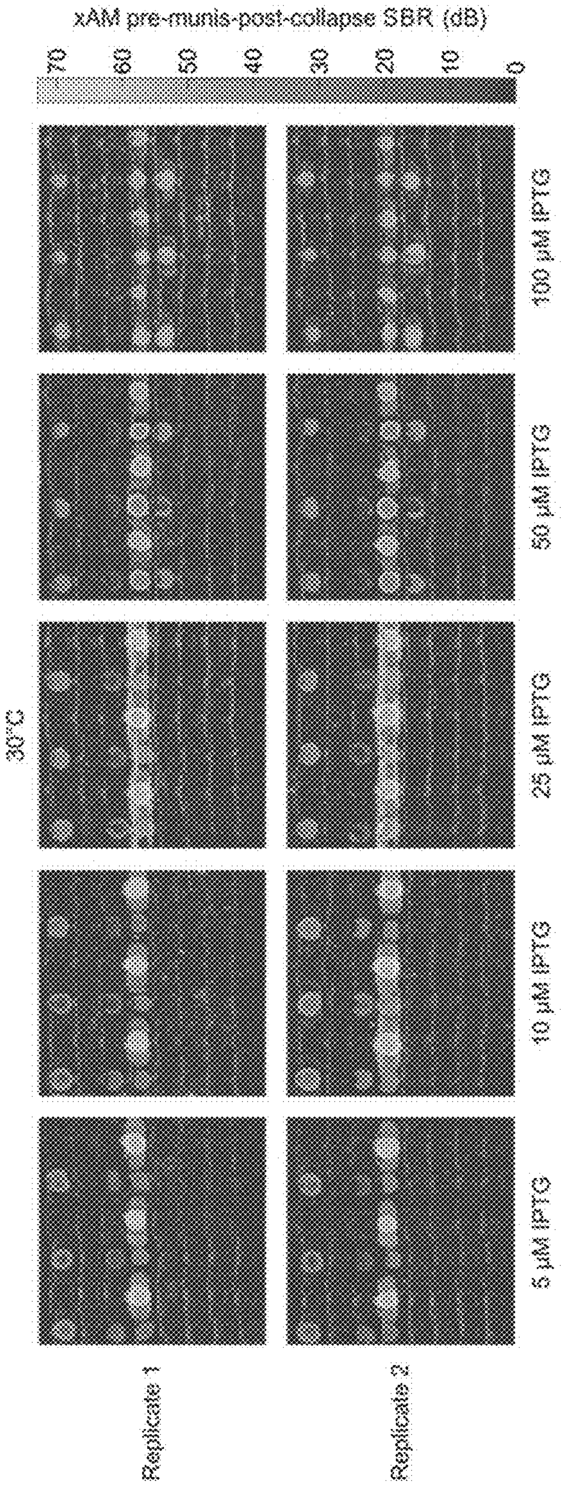
Figure 12D:
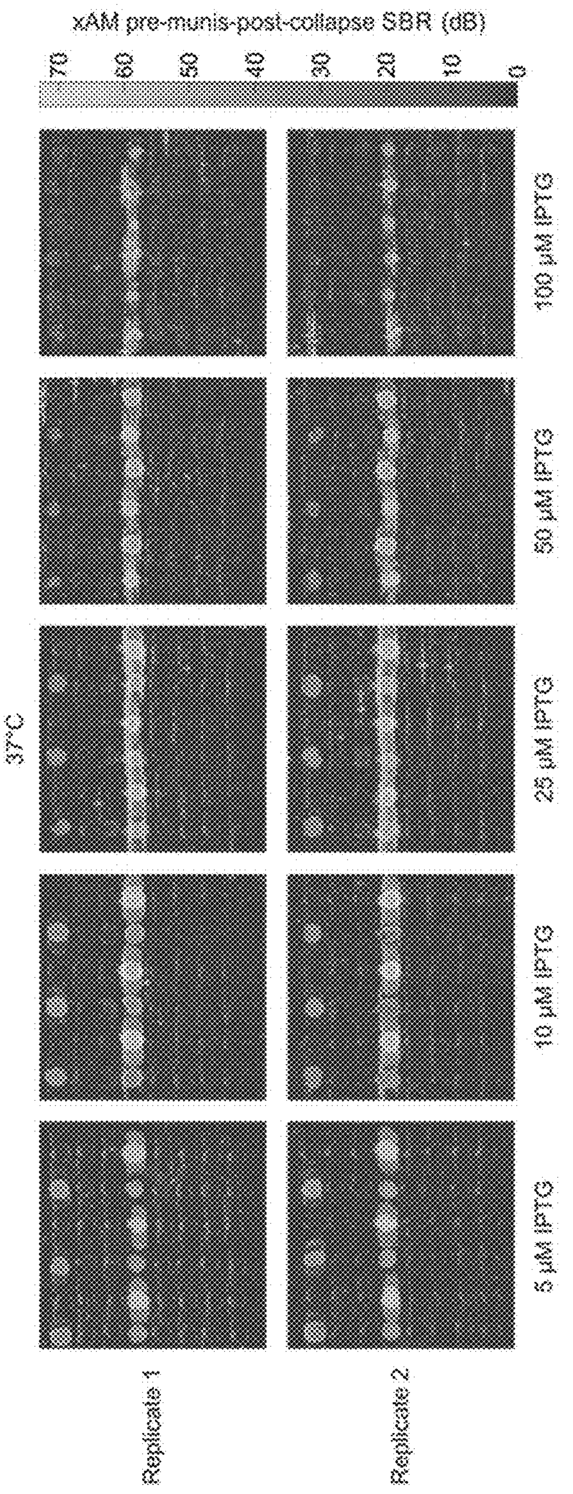

FIGS. 13A-13B depict data related to quantification of ultrasound signal for samples shown in FIGS. 12C-12D. (FIGS. 13A-13B) xAM SBR for the patches at 30° C. (FIG. 13A) and 37° C. (FIG. 13B) shown in FIGS. 12C-12D (n=6; lines represent the mean).

Figure 14B:
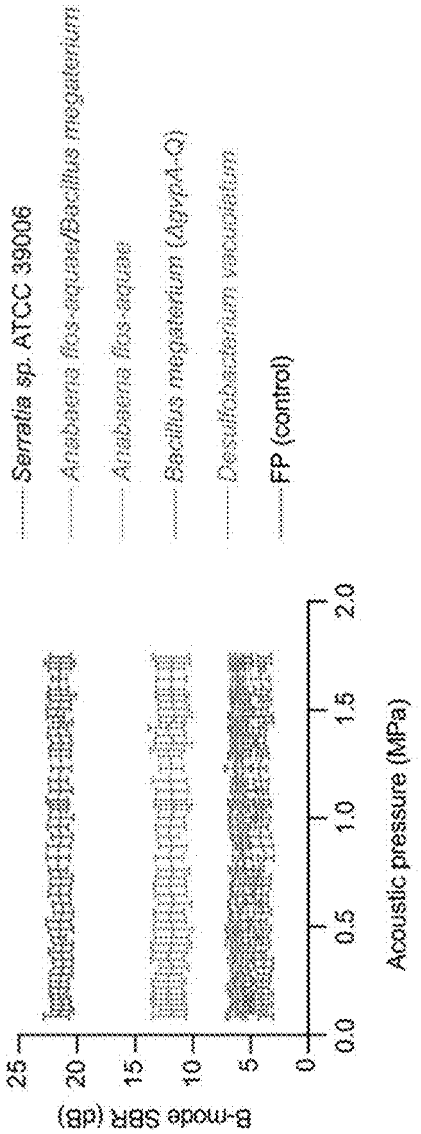
Figure 14A:
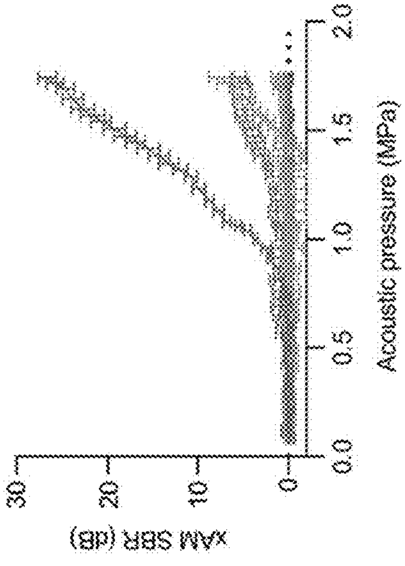
Figure 14C:
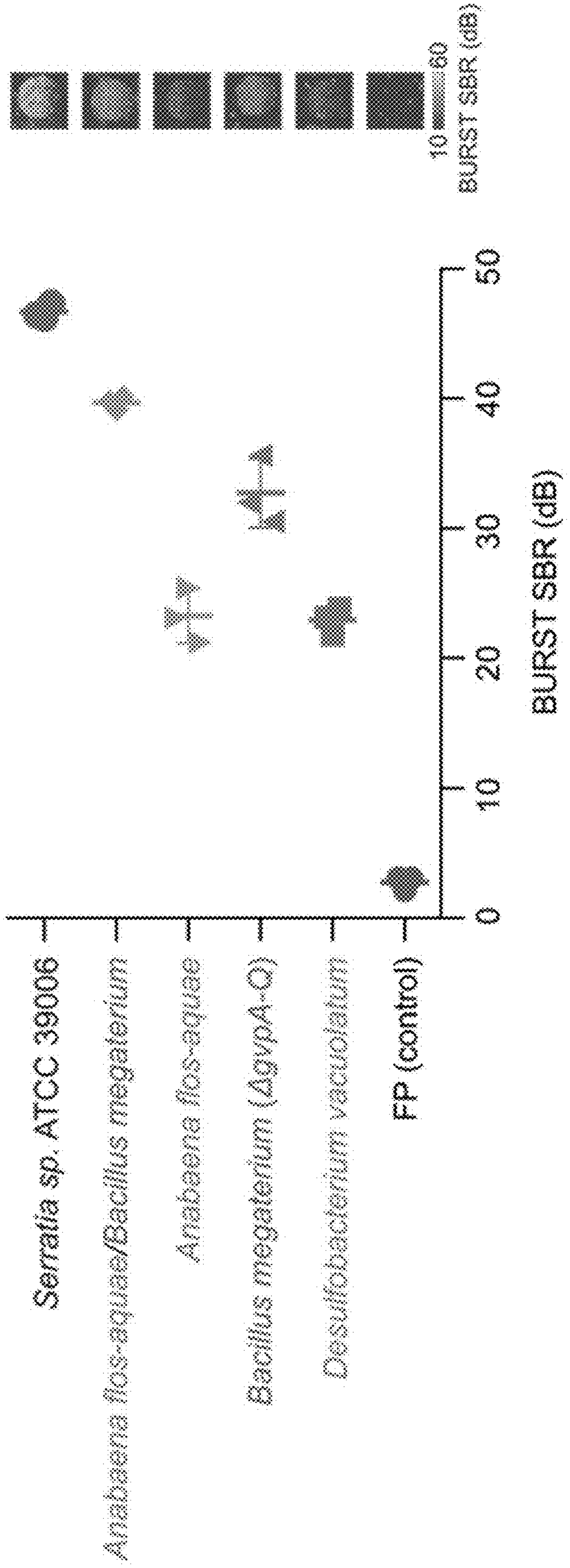
Figure 14D:
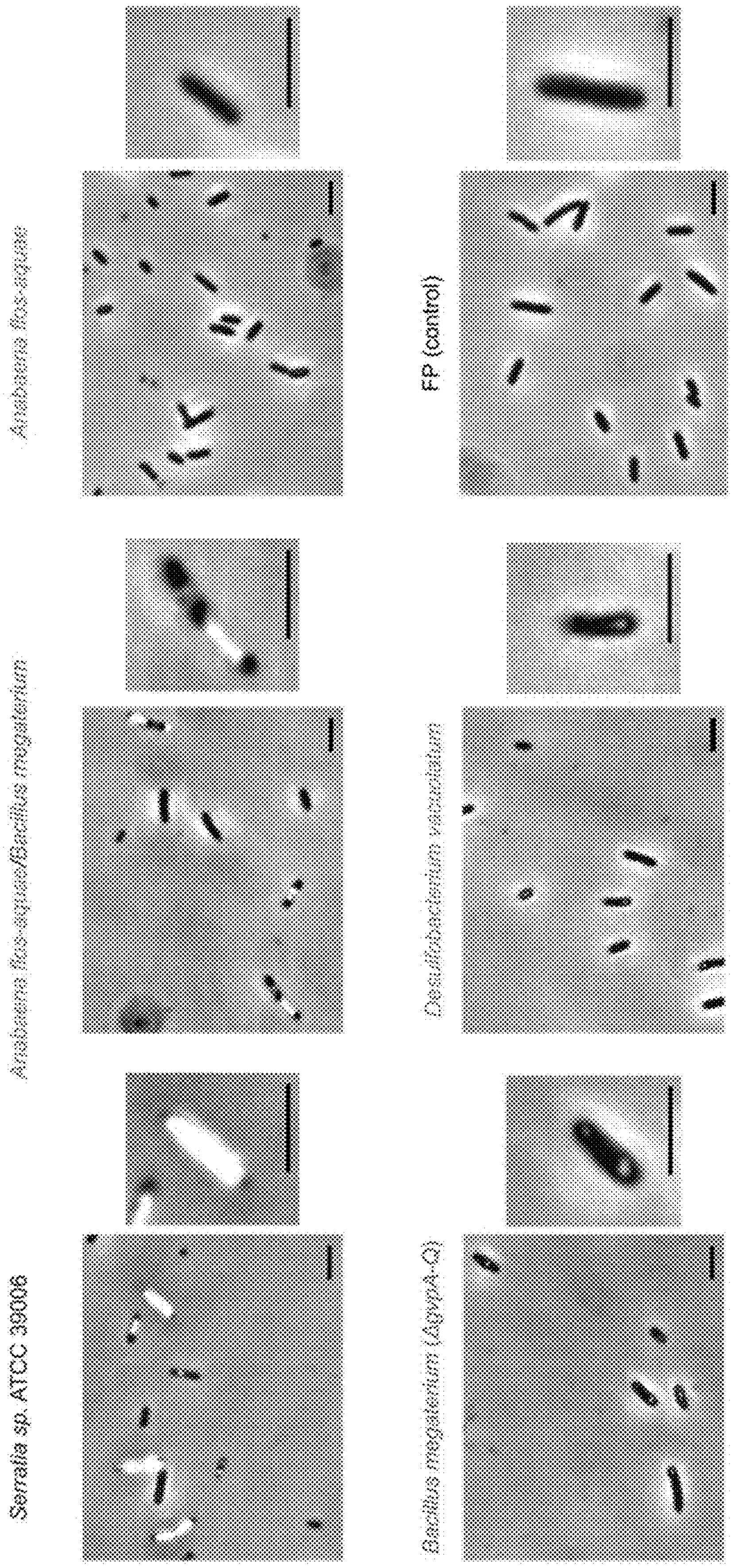

FIGS. 14A-14E depict data related to characterization of working GV clusters in BL21(DE3) *E. coli*. (FIGS. 14A-14D) xAM signal-to-background ratio (SBR) as a function of acoustic pressure (FIG. 14A), B-mode SBR at a constant pressure of 0.15 MPa after each increase in acoustic pressure in a (FIG. 14B), BURST SBRs and corresponding representative images (FIG. 14C), and representative phase contrast microscopy (PCM) images (FIG. 14D) of the working GV clusters expressed in BL21(DE3) *E. coli* at 30° C. on solid media. For ultrasound imaging (FIGS. 14A-14C), samples were normalized to $5\times10^{9}$ cells/mL in agarose phantoms. Curves and error bars represent the mean (n=3 biological replicates each with 2 technical replicates)±SD. (FIGS. 14A-14B) have the same legend. GV clusters in cells are visible by PCM for all clusters except for the cluster from *Anabaena flos-aquae* and the fluorescent protein (FP) control (FIG. 14D). (FIG. 14E) Representative TEM images of BL21(DE3) *E. coli* cells expressing *Serratia* GVs at varying levels of expression. Scale bars are 5 m in FIG. 14D and 500 nm in FIG. 14E.

FIGS. 15A-15F depict data related to effects of single-gene deletions on GV expression by the *Serratia* cluster. (FIG. 15A) Key for genotypes tested, repeated in 6 replicate columns on each plate. (FIGS. 15B-15D) xAM images (FIG. 15B), pre-minus-post-collapse xAM images (FIG. 15C), and optical images (FIG. 15D) of bacterial patches expressing single-gene deletions of the *Serratia* cluster. (FIGS. 15E-15F) Quantification of the xAM images (FIG. 15E) and pre-minus-post-collapse xAM images (FIG. 15F) shown in FIGS. 15B-15C (n=12).

Figure 16A:
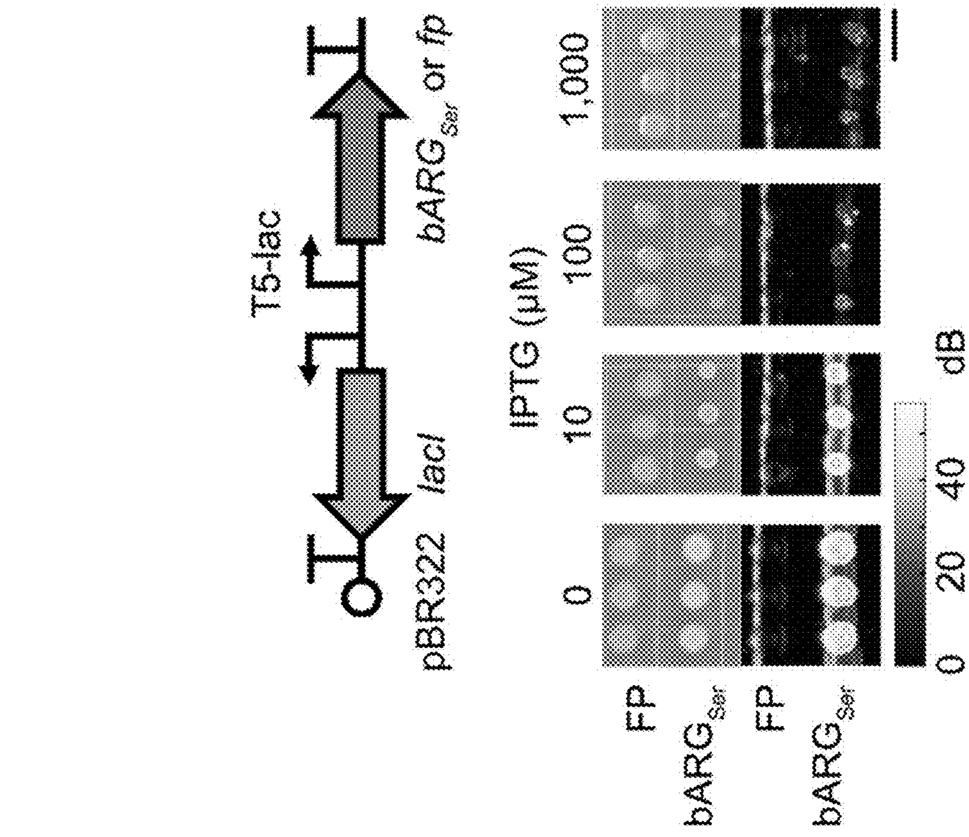
Figure 16B:
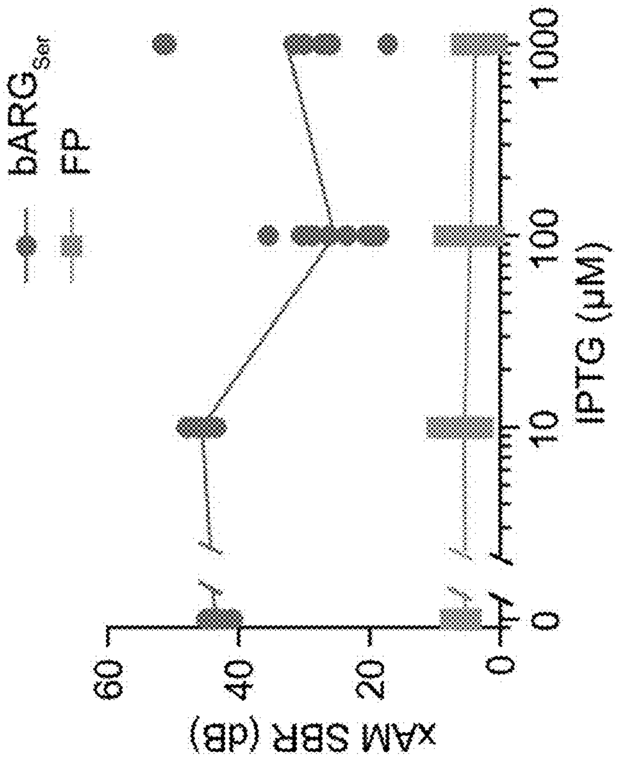
Figure 16C:
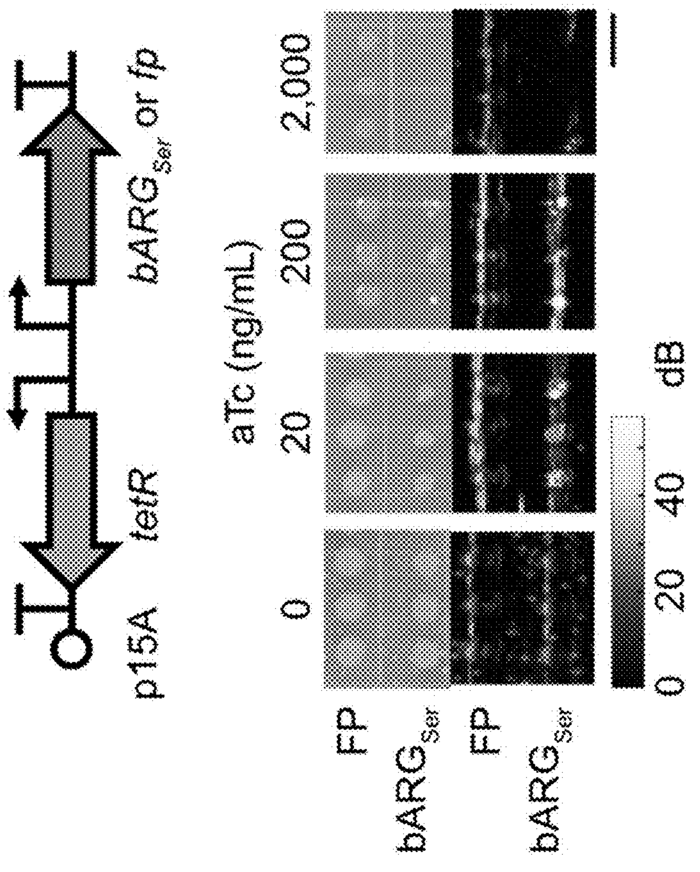
Figure 16D:
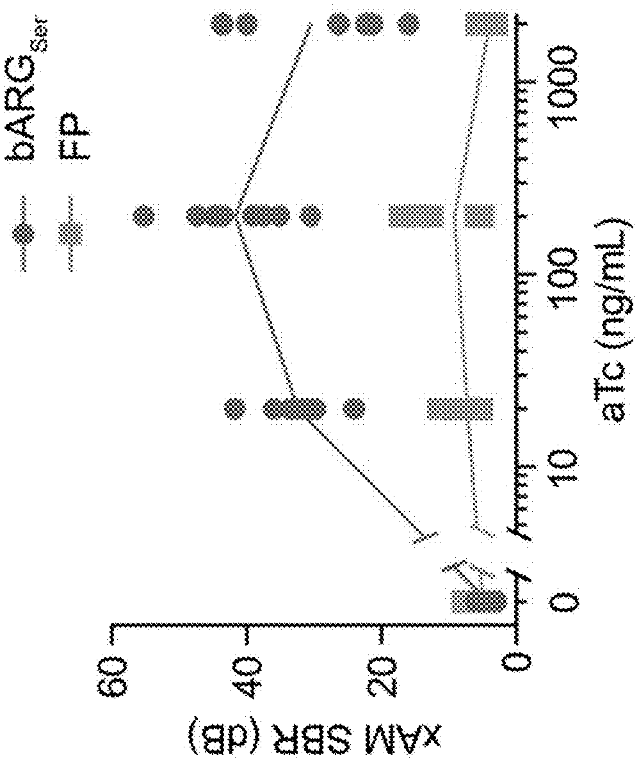

FIGS. 16A-16D depict non-limiting exemplary schematics and data related to testing $bARG_{Ser}$ expression in EcN with IPTG- and aTc-inducible gene circuits. (FIG. 16A) Diagram of the IPTG-inducible construct used to express $bARG_{Ser}$ in EcN (top), and representative optical and xAM images of $bARG_{Ser}$-expressing or fluorescent protein (FP)-expressing patches of EcN on solid media with varying IPTG concentrations at 37° C. (bottom). (FIG. 16B) Quantification of the xAM SBR of all patches from the experiment in (a) (n=8; curves represent the mean). (FIGS. 16C-16D) Same as in FIGS. 16A-16B but for the aTc-inducible construct. The scale bars in FIG. 16A, FIG. 16C represent 1 cm.

Figure 17A:
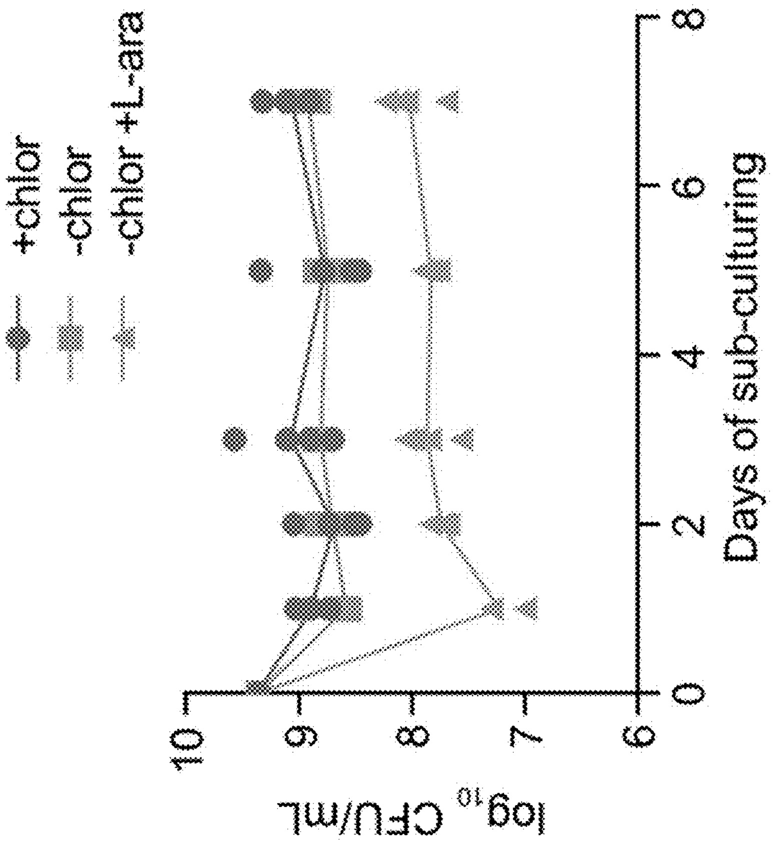
Figure 17B:
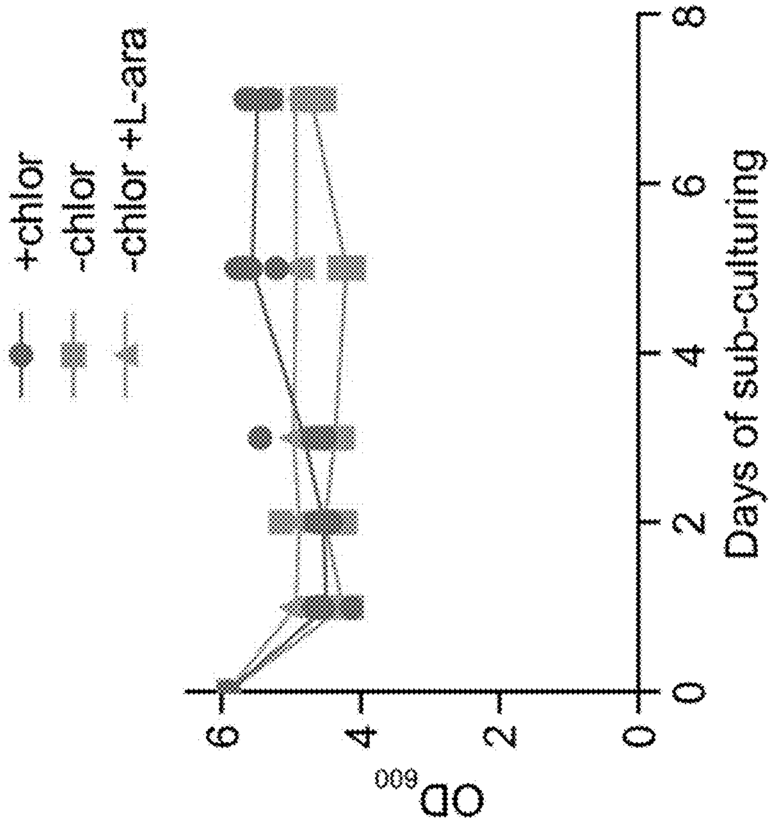

FIGS. 17A-17B depict data related to effect of induction on viability and $OD_{600}$ for $bARG_{Ser}$-expressing EcN in liquid culture. (FIGS. 17A-17B) Colony forming units (CFU) per mL of culture (FIG. 17A) and optical density at 600 nm (FIG. 17B) during daily sub-culturing into LB media with 25 μg/mL chloramphenicol (+chlor), without chloramphenicol (−chlor), or without chloramphenicol and with 0.1% (w/v) L-arabinose (−chlor +L-ara) using pBAD-$bARG_{Ser}$-AxeTxe EcN. Curves represent the mean of n=4 biological replicates.

Figures 18A, 18B:
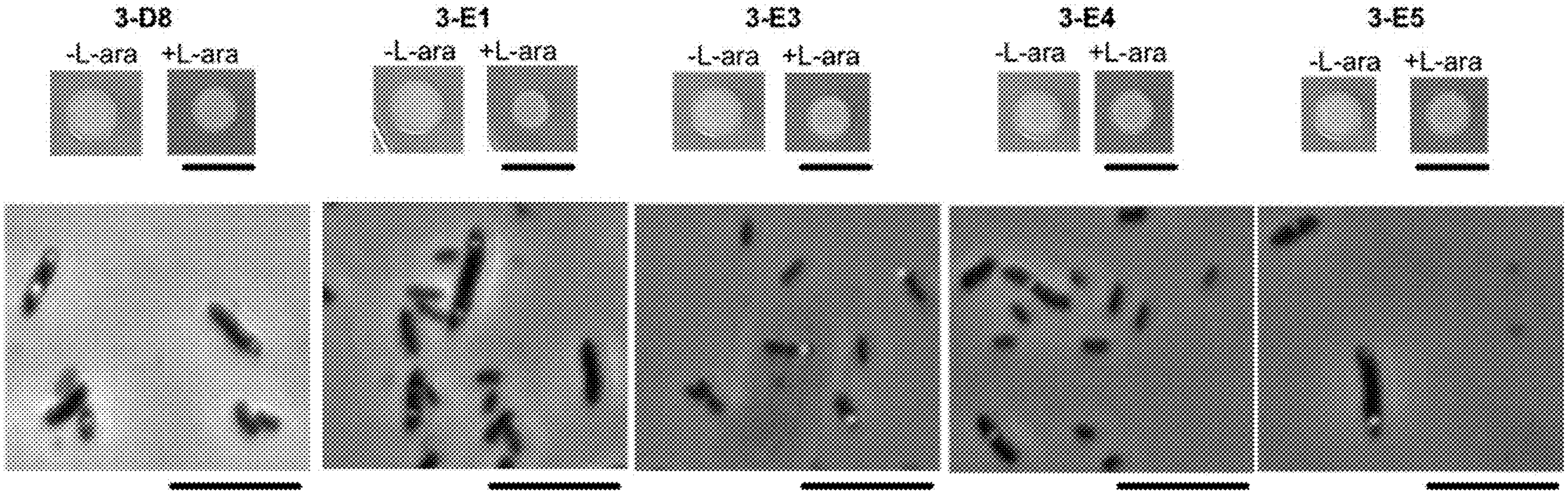
Figure 18B:
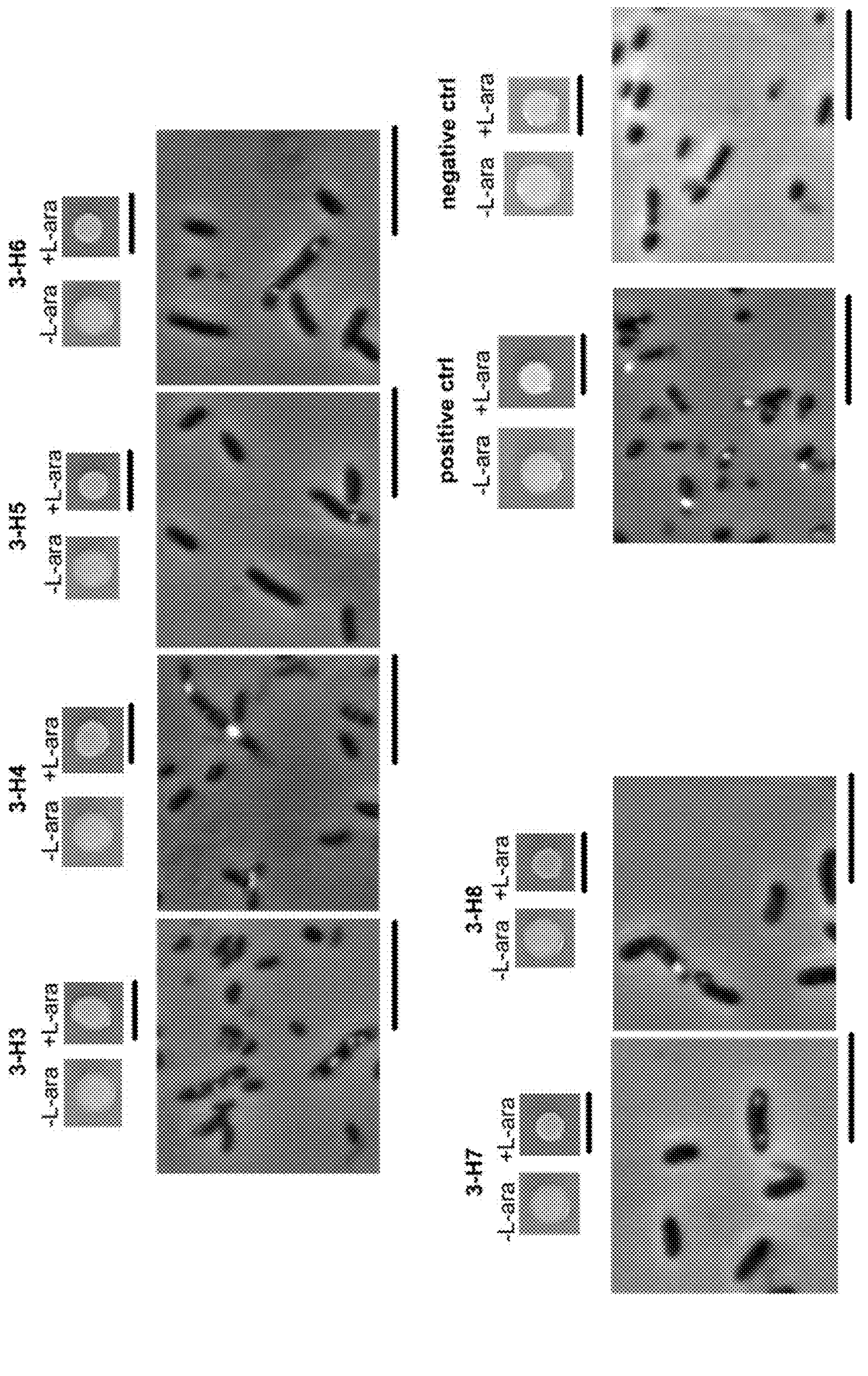

FIGS. 18A-18B depict data related to quantification and characterization of EcN mutants deficient in $bARG_{Ser}$ expression isolated from daily subculturing in vitro. (FIG. 18A) Numbers of non-white mutant colonies and total colonies screened on plates with 0.1% (w/v) L-arabinose from daily sub-culturing into LB media with 25 μg/mL chloramphenicol (+chlor), without chloramphenicol (−chlor), or without chloramphenicol and with 0.1% (w/v) L-arabinose (−chlor +L-ara) using pBAD-$bARG_{Ser}$-AxeTxe EcN. Cultures where mutants were found are indicated in red. (FIG. 18B) Optical images of patches (top rows) on fresh plates with 0.1% (w/v) L-arabinose (+L-ara) and without L-arabinose (−L-ara), and phase contrast microscopy images (bottom rows) from the 11 mutant colonies in FIG. 18A. Mutants 3-D3 and 3-E1 were from the culture −chlor +ara, replicate #2, day 3; mutants 3-E3, 3-E4, and 3-E5 were from the culture −chlor +ara, replicate #3, day 3; and mutants 3-H3 through 3-H8 were from the culture −chlor +ara, replicate #3, day 5. The positive and negative controls were wild-type pBAD-$bARG_{Ser}$-AxeTxe EcN and pBAD-FP-AxeTxe EcN, respectively. Scale bars are 1 cm for images of patches and 10 m for microscopy images.

Figure 19B:
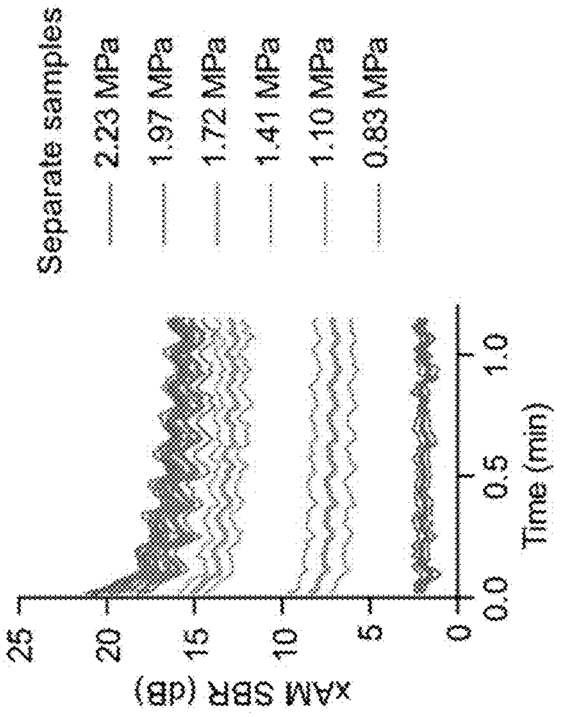
Figure 19A:
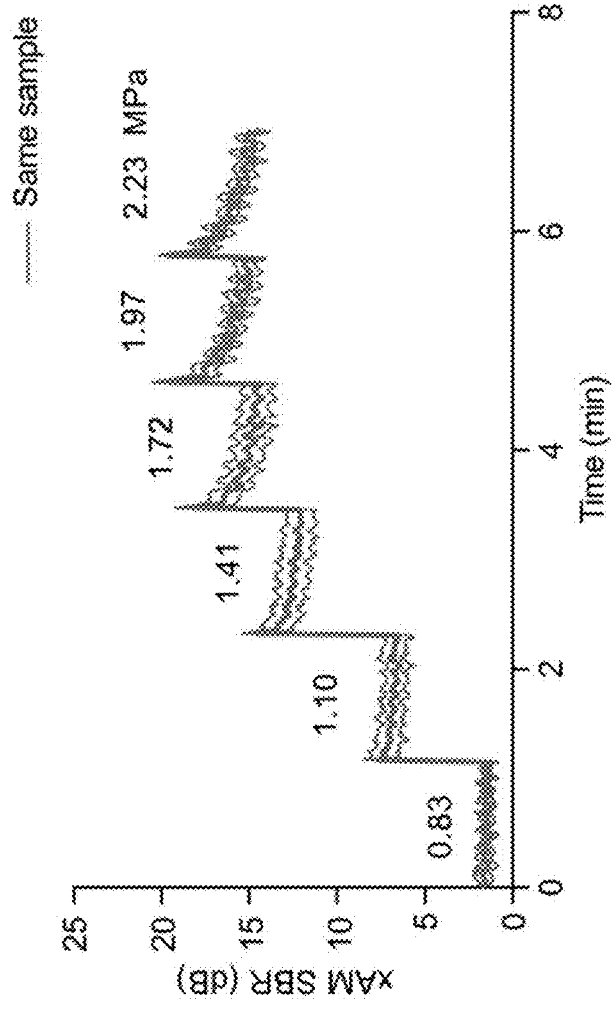
Figure 19C:
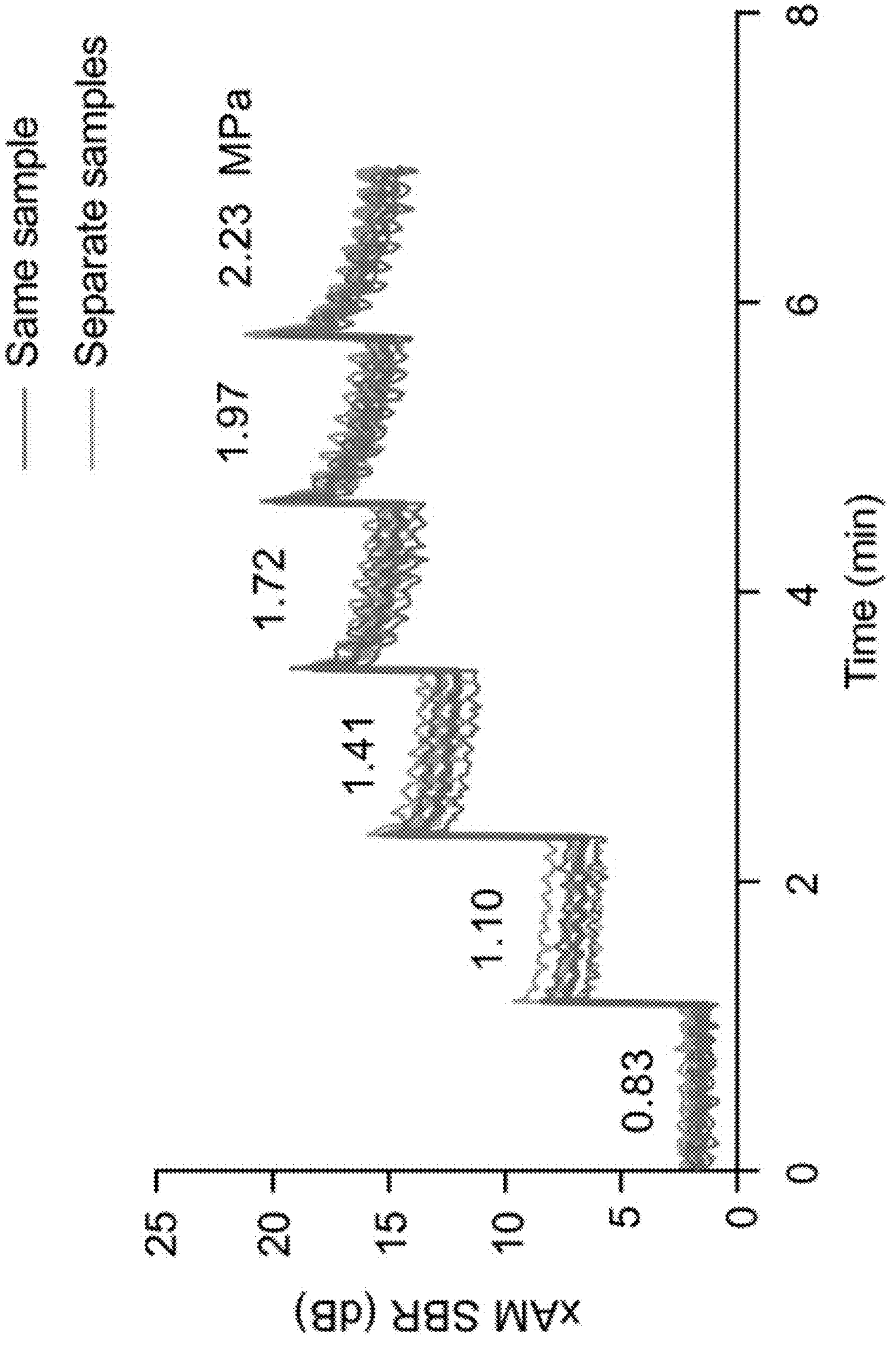

FIGS. 19A-19C depict data related to xAM ultrasound signal versus time at varying acoustic pressures applied sequentially to the same sample versus separate samples. (FIGS. 19A-19B) xAM SBR of $bARG_{Ser}$-expressing EcN measured over time at various acoustic pressures. In FIG. 19A, samples were subjected sequentially to 6 increasing acoustic pressures for approximately 70 sec each, whereas in FIG. 19B separate samples subjected to only one acoustic pressure for approximately 70 sec. (FIG. 19C) Overlay of xAM SBR curves for separate samples from FIG. 19B onto the curves for samples subjected to all pressures from FIG. 19A. There is no difference between these curves, indicating that the xAM SBR measured at a certain pressure was not significantly affected by collapse at a previously applied pressure. For FIGS. 19A-19C, pBAD-$bARG_{Ser}$-AxeTxe EcN were induced with 0.1% (w/v) L-arabinose for 24 hours at 37° C. in liquid culture, and were then normalized to $10^{9}$ cells/mL in agarose phantoms for ultrasound imaging. Bold lines represent the mean and thin lines represent±standard deviation; n=3 biological replicates, each with 2 technical replicates. Imaging was performed with an L22-v14X transducer, so the values for pressure and xAM SBR do not exactly match those in FIGS. 10A-10C where an L22-v14 transducer was used.

Figure 20A:
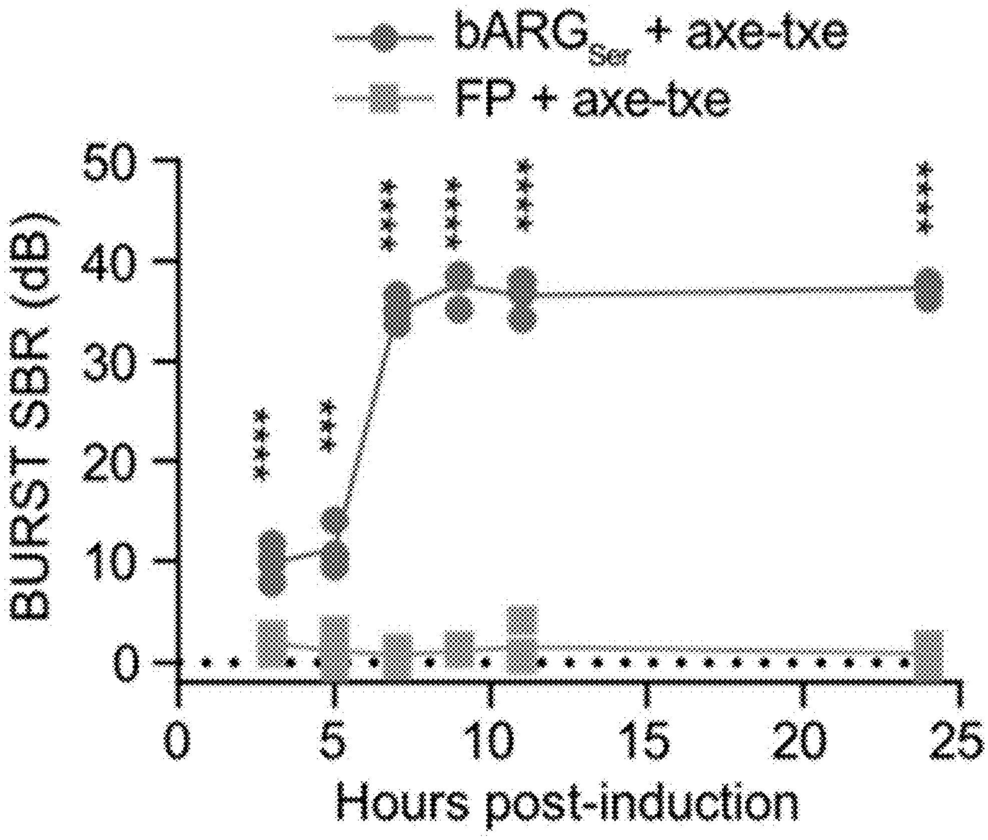
Figure 20B:
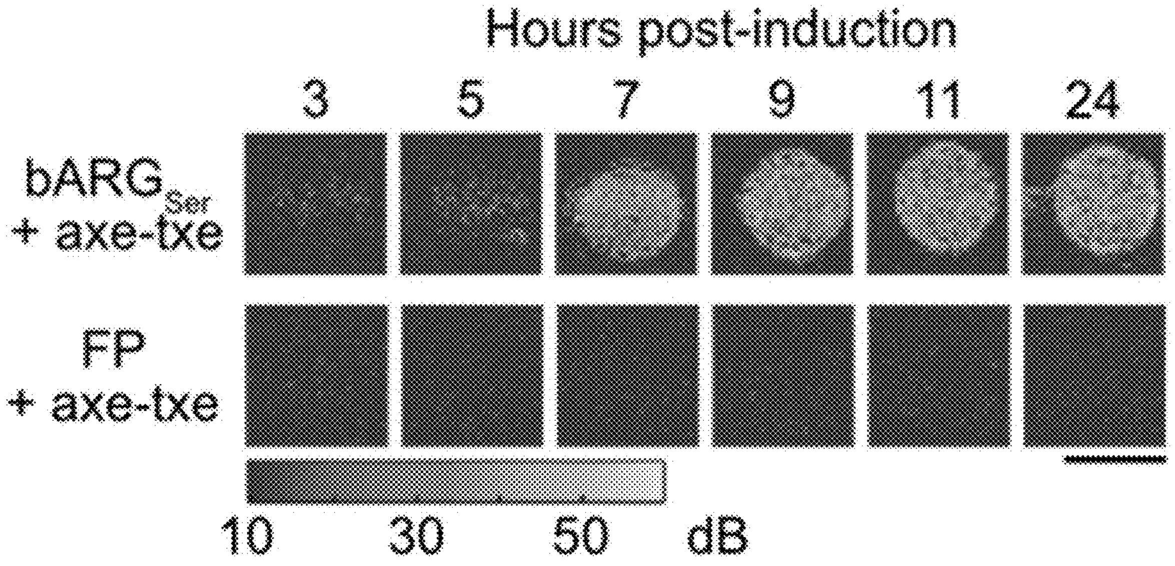
Figure 20C:
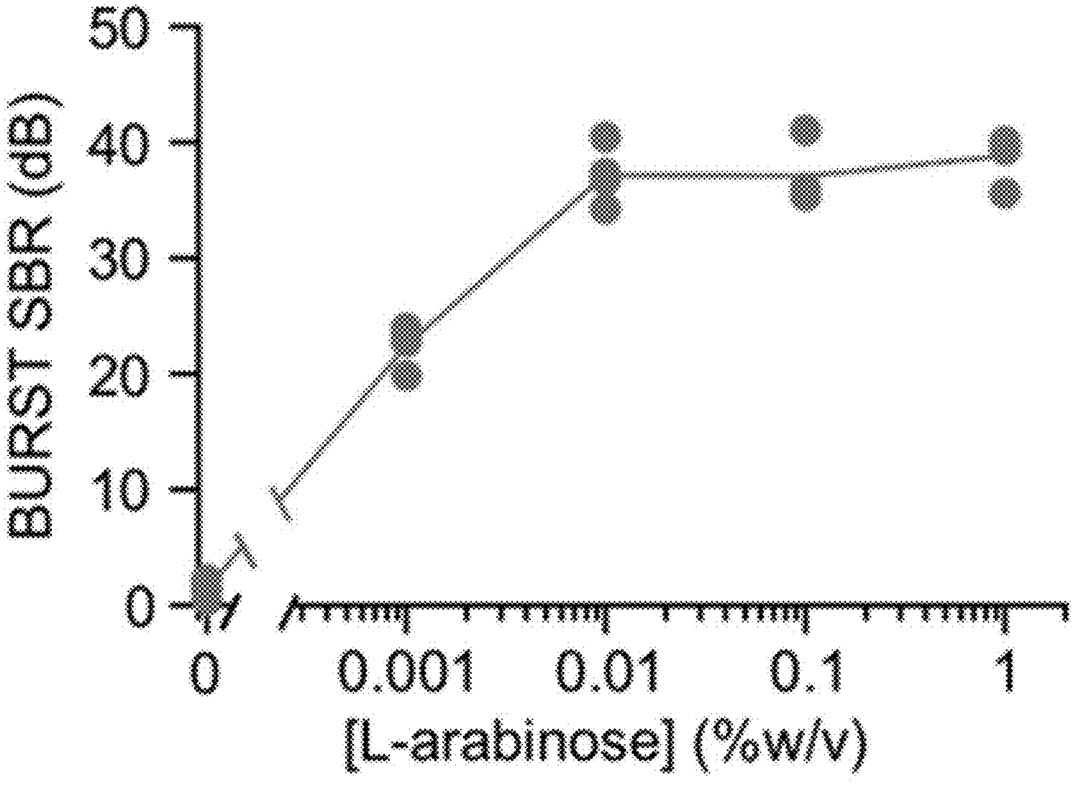
Figure 20D:
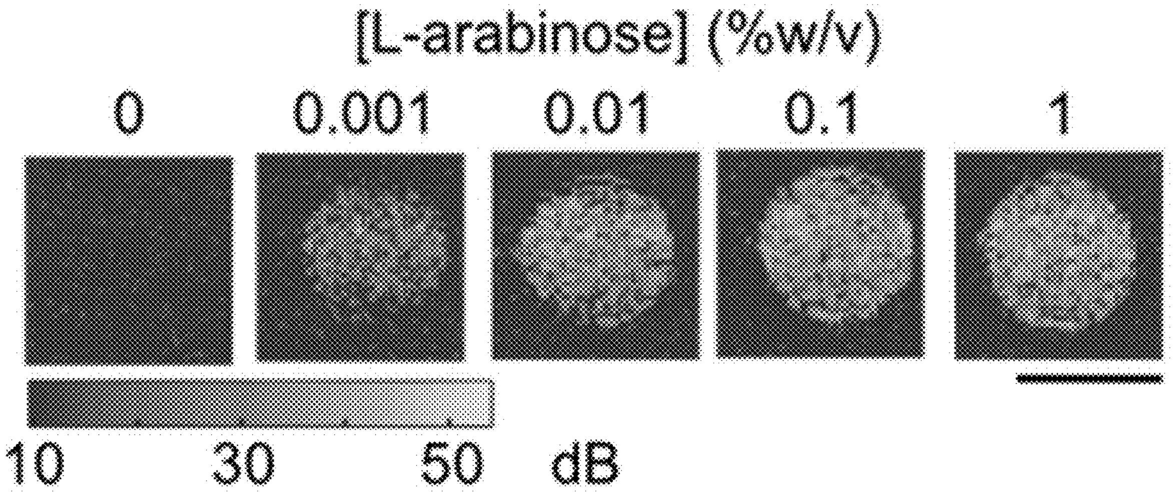
Figure 20E:
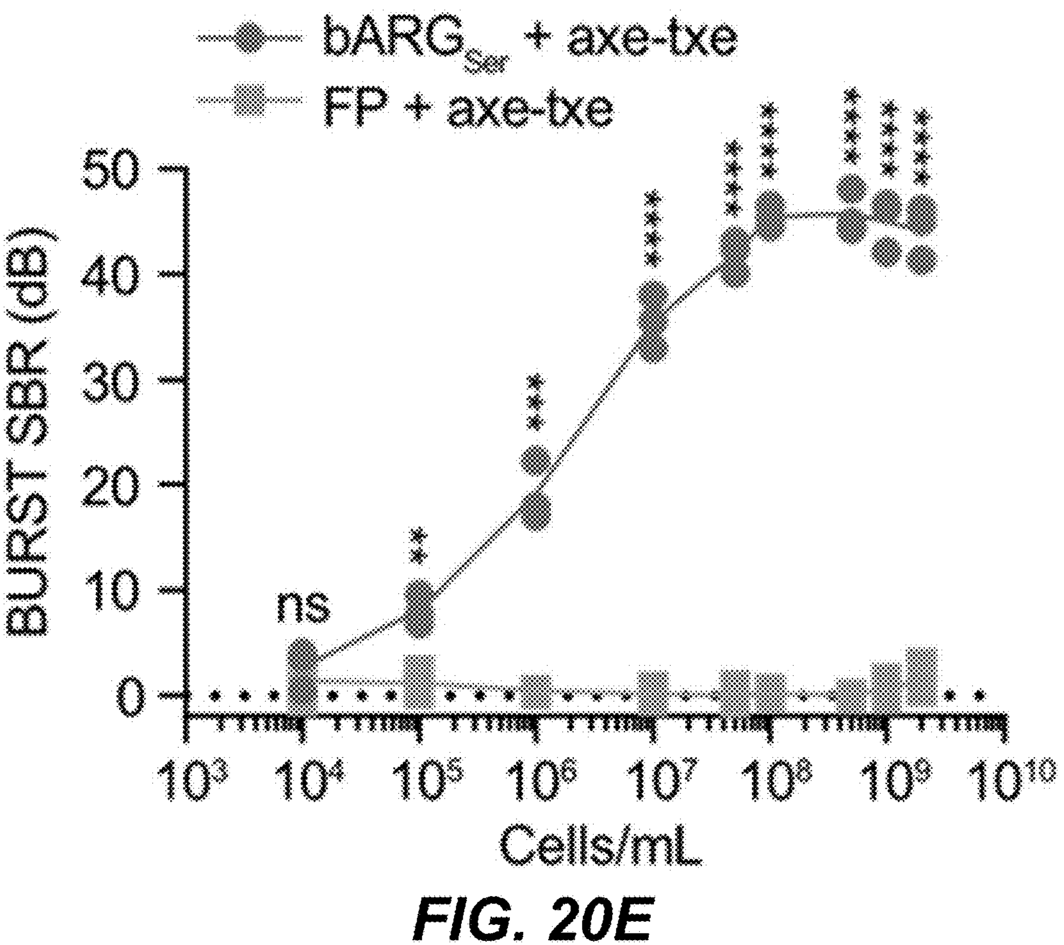
Figure 20F:
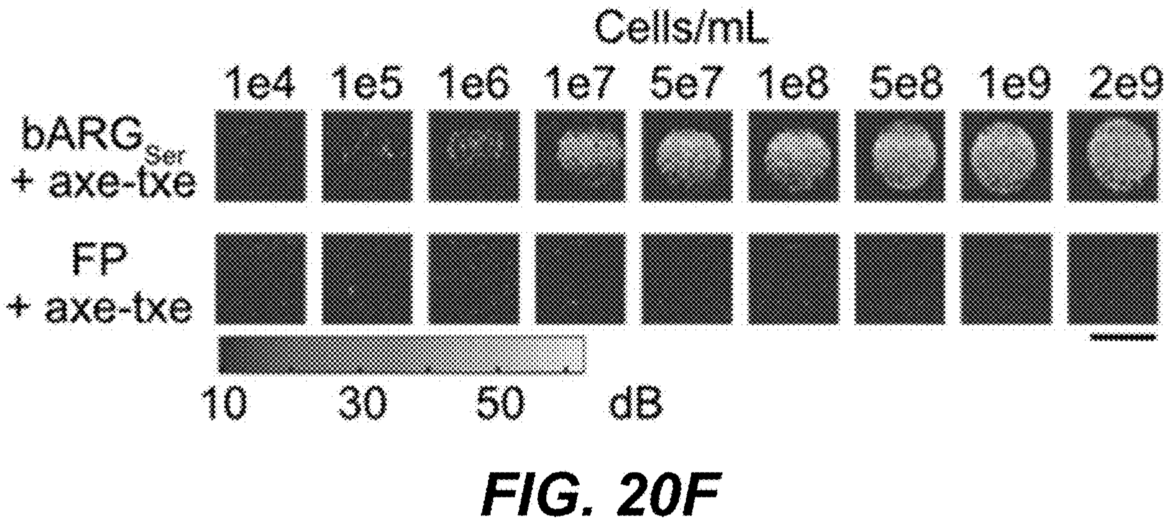
Figure 21G:
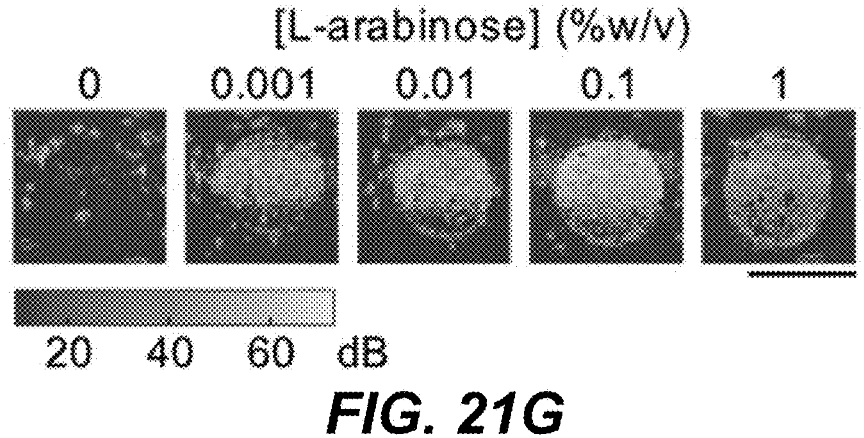
Figure 21H:
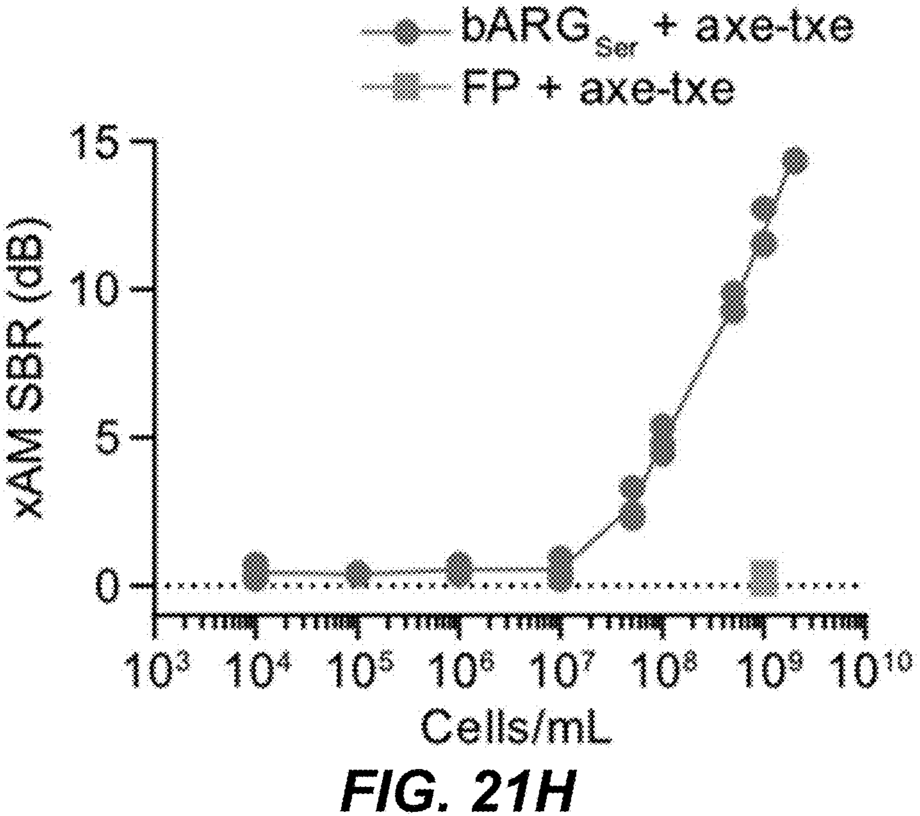
Figure 21I:
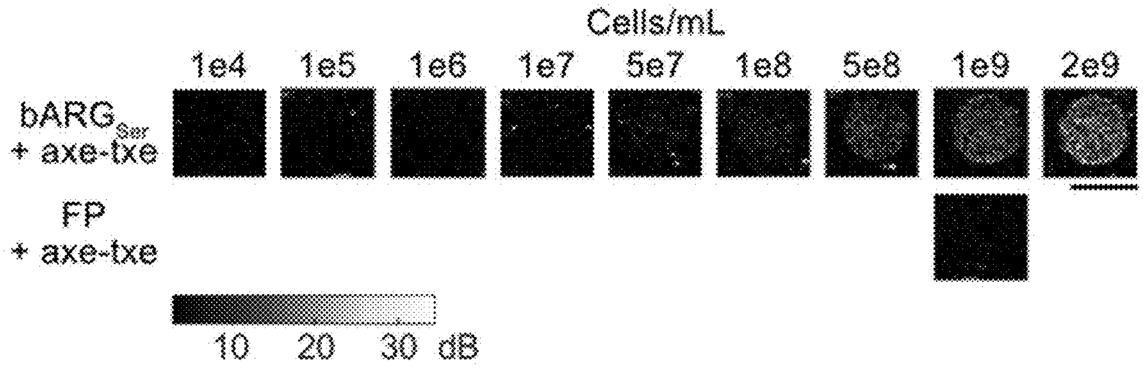
Figure 21J:
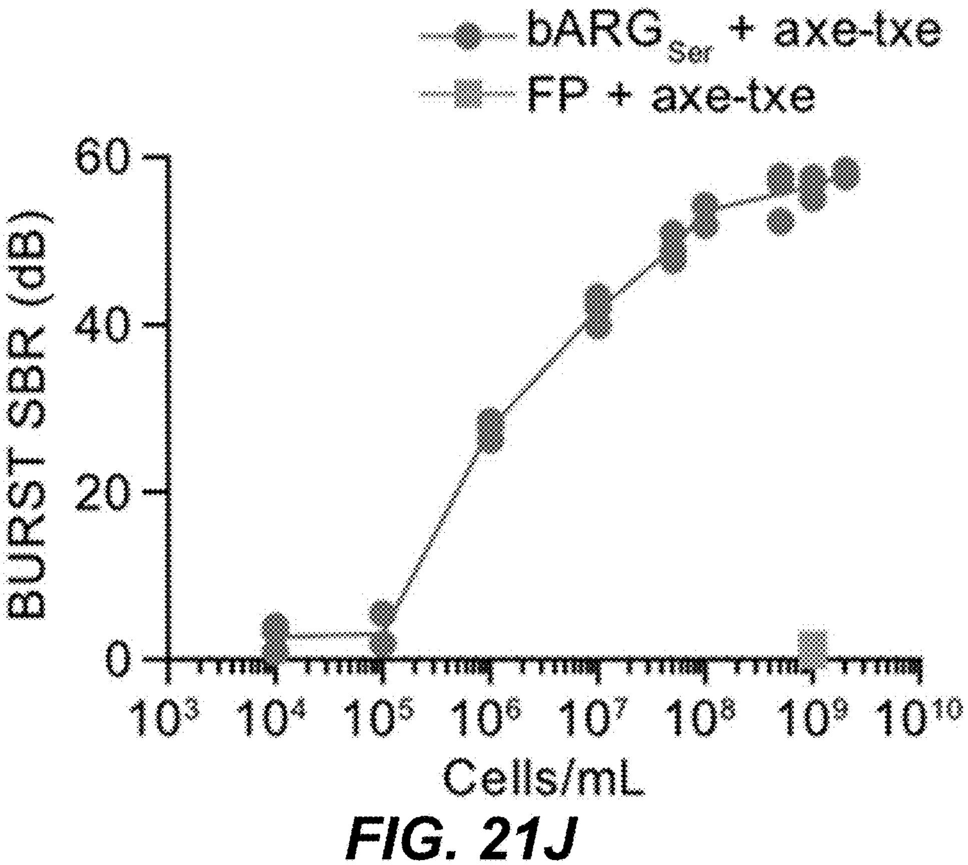
Figure 21K:
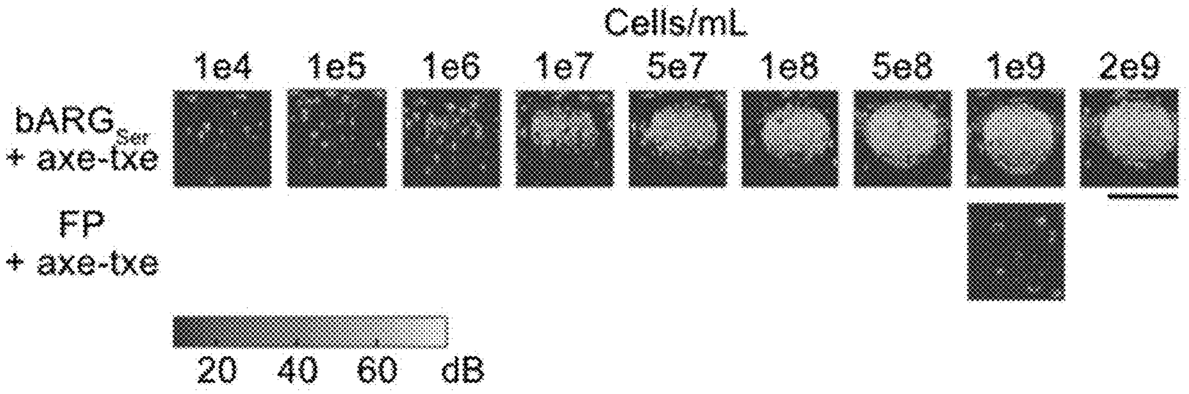

FIGS. 20A-20F depict data related to in vitro characterizations of bARG$_{Ser}$-expressing EcN with BURST ultrasound imaging. (FIGS. 20A-20B) BURST ultrasound signal-to-background ratio (SBR) versus time after inducing pBAD-bARG$_{Ser}$-AxeTxe and pBAD-FP-AxeTxe EcN strains with 0.1% L-arabinose in liquid culture at 37° C. (FIG. 20A) and the corresponding representative BURST images (FIG. 20B). (FIGS. 20C-20D) BURST ultrasound SBR versus L-arabinose concentration used to induce pBAD-bARG$_{Ser}$-AxeTxe EcN in liquid culture at 37° C. for 24 hours (FIG. 20C) and the corresponding representative BURST images. (FIGS. 20E-20F) BURST ultrasound SBR versus concentration of pBAD-bARG$_{Ser}$-AxeTxe or pBAD-FP-AxeTxe EcN cells induced for 24 hours at 37° C. with 0.1% L-arabinose in liquid culture (FIG. 20E) and the corresponding representative BURST images (FIG. 20F). Note that the BURST SBR saturated at 7 hours post-induction, 0.01% (w/v) L-arabinose, and $10^8$ cells/mL. All scale bars are 2 mm. For FIGS. 20A-20D, cells were normalized to $10^9$ cells/mL in agarose phantoms for ultrasound imaging. For FIG. 20A, FIG. 20C, FIG. 20E, each point is a biological replicate (n=4 for FIG. 20A and FIG. 20C; n=3 for FIG. 20E) that is the average of at least 2 technical replicates and curves indicate the mean. Asterisks represent statistical significance by two-tailed, unpaired Student's t-tests (**=p<0.0001, *=p<0.001, **=p<0.01, ns=no significance).

FIGS. 21A-21K depict data related to bARG$_{Ser}$ expression and acoustic characterization in *Salmonella enterica* serovar *typhimurium*. (FIG. 21A) Representative phase contrast microscopy image of bARG$_{Ser}$-expressing *S. typhimurium* cells. (FIG. 21B) xAM SBR as a function of transmitted acoustic pressure for bARG$_{Ser}$-expressing and FP-expressing S. *typhimurium* cells. (FIG. 21C) xAM SBRs measured over time when the transmitted acoustic pressure was increased approximately every 70 sec as indicated by the numbers above the curve for bARG$_{Ser}$-expressing *S. typhimurium*. Ultrasound was applied at a pulse repetition rate of 86.8 Hz. For FIGS. 21A-21C, pBAD-bARG$_{Ser}$-AxeTxe *S. typhimurium* cells were induced with 0.1% (w/v) L-arabinose for 24 hours at 37° C. in liquid culture, and were then diluted to $10^9$ cells/mL in agarose phantoms for ultrasound imaging. Bold lines represent the mean and thin lines represent±standard deviation; n=3 biological replicates, each with 2 technical replicates. (FIGS. 21D-21G) xAM ultrasound SBR (FIG. 21D) and corresponding representative ultrasound images (FIG. 21E), and BURST SBR (FIG. 21F) and corresponding representative images (FIG. 21G), using varying L-arabinose concentrations to induce pBAD-bARG$_{Ser}$-AxeTxe *S. typhimurium* in liquid culture at 37° C. for 24 hours. (FIGS. 21H-21K) xAM ultrasound SBR (FIG. 21H) and corresponding representative ultrasound images (FIG. 21I), and BURST SBR (FIG. 21J) and corresponding representative images (FIG. 21K), of varying concentrations of pBAD-bARG$_{Ser}$-AxeTxe or pBAD-FP-AxeTxe *S. typhimurium* cells induced for 24 hours at 37° C. with 0.1% (w/v) L-arabinose in liquid culture. Scale bars represent 5 μm in FIG. 21A and 2 mm in FIG. 21E, FIG. 21G, FIG. 21I, FIG. 21K. For FIGS. 21D-21G, cells were diluted to $10^9$ cells/mL in agarose phantoms for ultrasound imaging. For FIG. 21D, FIG. 21F, FIG. 21H, FIG. 21J, each point is a biological replicate (n=4 for FIG. 21D and FIG. 21F; n=3 for FIG. 21H and FIG. 21J) that is the average of at least 2 technical replicates, and curves represent the mean. All ultrasound imaging in this figure was performed with an L22-14vX transducer.

Figures 22A, 22B, 22C, 22D, 22E:
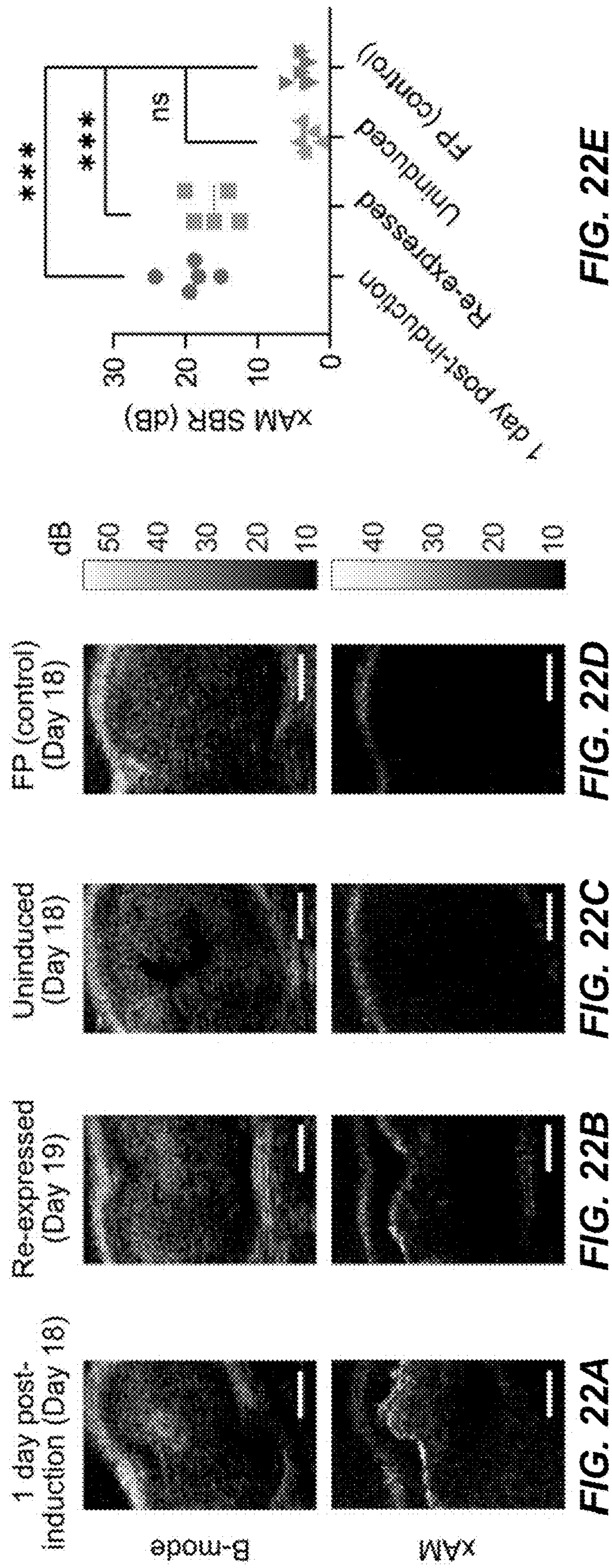

FIGS. 22A-22E depict data related to xAM ultrasound imaging of mouse tumors colonized by EcN. (FIGS. 22A-22C) Representative B-mode (top, grayscale) and xAM (bottom, hot-scale) ultrasound images of tumors colonized by pBAD-bARG$_{Ser}$-AxeTxe EcN at least 24 hours after induction with L-arabinose on day 18 (FIG. 22A), at least 24 hours after collapse and re-induction (day 19) (FIG. 22B), or uninduced on day 18 (FIG. 22C). (FIG. 22D) Representative ultrasound images of tumors colonized by pBAD-FP-AxeTxe EcN at least 24 hours after induction with L-arabinose on day 18. Scale bars in FIGS. 22A-22D represent 2 mm. (FIG. 22E) Quantification of the xAM SBR for the same conditions in FIGS. 22A-22D. Each group is n=5 mice and lines indicate the mean. Asterisks represent statistical significance by two-tailed, unpaired Student's t-tests (*=p<0.001, ns=no significance). See FIG. 4**A for the corresponding in vivo protocol.

Figure 23:
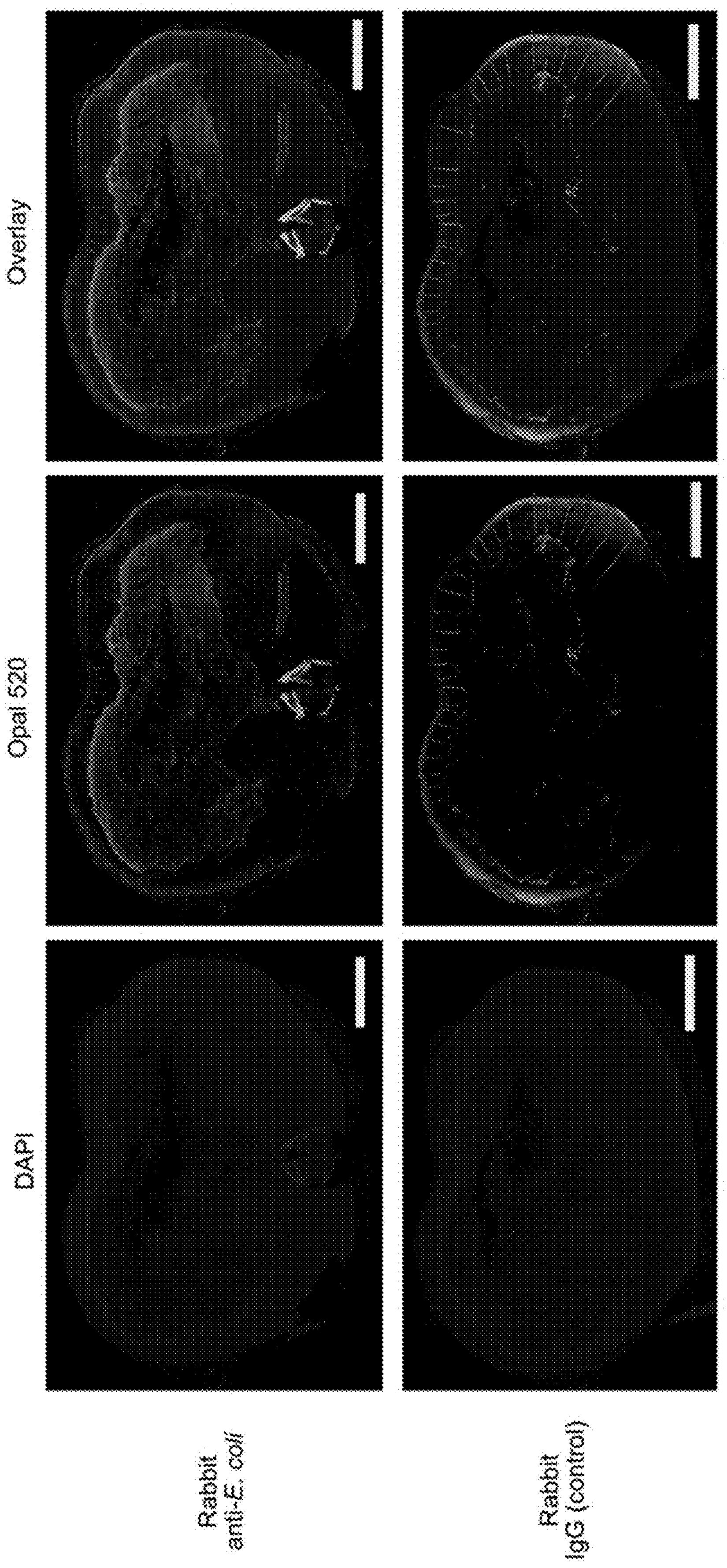

FIG. 23 depicts data related to histology of MC26 tumor colonized with bARG$_{Ser}$-expressing EcN. Fluorescent images of tissue sections after ultrasound imaging on day 19 (see FIG. 4A). Sections were incubated with either polyclonal rabbit anti-*E. coli* antibodies (top row) or non-reactive rabbit IgG isotype control antibody (bottom row) as a negative control. All sections were then incubated with an Opal 520 polymer anti-rabbit HRP antibody (Akoya biosciences) and counterstained with DAPI. The EcN are visible in the necrotic core in the Opal 520 channel (top middle panel); the edges of the tissue exhibit a high degree of background staining (bottom middle panel).

Figure 24A:
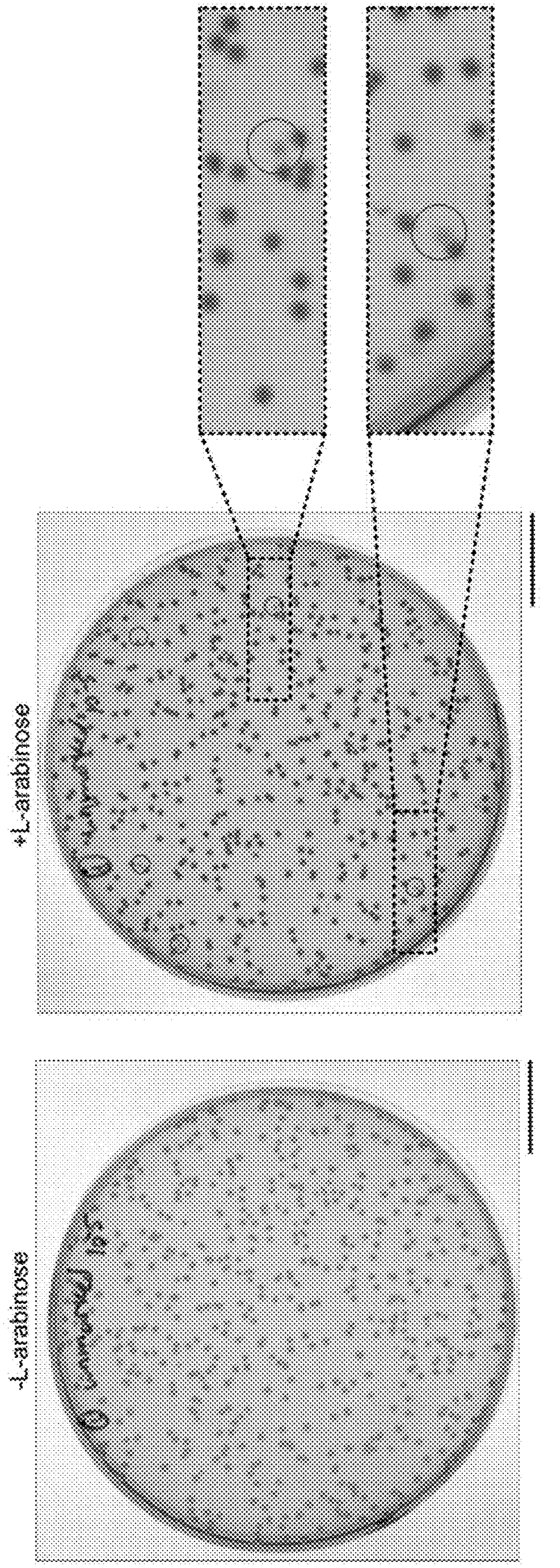
Figures 24B, 24C:
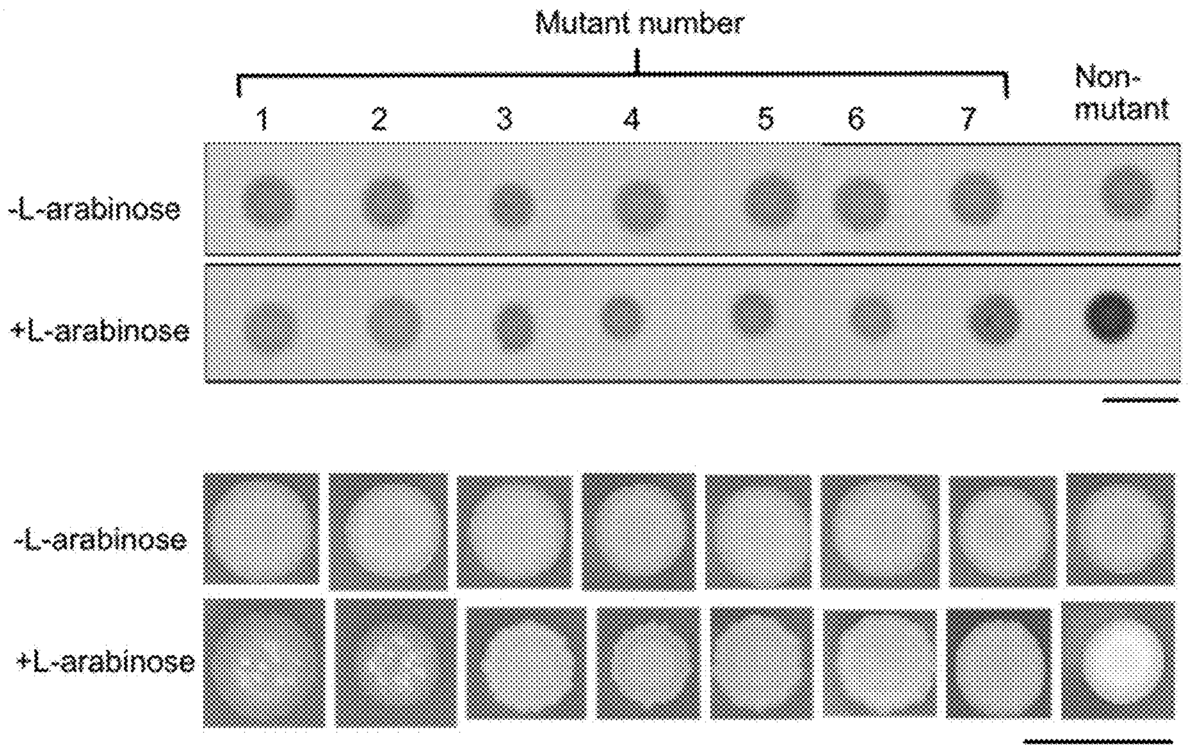

FIGS. 24A-24C depict data related to screening for EcN mutants defective in bARG$_{Ser}$ expression isolated from colonized tumors. (FIG. 24A) White light transmission images of plates with 0.1% (w/v) L-arabinose and without L-arabinose from plating a tumor (from mouse #5 in FIG. 24B) colonized by bARG$_{Ser}$-expressing EcN. Mutant colonies on the +L-arabinose plate appear lighter (more translucent) than wild-type opaque colonies and are indicated by red circles. (FIG. 24B) Numbers of non-white mutant colonies and total colonies screened on plates with 0.1% (w/v) L-arabinose for the ten mice injected with pBAD-bARG$_{Ser}$-AxeTxe EcN. (FIG. 24C) White light transmission images (top) and photographs (bottom) of patches on fresh plates with 0.1% (w/v) L-arabinose and without L-arabinose made from the seven translucent mutant colonies in red in FIG. 24B and an opaque non-mutant colony as a control. Mutants 1-2 were from mouse #2 and mutants 3-7 were from mouse #5. Scale bars are 2 cm in FIG. 24A and 1 cm in FIG. 24C.

FIGS. 25A-25G depict non-limiting exemplary schematics and data related to additional data on heterologous expression of the *A. flos-aquae* GV gene cluster in mammalian cells. (FIG. 25A) Schematic of the codon-optimized *A. flos-aquae* monocistronic plasmid set used in this study. (FIG. 25B) Representative BURST images (top) and SBR quantification (n=5, bottom) of transient GV expression in HEK293T cells 3 days after co-transfection of mixtures with varying gvpA fold excess relative to their respective assembly factor plasmids, with and without WPRE elements on the gvpA DNA. Gray lines connect the means of replicates. (FIG. 25C) BURST SBR quantification (n=6) of 293T cells expressing constructs tested in FIG. 5D. (FIG. 25D) FACS and flow cytometry data for production of the MDA-MB-231-mARG$_{Ana}$ cell line. rtTA expressing "High" cells were collected for subsequent mARG/transposase transduction.

Cells expressing gvpA and gvpNV were sorted twice to arrive at the final ~95% pure population. (FIG. 25E) TEM images of GVs purified from MDA-MB-231-mARG$_{Ana}$ detergent lysates after 1, 2, 4 and 6 days of 1 μg/ml doxycycline induction. Scalebars represent 0.5 μm. (FIG. 25F) Representative xAM images (top) and SBR quantification (n=4, bottom) of induced MDA-MB-231-mARG$_{Ana}$, 3T3-mARG$_{Ana}$ and HuH7-mARG$_{Ana}$ cells at 0.61 MPa as a function of cell concentration. Limit of detection was 300 k cells/mL for MDA-MB-231 and 3T3, and 30 k cells/mL for HuH7 with $p<0.05$ by unpaired t-tests. (FIG. 25G) Representative BURST images (top) and SBR quantification (n=4, bottom) of induced MDA-MB-231-mARG$_{Ana}$, 3T3-mARG$_{Ana}$ and HuH7-mARG$_{Ana}$ cells as a function of cell concentration. Limit of detection was 30 k cells/mL for MDA-MB-231 and HuH7, and 3 k cells/mL for 3T3 with $p<0.05$ by unpaired t-tests. For FIG. 25F and FIG. 25G, gray lines connect the means of the replicates and scalebars represent 1 mm. Percentages in parentheses represent mARG$_{Ana}$-positive cells.

Figure 26A:
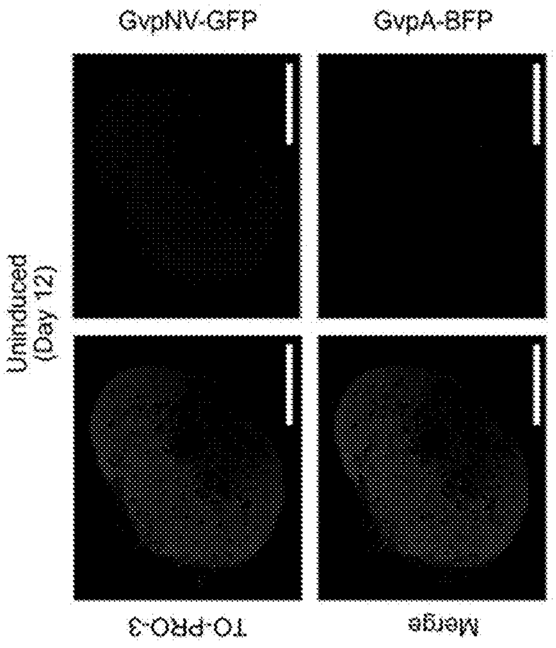
Figure 26B:
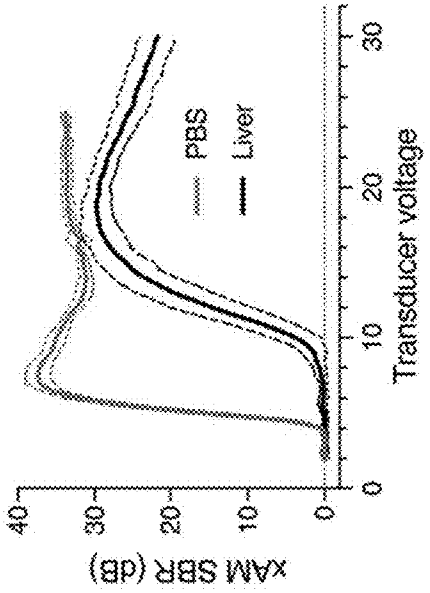
Figure 26C:
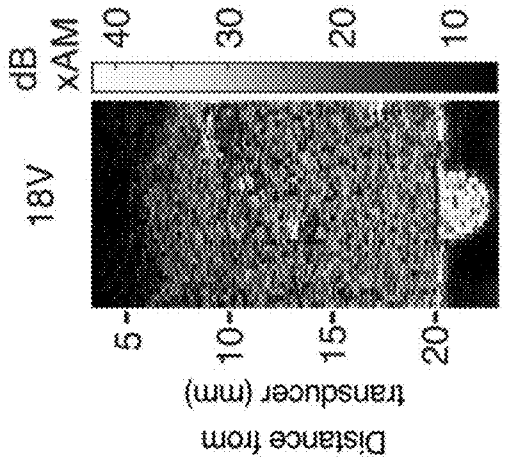

FIGS. 26A-26C depict data related to tumor histology and imaging through thick tissue. (FIG. 26A) Fluorescence micrograph of a 100 nm-thick tissue section from an uninduced tumor. The red color shows TO-PRO-3 nuclear stain; GFP and BFP fluorescence were not observed for this control tumor. Scale bars represent 2 mm. (FIG. 26B) Quantification of xAM SBR of MDA-MB-231-mARG$_{Ana}$ cells imaged under >1 cm of beef liver tissue (n=7) or under PBS (n=4) as a function of transducer voltage. Thick lines represent the mean of replicates and thin lines represent±standard deviation. (FIG. 26C) Representative xAM/B-mode overlay of MDA-MB-231-mARG$_{Ana}$ cells imaged under liver tissue using L10-5v transducer at 18V for xAM.

Figure 27:
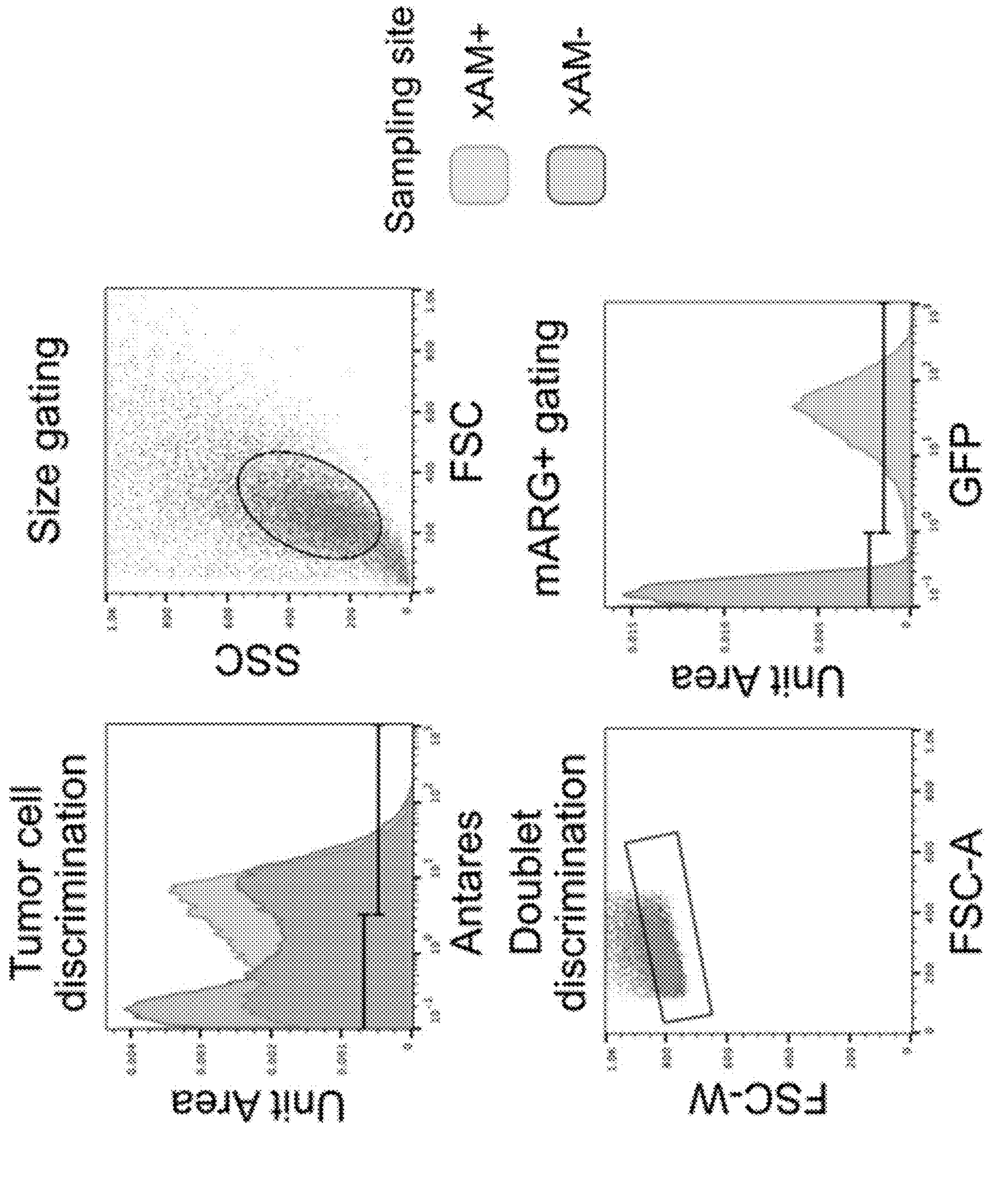

FIG. 27 depicts data related to flow cytometric gating strategy for chimeric tumor biopsy sample analyses. Events were first gated based on Antares expression to exclude endogenous mouse cells. Antares-positive cells were then gated by size. Single cells were gated based on FSC-W vs FSC-A plot. GFP-positive (mARG$_{Ana}$-positive) cells were gated from the resulting histograms.

Figure 28:
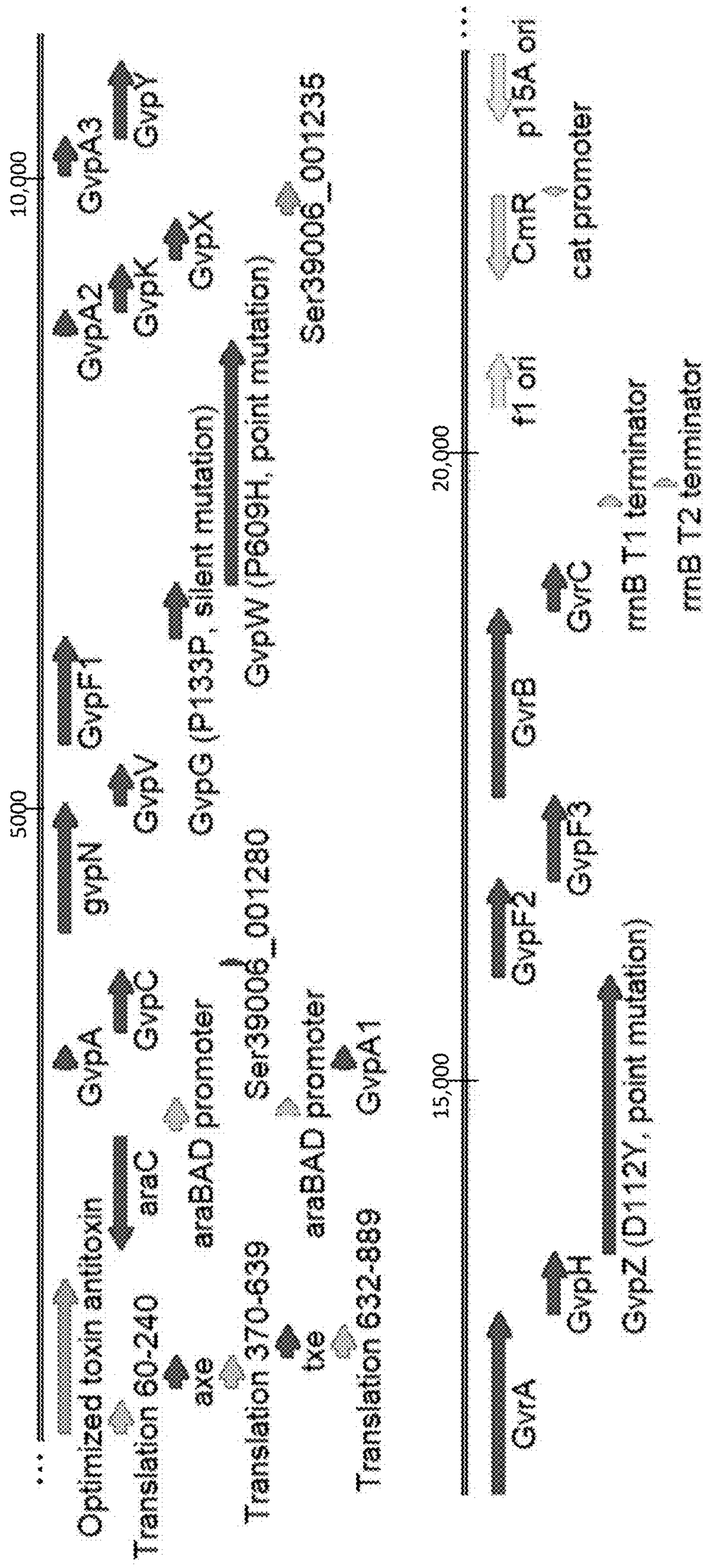

FIG. 28 depicts a non-limiting exemplary map of the bARG$_{Ser}$ construct (SEQ ID NO: 1).

Figure 29A:
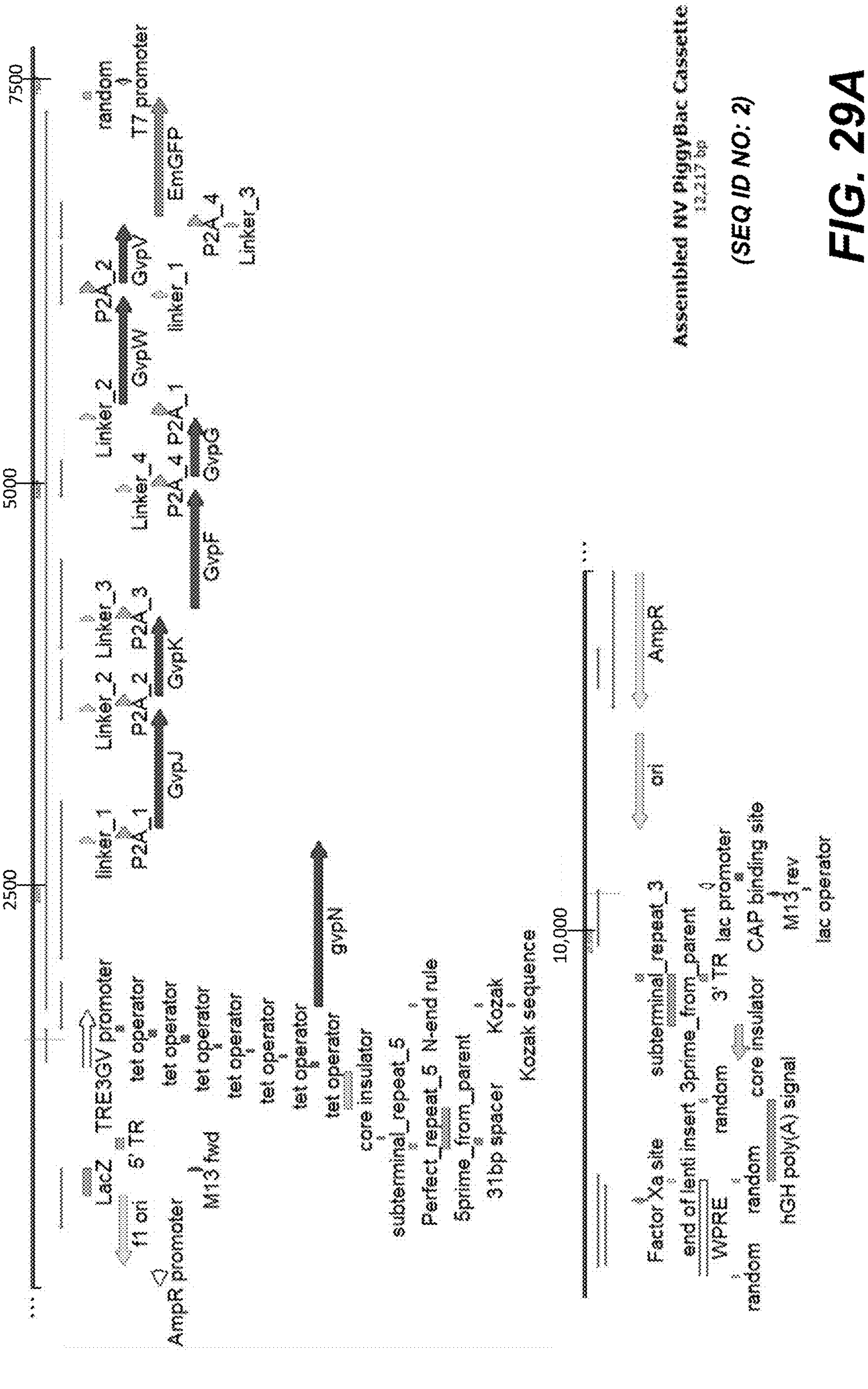
Figure 29B:
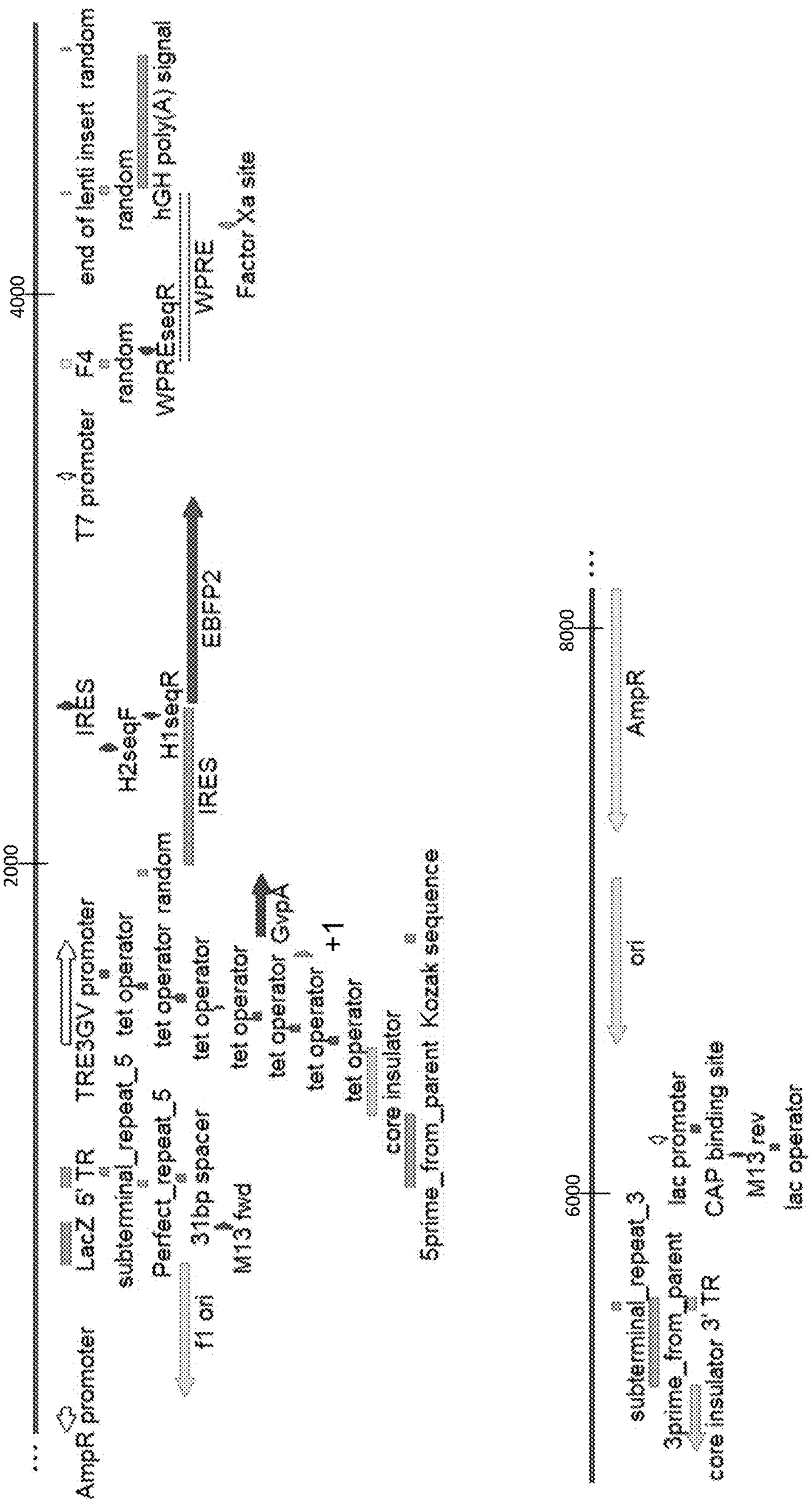

FIGS. 29A-29B depicts a non-limiting exemplary of the mARG$_{Ana}$ plasmid set: SEQ ID NO: 2 (FIG. 29A) and SEQ ID NO: 3 (FIG. 29B).

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

All patents, published patent applications, other publications, and sequences from GenBank, and other databases referred to herein are incorporated by reference in their entirety with respect to the related technology.

Disclosed herein include compositions (e.g, nucleic acid compositions, delivery compositions, mammalian cells, probiotic bacterial cells). In some embodiments, the composition comprises: a nucleic acid composition comprising one or more promoters operably connected to one or more gas vesicle (GV) polynucleotides comprising: one or more gas vesicle assembly (GVA) gene(s) encoding one or more GVA protein(s); and one or more gas vesicle structural (GVS) gene(s) encoding one or more GVS protein(s), wherein the one or more GVA protein(s) and the one or more GVS protein(s) are capable of forming gas vesicles (GVs) upon expression in a mammalian cell, and wherein said GVs are capable of producing nonlinear ultrasound contrast. In some embodiments, the composition comprises: a mammalian cell comprising one or more promoters operably connected to one or more gas vesicle (GV) polynucleotides comprising: one or more gas vesicle assembly (GVA) gene(s) encoding one or more GVA protein(s); and one or more gas vesicle structural (GVS) gene(s) encoding one or more GVS protein (s), wherein the one or more GVA protein(s) and the one or more GVS protein(s) are capable of forming gas vesicles (GVs) upon expression in the mammalian cell, and wherein said GVs are capable of producing nonlinear ultrasound contrast. In some embodiments, the composition comprises: a nucleic acid composition comprising one or more promoters operably connected to one or more gas vesicle (GV) polynucleotides comprising: one or more gas vesicle assembly (GVA) gene(s) encoding one or more GVA protein(s); and one or more gas vesicle structural (GVS) gene(s) encoding one or more GVS protein(s), wherein the one or more GVA protein(s) and the one or more GVS protein(s) are capable of forming gas vesicles (GVs) upon expression in a probiotic bacterial cell, and wherein said GVs are capable of producing nonlinear ultrasound contrast. In some embodiments, the composition comprises: a probiotic bacterial cell comprising one or more promoters operably connected to one or more gas vesicle (GV) polynucleotides comprising: one or more gas vesicle assembly (GVA) gene (s) encoding one or more GVA protein(s); and one or more gas vesicle structural (GVS) gene(s) encoding one or more GVS protein(s), wherein the one or more GVA protein(s) and the one or more GVS protein(s) are capable of forming gas vesicles (GVs) upon expression in a probiotic bacterial cell, and wherein said GVs are capable of producing nonlinear ultrasound contrast. In some embodiments, the composition comprises: a delivery composition comprising a nucleic acid composition disclosed herein, wherein the delivery composition is or comprises one or more vectors, a ribonucleoprotein (RNP) complex, a liposome, a nanoparticle, an exosome, a microvesicle, or any combination thereof.

Disclosed herein include methods of treating or preventing a disease or disorder in a subject. In some embodiments, the method comprises: administering to the subject an effective amount of a composition disclosed herein; and applying ultrasound (US) to a target site of the subject, thereby monitoring the treatment or prevention of the disease or disorder. In some embodiments, upon administration, the probiotic bacterial cells accumulate in one or more target sites of the subject, optionally hypoxic environments and/or immunosuppressive environments, further optionally the necrotic core of a solid tumor.

Disclosed herein include methods of monitoring a cell-based therapy. In some embodiments, the method comprises: administering to a subject an effective amount of the reporting therapeutic cell(s) disclosed herein; and applying ultrasound (US) to a target site of the subject, thereby monitoring the cell-based therapy. In some embodiments, monitoring the cell-based therapy comprises: monitoring the mass and/or function of the administered reporting therapeutic cells, and/or determining the ratio of functional reporting therapeutic cells post-administration. In some embodiments, the reporting therapeutic cells are administered to a target site of the subject. In some embodiments, the administering comprises transplantation of the reporting therapeutic cells, optionally transplantation at one or more target sites, optionally the target site comprises a site of disease or disorder or is proximate to a site of a disease or disorder. In some embodiments, the cell-based therapy is a transplant and/or tissue replacement. In some embodiments, the administering comprises implanting the reporting therapeutic cells into a target site of the subject.

Disclosed herein include methods of imaging a target site of a subject. In some embodiments, the method comprises: administering to the subject an effective amount of a composition disclosed herein; and applying ultrasound (US) to the target site of the subject to obtain a US image of the target site, optionally a nonlinear US image.

Disclosed herein include methods of imaging gene expression within a subject. In some embodiments, the method comprises: administering to the subject an effective amount of a composition disclosed herein; and applying ultrasound (US) to the target site of the subject to obtain a US image of gene expression at the target site, optionally a nonlinear US image.

Disclosed herein include methods of imaging gene expression within target cells. In some embodiments, the method comprises: administering to the subject an effective amount of a composition disclosed herein; and applying ultrasound (US) to said target cells to obtain a US image of gene expression of target cells at the target site, optionally a nonlinear US image.

Disclosed herein include methods of detecting a unique cell type and/or unique cell state within a subject. In some embodiments, the method comprises: administering to the subject an effective amount of a composition disclosed herein; and applying ultrasound (US) to the target site of the subject, thereby detecting the unique cell type and/or unique cell state within said subject.

DEFINITIONS

Unless defined otherwise, technical and scientific terms used herein have the same meaning as commonly understood by one of ordinary skill in the art to which the present disclosure belongs. See, e.g. Singleton et al., Dictionary of Microbiology and Molecular Biology 2nd ed., J. Wiley & Sons (New York, NY 1994); Sambrook et al., Molecular Cloning, A Laboratory Manual, Cold Spring Harbor Press (Cold Spring Harbor, NY 1989). For purposes of the present disclosure, the following terms are defined below.

As used herein, the terms "nucleic acid" and "polynucleotide" are interchangeable and can refer to any nucleic acid, whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sultone linkages, and combinations of such linkages. The terms "nucleic acid" and "polynucleotide" also specifically include nucleic acids composed of bases other than the five biologically occurring bases (adenine, guanine, thymine, cytosine and uracil).

The term "vector" as used herein, can refer to a vehicle for carrying or transferring a nucleic acid. Non-limiting examples of vectors include plasmids and viruses (for example, AAV viruses).

The term "construct," as used herein, can refer to a recombinant nucleic acid that has been generated for the purpose of the expression of a specific nucleotide sequence(s), or that is to be used in the construction of other recombinant nucleotide sequences.

As used herein, the term "plasmid" can refer to a nucleic acid that can be used to replicate recombinant DNA sequences within a host organism. The sequence can be a double stranded DNA.

The term "element" can refer to a separate or distinct part of something, for example, a nucleic acid sequence with a separate function within a longer nucleic acid sequence. The term "regulatory element" and "expression control element" are used interchangeably herein and refer to nucleic acid molecules that can influence the expression of an operably linked coding sequence in a particular host organism. These terms are used broadly to and cover all elements that promote or regulate transcription, including promoters, core elements required for basic interaction of RNA polymerase and transcription factors, upstream elements, enhancers, and response elements (see, e.g., Lewin, "Genes V" (Oxford University Press, Oxford) pages 847-873). Exemplary regulatory elements in prokaryotes include promoters, operator sequences and a ribosome binding sites. Regulatory elements that are used in eukaryotic cells can include, without limitation, transcriptional and translational control sequences, such as promoters, enhancers, splicing signals, polyadenylation signals, terminators, protein degradation signals, internal ribosome-entry element (IRES), 2A sequences, and the like, that provide for and/or regulate expression of a coding sequence and/or production of an encoded polypeptide in a host cell.

As used herein, the term "enhancer" refers to a type of regulatory element that can increase the efficiency of transcription, regardless of the distance or orientation of the enhancer relative to the start site of transcription.

The term "construct," as used herein, can refer to a recombinant nucleic acid that has been generated for the purpose of the expression of a specific nucleotide sequence(s), or that is to be used in the construction of other recombinant nucleotide sequences.

As used herein, the term "variant" can refer to a polynucleotide or polypeptide having a sequence substantially similar to a reference polynucleotide or polypeptide. In the case of a polynucleotide, a variant can have deletions, substitutions, additions of one or more nucleotides at the 5' end, 3' end, and/or one or more internal sites in comparison to the reference polynucleotide. Similarities and/or differences in sequences between a variant and the reference polynucleotide can be detected using conventional techniques known in the art, for example polymerase chain reaction (PCR) and hybridization techniques. Variant polynucleotides also include synthetically derived polynucleotides, such as those generated, for example, by using site-directed mutagenesis. Generally, a variant of a polynucleotide, including, but not limited to, a DNA, can have at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polynucleotide as determined by sequence alignment programs known by skilled artisans. In the case of a polypeptide, a variant can have deletions, substitutions, additions of one or more amino acids in comparison to the reference polypeptide. Similarities and/or differences in sequences between a variant and the reference polypeptide can be detected using conventional techniques known in the art, for example Western blot. Generally, a variant of a polypeptide, can have at least about 60%, about 65%, about 70%, about 75%, about 80%, about 85%, about 90%, about 91%, about 92%, about 93%, about 94%, about 95%, about 96%, about 97%, about 98%, about 99% or more sequence identity to the reference polypeptide as determined by sequence alignment programs known by skilled artisans.

As used herein, a "subject" refers to an animal that is the object of treatment, observation or experiment. "Animal" includes cold- and warm-blooded vertebrates and invertebrates such as fish, shellfish, reptiles, and in particular, mammals. "Mammal," as used herein, refers to an individual belonging to the class Mammalia and includes, but not limited to, humans, domestic and farm animals, zoo animals, sports and pet animals. Non-limiting examples of mammals include mice; rats; rabbits; guinea pigs; dogs; cats; sheep; goats; cows; horses; primates, such as monkeys, chimpanzees and apes, and, in particular, humans. In some embodiments, the mammal is a human. However, in some embodiments, the mammal is not a human. In some embodiments, the subject is a rodent (e.g., rat or mouse). In some embodiments, the subject is a primate (e.g., human or money).

As used herein, the term "effective amount" refers to an amount sufficient to effect beneficial or desirable imaging, biological, diagnostic, and/or clinical results.

As used herein, the term "treatment" refers to an intervention made in response to a disease, disorder or physiological condition manifested by a patient. The aim of treatment may include, but is not limited to, one or more of the alleviation or prevention of symptoms, slowing or stopping the progression or worsening of a disease, disorder, or condition and the remission of the disease, disorder or condition. The term "treat" and "treatment" includes, for example, therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. In some embodiments, "treatment" refers to both therapeutic treatment and prophylactic or preventative measures. Those in need of treatment include those already affected by a disease or disorder or undesired physiological condition as well as those in which the disease or disorder or undesired physiological condition is to be prevented. As used herein, the term "prevention" refers to any activity that reduces the burden of the individual later expressing those symptoms. This can take place at primary, secondary and/or tertiary prevention levels, wherein: a) primary prevention avoids the development of symptoms/disorder/condition; b) secondary prevention activities are aimed at early stages of the condition/disorder/symptom treatment, thereby increasing opportunities for interventions to prevent progression of the condition/disorder/symptom and emergence of symptoms; and c) tertiary prevention reduces the negative impact of an already established condition/disorder/symptom by, for example, restoring function and/or reducing any condition/disorder/symptom or related complications. The term "prevent" does not require the 100% elimination of the possibility of an event. Rather, it denotes that the likelihood of the occurrence of the event has been reduced in the presence of the compound or method.

As used herein, the term "effective amount" refers to an amount sufficient to effect beneficial or desirable biological and/or clinical results.

"Pharmaceutically acceptable" carriers are ones which are nontoxic to the cell or mammal being exposed thereto at the dosages and concentrations employed. "Pharmaceutically acceptable" carriers can be, but not limited to, organic or inorganic, solid or liquid excipients which is suitable for the selected mode of application such as oral application or injection, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins; hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as Tween™, polyethylene glycol (PEG), and Pluronics™. Auxiliary, stabilizer, emulsifier, lubricant, binder, pH adjustor controller, isotonic agent and other conventional additives may also be added to the carriers.

The term "autologous" shall be given its ordinary meaning, and shall also refer to any material derived from the same individual to whom it is later to be re-introduced into the individual.

The term "allogeneic" shall be given its ordinary meaning, and shall also refer to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

Acoustic Reporter Genes for Nondestructive In Vivo Imaging

There are provided, in some embodiments, compositions (e.g., nucleic acid compositions, probiotic bacterial cells, mammalian cell) and methods (e.g., imaging methods) employing next-generation ARGs disclosed herein. The capabilities of these next-generation ARGs provided herein were demonstrated by imaging in situ gene expression in mouse models of breast cancer and tumor-homing therapeutic bacteria, noninvasively revealing the unique spatial distributions of tumor growth and colonization by therapeutic cells in living subjects and providing real-time guidance for interventions such as needle biopsies (Example 1).

A major outstanding challenge in the fields of biological research, synthetic biology and cell-based medicine is the difficulty of visualizing the function of natural and engineered cells noninvasively inside opaque organisms. Ultrasound imaging has the potential to address this challenge as a widely available technique with a tissue penetration of several centimeters and spatial resolution below 100 μm. Recently, the first genetically encoded acoustic reporters were developed based on bacterial gas vesicles to link ultrasound signals to molecular and cellular function in mammalian cells. However, the properties of these first-generation mammalian acoustic reporter genes (mARGs)

resulted in limited sensitivity and specificity for imaging in the in vivo context. Herein are provided second-generation mARGs with greatly improved acoustic properties and expression characteristics, identified through a phylogenetic screen of candidate gene clusters from diverse bacteria and archaea. The resulting constructs offer major qualitative and quantitative improvements, including much stronger ultrasound contrast, the ability to produce nonlinear signals distinguishable from background tissue, and stable long-term expression. The utility of these next-generation mARGs was demonstrated by imaging in situ gene expression in mouse models of breast cancer, revealing the unique spatial distributions of tumor growth and tumor gene expression noninvasively in living subjects (Example 1).

Recently, the first genetically encoded acoustic reporters were developed based on bacterial gas vesicles to link ultrasound signals to molecular and cellular function in prokaryotes. However, the properties of these first-generation bacterial acoustic reporter genes (bARGs) resulted in limited sensitivity and specificity for imaging in the in vivo context. Herein are provided second-generation bARGs with greatly improved acoustic properties and expression characteristics. These bARGs were identified through a systematic phylogenetic screen of candidate gas vesicle gene clusters from diverse bacteria and archaea. The resulting constructs offer major qualitative and quantitative improvements, including the ability to produce nonlinear ultrasound contrast to distinguish their signals from those of background tissues, and a reduced burden of expression in probiotic hosts. The utility of these next-generation bARGs were demonstrated by imaging the in situ gene expression of tumor-homing probiotic bacteria, revealing the unique spatial distribution of tumor colonization by these cells noninvasively in living subjects (Example 1).

Provided herein include compositions (e.g, nucleic acid compositions, delivery compositions, mammalian cells, probiotic bacterial cells, GVs). In some embodiments, the composition comprises: a nucleic acid composition comprising one or more promoters operably connected to one or more gas vesicle (GV) polynucleotides comprising: one or more gas vesicle assembly (GVA) gene(s) encoding one or more GVA protein(s); and one or more gas vesicle structural (GVS) gene(s) encoding one or more GVS protein(s), wherein the one or more GVA protein(s) and the one or more GVS protein(s) are capable of forming gas vesicles (GVs) upon expression in a mammalian cell, and wherein said GVs are capable of producing nonlinear ultrasound contrast. In some embodiments, the composition comprises: a mammalian cell comprising one or more promoters operably connected to one or more gas vesicle (GV) polynucleotides comprising: one or more gas vesicle assembly (GVA) gene(s) encoding one or more GVA protein(s); and one or more gas vesicle structural (GVS) gene(s) encoding one or more GVS protein(s), wherein the one or more GVA protein(s) and the one or more GVS protein(s) are capable of forming gas vesicles (GVs) upon expression in the mammalian cell, and wherein said GVs are capable of producing nonlinear ultrasound contrast. In some embodiments, the composition comprises: a nucleic acid composition comprising one or more promoters operably connected to one or more gas vesicle (GV) polynucleotides comprising: one or more gas vesicle assembly (GVA) gene(s) encoding one or more GVA protein(s); and one or more gas vesicle structural (GVS) gene(s) encoding one or more GVS protein(s), wherein the one or more GVA protein(s) and the one or more GVS protein(s) are capable of forming gas vesicles (GVs) upon expression in a probiotic bacterial cell, and wherein said GVs are capable of producing nonlinear ultrasound contrast. In some embodiments, the composition comprises: a probiotic bacterial cell comprising one or more promoters operably connected to one or more gas vesicle (GV) polynucleotides comprising: one or more gas vesicle assembly (GVA) gene(s) encoding one or more GVA protein(s); and one or more gas vesicle structural (GVS) gene(s) encoding one or more GVS protein(s), wherein the one or more GVA protein(s) and the one or more GVS protein(s) are capable of forming gas vesicles (GVs) upon expression in a probiotic bacterial cell, and wherein said GVs are capable of producing nonlinear ultrasound contrast. In some embodiments, the composition comprises: a delivery composition comprising a nucleic acid composition disclosed herein, wherein the delivery composition is or comprises one or more vectors, a ribonucleoprotein (RNP) complex, a liposome, a nanoparticle, an exosome, a microvesicle, or any combination thereof. In some embodiments, the composition comprises: a GV encoded by a nucleic acid composition provided herein. Provided herein include cells (e.g., mammalian cells, probiotic bacterial cells) comprising a nucleic acid described herein.

The probiotic bacterial cell can comprise *Salmonella enterica* serovar *typhimurium* and/or *E. coli* Nissle 1917 (EcN). The probiotic bacterial cell can comprise tumor-homing bacteria. The tumor-homing bacteria can comprise *Bifidobacterium, Caulobacter, Clostridium, Escherichia coli, Listeria, Mycobacterium, Salmonella, Streptococcus*, and *Vibrio*, e.g., *Bifidobacterium adolescentis, Bifidobacterium bifidum, Bifidobacterium breve* UCC2003, *Bifidobacterium infantis, Bifidobacterium longum, Clostridium acetobutylicum, Clostridium butyricum, Clostridium butyricum* M-55, *Clostridium butyricum miyairi, Clostridium cochlearum, Clostridium felsineum, Clostridium histolyticum, Clostridium multifermentans, Clostridium novyi*-NT, *Clostridium paraputrificum, Clostridium pasteureanum, Clostridium pectinovorum, Clostridium perfringens, Clostridium roseum, Clostridium sporogenes, Clostridium tertium, Clostridium tetani, Clostridium tyrobutyricum, Corynebacterium parvum, Escherichia coli* MG1655, *Escherichia coli* Nissle 1917, *Listeria monocytogenes, Mycobacterium bovis, Salmonella choleraesuis, Salmonella typhimurium*, and *Vibrio cholera*, variants thereof, derivatives thereof, or any combination thereof. The probiotic bacterial cell can be an obligate anaerobic, facultative anaerobic, aerobic, Gram-positive, Gram-negative, commensal, or any combination thereof. The probiotic bacterial cell can comprise naturally pathogenic bacteria that are modified or mutated to reduce or eliminate pathogenicity.

The mammalian cell can comprise a cancer cell, an immortalized cell line, an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, a zymogenic cell, or any combination thereof. The stem cell can comprise an embryonic stem cell, an induced pluripotent stem cell (iPSC), a hematopoietic stem/progenitor cell (HSPC), or any combination thereof. The mammalian cell can be a reporting therapeutic cell configured to treat a disease or disorder of a subject upon administration. The presence and/or functionality of the reporting therapeutic cell can be capable of being monitored in vivo by application of ultrasound (US). The reporting therapeutic cell can be a replacement for a cell that is absent, diseased, infected, and/or involved in maintaining, promoting, or causing a disease or condition in a subject in need. The disease can be a metabolic disease, e.g., selected from the group consisting of T1D (type-1 diabetes), T2D (type-2 diabetes), diabetic ketoacidosis, obesity, cardiovascular disease, the metabolic syndrome and cancer. The reporting therapeutic cell can be autologous, allogenic, or xenogenic.

Provided herein are engineered gas-filled protein structures (GVPS), also referred to as "gas vesicles" (GVs). The phrases "gas vesicles protein structure" or "GV", "GVP", "GVPS" or "Gas Vesicles" as used herein shall be given their ordinary meaning, and shall also refer to a gas-filled protein structure intracellularly expressed by certain bacteria or archea as a mechanism to regulate cellular buoyancy in aqueous environments. GVs are described in Walsby, A. E. ((1994). Gas vesicles. Microbiology and Molecular Biology Reviews, 58(1), 94-144) hereby incorporated by reference in its entirety. The term Gas Vesicle Structural (GVS) proteins as used herein indicates proteins forming part of a gas-filled protein structure intracellularly expressed by certain bacteria or archaea and can be used as a mechanism to regulate cellular buoyancy in aqueous environments. In particular, GVS shell comprises a GVS identified as gvpA or gvpB (herein also referred to as gvpA/B) and optionally also a GVS identified as gvpC. The compositions, methods and systems described herein can be used with compositions, methods and systems (e.g., gas vesicle compositions and ultrasonic methods) previously described in U.S. Patent Application Publication Nos. 2014/0288411, 2014/0288421, 2018/0030501, 2018/0038922, 2019/0175763, 2019/0314001, 2020/0164095, 2020/0237346, 2021/0060185, and International Patent Application Publication WO2020/146379; the content of each of these applications is incorporated herein by reference in its entirety.

The systems, methods, compositions, and kits provided herein can, in some embodiments, be employed in concert with the systems, methods, compositions, and kits comprising recombinant adeno-associated virus (rAAV) comprising an AAV acoustic targeting peptide exhibiting increased transduction at site(s) of focused ultrasound blood-brain barrier opening (FUS-BBBO), increased neuronal tropism, and diminished transduction of peripheral organs described in U.S. patent application Ser. No. 17/814,384, entitled, "VIRAL VECTORS FOR ENHANCED ULTRASOUND-MEDIATED DELIVERY TO THE BRAIN," filed Jul. 22, 2022, the content of which is incorporated herein by reference in its entirety.

GV production requires the co-expression of multiple GV proteins (Gvps), which in prokaryotes are expressed from polycistronic operons at specific ratios determined by the strength of their respective ribosome binding sites or other regulatory mechanisms. The systems, methods, compositions, and kits provided herein can, in some embodiments, be employed in concert with the systems, methods, compositions, and kits expression of multiple proteins from a single mRNA with a predetermined stoichiometry described in U.S. patent application Ser. No. 17/866,240, entitled "STOICHIOMETRIC EXPRESSION OF MESSENGER POLYCISTRONS", filed Jul. 15, 2022, the content of which is incorporated herein by reference in its entirety. The systems, methods, compositions, and kits provided herein can, in some embodiments, be employed in concert with the systems, methods, compositions, and kits described in U.S. patent application Ser. No. 17/936,286, entitled, "VIRAL DELIVERY OF GAS VESICLE GENES," filed Sep. 28, 2022, the content of which is incorporated herein by reference in its entirety.

The systems, methods, compositions, and kits provided herein can, in some embodiments, be employed in concert with the systems, methods, compositions, and kits described in U.S. patent application Ser. No. 17/937,975, entitled, "ULTRASONIC GENETICALLY ENCODED CALCIUM INDICATORS," filed Oct. 4, 2022, the content of which is incorporated herein by reference in its entirety. The systems, methods, compositions, and kits provided herein can, in some embodiments, be employed in concert with the systems, methods, compositions, and kits described in U.S. patent application Ser. No. 18/073,102, entitled, "GENETICALLY ENCODED ACTUATORS FOR ACOUSTIC MANIPULATION," filed Dec. 1, 2022, the content of which is incorporated herein by reference in its entirety. Nucleic acid compositions and methods are provided in Hurt et al ("Genomically mined acoustic reporter genes enable real-time in vivo monitoring of tumors and tumor-homing probiotics", *bioRxiv* (2022)), the content of which is incorporated herein by reference in its entirety.

In particular, a GV in the sense of the disclosure is a structure intracellularly expressed by bacteria or archaea forming a hollow structure wherein a gas is enclosed by a protein shell, which is a shell substantially made of protein (up at least 95% protein). In gas vesicles in the sense of the disclosure, the protein shell is formed by a plurality of proteins herein also indicated as Gyp proteins or Gvps, which are expressed by the bacteria or archaea and form in the bacteria or archaea cytoplasm a gas permeable and liquid impermeable protein shell configuration encircling gas. Accordingly, a protein shell of a GV is permeable to gas but not to surrounding liquid such as water. For example, GVs' protein shells exclude liquid water but permit gas to freely diffuse in and out from the surrounding media making them physically stable despite their usual nanometer size.

GV structures are typically nanostructures with widths and lengths of nanometer dimensions (in particular with widths of 45-250 nm and lengths of 100-800 nm) but can have lengths as large as the dimensions of a cell in which they are expressed, as will be understood by a skilled person. GVs and methods are described in Farhadi et al, Science, 2019, hereby incorporated by reference. In some embodiments, the gas vesicles protein structure have average dimensions of 1000 nm or less, such as 900 nm or less, including 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less. For example, the average diameter of the gas vesicles may range from 10 nm to 1000 nm, such as 25 nm to 500 nm, including 50 nm to 250 nm, or 100 nm to 250 nm. By "average" is meant the arithmetic mean.

GVs in the sense of the disclosure have different shapes depending on their genetic origins. For example, GVs in the sense of the disclosure can be substantially spherical, ellipsoid, cylindrical, or have other shapes such as football shape or cylindrical with cone shaped end portions depending on the type of bacteria providing the gas vesicles.

The term Gas Vesicle Structural (GVS) proteins as used herein indicates proteins forming part of a gas-filled protein structure intracellularly expressed by certain bacteria or archaea and can be used as a mechanism to regulate cellular buoyancy in aqueous environments. In particular, GVS shell comprises a GVS identified as gvpA or gvpB (herein also referred to as Gyp A/B) and optionally also a GVS identified as gvpC. GvpA is a structural protein that assembles through repeated unites to make up the bulk of GVs. GvpC is a scaffold protein with 5 repeat units that assemble on the outer shell of GVs. GvpC can be engineered to tune the mechanical and acoustic properties of GVs as well as act as a handle for appending moieties on to. A gvpC protein is a hydrophilic protein of a GV shell, which includes repetitions of one repeat region flanked by an N-terminal region and a C terminal region. The term "repeat region" or "repeat" as used herein with reference to a protein can refer to the minimum sequence that is present within the protein in multiple repetitions along the protein sequence without any gaps. Accordingly, in a gvpC multiple repetitions of a same repeat is flanked by an N-terminal region and a C-terminal region. In a same gvpC, repetitions of a same repeat in the gvpC protein can have different lengths and different sequence identity one with respect to another.

The optional gvpC gene encodes for a gvpC protein which is a hydrophilic protein of a GV shell, including repetitions of one repeat region flanked by an N-terminal region and a C terminal region. The term "repeat region" or "repeat" as used herein with reference to a protein can refer to the minimum sequence that is present within the protein in multiple repetitions along the protein sequence without any gaps. Accordingly, in a gvpC multiple repetitions of a same repeat is flanked by an N-terminal region and a C-terminal region. In a same gvpC, repetitions of a same repeat in the gvpC protein can have different lengths and different sequence identity one with respect to another. In performing alignment steps sequence are identified as repeat when the sequence shows at least 3 or more of the characteristics described in U.S. application Ser. No. 15/663,635 published as US 2018/0030501 (incorporated herein by reference in its entirety) which also include additional features of gvpC proteins and the related identification.

The phrase "GV type" as used herein shall be given its ordinary meaning, and shall also refer to a gas vesicle having dimensions and shape resulting in distinctive mechanical, acoustic, surface and/or magnetic properties as will be understood by a skilled person upon reading of the present disclosure. In particular, a skilled person will understand that different shapes and dimensions will result in different properties in view of the indications in provided in U.S. application Ser. No. 15/613,104 and U.S. Ser. No. 15/663,600 and additional indications identifiable by a skilled person. In some embodiments, the nucleic acid compositions provided herein encode a combination of different GV types and/or variants thereof, with each expressed GV exhibiting a different acoustic collapse profile with progressively decreased midpoint collapse pressure values. In some embodiments, the percentage difference between the midpoint collapse pressure values of any given two expressed GVs types is at least twenty percent.

In some embodiments, GVs are capable of withstanding pressures of several kPa. but collapse irreversibly at a pressure at which the GV protein shell is deformed to the point where it flattens or breaks, allowing the gas inside the GV to dissolve irreversibly in surrounding media, herein also referred to as a critical collapse pressure, or selectable critical collapse pressure, as there are various points along a collapse pressure profile (e.g., peak acoustic pressure).

A collapse pressure profile (e.g., peak acoustic pressure) as used herein indicates a range of pressures over which collapse of a population of GVs of a certain type occurs. In particular, a collapse pressure profile in the sense of the disclosure comprise increasing acoustic collapse pressure values, starting from an initial collapse pressure value at which the GV signal/optical scattering by GVs starts to be erased to a complete collapse pressure value at which the GV signal/optical scattering by GVs is completely erased. The collapse pressure profile of a set type of GV is thus characterized by a mid-point pressure where 50% of the GVs of the set type have been collapsed (also known as the "midpoint collapse pressure"), an initial collapse pressure where 5% or lower of the GVs of the type have been collapsed, and a complete collapse pressure where at least 95% of the GVs of the type have been collapsed. In some embodiments herein described a selectable critical collapse pressure can be any of these collapse pressures within a collapse pressure profile, as well as any point between them. The critical collapse pressure profile of a GV is functional to the mechanical properties of the protein shell and the diameter of the shell structure. U.S. Patent Application Publication No. 2020/0164095 describes gas vesicles, protein variants and related compositions methods and systems for singleplexed and/or multiplexed ultrasonic methods (e.g., imaging of a target site in which a gas vesicle provides contrast for the imaging) which is modifiable by application of a selectable acoustic collapse pressure value of the gas vesicle, the content of which is hereby expressly incorporated by reference in its entirety.

The acoustic collapse pressure profile (e.g., peak acoustic pressure) of a given GV type can be determined by imaging GVs with imaging ultrasound energy after collapsing portions of the given GV type population with a collapsing ultrasound energy (e.g. ultrasound pulses) with increasing peak positive pressure amplitudes to obtain acoustic pressure data point of acoustic pressure values, the data points forming an acoustic collapse curve. The acoustic collapse pressure function f(p) can be derived from the acoustic collapse curve by fitting the data with a sigmoid function such as a Boltzmann sigmoid function. An acoustic collapse pressure profile in the sense of the disclosure can include a set of initial collapse pressure values, a midpoint collapse pressure value and a set of complete collapse pressure values. The initial collapse pressures are the acoustic collapse pressures at which 5% or less of the GV signal is erased. A midpoint collapse pressure is the acoustic collapse pressure at which 50% of the GV signal is erased. Complete collapse pressures are the acoustic collapse pressures at which 95% or more of the GV signal is erased. The pressure can be peak pressure. In some embodiments, the peak pressure is peak positive pressure. In some embodiments, the peak pressure is peak negative pressure.

U.S. Patent Application Publication No. 2018/0030501 describes hybrid gas vesicle gene cluster (GVGC) configured for expression in a prokaryotic host comprising gas vesicle assembly (GVA) genes native to a GVA prokaryotic species and capable of being expressed in a functional form in the prokaryotic host, as well as one or more gas vesicle structural (GVS) genes native to one or more GVS prokaryotic species, at least one of the one or more GVS prokaryotic species different from the GVA prokaryotic species, and related gas vesicle reporting (GVR) genetic circuits, genetic, vectors, engineered cells, and related compositions methods and systems to produce GVs, hybrid GVGC and/or image a target site, the content of which is hereby expressly incorporated by reference in its entirety. The term "Gas Vesicle Genes Cluster" or "GVGC" as described herein indicates a gene cluster encoding a set of GV proteins capable of providing a GV upon expression within a cell. In some embodiments, the nucleic acid compositions provided herein encode some or all elements of a GVGC. The term "gene cluster" as used herein means a group of two or more genes found within an organism's DNA that encode two or more polypeptides or proteins, which collectively share a generalized function or are genetically regulated together to produce a cellular structure and are often located within a few thousand base pairs of each other. The size of gene clusters can vary significantly, from a few genes to several hundred genes. Portions of the DNA sequence of each gene within a gene cluster are sometimes found to be similar or identical; however, the resulting protein of each gene is distinctive from the resulting protein of another gene within the cluster. Genes found in a gene cluster can be observed near one another on the same chromosome or native plasmid DNA, or on different, but homologous chromosomes. An example of a gene cluster is the Hox gene, which is made up of eight genes and is part of the Homeobox gene family. In the sense of the disclosure, gene clusters as described herein also comprise gas vesicle gene clusters, wherein the expressed proteins thereof together are able to form gas vesicles.

Engineered GVs and methods of tuning the acoustic properties thereof are provided in U.S. Patent Application Publication No. 2020/0164095, the content of which is incorporated herein by reference in its entirety. In some embodiments, the GVs can be engineered to modulate the GV mechanical, acoustic, surface and targeting properties in order to achieve enhanced harmonic responses and multiplexed imaging to be better distinguished from background tissues. In some embodiments herein described Gas vesicles protein structures can be provided by Gyp genes endogenously expressed in bacteria or archaea. Endogenous expression can refer to expression of Gyp proteins forming the protein shell of the GV in bacteria or archaea that naturally produce gas vesicles encoded (e.g. in their genome or native plasmid DNA). Gyp proteins expressed by bacteria or archaea typically include two primary structural proteins, here also indicated as GvpA and GvpC, and several putative minor components and chaperones as would be understood by a person skilled in the art. In some embodiments, heterologously expressed Gyp proteins to provide a GV type have independently at least 50% sequence identity, preferably at least 80%, more preferably at least 90%, most preferably at least 95% sequence identity compared to a reference sequence of corresponding Gyp protein using one of the alignment programs described using standard parameters. In some embodiments, multiplexed imaging methods are provided. The term "multiplex" can refer to the presence of two or more distinct GVPS types, each of which exhibits an acoustic collapse and/or buckling pressure profile distinct from one another. The two or more distinct GVPSs can be derived from different organisms or variants of GVPSs from the same or different organisms (e.g., archaea).

The expression of the GVs within the probiotic bacterial cell and/or mammalian cell can be capable of being detected via dynamic non-destructive imaging, such as, for example, (i) nonlinear ultrasound imaging, optionally cross-propagating amplitude modulation pulse sequence (xAM) imaging and/or parabolic AM (pAM) imaging, (ii) at an acoustic pressure of about 0.3 MPa, to about 1.75 MPa, (iii) nonlinear ultrasound signal is proportional to cell concentration, further optionally between about $10^2$ cells/mL and $10^9$ cells/mL, and/or (iv) about 3 hours upon induction of expression. The GVs can be capable of producing at least about 1.1-fold (e.g., 1.1-fold, 1.2-fold, 1.3-fold, 1.4-fold, 1.5-fold, 1.6-fold, 1.7-fold, 1.8-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values) greater non-linear ultrasound signals as compared to GVs expressed from first generation acoustic reporter genes (ARGs) in the probiotic bacterial cell and/or a mammalian cell, optionally said first generation ARGs comprise bARG1 or $mARG_{Mega}$. The probiotic bacterial cell and/or mammalian cell can be capable of exhibiting an about 5 dB to about 50 dB enhancement in nonlinear ultrasound contrast as compared to a probiotic bacterial cell and/or a mammalian cell comprising first generation acoustic reporter genes (ARGs), optionally said first generation ARGs comprise bARG1 or $mARG_{Mega}$.

The probiotic bacterial cell and/or mammalian cell can be capable of exhibiting an at least about 1.1-fold (e.g., 1.1-fold, 1.2-fold, 1.3-fold, 1.4-fold, 1.5-fold, 1.6-fold, 1.7-fold, 1.8-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values) increase in contrast to noise ratio (CNR) as compared to a probiotic bacterial cell and/or a mammalian cell comprising first generation acoustic reporter genes (ARGs), optionally said first generation ARGs comprise bARG1 or $mARG_{Mega}$. In some embodiments, the probiotic bacterial cell and/or mammalian cell exhibits a growth rate within about 20 percent of the growth rate of a probiotic bacterial cell and/or a mammalian cell (i) comprising first generation acoustic reporter genes (ARGs) or (ii) not comprising GVA genes and GVS genes, optionally said first generation ARGs comprise bARG1 or $mARG_{Mega}$, further optionally in vitro growth rate and/or in vivo growth rate. The mammalian cell can be capable of expressing an at least about 1.1-fold (e.g., 1.1-fold, 1.2-fold, 1.3-fold, 1.4-fold, 1.5-fold, 1.6-fold, 1.7-fold, 1.8-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values) greater amount of GVs as compared to a mammalian cell comprising first generation acoustic reporter genes (ARGs), optionally $mARG_{Mega}$. The probiotic bacterial cell can be capable of expressing an at least about 1.1-fold (e.g., 1.1-fold, 1.2-fold, 1.3-fold, 1.4-fold, 1.5-fold, 1.6-fold, 1.7-fold, 1.8-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values) greater amount of GVs as compared to a probiotic bacterial cell comprising first generation acoustic reporter genes (ARGs), optionally bARG1. In some embodiments, less than about 10 percent of cells of a population the probiotic bacterial cells and/or mammalian cells express less than a threshold amount of the GVs, optionally the threshold amount of the GVs is the threshold amount of the GVs detectable via nonlinear ultrasound imaging.

The one or more GVS gene(s) and/or the one or more GVA gene(s) can be derived from *Serratia* sp. ATAC 39006, optionally gvpA, gvpC, gvpN, gvpV, gvpF1, gvpG, gvpW, gvpJ1, gvpK, gvpX, gvpJ2, gvpY, gvrA, gvpH, gvpZ, gvpF2, gvpF3, gvrB, gvrC, or any combination thereof. The one or more GVS gene(s) and/or the one or more GVA gene(s) can be derived from *Desulfobacterium vacuolatum*, optionally gvrA, gvpH, gvpZ, gvpF2, gvpF3, gvrB, gvrC, gvpA, gvpC, gvpN, gvpV, gvpF1, gvpG, gvpW, gvpJ1, gvpK, gvpJ2, or any combination thereof. The one or more GVS gene(s) can comprise gvpA and/or gvpC of *Anabaena flos-aquae* and the one or more GVA gene(s) can be derived from *Bacillus megaterium*, optionally gvpR, gvpN, gvpF, gvpG, gvpL, gvpS, gvpK, gvpJ, gvpT, gvpU, or any combination thereof. The one or more GVA gene(s) and/or the one or more GVA gene(s) can be derived from *Anabaena flos-aquae*, optionally gvpA, gvpC, gvpN, gvpJ, gvpK, gvpF, gvpG, gvpV, gvpW, or any combination thereof. The one or more GVA gene(s) and/or the one or more GVA gene(s) can be derived from *Bacillus megaterium*, optionally gvpB, gvpR, gvpN, gvpF, gvpG, gvpL, gvpS, gvpK, gvpJ, gvpT, gvpU, or any combination thereof.

In some embodiments, the nucleic acid composition and/or mammalian cell comprises: a first GV polynucleotide encoding GvpA, a second GV polynucleotide encoding GvpN, a third GV polynucleotide encoding GvpJ, a fourth GV polynucleotide encoding GvpK, a fifth GV polynucleotide encoding GvpF, a sixth GV polynucleotide encoding GvpG, a seventh GV polynucleotide encoding GvpW, and an eighth GV polynucleotide encoding GvpV, optionally two or more of the GV polynucleotides are operably connected to a tandem gene expression element. In some embodiments, the one or more GV polynucleotides do not comprise Ser39006_001280.

As used herein, the term "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A promoter can be inducible, repressible, and/or constitutive. Inducible promoters initiate increased levels of transcription from DNA under their control in response to some change in culture conditions, such as a change in temperature.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

The promoter (e.g., first promoter, context-dependent promoter) can vary in length, for example be less than 1 kb. In other embodiments, the promoter (e.g., first promoter, context-dependent promoter) is greater than 1 kb. The promoter can have a length of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800 bp, or a number or a range between any two of these values, or more than 800 bp.

The one or more promoters can comprise one or more first promoters, one or more inducible promoters, and/or one or more context-dependent promoters, optionally: one or more inducible promoters is operably connected to one or more GV polynucleotides comprising GVS gene(s) and one or more first promoters is operably connected to one or more GV polynucleotides comprising GVA gene(s); or one or more context-dependent promoters is operably connected to one or more GV polynucleotides comprising GVS gene(s) and one or more first promoters is operably connected to one or more GV polynucleotides comprising GVA gene(s). At least two of the GV polynucleotides can be operably connected to a tandem gene expression element selected from the group comprising an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A), or any combination thereof. At least one of the one or more promoters can be an inducible promoter, such as, for example, an anhydrotetracycline-inducible promoter, an IPTG-inducible promoter, a rhamnose-inducible promoter, or an arabinose-inducible promoter. The inducible promoter can be induced by the cellular event. The cellular event can be marked by a stimulus received by the cell. The stimulus can be a small molecule, a protein, a peptide, an amino acid, a metabolite, an inorganic molecule, an organometallic molecule, an organic molecule, a drug or drug candidate, a sugar, a lipid, a metal, a nucleic acid, a molecule produced during the activation of an endogenous or an exogenous signaling cascade, light, heat, sound, pressure, mechanical stress, shear stress, or a virus or other microorganism, change in pH, or change in oxidation/reduction state.

At least one of the one or more promoters can comprise the TlpA operator/promoter, lambda phage pL, lambda phage pR, lambda phage pRM, or any combination thereof. At least one of the one or more promoters can be a promoter selected from the group comprising: a bacteriophage promoter, optionally Pls1con, T3, T7, SP6, or PL; a bacterial promoter, optionally Pbad, PmgrB, Ptrc2, Plac/ara, Ptac, or Pm; and/or a bacterial-bacteriophage hybrid promoter, optionally PLlacO or PLtetO. At least one of the one or more promoters can be a positively regulated *E. coli* promoter selected from the group comprising: a $\sigma^{70}$ promoter, optionally inducible pBad/araC promoter, Lux cassette right promoter, modified lamdba Prm promoter, plac Or2-62 (positive), pBad/AraC with extra REN sites, pBad, P(Las) TetO, P(Las) CIO, P(Rhl), Pu, FecA, pRE, cadC, hns, pLas, or pLux; a $\sigma^{S}$ promoter, optionally Pdps; a $\sigma^{32}$ promoter, optionally heat shock; and/or a $\sigma^{54}$ promoter, optionally glnAp2. At least one of the one or more promoters can be a negatively regulated *E. coli* promoter selected from the group comprising: a $\sigma^{70}$ promoter, optionally Promoter (PRM+), modified lamdba Prm promoter, TetR-TetR-4C P(Las) TetO, P(Las) CIO, P(Lac) IQ, RecA_DlexO_D-LacO1, dapAp, FecA, Pspac-hy, pcI, plux-cI, plux-lac, CinR, CinL, glucose controlled, modifed Pr, modifed Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, or RcnR; a as promoter, optionally Lutz-Bujard LacO with alternative sigma factor $\sigma^{38}$; a $\sigma^{32}$ promoter, optionally Lutz-Bujard LacO with alternative sigma factor $\sigma^{32}$; and/or a $\sigma^{54}$ promoter, optionally glnAp2. At least one of the one or more promoters can be a P7 promoter. At least one of the one or more promoters can be a heat-shock promoter, optionally pTSR, pR-pL, GrpE, HtpG, Lon, RpoH, Clp, and/or DnaK. At least one of the one or more promoters can be a constitutive promoter, optionally selected from the group comprising: a constitutive *Escherichia coli* $\sigma^{S}$ promoter, optionally osmY promoter (BBa_J45993); a constitutive *Escherichia coli* $\sigma^{32}$ promoter, optionally htpG heat shock promoter (BBa_J45504); a constitutive *Escherichia coli* $\sigma^{70}$ promoter, optionally lacq promoter (BBa_J54200 or BBa_J56015), *E. coli* CreABCD phosphate sensing operon promoter (BBa_J64951), GlnRS promoter (BBa_K088007), lacZ promoter (BBa_K119000 or BBa_K119001), M13K07 gene I promoter (BBa_M13101), M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), or M13110 (BBa_M13110); a constitutive *Bacillus subtilis* $\sigma^{A}$ promoter, optionally promoter veg (BBa_K143013), promoter 43 (BBa_K143013), $P_{liaG}$ (BBa_K823000), $P_{lepA}$ (BBa_K823002), or $P_{veg}$ (BBa_K823003); a constitutive *Bacillus subtilis* $\sigma^{B}$ promoter, optionally promoter ctc (BBa_K143010) or promoter gsiB (BBa_K143011)), a *Salmonella* promoter, optionally Pspv2 from *Salmonella* (BBa_K112706) or Pspv from *Salmonella* (BBa_K112707); a bacteriophage T7 promoter, optionally BBa_I712074, BBa_I719005, BBa_J34814, BBa_J64997, BBa_K113010, BBa_K113011, BBa_K113012, BBa_R0085, BBa_R0180, BBa_R0181, BBa_R0182, BBa_R0183, BBa_Z0251, BBa_Z0252, or BBa_Z0253; and/or a bacteriophage SP6 promoter, optionally SP6 promoter (BBa_J64998). At least one of the one or more promoters can comprise at least one −10 element and/or at least one −35 element.

In some embodiments, the one or more first promoters comprise: a minimal promoter, optionally TATA, miniCMV, and/or miniPromo; a tissue-specific promoter and/or a lineage-specific promoter; and/or a ubiquitous promoter, optionally a minEf1a promoter, a cytomegalovirus (CMV) immediate early promoter, a CMV promoter, a viral simian virus 40 (SV40) (e.g., early or late), a Moloney murine leukemia virus (MoMLV) LTR promoter, a Rous sarcoma virus (RSV) LTR, an RSV promoter, a herpes simplex virus (HSV) (thymidine kinase) promoter, H5, P7.5, and P11 promoters from vaccinia virus, an elongation factor 1-alpha (EF1a) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus, a Ubiquitin C promoter (UBC), a phosphoglycerate kinase-1 (PGK) promoter, 3-phosphoglycerate kinase promoter, a cytomegalovirus enhancer, human β-actin (HBA) promoter, chicken β-actin (CBA) promoter, a CAG promoter, a CASI promoter, a CBH promoter, or any combination thereof. In some embodiments, the activity of the context-dependent promoter and/or the degree of expression of the GVs operably connected to a context-dependent promoter is associated with the presence and/or amount a unique cell type and/or a unique cell state.

In some embodiments, the composition comprises: a context-dependent promoter operably linked to a transactivator polynucleotide comprising a transactivator gene, wherein the context-dependent promoter is capable of inducing transcription of the transactivator gene to generate a transactivator transcript, wherein the transactivator transcript is capable of being translated to generate a transactivator, wherein the activity of the context-dependent promoter and/or the degree of expression of the transactivator is associated with the presence and/or amount a unique cell type and/or a unique cell state, wherein, in the presence of the transactivator and a transactivator-binding compound, the first promoter is capable of inducing transcription of the one or more GV polynucleotides to generate GV transcript (s), and wherein the GV transcript(s) are capable of being translated to generate GVA protein(s) and/or GVS protein (s). The first promoter can comprise one or more copies of a transactivator recognition sequence the transactivator is capable of binding to induce transcription, and wherein the transactivator is incapable of binding the transactivator recognition sequence in the absence of the transactivator-binding compound, optionally the one or more copies of a transactivator recognition sequence comprise one or more copies of a tet operator (TetO). The one or more copies of a transactivator recognition sequence can comprise one or more copies of a tet operator (TetO). The first promoter can comprise a tetracycline response element (TRE), and the TRE can comprise one or more copies of a tet operator (TetO). The transactivator can comprise reverse tetracycline-controlled transactivator (rtTA). The transactivator can comprise tetracycline-controlled transactivator (tTA). The transactivator-binding compound can comprise tetracycline, doxycycline or a derivative thereof. The transactivator can comprise a constitutive signal peptide for protein degradation, optionally PEST.

In some embodiments, one or more GV polynucleotides and/or transactivator polynucleotide comprise: a 5'UTR and/or a 3'UTR; a tandem gene expression element selected from the group comprising an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A), or any combination thereof; and/or a transcript stabilization element (e.g., woodchuck hepatitis post-translational regulatory element (WPRE), bovine growth hormone polyadenylation (bGH-polyA) signal sequence, human growth hormone polyadenylation (hGH-polyA) signal sequence, or any combination thereof).

The unique cell state can comprise activation of one or more cellular activities of interest. A unique cell type and/or a unique cell state can be caused by hereditable, environmental, and/or idiopathic factors. A unique cell type and/or a unique cell state can be caused by and/or associated with the expression of one or more endogenous proteins whose expression is regulated by the endogenous context-dependent promoter. The unique cell state and/or unique cell type can be characterized by signaling of one or more endogenous signal transducer(s), optionally signal transducer(s) regulated by the endogenous context-dependent promoter. In some embodiments, the unique cell type and/or the cell in the unique cell state (i) causes and/or aggravates a disease or disorder and/or (ii) is associated with the pathology of a disease or disorder.

The unique cell state and/or unique cell type can be characterized by aberrant signaling of one or more signal transducer(s). In some embodiments, the aberrant signaling involves: an overactive signal transducer; a constitutively active signal transducer over a period of time; an active signal transducer repressor and an active signal transducer; an inactive signal transducer activator and an active signal transducer; an inactive signal transducer; an underactive signal transducer; a constitutively inactive signal transducer over a period of time; an inactive signal transducer repressor and an inactive signal transducer; and/or an active signal transducer activator and an inactive signal transducer. The aberrant signaling can comprise an aberrant signal of at least one signal transduction pathway regulating cell survival, cell growth, cell proliferation, cell adhesion, cell migration, cell metabolism, cell morphology, cell differentiation, apoptosis, or any combination thereof. The signal transduscer(s) can be AKT, PI3K, MAPK, p44/42 MAP kinase, TYK2, p38 MAP kinase, PKC, PKA, SAPK, ELK, INK, cJun, RAS, Raf, MEK 1/2, MEK 3/6, MEK 4/7, ZAP-70, LAT, SRC, LCK, ERK 1/2, Rsk 1, PYK2, SYK, PDK1, GSK3, FKHR, AFX, PLCγ, PLCy, NF-kB, FAK, CREB, αIIIβ3, FcεRI, BAD, p70S6K, STAT1, STAT2, STAT3, STAT5, STAT6, or any combination thereof. The disease or disorder can be characterized by an aberrant signaling of the first transducer.

In some embodiments, the unique cell state comprises: a physiological state, optionally a cell cycle state, a differentiation state, a development state, a metabolic state, or a combination thereof; and/or a pathological state, optionally a disease state, a human disease state, a diabetic state, an immune disorder state, a neurodegenerative disorder state, an oncogenic state, or a combination thereof. The unique cell state and/or unique cell type can be characterized by one or more of cell proliferation, stress pathways, oxidative stress, stress kinase activation, DNA damage, lipid metabolism, carbohydrate regulation, metabolic activation including Phase I and Phase II reactions, Cytochrome P-450 induction or inhibition, ammonia detoxification, mitochondrial function, peroxisome proliferation, organelle function, cell cycle state, morphology, apoptosis, DNA damage, metabolism, signal transduction, cell differentiation, cell-cell interaction and cell to non-cellular compartment. The unique cell state and/or unique cell type can be characterized by one or more of acute phase stress, cell adhesion, AH-response, anti-apoptosis and apoptosis, antimetabolism, anti-proliferation, arachidonic acid release, ATP depletion, cell cycle disruption, cell matrix disruption, cell migration, cell proliferation, cell regeneration, cell-cell communication, cholestasis, differentiation, DNA damage, DNA replication, early response genes, endoplasmic reticulum stress, estogenicity, fatty liver, fibrosis, general cell stress, glucose deprivation, growth arrest, heat shock, hepatotoxicity, hypercholesterolemia, hypoxia, immunotox, inflammation, invasion, ion transport, liver regeneration, cell migration, mitochondrial function, mitogenesis, multidrug resistance, nephrotoxicity, oxidative stress, peroxisome damage, recombination, ribotoxic stress, sclerosis, steatosis, teratogenesis, transformation, disrupted translation, transport, and tumor suppression. The unique cell state and/or unique cell type can be characterized by one or more of nutrient deprivation, hypoxia, oxidative stress, hyperproliferative signals, oncogenic stress, DNA damage, ribonucleotide depletion, replicative stress, and telomere attrition, promotion of cell cycle arrest, promotion of DNA-repair, promotion of apoptosis, promotion of genomic stability, promotion of senescence, and promotion of autophagy, regulation of cell metabolic reprogramming, regulation of tumor microenvironment signaling, inhibition of cell stemness, survival, and invasion.

In some embodiments, the cell type is: an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, a zymogenic cell, or any combination thereof. The stem cell can comprise an embryonic stem cell, an induced pluripotent stem cell (iPSC), a hematopoietic stem/progenitor cell (HSPC), or any combination thereof.

The context-dependent promoter can comprise a tissue-specific promoter and/or a lineage-specific promoter. The tissue specific promoter can be a liver-specific thyroxin binding globulin (TBG) promoter, an insulin promoter, a glucagon promoter, a somatostatin promoter, a pancreatic polypeptide (PPY) promoter, a synapsin-1 (Syn) promoter, a creatine kinase (MCK) promoter, a mammalian desmin (DES) promoter, a hSynapsin promoter, a α-myosin heavy chain (a-MIC) promoter, or a cardiac Troponin T (cTnT) promoter. The tissue specific promoter can be a neuronal activity-dependent promoter and/or a neuron-specific promoter, optionally a synapsin-1 (Syn) promoter, a CaMKIIa promoter, a calcium/calmodulin-dependent protein kinase II a promoter, a tubulin alpha I promoter, a neuron-specific enolase promoter, a platelet-derived growth factor beta chain promoter, TRPV1 promoter, a $Na_v1.7$ promoter, a $Na_v1.8$ promoter, a $Na_v1.9$ promoter, or an Advillin promoter. The tissue specific promoter can be a muscle-specific promoter, optionally the muscle-specific promoter comprises a creatine kinase (MCK) promoter. The expression of a payload protein can be linked to the expression of a GVS protein via a tandem gene expression element, optionally a tandem gene expression element selected from the group comprising an internal ribosomal entry site (IRES), foot-and-mouth disease virus 2A peptide (F2A), equine rhinitis A virus 2A peptide (E2A), porcine teschovirus 2A peptide (P2A) or Thosea asigna virus 2A peptide (T2A), or any combination thereof. In some embodiments, the GVA genes and GVS genes have sequences codon optimized for expression in a eukaryotic cell. The GVs can comprise a GVS variant engineered to present a tag enabling clustering in the cell.

Nucleic acid composition can be complexed or associated with one or more lipids or lipid-based carriers, thereby forming liposomes, lipid nanoparticles (LNPs), lipoplexes, and/or nanoliposomes, optionally encapsulating the nucleic acid composition. The nucleic acid composition is, comprises, or further comprises, one or more vectors. At least one of the one or more vectors can be a viral vector, a plasmid, a transposable element, a naked DNA vector, a lipid nanoparticle (LNP), or any combination thereof. The viral vector can be an AAV vector, a lentivirus vector, a retrovirus vector, an adenovirus vector, a herpesvirus vector, a herpes simplex virus vector, a cytomegalovirus vector, a vaccinia virus vector, a MVA vector, a baculovirus vector, a vesicular stomatitis virus vector, a human papillomavirus vector, an avipox virus vector, a Sindbis virus vector, a VEE vector, a Measles virus vector, an influenza virus vector, a hepatitis B virus vector, an integration-deficient lentivirus (IDLV) vector, or any combination thereof. The transposable element can be piggybac transposon or sleeping beauty transposon. The one or more gas vesicle (GV) polynucleotides can be situated on the same vector or two or more separate vectors.

The plasmid can comprise an origin of replication, optionally a low-copy, a medium-copy, or a high-copy origin of replication, further optionally the origin of replication is selected from the group comprising a low copy number modified pSC101 origin of replication, a RK2 origin of replication, a wildtype pSC101 origin of replication, a p15a origin of replication, and a pACYC origin of replication, derivatives thereof, or any combination thereof. The vector can be capable of being maintained within the probiotic bacterial cell in the absence of antibiotic selection for at least five days, optionally the probiotic bacterial cell comprises a toxin-antitoxin stability cassette, further optionally Axe-Txe. The composition can comprise: a polynucleotide encoding a toxin and/or an antitoxin, optionally one or more elements of the Axe-Txe type II toxin anti-toxin system, further optionally the nucleic acid composition is capable of being retained in a probiotic bacterial cell without antibiotic selection for at least about 10 days, about 20 days, about 40 days, about 80 days, about 80 days, or about 100 days. The probiotic bacterial cell chromosome can comprise a polynucleotide encoding a toxin and/or antitoxin, optionally one or more elements of the Axe-Txe type II toxin anti-toxin system. The probiotic bacterial cell can comprise a polynucleotide conferring resistance to an antibiotic, optionally the antibiotic is selected from the group comprising phleomycin D1 (ZEOCIN™), kanamycin, spectinomycin, streptomycin, ampicillin, carbenicillin, bleomycin, erythromycin, polymyxin B, tetracycline and chloramphenicol, further optionally the nucleic acid composition comprises said polynucleotide conferring resistance to an antibiotic.

The composition can comprise: one or more gene(s) encoding one or more detectable protein(s), optionally a detectable protein selected from the group comprising green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), TagRFP, Dronpa, Padron, mScarlet, mApple, mCitrine, mCherry, mruby3, rsCherry, rsCherryRev, derivatives thereof, or any combination thereof, further optionally said one or more detectable protein(s) are co-expressed with the one or more GVS gene(s) and/or the one or more GVA gene(s).

The nucleic acid composition can be configured to express the GVS gene(s) at a higher stoichiometry relative to the GVA gene(s), optionally about 1.1-fold to about 9-fold higher (e.g., 1.1-fold, 1.2-fold, 1.3-fold, 1.4-fold, 1.5-fold, 1.6-fold, 1.7-fold, 1.8-fold, 1.8-fold, 1.9-fold, 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, or a number or a range between any of these values) stoichiometry. The probiotic bacterial cell and/or mammalian cell can be robust to mutations reducing or abrogating GV expression. The probiotic bacterial cell and/or mammalian cell can be robust to said mutations for at least about 5 days, about 10 days, about 20 days, about 40 days, about 80 days, about 80 days, or about 100 days, of continuous culture and/or presence in a subject. In some embodiments, the GVs do not comprise GvpC, and wherein the absence of the GvpC enhances the nonlinear signal in xAM imaging of said GVs. The GVs can comprise a GvpC variant. The GvpC variant can comprise: a protease-sensing GvpC protein comprising at least one protease recognition site inserted within the central portion and/or attached to at least one of the N-terminus and the C-terminus of the Gyp; and/or a $Ca^{2+}$-sensing GvpC protein comprising a $Ca^{2+}$-binding domain and an interaction domain.

The nucleic acid composition and/or probiotic bacterial cell can comprise a DNA sequence that is at least 80%, 85%, 90%, 95%, 98%, 99%, or 100% identical to SEQ ID NO: 1, or a portion thereof. The nucleic acid composition and/or mammalian cell can comprise a DNA sequence that is at least 80%, 85%, 90%, 95%, 98%, 99%, or 100% identical to SEQ ID NO: 2 and/or SEQ ID NO: 3, or a portion thereof. The nucleic acid compositions provided herein can comprise one or more components/features (e.g., promoter, GVA gene, GVS gene, tandem gene expression element, terminator, operators) of the $bARG_{Ser}$ construct (SEQ ID NO: 1;

FIG. 28) or the mARG$_{Ana}$ plasmid set: SEQ ID NO: 2 (FIG. 29A) and SEQ ID NO: 3 (FIG. 29B). Provided herein are nucleic acids that are at least 80%, 85%, 90%, 95%, 98%, 99%, or 100% identical to SEQ ID NOS: 1-3, portions thereof, and/or complements thereof. Also provided herein are nucleic acids that comprise at least about 5 consecutive nucleotides (e.g., about 5 nt, about 10 nt, about 15 nt, about 20 nt, 25 nt, 30 nt, 35 nt, 40 nt, 45 nt, 50 nt, 60 nt, 70 nt, 80 nt, 90 nt, 100 nt, 110 nt, 120 nt, 128 nt, 130 nt, 140 nt, 150 nt, 160 nt, 170 nt, 180 nt, 190 nt, 200 nt, 210 nt, 220 nt, 230 nt, 240 nt, 250 nt, 260 nt, 270 nt, 280 nt, 290 nt, 300 nt, 310 nt, 320 nt, 330 nt, 340 nt, 350 nt, 360 nt, 370 nt, 380 nt, 390 nt, 400 nt, 410 nt, 420 nt, 430 nt, 440 nt, 450 nt, 460 nt, 470 nt, 480 nt, 490 nt, 500 nt, 510 nt, 520 nt, 530 nt, 540 nt, 550 nt, 560 nt, 570 nt, 580 nt, 590 nt, 600 nt, 610 nt, 620 nt, 630 nt, 640 nt, 650 nt, 660 nt, 670 nt, 680 nt, 690 nt, 700 nt, 710 nt, 720 nt, 730 nt, 740 nt, 750 nt, 760 nt, 770 nt, 780 nt, 790 nt, 800 nt, 810 nt, 820 nt, 830 nt, 840 nt, 850 nt, 860 nt, 870 nt, 880 nt, 890 nt, 900 nt, 910 nt, 920 nt, 930 nt, 940 nt, 950 nt, 960 nt, 970 nt, 980 nt, 990 nt, 10000 nt, 50000 nt, or a number or a range between any two of these values) of a sequence described by SEQ ID NOS: 1-3, or a complement thereof. The sequence identity between a component/feature (e.g., promoter, promoter, GVA gene, GVS gene, tandem gene expression element, terminator, operators) of the disclosed construct and the sequence of a feature of any one of SEQ ID NOS: 1-3 can be, or be about, 0.000000001%, 0.00000001%, 0.0000001%, 0.000001%, 0.00001%, 0.0001%, 0.001%, 0.01%, 0.1%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, or a number or a range between any two of these values.

The nucleic acid composition can comprise: a polynucleotide encoding a toxin and/or an antitoxin, such as one or more elements of the Axe-Txe type II toxin anti-toxin system. The nucleic acid composition can be capable of being retained in a probiotic cell without antibiotic selection for at least about 10 days, about 20 days, about 40 days, about 80 days, about 80 days, about 100 days, or a number or a range between any two of the values.

Vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

The nucleic acid composition can be single-stranded or double-stranded. The nucleic acid composition can contain two or more nucleic acids. The two or more nucleic acids can be in the same form (e.g., a first plasmid and a second plasmid) or different in forms (e.g., a first plasmid and a first viral vector). In some embodiments, the probiotic cells described herein also comprise a kill switch. Suitable kill switches are described in International Patent Application PCT/US2016/39427, filed Jun. 24, 2016, published as WO2016/210373, the contents of which are herein incorporated by reference in their entirety. The kill switch is intended to actively kill engineered microbes in response to external stimuli. As opposed to an auxotrophic mutation where bacteria die because they lack an essential nutrient for survival, the kill switch is triggered by a particular factor in the environment that induces the production of toxic molecules within the microbe that cause cell death.

The composition can comprise: one or more promoters operably connected to one or more secondary gas vesicle (sGV) polynucleotides comprising: one or more gas vesicle assembly (GVA) gene(s) encoding one or more GVA protein (s); and one or more gas vesicle structural (GVS) gene(s) encoding one or more GVS protein(s), wherein the one or more GVA protein(s) and the one or more GVS protein(s) are capable of forming secondary gas vesicles (sGVs) upon expression in a probiotic bacterial cell and/or a mammalian cell, wherein the GVs and the sGVs differ in composition with respect to at least one GVA protein and/or GVS protein, and wherein the sGVs comprise distinctive mechanical, acoustic, surface and/or magnetic properties as compared to the GVs. The GVs and sGVs can be configured to be expressed in different cell types and/or different cell states.

In some embodiments, the GVs have a first buckling pressure profile. The first buckling pressure profile can comprise a buckling function from which a GV buckling amount can be determined for a given pressure value. The buckling amount can comprise the amount of nonlinear contrast. The first buckling pressure profile can comprise a first buckling threshold pressure where a GV starts to buckle and produce nonlinear contrast, a first optimum buckling pressure where a GV exhibits maximum buckling and produces the highest level of nonlinear contrast, a first collapse pressure wherein a GV collapses, any pressure between the first buckling threshold pressure and the first optimum buckling pressure, and any pressure between the first optimum buckling pressure and the first collapse pressure. The sGV can have a second buckling pressure profile. The second buckling pressure profile can comprise a buckling function from which a sGV buckling amount can be determined for a given pressure value. The buckling amount can comprise the amount of nonlinear contrast. The second buckling pressure profile can comprise a second buckling threshold pressure where a sGV starts to buckle and produce nonlinear contrast, a second optimum buckling pressure where a sGV exhibits maximum buckling and produces the highest level of nonlinear contrast, a second collapse pressure wherein a sGV collapses, any pressure between the second buckling threshold pressure and the second optimum buckling pressure, and any pressure between the second optimum buckling pressure and the second collapse pressure. The first buckling pressure profile and the second buckling pressure profile can be different. A selectable buckling pressure can be the pressure value which produces the maximal difference in buckling between a GV and a sGV. The selectable buckling pressure can be: from about 40 kPa to about 1500 kPa; any collapse pressure within the first buckling pressure profile; any collapse pressure within the second buckling pressure profile; the first optimum buckling pressure; and/or the second optimum buckling pressure.

The GV can have a first collapse pressure profile. The first collapse pressure profile can comprise a collapse function from which a GV collapse amount can be determined for a given pressure value. The first collapse pressure profile can comprise a first initial collapse pressure where 5% or lower of a plurality of GVs are collapsed, a first midpoint collapse pressure where 50% of a plurality of GVs are collapsed, a first complete collapse pressure where at least 95% of a plurality of GVs are collapsed, any pressure between the first initial collapse pressure and the first midpoint collapse pressure, and any pressure between the first midpoint collapse pressure and the first complete collapse pressure. In some embodiments, a first selectable collapse pressure is: any collapse pressure within the first collapse pressure profile; selected from the first collapse pressure profile at a value between 0.05% collapse of a plurality of GVs and 95% collapse of a plurality of GVs; equal to or greater than the first initial collapse pressure; equal to or greater than the first midpoint collapse pressure; and/or equal to or greater than the first complete collapse pressure. The sGV can have a second collapse pressure profile. The second collapse pressure profile can comprise a collapse function from which a sGV collapse amount can be determined for a given pressure value. The first collapse pressure profile and the second collapse pressure profile can be different. A midpoint of the second collapse profile can have a higher pressure component than a midpoint of the first collapse profile. The second collapse pressure profile can comprise a second initial collapse pressure where 5% or lower of a plurality of sGVs are collapsed, a second midpoint collapse pressure where 50% of a plurality of sGVs are collapsed, a second complete collapse pressure where at least 95% of a plurality of sGVs are collapsed, any pressure between the second initial collapse pressure and the second midpoint collapse pressure, and any pressure between the second midpoint collapse pressure and the second complete collapse pressure. In some embodiments, a second selectable collapse pressure is: any collapse pressure within the second collapse pressure profile; selected from the second collapse pressure profile at a value between 0.05% collapse of a plurality of sGVs and 95% collapse of a plurality of sGVs; equal to or greater than the second initial collapse pressure; equal to or greater than the second midpoint collapse pressure; and/or equal to or greater than the second complete collapse pressure.

Methods of Imaging and Treatment

Disclosed herein include methods of treating or preventing a disease or disorder in a subject. In some embodiments, the method comprises: administering to the subject an effective amount of a composition disclosed herein; and applying ultrasound (US) to a target site of the subject, thereby monitoring the treatment or prevention of the disease or disorder. In some embodiments, upon administration, the probiotic bacterial cells accumulate in one or more target sites of the subject, optionally hypoxic environments and/or immunosuppressive environments, further optionally the necrotic core of a solid tumor.

Disclosed herein include methods of monitoring a cell-based therapy. In some embodiments, the method comprises: administering to a subject an effective amount of the reporting therapeutic cell(s) disclosed herein; and applying ultrasound (US) to a target site of the subject, thereby monitoring the cell-based therapy. In some embodiments, monitoring the cell-based therapy comprises: monitoring the mass and/or function of the administered reporting therapeutic cells, and/or determining the ratio of functional reporting therapeutic cells post-administration. The reporting therapeutic cells can be administered to a target site of the subject. The administering can comprise transplantation of the reporting therapeutic cells, optionally transplantation at one or more target sites, optionally the target site comprises a site of disease or disorder or is proximate to a site of a disease or disorder. In some embodiments, the cell-based therapy is a transplant and/or tissue replacement. The administering can comprise implanting the reporting therapeutic cells into a target site of the subject.

Disclosed herein include methods of imaging a target site of a subject. In some embodiments, the method comprises: administering to the subject an effective amount of a composition disclosed herein; and applying ultrasound (US) to the target site of the subject to obtain a US image of the target site, optionally a nonlinear US image.

Disclosed herein include methods of imaging gene expression within a subject. In some embodiments, the method comprises: administering to the subject an effective amount of a composition disclosed herein; and applying ultrasound (US) to the target site of the subject to obtain a US image of gene expression at the target site, optionally a nonlinear US image.

Disclosed herein include methods of imaging gene expression within target cells. In some embodiments, the method comprises: administering to the subject an effective amount of a composition disclosed herein; and applying ultrasound (US) to said target cells to obtain a US image of gene expression of target cells at the target site, optionally a nonlinear US image.

Disclosed herein include methods of detecting a unique cell type and/or unique cell state within a subject. In some embodiments, the method comprises: administering to the subject an effective amount of a composition disclosed herein; and applying ultrasound (US) to the target site of the subject, thereby detecting the unique cell type and/or unique cell state within said subject.

In some embodiments, the administering step comprises: (i) isolating target cells from the subject; introducing a nucleic acid composition and/or a delivery composition disclosed herein into said target cells; and administering to the subject an effective amount of said target cells; (ii) administering to the subject an effective amount of the probiotic bacterial cells, the reporting therapeutic cell(s), and/or the mammalian cells of disclosed herein; and/or (iii) administering to the subject an effective amount of the delivery composition disclosed herein. In some embodiments, the target cells are situated within a target site of a subject, and wherein applying US comprises applying US to the target site to obtain a US image of the target site; the target cells are situated within a plurality of target sites of a subject, and wherein applying US comprises applying US to the plurality of target sites to obtain US images of the plurality of target sites, and/or applying US to the target site comprises applying US to a plurality of target sites of a subject, optionally the target cells comprise the probiotic bacterial cells, the reporting therapeutic cell(s), and/or the mammalian cells disclosed herein. In some embodiments, the target cells are situated within a target site of a subject, and wherein applying US comprises applying US to the target site to obtain a US image of the target site.

In some embodiments, the target cells in a unique cell type and/or a unique cell state express GVs, and wherein said GVs produce nonlinear ultrasound contrast. In some embodiments, applying US causes the production of unique cell type-dependent and/or unique cell state-dependent nonlinear ultrasound contrast. In some embodiments, detecting a unique cell type and/or unique cell state can comprise detecting an at least about 1 dB enhancement in nonlinear ultrasound contrast.

The term "contrast enhanced imaging" or "imaging", as used herein indicates a visualization of a target site performed with the aid of a contrast agent administered to the target site to improve the visibility of structures or fluids by devices process and techniques suitable to provide a visual representation of a target site. Accordingly a contrast agent is a substance that enhances the contrast of structures or fluids within the target site, producing a higher contrast image for evaluation.

The term "ultrasound imaging" or ultrasound scanning" or "sonography" as used herein indicate imaging performed with techniques based on the application of ultrasound. Ultrasound can refer to sound with frequencies higher than the audible limits of human beings, typically over 20 kHz. Ultrasound devices typically can range up to the gigahertz range of frequencies, with most medical ultrasound devices operating in the 1 to 18 MHz range. The amplitude of the waves relates to the intensity of the ultrasound, which in turn relates to the pressure created by the ultrasound waves. Applying ultrasound can be accomplished, for example, by sending strong, short electrical pulses to a piezoelectric transducer directed at the target. Ultrasound can be applied as a continuous wave, or as wave pulses as will be understood by a skilled person.

Accordingly, the wording "ultrasound imaging" as used herein can refer to in particular to the use of high frequency sound waves, typically broadband waves in the megahertz range, to image structures in the body. The image can be up to 3D with ultrasound. In particular, ultrasound imaging typically involves the use of a small transducer (probe) transmitting high-frequency sound waves to a target site and collecting the sounds that bounce back from the target site to provide the collected sound to a computer using sound waves to create an image of the target site. Ultrasound imaging allows detection of the function of moving structures in real-time. Ultrasound imaging works on the principle that different structures/fluids in the target site will attenuate and return sound differently depending on their composition. A contrast agent sometimes used with ultrasound imaging are microbubbles created by an agitated saline solution, which works due to the drop in density at the interface between the gas in the bubbles and the surrounding fluid, which creates a strong ultrasound reflection. Ultrasound imaging can be performed with conventional ultrasound techniques and devices displaying 2D images as well as three-dimensional (3-D) ultrasound that formats the sound wave data into 3-D images. In addition to 3D ultrasound imaging, ultrasound imaging also encompasses Doppler ultrasound imaging, which uses the Doppler Effect to measure and visualize movement, such as blood flow rates. Types of Doppler imaging includes continuous wave Doppler, where a continuous sinusoidal wave is used; pulsed wave Doppler, which uses pulsed waves transmitted at a constant repetition frequency, and color flow imaging, which uses the phase shift between pulses to determine velocity information which is given a false color (such as red=flow towards viewer and blue=flow away from viewer) superimposed on a grey-scale anatomical image. Ultrasound imaging can use linear or non-linear propagation depending on the signal level. Harmonic and harmonic transient ultrasound response imaging can be used for increased axial resolution, as harmonic waves are generated from non-linear distortions of the acoustic signal as the ultrasound waves insonate tissues in the body. Other ultrasound techniques and devices suitable to image a target site using ultrasound would be understood by a skilled person.

The basic physics of sound waves enables ultrasound to visualize biological tissues with high spatial and temporal resolution. This capability has been enhanced by the development of acoustic biomolecules proteins with physical properties enabling them to scatter sound. The first acoustic biomolecules developed as contrast agents in ultrasound imaging, analogous to GFPs used in optical imaging, were based on a unique class of air-filled protein nanostructures called gas vesicles (GVs). The advancement of GVs has made it possible to use ultrasound to visualize the functions of cells deep inside tissues.

The term "ultrasound" can refer to sound with frequencies higher than the audible limits of human beings, typically over 20 kHz. Ultrasound devices typically can range up to the gigahertz range of frequencies, with most medical ultrasound devices operating in the 0.2 to 18 MHz range. The amplitude of the waves relates to the intensity of the ultrasound, which in turn relates to the pressure created by the ultrasound waves. Applying ultrasound can be accomplished, for example, by sending strong, short electrical pulses to a piezoelectric transducer directed at the target. Ultrasound can be applied as a continuous wave, or as wave pulses as will be understood by a person skilled in focused ultrasound. U.S. Patent Application Publication No. 2020/0237346 describes methods comprising the application of a step function increase in acoustic pressure during ultrasound imaging using gas vesicle contrast, along with capturing successive frames of ultrasound imaging and extracting time-series vectors for pixels of the frames, the content of which is hereby expressly incorporated by reference in its entirety. In some embodiments, the first, second, third, fourth, fifth, and/or sixth US pulse(s) each comprise a set of pulses.

Focused ultrasound ("FUS") can refer to the technology that uses ultrasound energy to target specific areas of a subject, such as a specific area of a brain or body. FUS focuses acoustic waves by employing concave transducers that usually have a single geometric focus, or an array of ultrasound transducer elements which are actuated in a spatiotemporal pattern such as to produce one or more focal zones. At this focus or foci most of the power is delivered during sonication in order to induce mechanical effects, thermal effects, or both. The frequencies used for focused ultrasound are in the range of 200 KHz to 8000 KHz.

As used herein, the term "harmonic signal" or "harmonic frequency" can refer to a frequency in a periodic waveform that is an integer multiple of the frequency of the fundamental signal. In addition, this term encompasses subharmonic signals, which are signals with a frequency equal to an integral submultiple of the frequency of the fundamental signal. In ultrasound imaging, the transmitted pulse is typically centered around a fundamental frequency, and received signals may be processed to isolate signals centered around the fundamental frequency or one or more harmonic frequencies.

The term "fundamental signal" or "fundamental wave" can refer to the primary frequency of the transmitted ultrasound pulse. All GVs can backscatter ultrasound at the fundamental frequency, allowing their detection by ultrasound.

The term "non-linear signal" can refer to a signal that does not obey superposition and scaling properties, with regards to the input. The term "linear signal" can refer to a signal that does obey those properties. One example of non-linearity is the production of harmonic signals in response to ultrasound excitation at a certain fundamental frequency. Another example is a non-linear response to acoustic pressure. One embodiment of such a non-linearity is the acoustic collapse profile of GVs, in which there is a non-linear relationship between the applied pressure and the disappearance of subsequent ultrasound contrast from the GVs as they collapse. Another example of a non-linear signal that does not involve the destruction of GVs, is the increase in both fundamental and harmonic signals with increasing pressure of the transmitted imaging pulse, wherein certain GVs exhibit a super-linear relationship between these signals and the pulse pressure.

The term "applying ultrasound" shall be given its ordinary meaning, and shall also refer to sending ultrasound-range acoustic energy to a target. The sound energy produced by the piezoelectric transducer can be focused by beamforming, through transducer shape, lensing, or use of control pulses. The soundwave formed is transmitted to the body, then partially reflected or scattered by structures within a body; larger structures typically reflecting, and smaller structures typically scattering. The return sound energy reflected/scattered to the transducer vibrates the transducer and turns the return sound energy into electrical signals to be analyzed for imaging. The frequency and pressure of the input sound energy can be controlled and are selected based on the needs of the particular imaging/delivery task and, in some methods described herein, collapsing GVs. To create images, particularly 2D and 3D imaging, scanning techniques can be used where the ultrasound energy is applied in lines or slices which are composited into an image.

In certain embodiments, the method includes applying a set of imaging pulses from an ultrasound transmitter to the target site, and receiving ultrasound signal at a receiver. In certain instances, the ultrasound signal detected by the receiver includes an ultrasound echo signal. Additional information of ultrasound systems and methods can be found in related publications as will be understood by a person skilled in the art.

Methods for performing ultrasound imaging are known in the art and can be employed in methods of the current disclosure. In certain aspects, an ultrasound transducer, which comprises piezoelectric elements, transmits an ultrasound imaging signal (or pulse) in the direction of the target site. Variations in the acoustic impedance (or echogenicity) along the path of the ultrasound imaging signal causes backscatter (or echo) of the imaging signal, which is received by the piezoelectric elements. The received echo signal is digitized into ultrasound data and displayed as an ultrasound image. Conventional ultrasound imaging systems comprise an array of ultrasonic transducer elements that are used to transmit an ultrasound beam, or a composite of ultrasonic imaging signals that form a scan line. The ultrasound beam is focused onto a target site by adjusting the relative phase and amplitudes of the imaging signals. The imaging signals are reflected back from the target site and received at the transducer elements. The voltages produced at the receiving transducer elements are summed so that the net signal is indicative of the ultrasound energy reflected from a single focal point in the subject. An ultrasound image is then composed of multiple image scan lines.

In some embodiments, imaging the target site is performed by applying or transmitting an imaging ultrasound signal from an ultrasound transmitter to the target site and receiving a set of ultrasound data at a receiver. The ultrasound data can be obtained using a standard ultrasound device, or can be obtained using an ultrasound device configured to specifically detect the contrast agent used. Obtaining the ultrasound data can include detecting the ultrasound signal with an ultrasound detector. In some embodiments, the imaging step further comprises analyzing the set of ultrasound data to produce an ultrasound image.

In certain embodiments, the ultrasound signal has a transmit frequency of at least 1 MHz, 5 MHz, 10 MHz, 20 MHz, 30 MHz, 40 MHz or 50 MHz. For example, an ultrasound data is obtained by applying to the target site an ultrasound signal at a transmit frequency from 4 to 11 MHz, or at a transmit frequency from 14 to 22 MHz. In some instances, the imaging frequency is selected so as to maximize the contrast generated by the administered contrast agent. In some embodiments, applying ultrasound (US) to the target site of the subject comprises applying US to a plurality of target sites of the subject.

In the embodiments herein described, the collapsing ultrasound and imaging ultrasound are selected to have a collapsing pressure and an imaging pressure amplitude based on the acoustic collapse pressure profile (e.g., peak acoustic pressure) of the GVPS type used. In some instances, the ultrasound pressure, including the collapsing ultrasound pressure and the imaging ultrasound pressure can be referred to as the "peak positive pressure" of the ultrasound pulses. The term "peak positive pressure" can refer to the maximum pressure amplitude of the positive pulse of a pressure wave, typically in terms of the difference between the peak pressure and the ambient pressure at the location in the person or specimen that is being imaged.

In some embodiments, imaging gene expression comprises: detecting an at least about 1 dB enhancement in nonlinear ultrasound contrast; and/or quantified GV expression over time as a volumetric sum of xAM signal over all acquired image planes. Applying US can comprise nonlinear US imaging. Applying US can comprise applying one or more US pulse(s) over a duration of time. The duration of time can be about 48 hours, about 44 hours, about 40 hours, about 35 hours, about 30 hours, about 25 hours, 20 hours, 15 hours, 10 hours, about 8 hours, about 8 hours, 8 hours, about 7 hours, about 6 hours, about 5 hours, about 4 hours, about 3 hours, about 2 hours, about 1 hour, about 30 minutes, about 15 minutes, about 10 minutes, or about 5 minutes. In some embodiments, the one or more US pulse(s) each have a pulse duration of about 1 hour, about 30 minutes, about 15 minutes, about 10 minutes, about 5 minutes, about 1 minute, about 1 second, or about 1 millisecond. Applying one or more US pulse(s) can comprise applying one or more focused US pulse(s). Applying one or more US pulse(s) can comprise applying US at a frequency of 100 kHz to 100 MHz. Applying one or more US pulse(s) can comprise applying ultrasound at a frequency of 0.2 to 1.5 mHz. Applying one or more US pulse(s) can comprise applying ultrasound having a mechanical index in a range between 0.2 and 0.6. The one or more US pulse(s) can comprise a peak pressure of about 40 kPa to about 800 kPa. The one or more US pulse(s) can comprise a peak pressure of about 70 kPa to about 150 kPa, and/or about 440 kPa to about 605 kPa. The one or more US pulse(s) can comprise a pressure value that is: the selectable buckling pressure; the first optimum buckling pressure; and/or equal to or less than the first initial collapse pressure. In some embodiments, the one or more US pulse(s) induces collapse of GVs, and wherein the one or more US pulse(s) comprise a pressure value that is the first selectable collapse pressure. The nonlinear ultrasound imaging can comprise cross-amplitude modulation (x-AM) ultrasound imaging or parabolic amplitude modulation (pAM) ultrasound imaging. The nonlinear ultrasound imaging can comprise differential nonlinear ultrasound imaging. In some embodiments, differential nonlinear ultrasound imaging can comprise imaging of the second and/or higher harmonics with the first harmonic signal subtracted out, further optionally cross-phase modulation imaging and/or harmonic imaging. The nonlinear ultrasound imaging can comprise providing amplitude modulation (AM) ultrasound pulse sequences.

In some embodiments, the nonlinear ultrasound imaging comprises: pairs of cross-propagating plane waves to elicit nonlinear scattering from buckling GVs at the wave intersection; subtracting the signal generated by transmitting each wave on its own; and quantifying the resulting contrast. In some embodiments, the signals generated by transmitting each wave on its own has linear characteristics and/or lower nonlinear characteristics than the combined transmission of both plane waves produced at their intersection. In some embodiments, the nonlinear ultrasound imaging comprises: a peak positive pressure of two single tilted plane waves exciting the GV in a linear scattering regime; a doubled X-wave intersection amplitude exciting the GV in a nonlinear scattering regime; summing the echoes from the two single tilted plane-wave transmissions to generate a sum; and subtracting the sum from the echoes of the X-wave transmissions to derive nonzero differential GV signals. Applying US can comprise detecting scattering of the one or more US pulse(s) by gas vesicles, optionally nonlinear scattering of the US by buckling gas vesicles. In some embodiments, detecting scattering comprises: detecting backscattered echoes of two half-amplitude transmissions at applied pressures below the buckling threshold of the GV, optionally said two half-amplitude transmissions trigger largely linear scattering, detecting backscattered echoes of a third full-amplitude transmission at pressures above the buckling threshold of the gas vesicles, optionally said third full-amplitude transmission triggers harmonic and nonlinear scattering, optionally the method comprises subtracting the backscattered echoes of the two half-amplitude transmissions from the backscattered echoes of the third full-amplitude transmission.

In some embodiments, the GVs have an acoustic collapse pressure threshold, and wherein applying ultrasound comprises: applying ultrasound to the target site at a peak positive pressure less than the acoustic collapse pressure threshold; increasing peak positive pressure (PPP) to above the selective acoustic collapse pressure value as a step function; and imaging the target site in successive frames during the increasing; and extracting a time-series vector for each of at least one pixel of the successive frames. The method can comprise: performing a signal separation algorithm on the time-series vectors using at least one template vector. In some embodiments, the signal separation algorithm includes template projection and/or template unmixing. In some embodiments, the at least one template vector includes linear scatterers, noise, gas vesicles, or a combination thereof. The successive frames can comprise a frame prior to GVs collapse, a frame during GVs collapse, and a frame after GVs collapse. In some embodiments, the increasing includes increasing the PPP to a hiBURST regime, optionally the PPP in hiBURST regime is 4.3 MPa or higher. In some embodiments, the increasing includes increasing the PPP to a loBURST regime, optionally the PPP in loBURST regime is no higher than 3.7 MPa. In some embodiments, the method comprises: single-cell imaging; and/or imaging a large volume in deep tissue. The method can comprise US imaging with a spatiotemporal resolution of less than about 100 μm and less than about 1 ms. In some embodiments, the target site comprises: a volume larger than about 1 mm3; a depth deeper than about 1 mm; a depth and/or a volume inaccessible via optical imaging and/or fiber photometry; and/or the entire brain or a portion thereof.

The disease or disorder can be associated with expression of a tumor antigen. The disease associated with expression of a tumor antigen can be selected from the group consisting of a proliferative disease, a precancerous condition, a cancer, and a non-cancer related indication associated with expression of the tumor antigen. The disease or disorder can be a blood disease, an immune disease, a neurological disease or disorder, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or any combination thereof, optionally a solid tumor. The cancer can be selected from the group consisting of colon cancer, rectal cancer, renal-cell carcinoma, liver cancer, non-small cell carcinoma of the lung, cancer of the small intestine, cancer of the esophagus, melanoma, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin lymphoma, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers, combinations of said cancers, and metastatic lesions of said cancers. The cancer can be a hematologic cancer chosen from one or more of chronic lymphocytic leukemia (CLL), acute leukemias, acute lymphoid leukemia (ALL), B-cell acute lymphoid leukemia (B-ALL), T-cell acute lymphoid leukemia (T-ALL), chronic myelogenous leukemia (CML), B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablastic lymphoma, plasmacytoid dendritic cell neoplasm, Waldenstrom macroglobulinemia, or pre-leukemia.

The method can comprise performing one or more biopsies guided on the basis of one or more US images, optionally said one or more biopsies and applying US are performed concurrently, further optionally biopsies targeting either the xAM-positive and/or the xAM-negative regions of a target site. The subject can have a disease of the GI tract. The disease of the GI tract can be an inflammatory bowel disease. The inflammatory bowel disease can comprise Crohn's disease, ulcerative colitis, irritable bowel syndrome, microscopic colitis, lymphocytic-plasmocytic enteritis, coeliac disease, collagenous colitis, lymphocytic colitis and eosinophilic enterocolitis, indeterminate colitis, infectious colitis, pseudomembranous colitis, ischemic inflammatory bowel disease or Behcet's disease. The target site can comprise a section or subsection of the GI tract. The section or subsection of the GI tract can be selected from the group consisting of the stomach, proximal duodenum, distal duodenum, proximal jejunum, distal jejunum, proximal ileum, distal ileum, proximal cecum, distal cecum, proximal ascending colon, distal ascending colon, proximal transverse colon, distal transverse colon, proximal descending colon and distal descending colon, or any combination thereof. In some embodiments, the target site comprises: (i) a site of disease or disorder or is proximate to a site of a disease or disorder, optionally the location of the one or more sites of a disease or disorder is predetermined, is determined during the method, or both, further optionally the target site is an immunosuppressive environment; (ii) target cell(s); and/or (iii) a tissue, optionally the tissue is inflamed tissue and/or infected tissue. The tissue can comprise adrenal gland tissue, appendix tissue, bladder tissue, bone, bowel tissue, brain tissue, breast tissue, bronchi, coronal tissue, ear tissue, esophagus tissue, eye tissue, gall bladder tissue, genital tissue, heart tissue, hypothalamus tissue, kidney tissue, large intestine tissue, intestinal tissue, larynx tissue, liver tissue, lung tissue, lymph nodes, mouth tissue, nose tissue, pancreatic tissue, parathyroid gland tissue, pituitary gland tissue, prostate tissue, rectal tissue, salivary gland tissue, skeletal muscle tissue, skin tissue, small intestine tissue, spinal cord, spleen tissue, stomach tissue, thymus gland tissue, trachea tissue, thyroid tissue, ureter tissue, urethra tissue, soft and connective tissue, peritoneal tissue, blood vessel tissue and/or fat tissue. In some embodiments, the tissue comprises: (i) grade I, grade II, grade III or grade IV cancerous tissue; (ii) metastatic cancerous tissue; (iii) mixed grade cancerous tissue; (iv) a sub-grade cancerous tissue; (v) healthy or normal tissue; and/or (vi) cancerous or abnormal tissue.

The target cell can comprise an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, a zymogenic cell, or any combination thereof, further optionally the stem cell comprises an embryonic stem cell, an induced pluripotent stem cell (iPSC), a hematopoietic stem/progenitor cell (HSPC), or any combination thereof.

The method can comprise: administering an effective amount of a transactivator-binding compound and/or chemical inducer to the subject. The transactivator-binding compound can comprise tetracycline, doxycycline or a derivative thereof, optionally the chemical inducer is L-arabinose or a derivative thereof. The administering can comprise systemic administration, optionally the systemic administration is intravenous, intramuscular, intraperitoneal, or intraarticular. Administering can comprise intracranial delivery, intrathecal administration, intracranial injection, aerosol delivery, nasal delivery, vaginal delivery, direct injection to any tissue in the body, intraventricular delivery, intraocular delivery, rectal delivery, buccal delivery, ocular delivery, local delivery, topical delivery, intracisternal delivery, intraperitoneal delivery, oral delivery, intramuscular injection, intravenous injection, subcutaneous injection, intranodal injection, intratumoral injection, intraperitoneal injection, intradermal injection, or any combination thereof. The period of time between the administering and applying can be about 21 days, about 14 days, about 7 days, about 3 days, about 48 hours, about 44 hours, about 40 hours, about 35 hours, about 30 hours, about 25 hours, 20 hours, 15 hours, 10 hours, about 8 hours, about 7 hours, about 6 hours, about 5 hours, about 4 hours, about 3 hours, about 2 hours, about 1 hour, about 30 minutes, about 15 minutes, about 10 minutes, or about 5 minutes. The subject can be a mammal, optionally the subject is not anesthetized. In some embodiments, the method does not comprise pre-expression of GVs under ideal laboratory conditions prior to the administering and/or the use of a global epigenetic activator.

The method can comprise: administering one or more additional agents to the subject, optionally a prodrug or a pro-death agent. The one or more additional agents can comprise a protein phosphatase inhibitor, a kinase inhibitor, a cytokine, an inhibitor of an immune inhibitory molecule, and/or or an agent that decreases the level or activity of a TREG cell. The one or more additional agents can comprise an immune modulator, an anti-metastatic, a chemotherapeutic, a hormone or a growth factor antagonist, an alkylating agent, a TLR agonist, a cytokine antagonist, a cytokine antagonist, or any combination thereof. The one or more additional agents can comprise a therapeutic agent useful for treating a disease of the GI tract, such as, for example: one of the following classes of compounds: 5-aminosalicyclic acids, corticosteroids, thiopurines, tumor necrosis factor-alpha blockers and JAK inhibitors; and/or one or more of Prednisone, Humira, Lialda, Imuran, Sulfasalazine, Pentasa, Mercaptopurine, Azathioprine, Apriso, Simponi, Enbrel, Humira Crohn's Disease Starter Pack, Colazal, Budesonide, Azulfidine, Purinethol, Proctosol HC, Sulfazine EC, Delzicol, Balsalazide, Hydrocortisone acetate, Infliximab, Mesalamine, Proctozone-HC, Sulfazine, Orapred ODT, Mesalamine, Azasan, Asacol HD, Dipentum, Prednisone Intensol, Anusol-HC, Rowasa, Azulfidine EN-tabs, Veripred 20, Uceris, Adalimumab, Hydrocortisone, Colocort, Pediapred, Millipred, Azathioprine injection, Prednisolone sodium phosphate, Flo-Pred, Aminosalicylic acid, Procto-Cream-HC, 5-aminosalicylic acid, Millipred DP, Golimumab, Prednisolone acetate, Rayos, Proctocort, Paser, Olsalazine, Procto-Pak, Purixan, Cortenema, Giazo, Vedolizumab, Entyvio, Micheliolide, and Parthenolide. The disease of the GI tract can be an inflammatory bowel disease.

Also disclosed herein are pharmaceutical compositions comprising one or more of the compositions (e.g, nucleic acid compositions, delivery compositions, mammalian cells, probiotic bacterial cells) disclosed herein and one or more pharmaceutically acceptable carriers. The compositions can also comprise additional ingredients such as diluents, stabilizers, excipients, and adjuvants. As used herein, "pharmaceutically acceptable" carriers, excipients, diluents, adjuvants, or stabilizers are nontoxic to the cell or subject being exposed thereto (preferably inert) at the dosages and concentrations employed or that have an acceptable level of toxicity as determined by the skilled practitioners. The carriers, diluents and adjuvants can include buffers such as phosphate, citrate, or other organic acids: antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, di saccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution An effective amount of the engineered cells (e.g., reporting therapeutic cells, mammalian cells, probiotic bacterial cells) can be at least about $10^4$ cells, at least about $10^6$ cells, at least about $10^6$ cells, at least about $10^7$ cells, at least about $10^8$ cells, at least about $10^9$, or at least about $10^{10}$. In another embodiment, the effective amount of the engineered cells (e.g., reporting therapeutic cells, mammalian cells, probiotic bacterial cells) is about $10^4$ cells, about $10^5$ cells, about $10^6$ cells, about $10^7$ cells, or about 10 cells. In one particular embodiment, the effective amount of the engineered cells (e.g., reporting therapeutic cells, mammalian cells, probiotic bacterial cells) is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg. In some embodiments, the administering step comprises administering a vector (e.g., viral vector) comprising a nucleic acid composition provided herein. The compositions (e.g, nucleic acid compositions, delivery compositions, mammalian cells, probiotic bacterial cells) disclosed herein may be included in a composition for administration. The composition may include a pharmaceutical composition and further include a pharmaceutically acceptable carrier.

EXAMPLES

Some aspects of the embodiments discussed above are disclosed in further detail in the following examples, which are not in any way intended to limit the scope of the present disclosure.

Example 1

Genomically Mined Acoustic Reporter Genes Enable Real-Time In Vivo Monitoring of Tumors and Tumor-Homing Probiotics As provided and discussed above, there is a need for next-generation ARGs that, when expressed heterologously in either probiotic bacterial strains or mammalian cancer cell lines, can produce GVs with strong nonlinear ultrasound contrast and enable robust, sustained expression under physiological conditions. These qualities would enable long-term noninvasive imaging of gene expression in a broad range of in vivo applications. It was hypothesized that a genomic mining approach—previously applied to improving fluorescent proteins, opsins Cas proteins, and other biotechnology tools—would yield ARGs with improved properties, which could be further optimized through genetic engineering. By cloning and screening 15 distinct polycistronic operons from a diverse set of GV-expressing species representing a broad phylogeny, two GV gene clusters were identified—from *Serratia* sp. 39006 and *Anabaena flos-aquae*—that produce vastly more linear and nonlinear acoustic contrast than previously tested clusters when expressed in several types of bacteria and mammalian cells, respectively. The bacterial ARG adapted from *Serratia* sp. 39006 ($bARG_{Ser}$), when expressed in the widely used probiotic bacterium *E. coli* Nissle 1917 (EcN), enabled noninvasive ultrasound imaging of these probiotic agents colonizing tumors, providing direct visualization of the microscale in vivo distribution of this rapidly emerging class of anti-cancer therapy. The mammalian ARG adapted from *A. flos-aquae* ($mARG_{Ana}$), when expressed in human breast cancer cells, enabled both the noninvasive, in situ microscale imaging and long-term monitoring of heterologous gene expression in developing orthotopic tumors, and the ultrasound-guided biopsy of a genetically defined subpopulation of these tumor cells. The properties and performance of these second-generation ARGs represent a fundamental advance in the utility of acoustic proteins for a wide range of in vivo research.

Results

Genomic Mining of Gas Vesicle Gene Clusters Reveals Homologs with Improved Ultrasound Performance in *E. coli*

GVs are encoded by polycistronic gene clusters comprising one or more copies of the primary structural gene gvpA and 7 to 20+ other genes encoding minor constituents, assembly factors or reinforcing proteins, which together help assemble the GVs' protein shells. Hundreds of organisms have GV genes in their genomes, but only a small subset have been shown to produce GVs. Given the labor involved in cloning and testing polycistronic clusters, the phylogenetic search was limited to organisms with confirmed GV production and sequenced operons. 11 representative species were selected, broadly sampling phylogenetic space, cluster architecture and organismal characteristics (i.e., halophilic, thermophilic and mesophilic) (FIG. 1A and FIG. 8). Each species was obtained from culture repositories, amplified GV operons from their genomes, and cloned them into a bacterial expression vector.

Each operon was then expressed in confluent *E. coli* patches at several temperatures and inducer concentrations (FIG. 1B), comparing them to two bacterial ARG constructs previously shown (Bourdeau et al. "Acoustic reporter genes for noninvasive imaging of microorganisms in mammalian hosts." Nature 553.7686 (2018): 86-90) to work in *E. coli*—bARG1 (*Anabaena flos-aquae Bacillus megaterium* hybrid) and *Bacillus megaterium* ΔgvpA-Q, as well as the full *Bacillus megaterium* gene cluster (FIGS. 1C-1G, FIGS. 9A-9E, FIGS. 10A-10C, FIGS. 11A-11B, FIGS. 12A-12D, FIGS. 13A-13B). These patches were scanned using a home-built robotic ultrasound imaging apparatus, applying a cross-propagating amplitude modulation pulse sequence (xAM). This pulse sequence enhances signals specific to nonlinear contrast agents such as GVs while cancelling linear background scattering. Importantly, unlike pulse sequences that relied on the irreversible collapse of GVs to obtain GV-specific contrast, xAM is nondestructive. In addition, the optical opacity of the patches was examined, which can be increased by sufficient levels of GV expression.

Figure 1C:
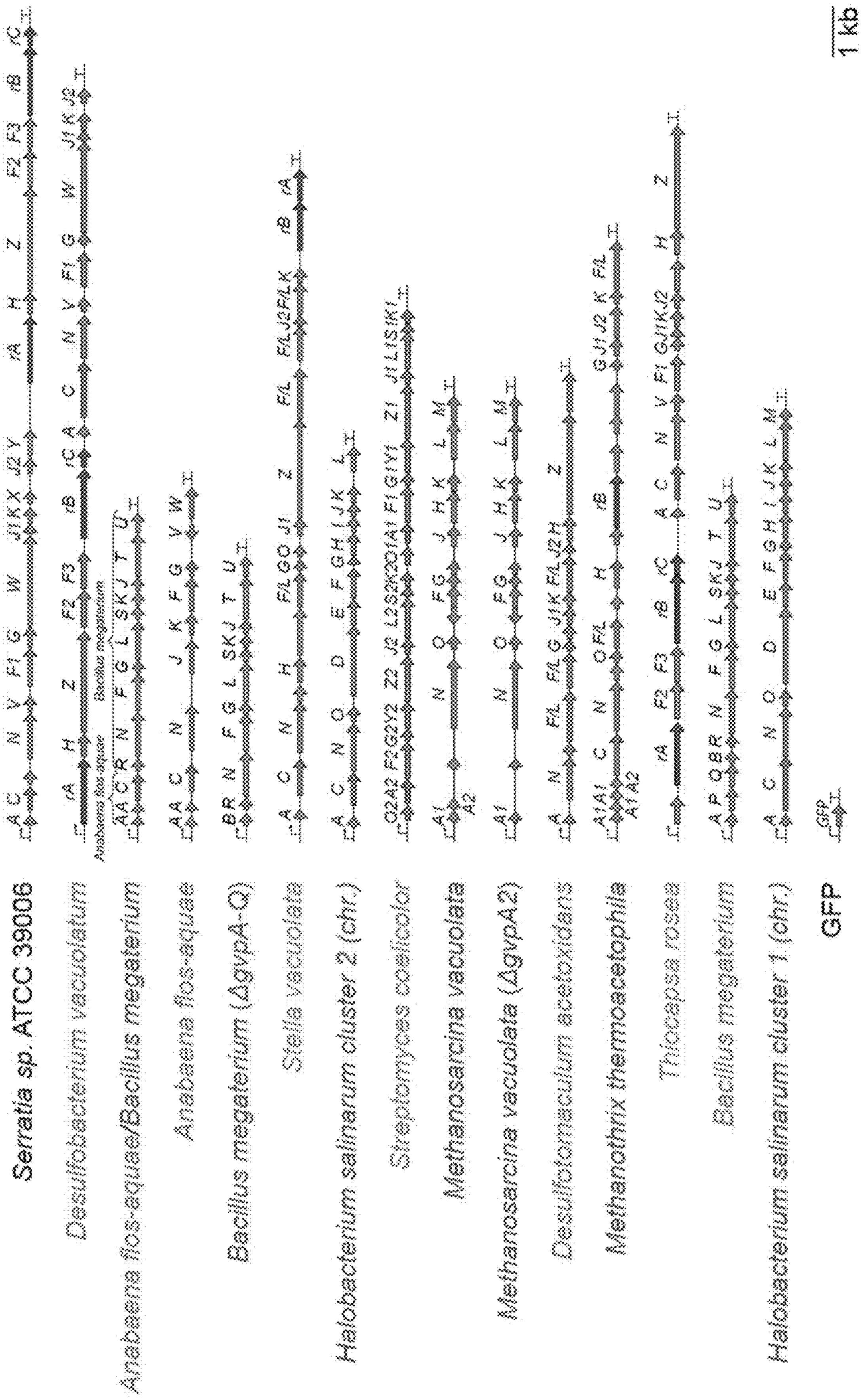
Figure 1E:
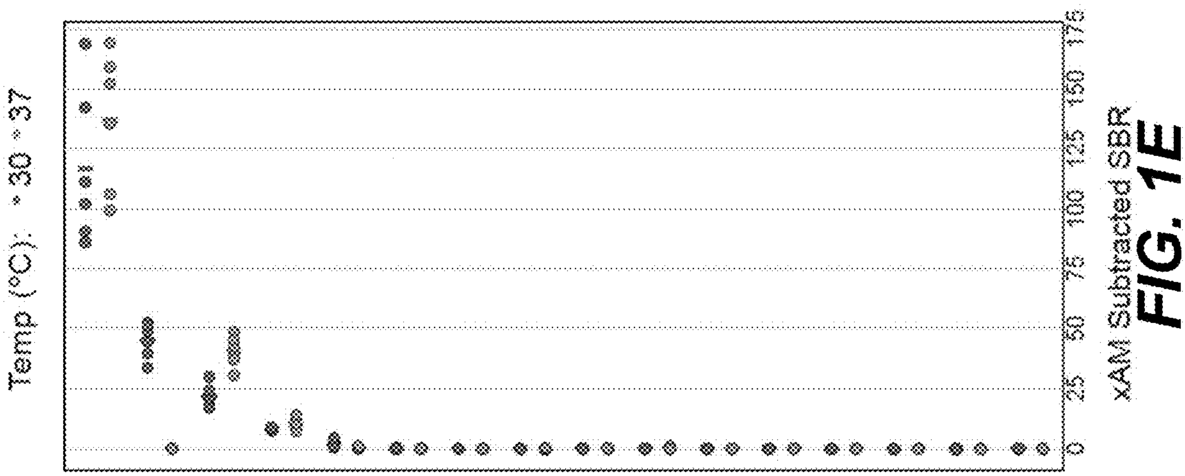
Figure 1D:
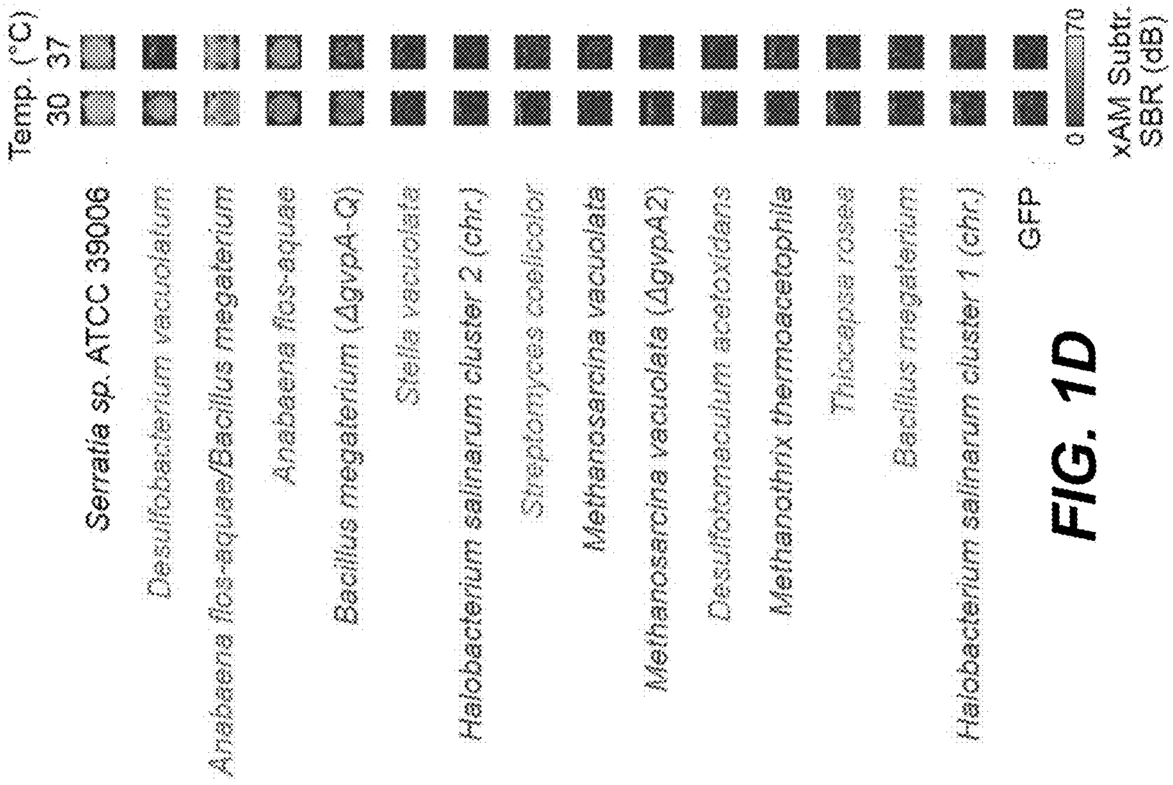
Figure 10D:
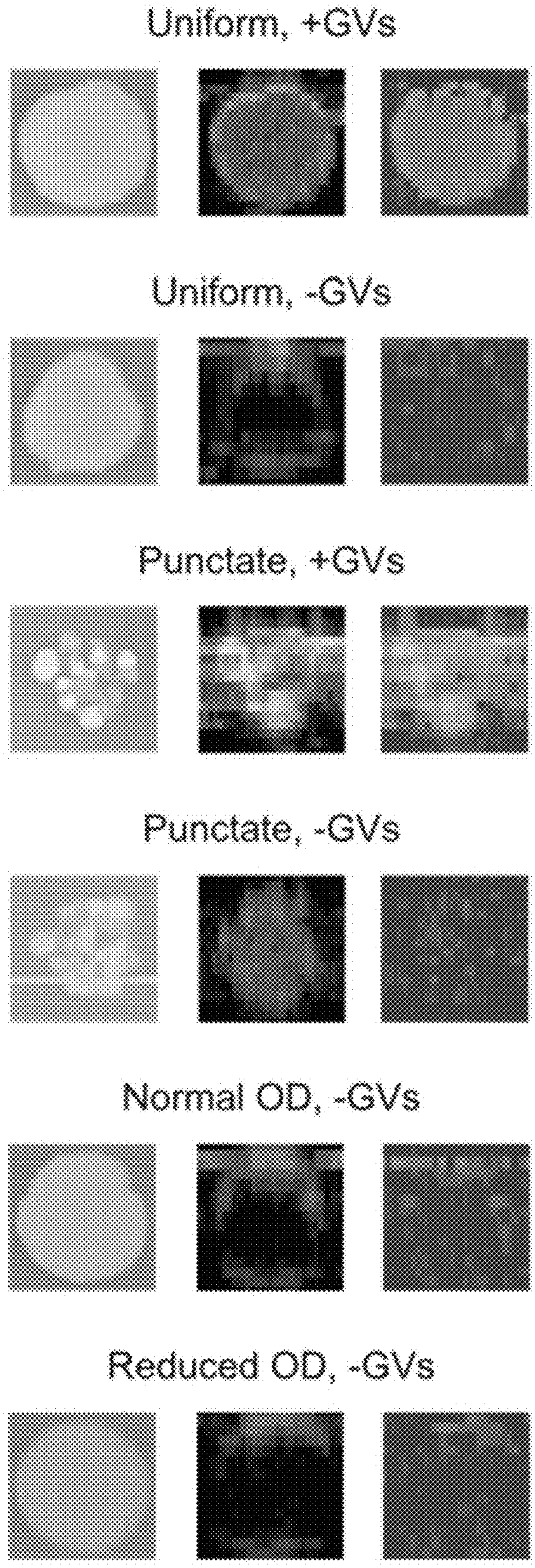

Of the 15 gene clusters tested, only 3 showed significant xAM signal when expressed at 37° C., and 5 showed significant xAM signal at 30° C. (FIGS. 1C-1E). Even though all operons tested are from organisms reported to produce GVs in their native hosts, only the *A. flos-aquae, B. megaterium* ΔgvpA-Q, bARG1*, Desulfobacterium vacuolatum*, and *Serratia* sp. 39006 (*Serratia*) clusters produced detectable GVs heterologously in *E. coli*. Several other operons produced a small amount of ultrasound contrast under certain conditions, which did not arise from GV expression but reflected a rough patch morphology likely due to cellular toxicity (FIG. 10D). The failure of most tested gene clusters to produce GVs in *E. coli* is not surprising given the complexity of polycistronic heterologous expression, which requires each component to fold and function properly in a new host with a potentially different cytoplasmic environment, growth temperature and turgor pressure. In addition, it is possible that some genes included in the clusters act as cis-regulators, limiting expression absent a specific trans input, or that some additional genes are required beyond the annotated operons.

In patch format, the strongest acoustic performance was observed with the genes from *Serratia*, bARG1, *A. flos-aquae, B. megateriaum*, and *D. vacuolatum*. Because patch experiments do not control for the density of cells in each sample, the performance of these clusters in resuspended samples was further compared. Each operon was expressed on solid media at 30° C.—a temperature at which all five operons produced GVs—then scraped, resuspended, and normalized for cell concentration. These samples were imaged in hydrogels using both xAM (FIGS. 1F-1G and FIGS. 14A-14B) and a more sensitive but destructive imaging method called BURST (FIG. 14C), and examined optically with phase-contrast microscopy (PCM), which reveals the presence of GVs due to the refractive index difference between GVs and water (FIG. 14D). Three of the clusters produced xAM signals, and all clusters produced BURST signals significantly stronger than the negative control. All clusters except *A. flos-aquae* exhibited sufficient GV expression to be visible by PCM.

Figure 1F:
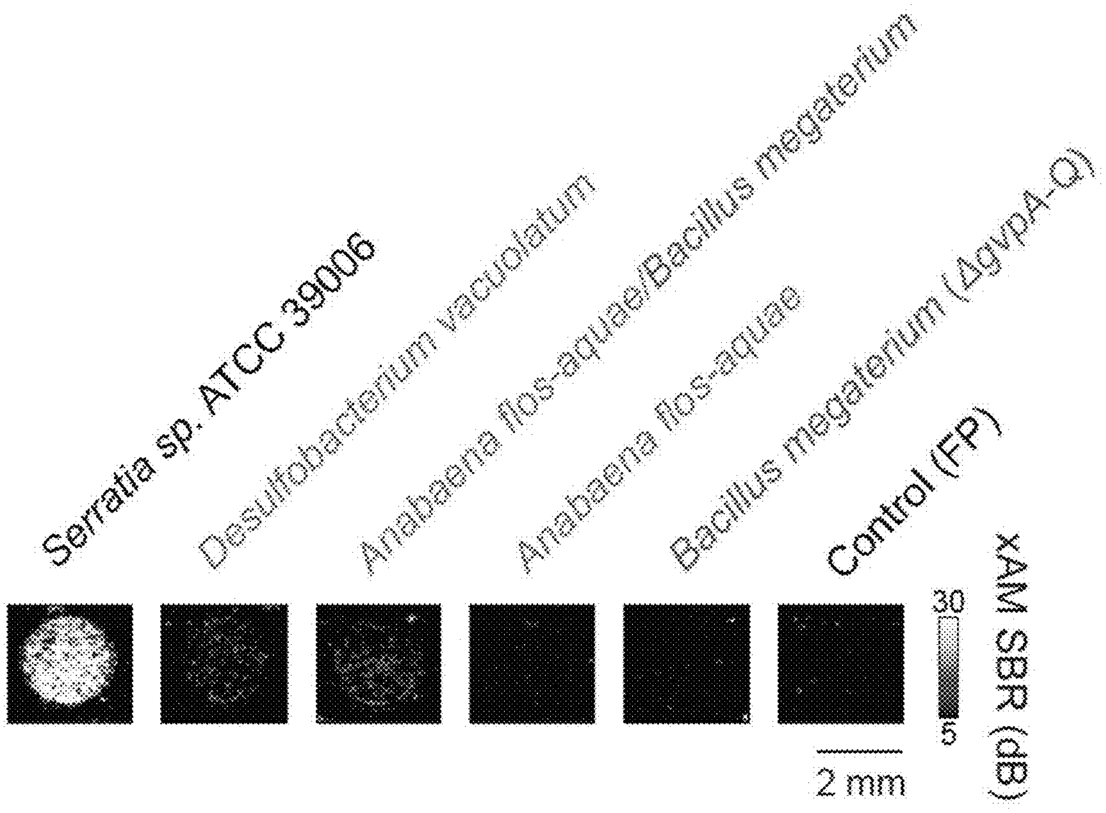
Figure 1G:
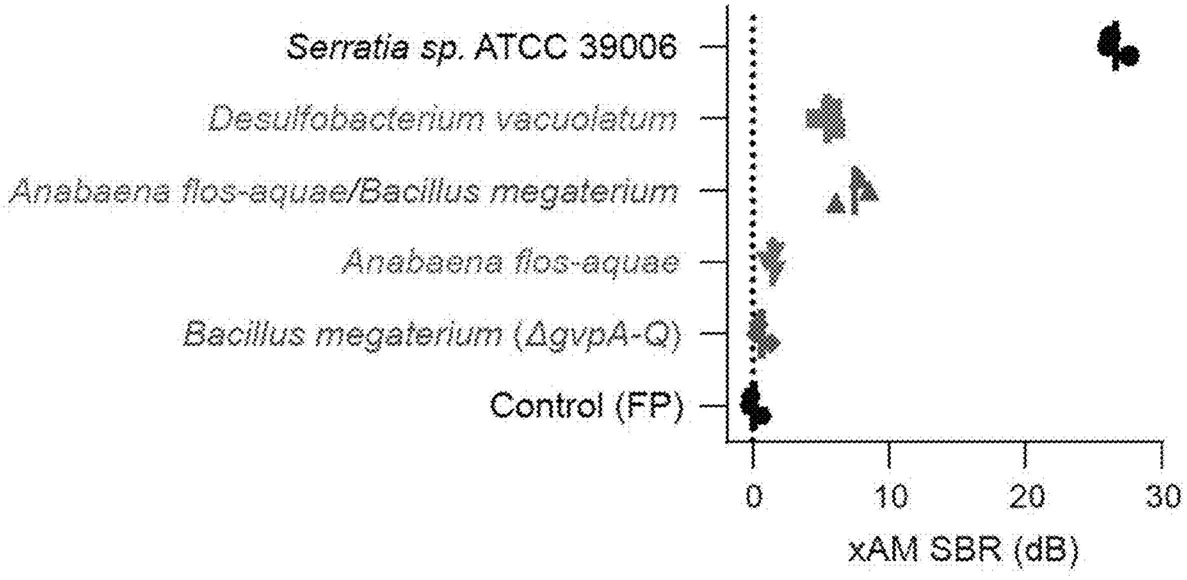
Figure 14E:
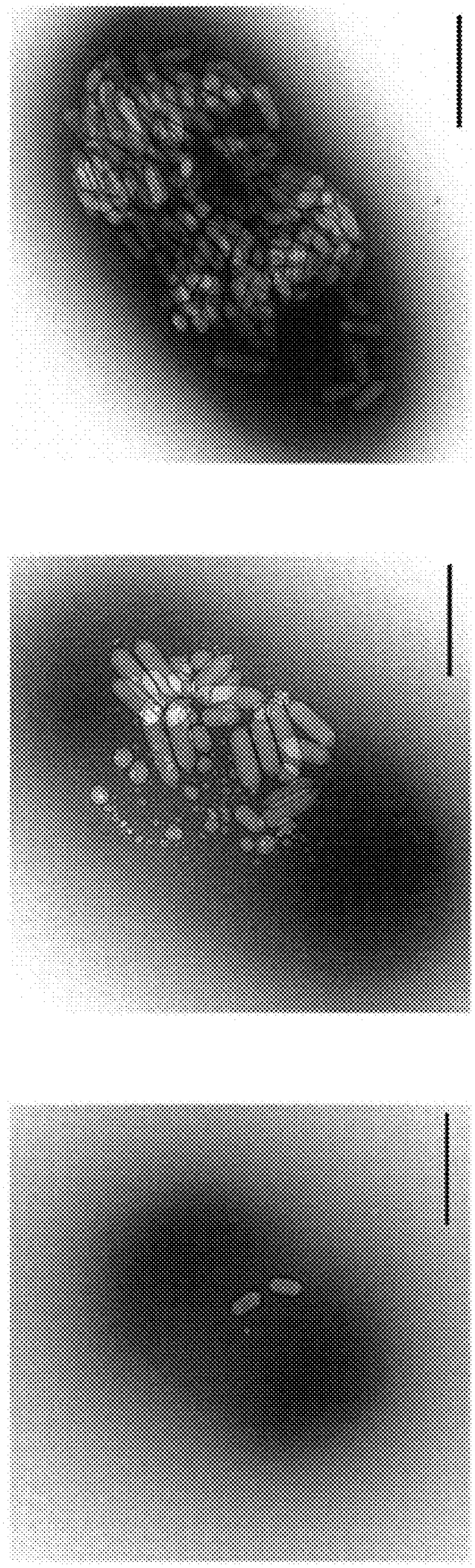

Cells expressing the *Serratia* cluster produced the strongest ultrasound signals, 19.2 dB above the next brightest cluster, bARG1, under xAM imaging at an applied acoustic pressure of 1.74 MPa: an 83-fold gain in signal intensity (FIG. 1F). Additionally, PCM images (FIG. 14D) showed that cells expressing the *Serratia* cluster had the highest levels of GV expression, as also seen in whole-cell transmission electron microscopy (TEM) (FIG. 14E). Based on the large improvement in ultrasound contrast provided by the *Serratia* GV operon relative to the other gene clusters, this operon was selected for further optimization as a second-generation bacterial ARG.

Figure 15B:
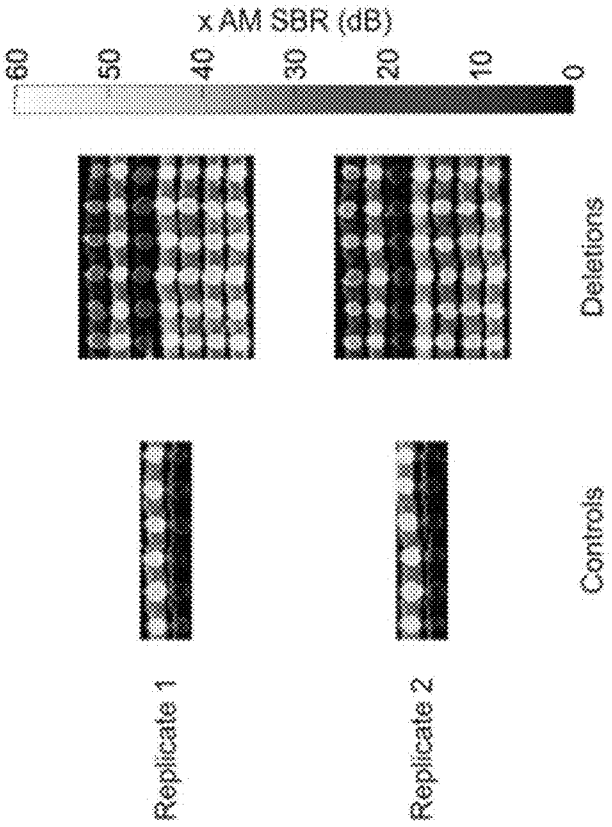
Figure 15A:
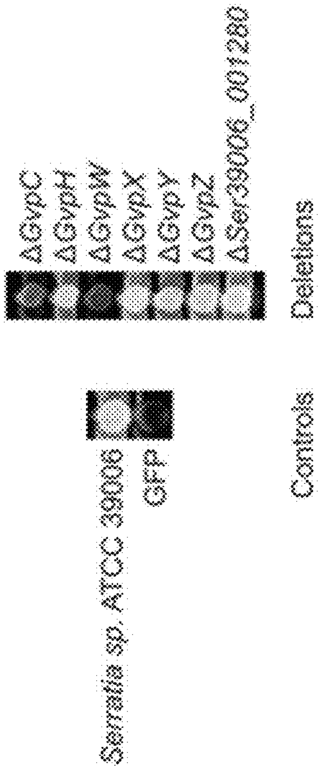
Figure 15D:
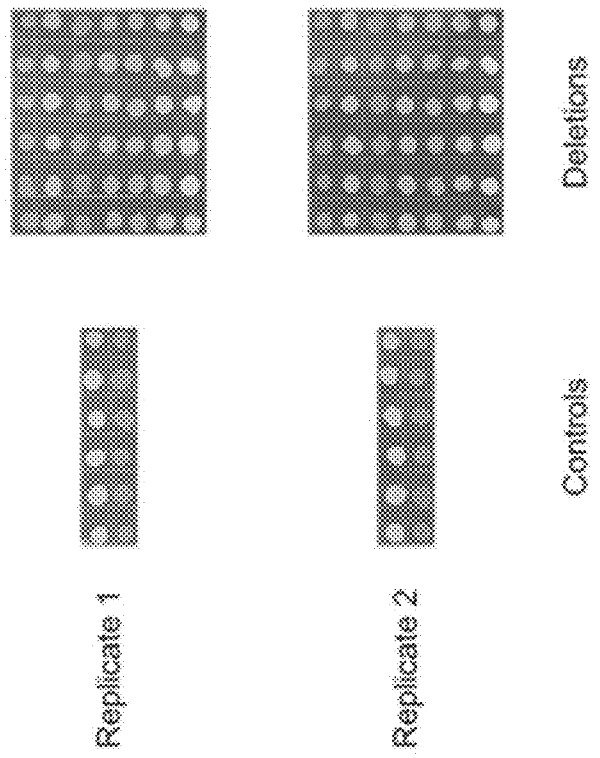
Figure 15C:
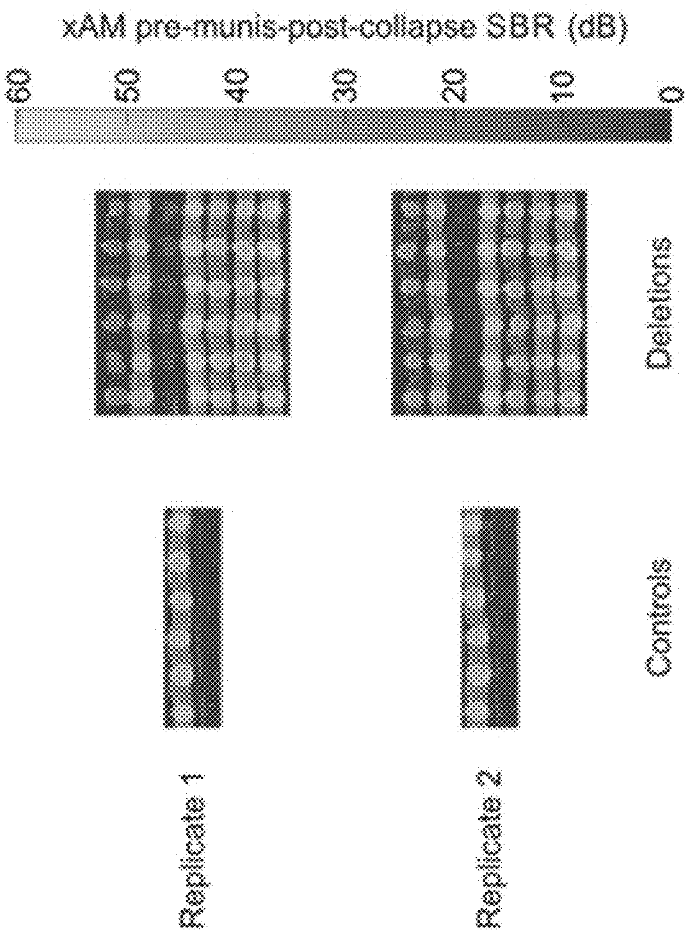
Figure 15E:
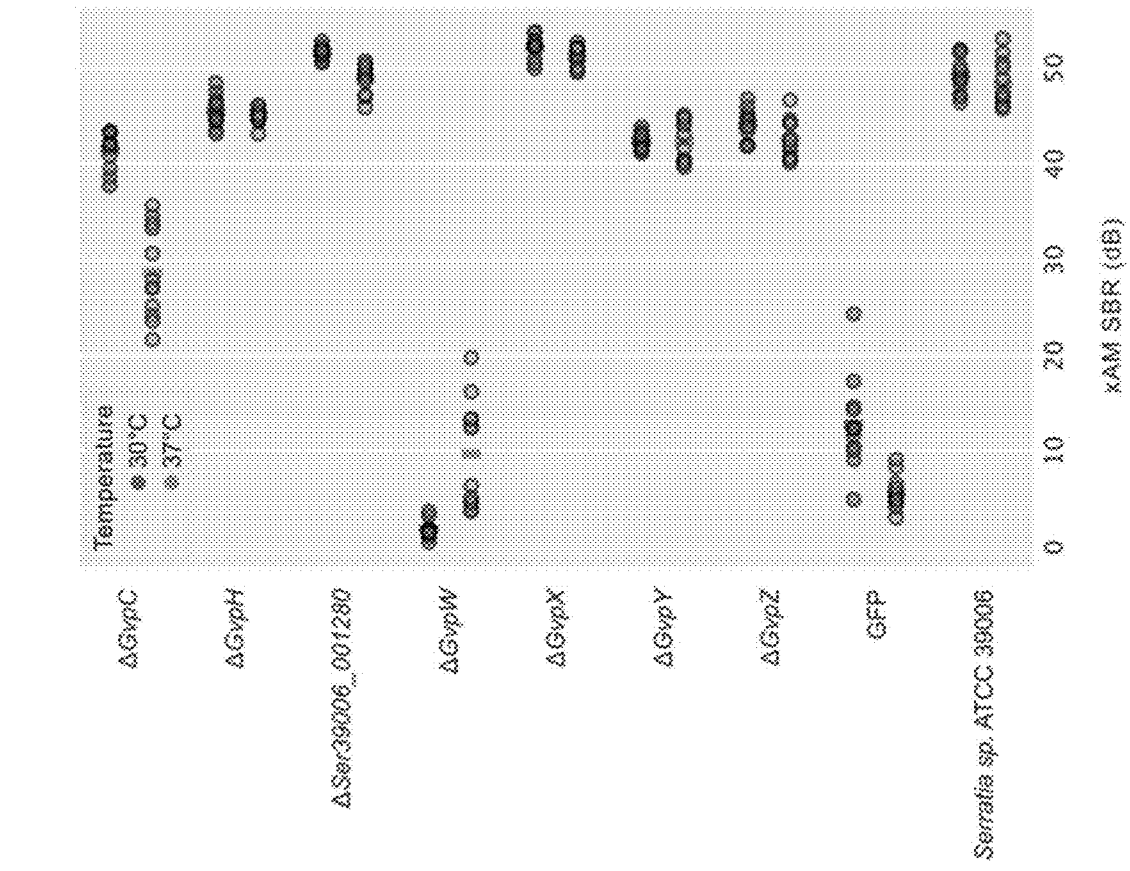
Figure 15F:
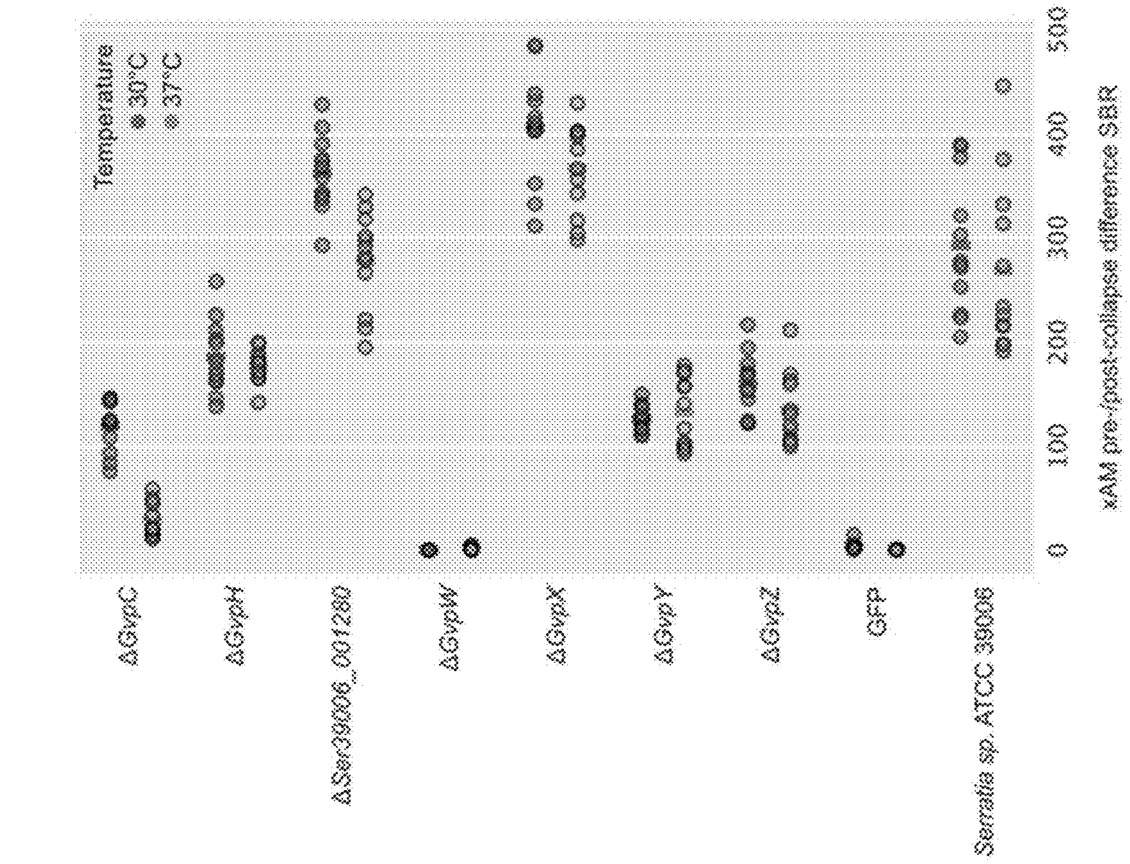

Because overexpression of any protein imposes a metabolic demand on the host cell, it was reasoned that deletion of non-essential genes could improve GV expression from the *Serratia* cluster, and therefore the xAM signal. Previous work showed that deletions of gvpC, gvpW, gvpX, gvpY, gvpH, or gvpZ preserve GV formation in the native organism. These deletions were tested, as well as the deletion of an unannotated hypothetical protein (Ser39006_001280) encoded between the gvpC and gvpN coding sequences (FIG. 15A). When expressed in *E. coli*, deletions of gvpC, gvpH, gvpW, gvpY, or gvpZ reduced or eliminated xAM signal (FIGS. 15B-15C) and patch opacity (FIG. 15D). Deletion of gvpX increased xAM signal but decreased opacity, and deletion of Ser39006_001280 increased both xAM signal and opacity. Based on these results, the *Serratia* ΔSer39006_001280 operon was selected for subsequent in vitro and in vivo experiments. This new genetic construct was called bARG$_{Ser}$—a bacterial acoustic reporter gene derived from *Serratia*.

bARG$_{Ser}$ Shows Robust Expression, Contrast, and Stability in *E. coli* Nissle bARG$_{Ser}$ was transferred into EcN, a strain of *E. coli* that is widely used in in vivo biotechnology applications due to its ability to persist in the gastrointestinal tract and colonize tumors. EcN has been intensely investigated as a chassis for anti-tumor therapy delivery, and is currently the most commonly used species in this application. Three different inducible promoter architectures were first tested in EcN on solid media at 37° C., examining xAM ultrasound contrast and patch opacity as a function of inducer concentration. It was found that the L-arabinose-inducible pBAD promoter provided the most robust control over GV expression without obvious burden (FIGS. 2A-2B, FIGS. 16A-16D). Based on these results, the pBAD-bARG$_{Ser}$ EcN strain was selected for subsequent experiments.

Figure 2A:
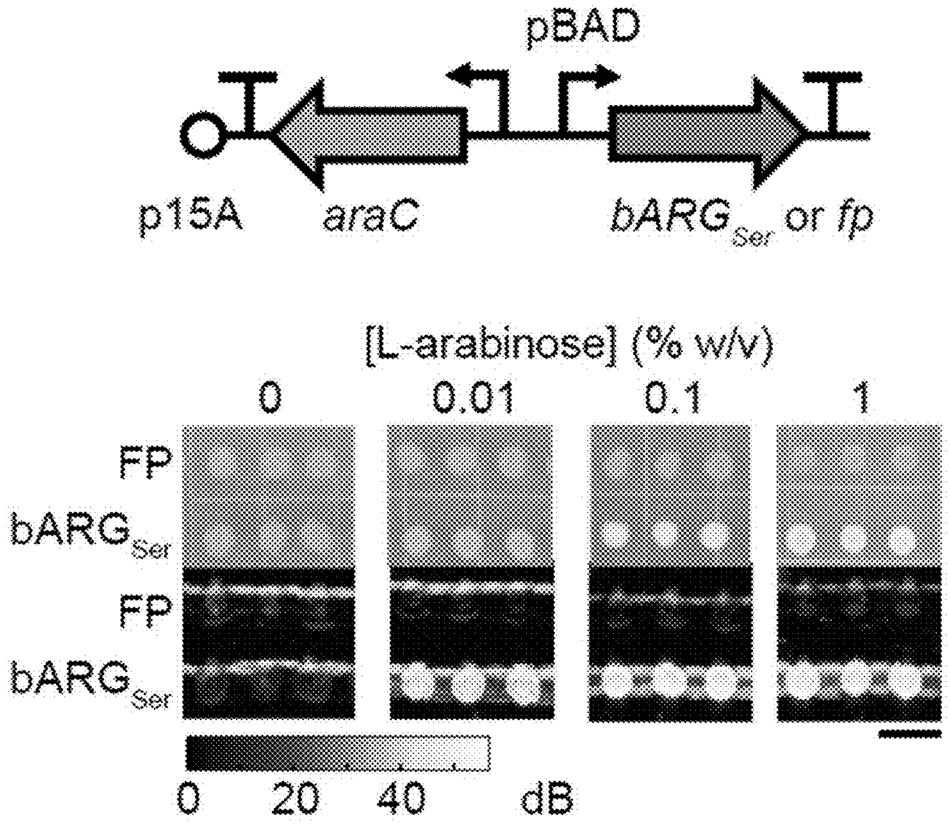
FIGS. 2A-2I depict non-limiting exemplary schematics and data related to genetic engineering and expression of $bARG_{Ser}$ in the probiotic bacterium *E. coli* Nissle (EcN).
Figure 2B:
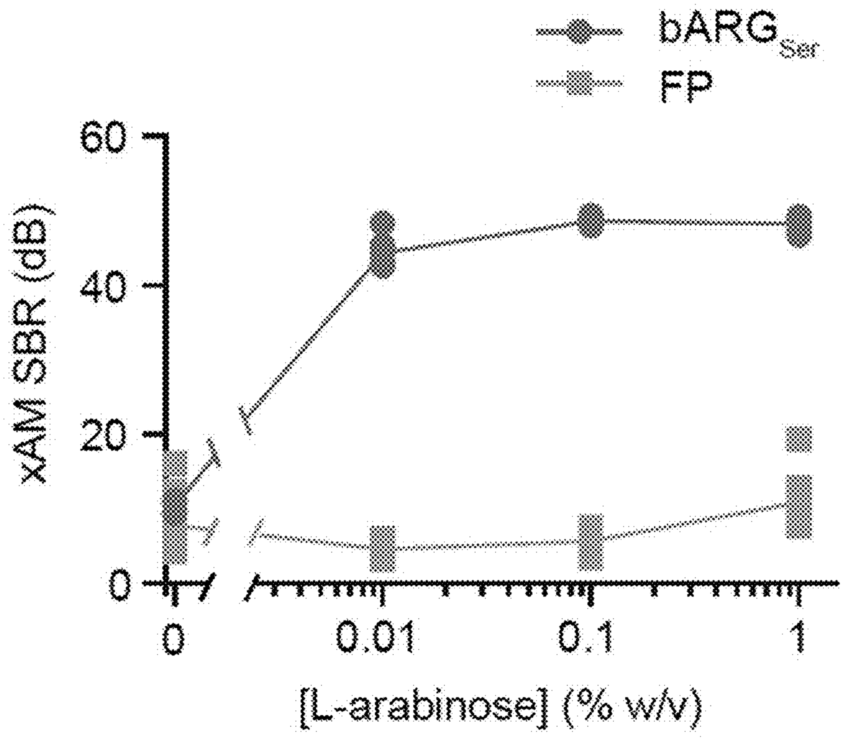
Figure 2C:
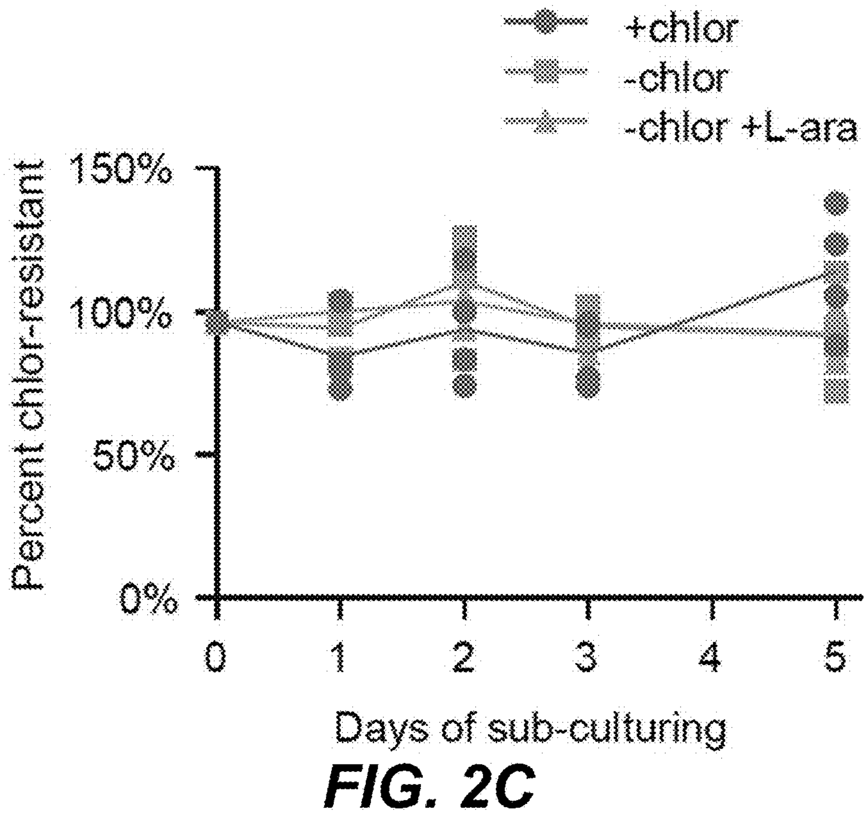
Figure 2D:
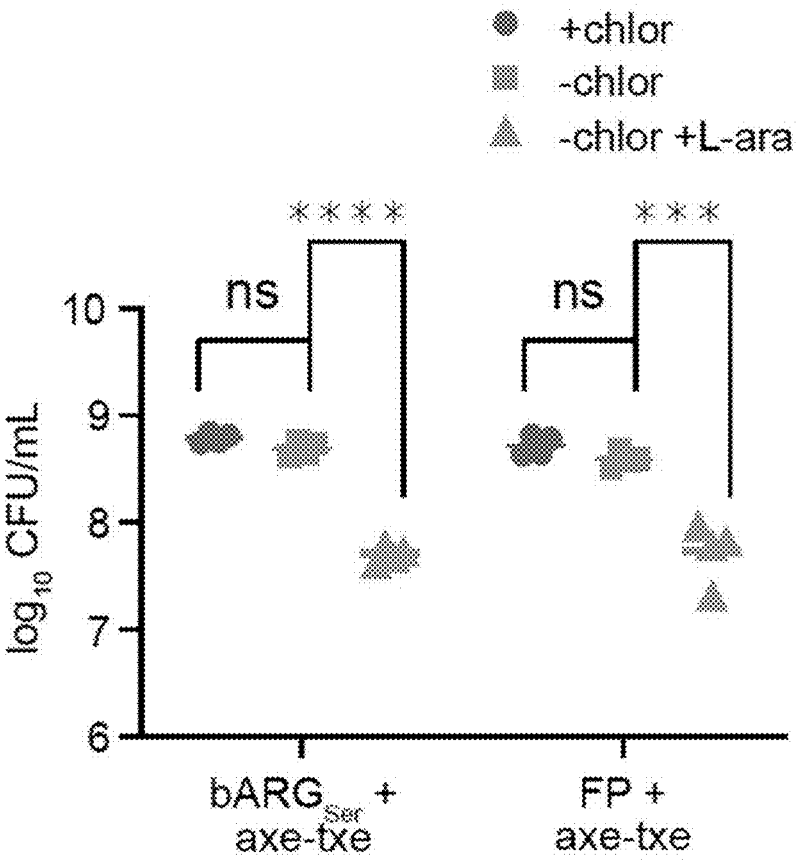

To ensure that the pBAD-bARG$_{Ser}$ plasmid is maintained in the absence of antibiotic selection, as required in certain in vivo applications, the toxin-antitoxin stability cassette Axe-Txe was added. This enabled the pBAD-bARG$_{Ser}$-AxeTxe plasmid to be maintained in EcN for up to 5 days of daily sub-culturing in liquid media without antibiotics, both with and without induction of ARG expression (FIG. 2C).

Figure 2E:
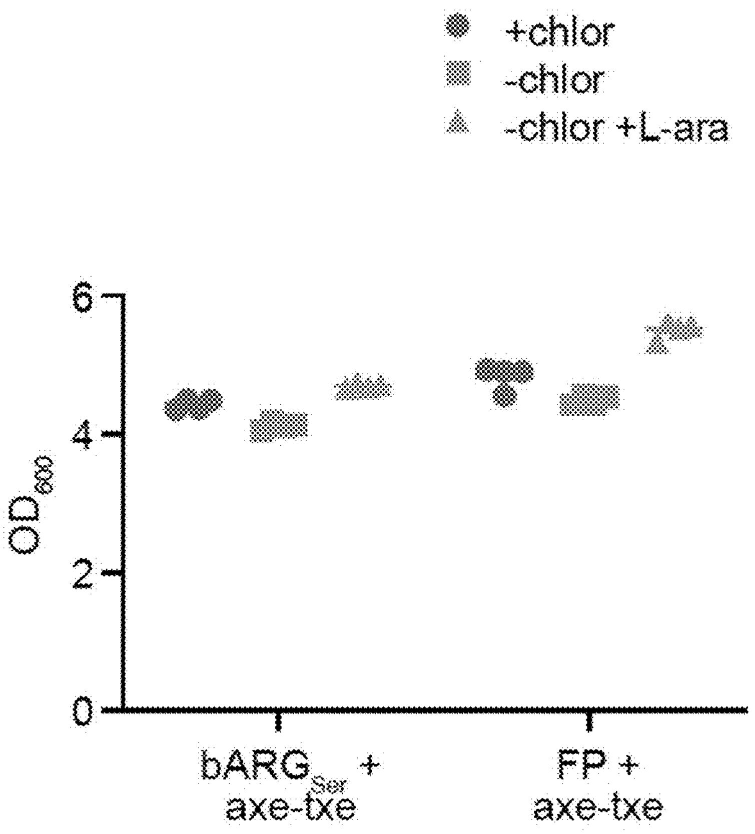
Figure 2F:
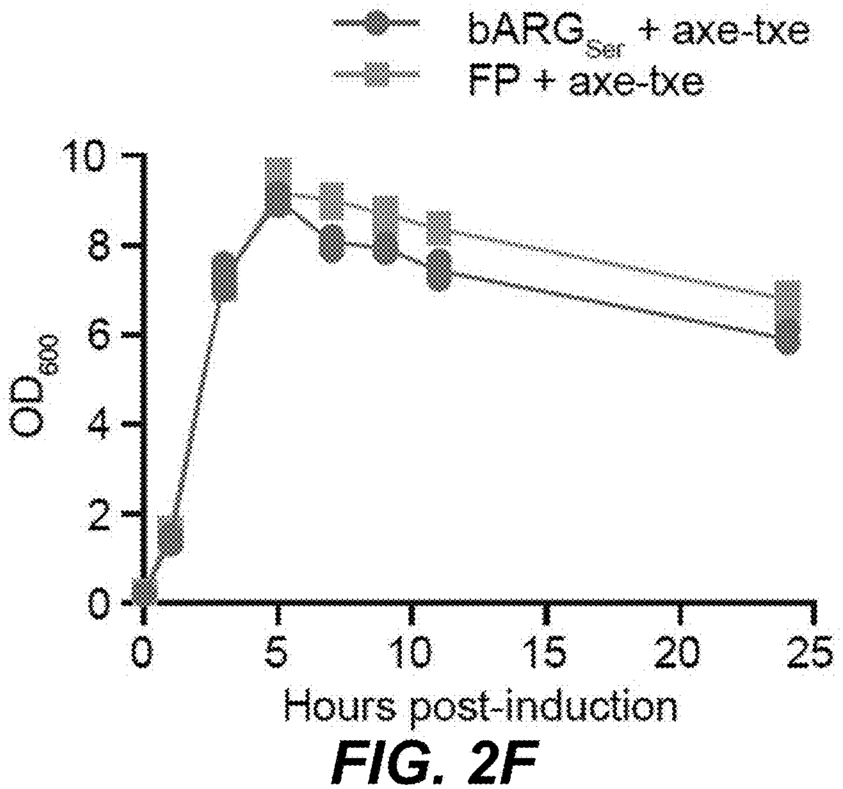
Figure 2G:
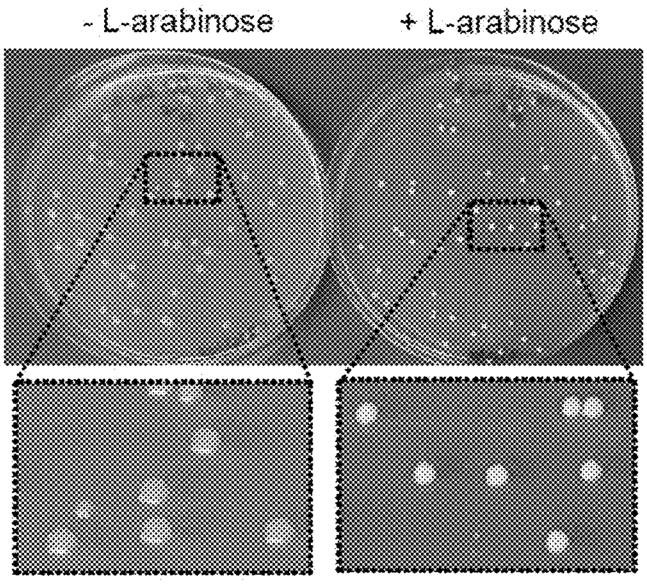

The expression of most heterologous genes, including widely used reporter genes such as fluorescent proteins (FPs), results in some degree of metabolic burden on engineered cells. Consistent with this expectation, the induction of pBAD-bARG$_{Ser}$ EcN resulted in reduced colony formation to an extent similar to the expression of a FP (FIG. 2D and FIG. 17A), even as the culture density measured by $OD_{600}$ remained relatively unchanged (FIG. 2E and FIG. 17B). When the $OD_{600}$ was measured after inducing cultures with L-arabinose, the growth curves of bARG$_{Ser}$-expressing and FP-expressing EcN were indistinguishable during the growth phase (0 to 5 hours), indicating that the two strains have similar growth rates (FIG. 2F). Collectively, these results suggest that overexpression of bARG$_{Ser}$ using the pBAD expression system in EcN is not significantly more burdensome than that of FPs, which are widely accepted as relatively non-perturbative indicators of cellular function.

Figure 2H:
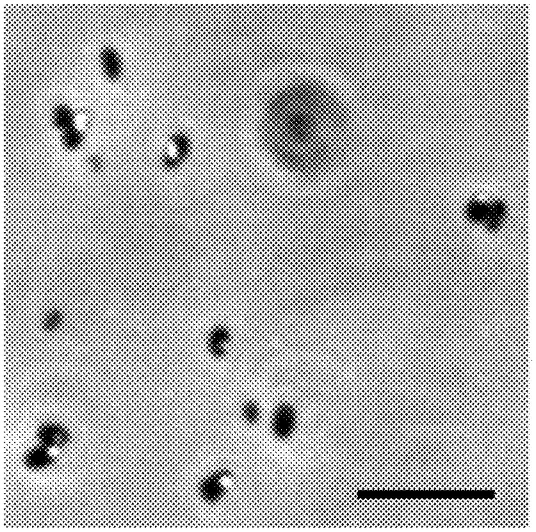
Figure 2I:
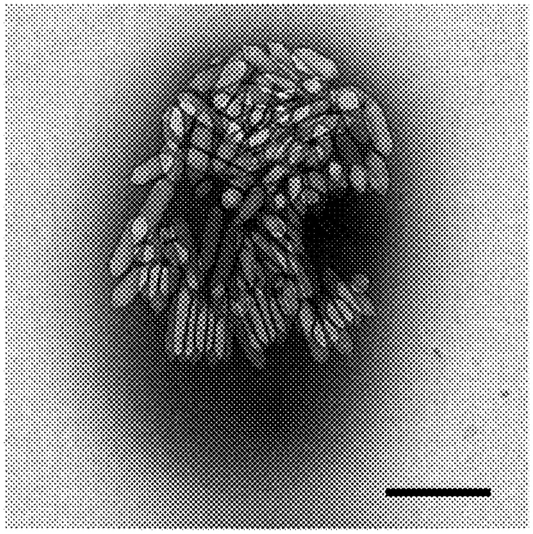

To further examine the genetic stability of bARG$_{Ser}$ constructs, cells were plated from daily sub-cultures onto agar with 0.1% (w/v) L-arabinose and examined colony opacity (FIG. 2G) as a measure of retained GV expression. Of a total of 3824 colonies, nearly all were opaque (FIG. 2G), with GV expression confirmed by PCM and TEM (FIGS. 2H-2I). Only 11 colonies (<0.3% after ~35 cell generations) exhibited a reduced opacity (FIG. 18A), representing a mutated phenotype confirmed by growing these cells on fresh media (FIG. 18B). PCM revealed that these rare mutants still produced GVs, but at lower levels than non-mutants. These results indicate that mutational inactivation of GV production is not a major issue for pBAD-bARG$_{Ser}$-AxeTxe EcN under typical conditions.

After establishing construct stability, the acoustic properties of $bARG_{Ser}$-expressing EcN were characterized. For cells induced in liquid culture with 0.1% L-arabinose for 24 hours and suspended at $10^9$ cells/mL in agarose phantoms, an xAM signal was detected at acoustic pressures above 0.72 MPa, rising with increasing pressure up to the tested maximum of 1.74 MPa (FIG. 3A). To characterize the physical stability of GVs in these cells during ultrasound exposure, the xAM signal was measured over time at a series of increasing acoustic pressures (FIG. 3B and FIGS. 19A-19C). The xAM signal was steady at pressures up to 0.96 MPa, above which a slow decrease was observed, indicating that some of the GVs gradually collapsed despite sustained high xAM signals. The cells were also imaged with parabolic pulses, which can transmit higher pressures than xAM, and thus can be helpful in vivo to compensate for attenuation at tissue interfaces. When imaged with parabolic B-mode at varying acoustic pressures, the GVs started to collapse slowly at 1.02 MPa and more rapidly at 1.33 MPa and above (FIG. 3C). Based on these results, an acoustic pressure of 1.29 MPa was selected for xAM and 1.02 MPa for parabolic AM (pAM) imaging in subsequent experiments to obtain the strongest signals while minimizing GV collapse.

Figure 3D:
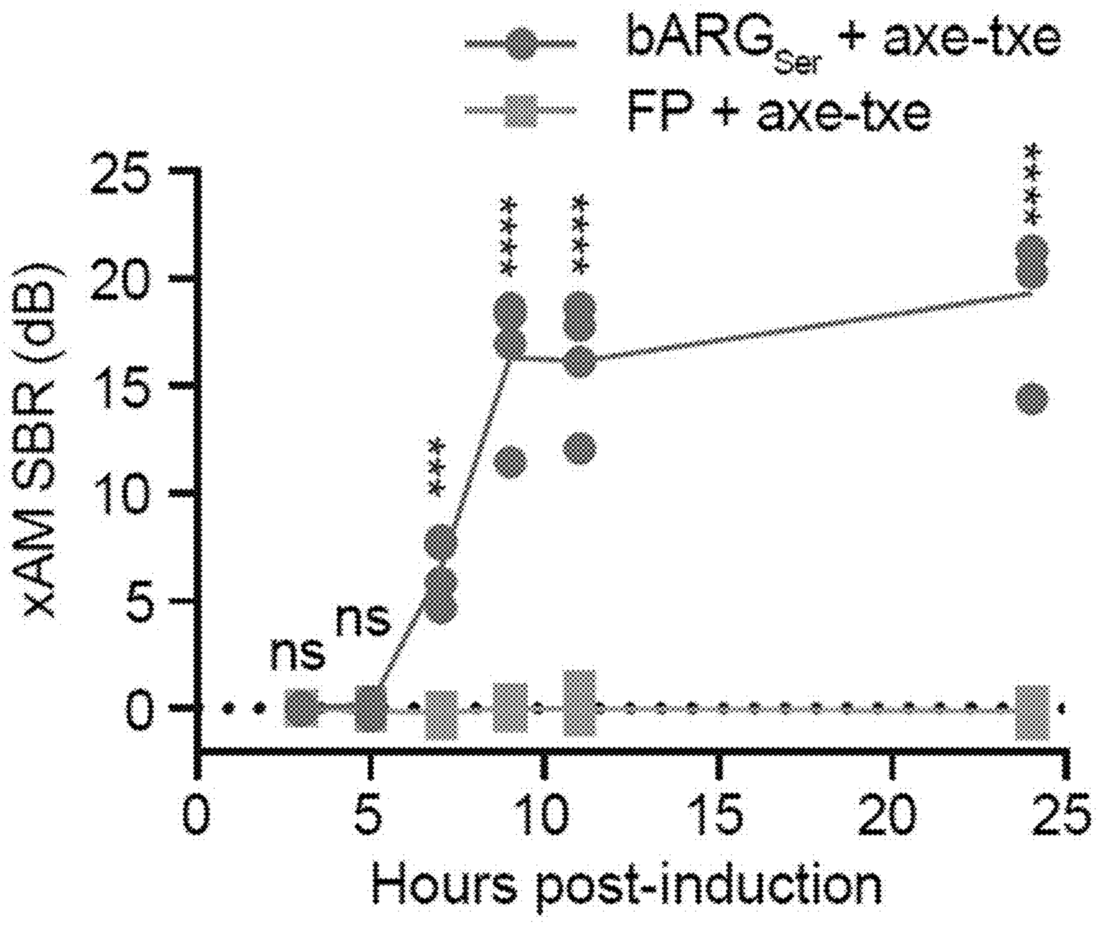
Figure 3E:
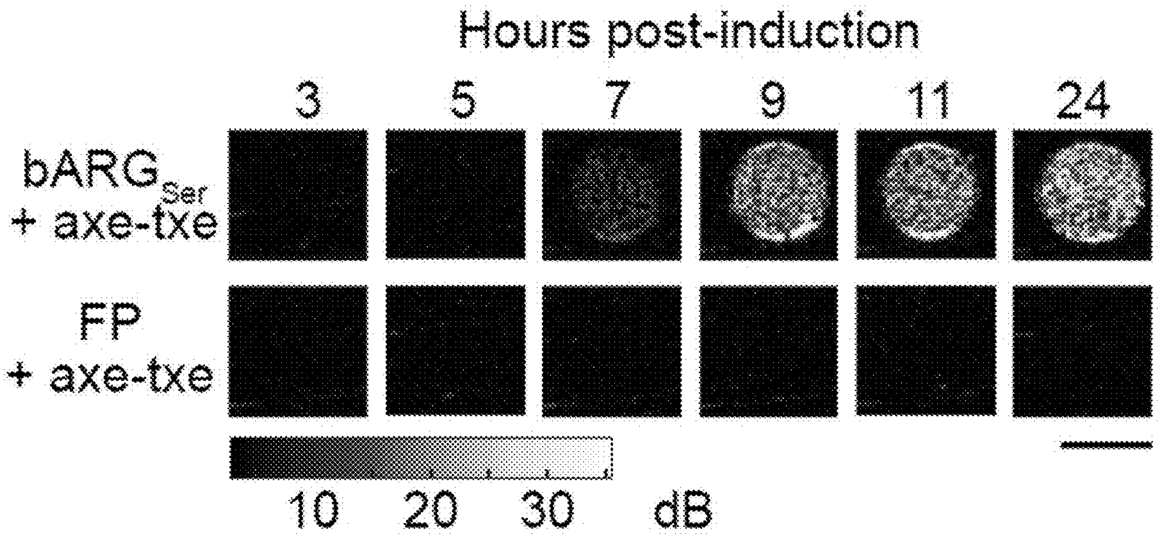
Figure 3F:
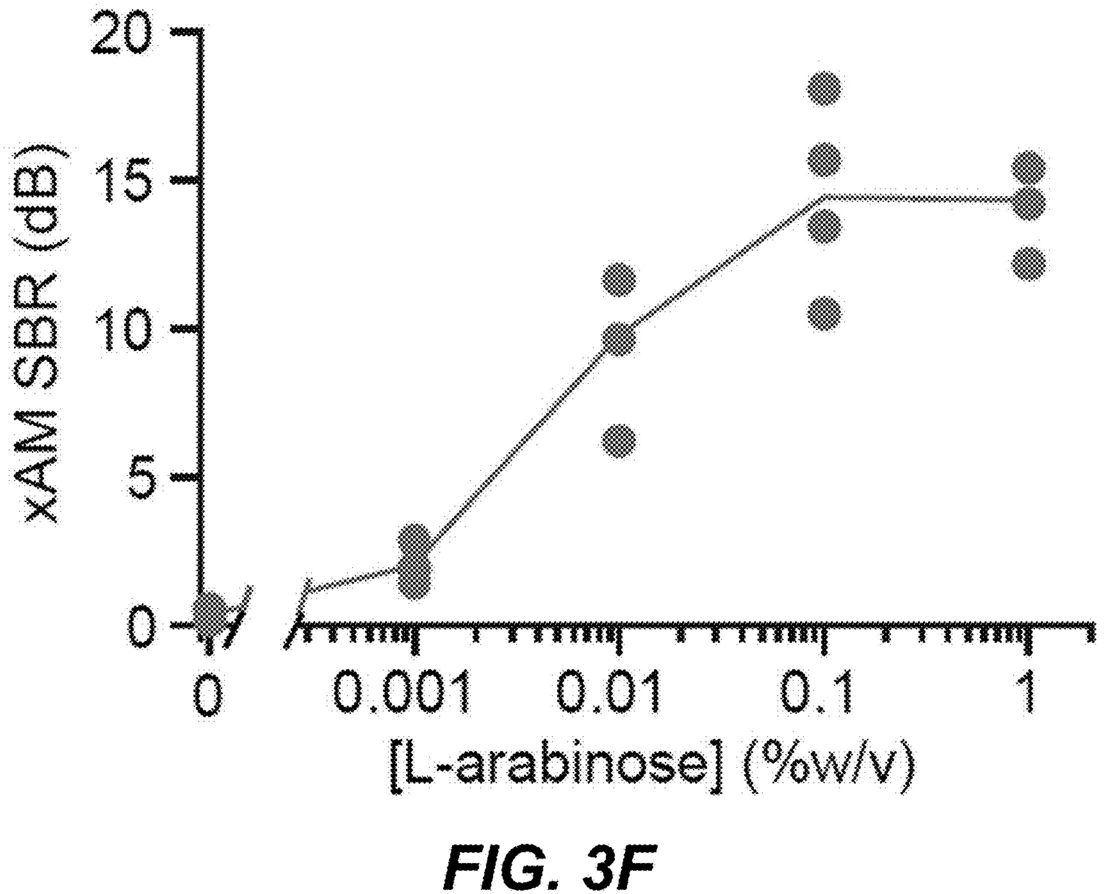
Figure 3G:
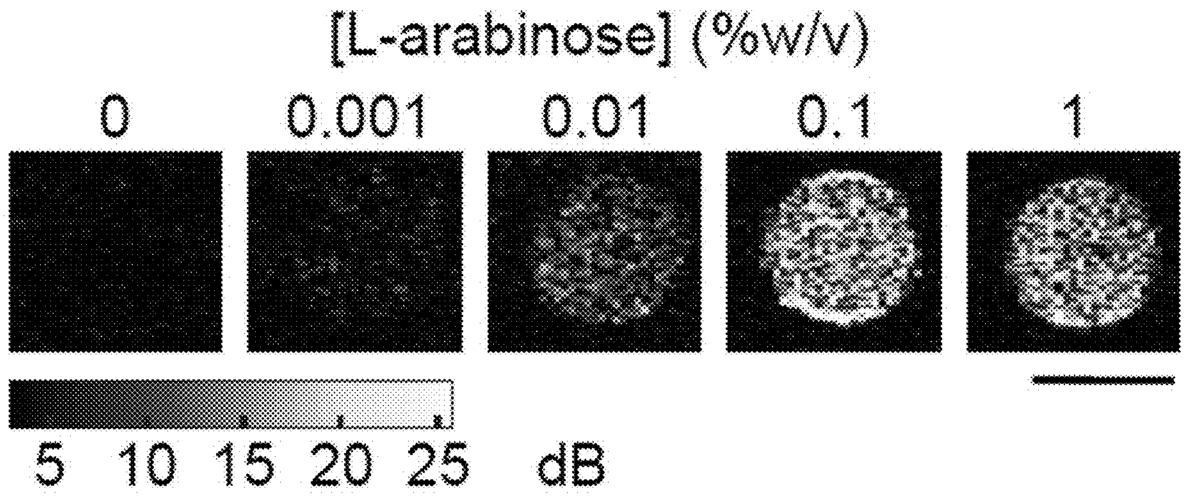
Figure 3H:
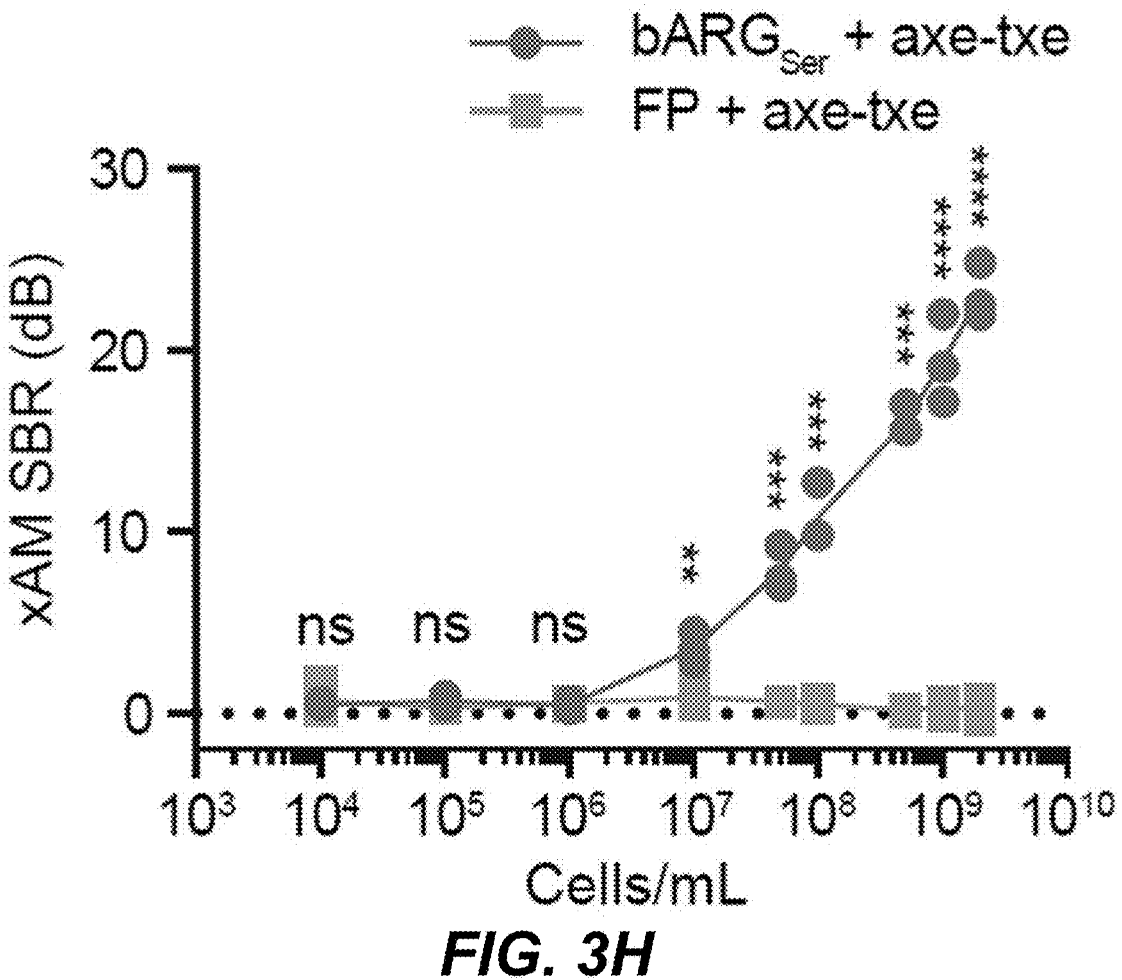
Figure 3I:
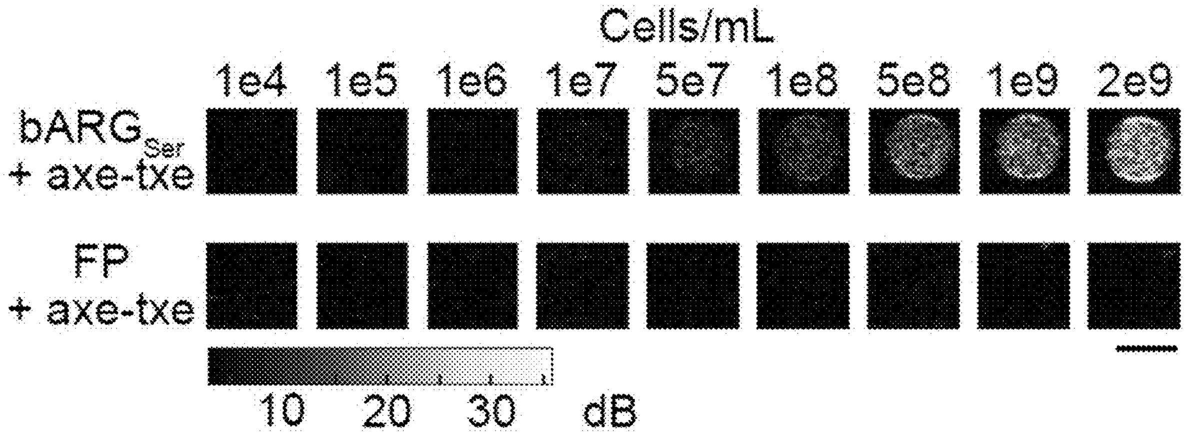

Next, to characterize the dynamics and inducibility of $bARG_{Ser}$ in EcN and determine the ultrasound detection limit of $bARG_{Ser}$-expressing EcN, xAM signal was measured as a function of induction time, inducer concentration, and cell concentration. At a density of $10^9$ cells/mL, xAM signal could first be observed 7 hours after induction with 0.1% L-arabinose and leveled off by 9 hours post-induction (FIGS. 3D-3E). Keeping the induction time constant at 24 hours while varying the L-arabinose concentration, GV expression was detected with as little as 0.001% L-arabinose, and the highest ultrasound signal was observed for 0.1-1% L-arabinose (FIGS. 3F-3G). When cells induced for 24 hours with 0.1% L-arabinose were diluted, they were detectable by ultrasound down to $10^7$ cells/mL (FIGS. 3H-3I). Critically, this detection was achieved non-destructively with nonlinear imaging, compared to previous bacterial ARGs, which required a destructive linear imaging approach. The $bARG_{Ser}$ xAM signal was proportional to the cell concentration between $10^7$ cells/mL and $2\times10^9$ cells/mL (FIGS. 3H-3I). The cells were also imaged using BURST imaging, which provides greater sensitivity at the cost of collapsing the GVs. BURST enabled $bARG_{Ser}$-expressing EcN to be detected as early as 3 hours post-induction (FIGS. 20A-20B), with as little as 0.001% L-arabinose FIGS. 20C-20D), and at a density as low as $10^5$ cells/mL (FIGS. 20E-20F). Taken together, in vitro experiments provided herein indicated that the reporter gene construct pBAD-$bARG_{Ser}$-AxeTxe is robust and stable in EcN and enables gene expression in these cells to be imaged with high contrast and sensitivity.

To test whether this ARG construct can function in other bacterial species, pBAD-$bARG_{Ser}$-AxeTxe was transformed into an attenuated strain of *Salmonella enterica* serovar *typhimurium*, which has been used in bacterial anti-tumor therapies. After inducing expression with L-arabinose, *S. typhimurium* cells produced GVs, as observed with PCM (FIG. 21A), and generated strong contrast in xAM imaging (FIGS. 21B-21C). *S. typhimurium* cells exhibited similar detection limits to EcN with both xAM and BURST imaging (FIGS. 21D-21K).

$bARG_{Ser}$ Enables In Situ Imaging of Tumor-Colonizing Bacteria

Tumor-homing bacteria are a major emerging class of cancer therapy, taking advantage of the ability of cells such as EcN to infiltrate tumors and proliferate in their immunosuppressed microenvironment. Major synthetic biology efforts have been undertaken to turn tumor-homing EcN cells into effective therapies for solid tumors. However, despite the promise of this technology and the importance of appropriate microscale biodistribution of the bacteria inside tumors, no effective methods currently exist to visualize this biodistribution in situ in living animals.

Figure 4A:
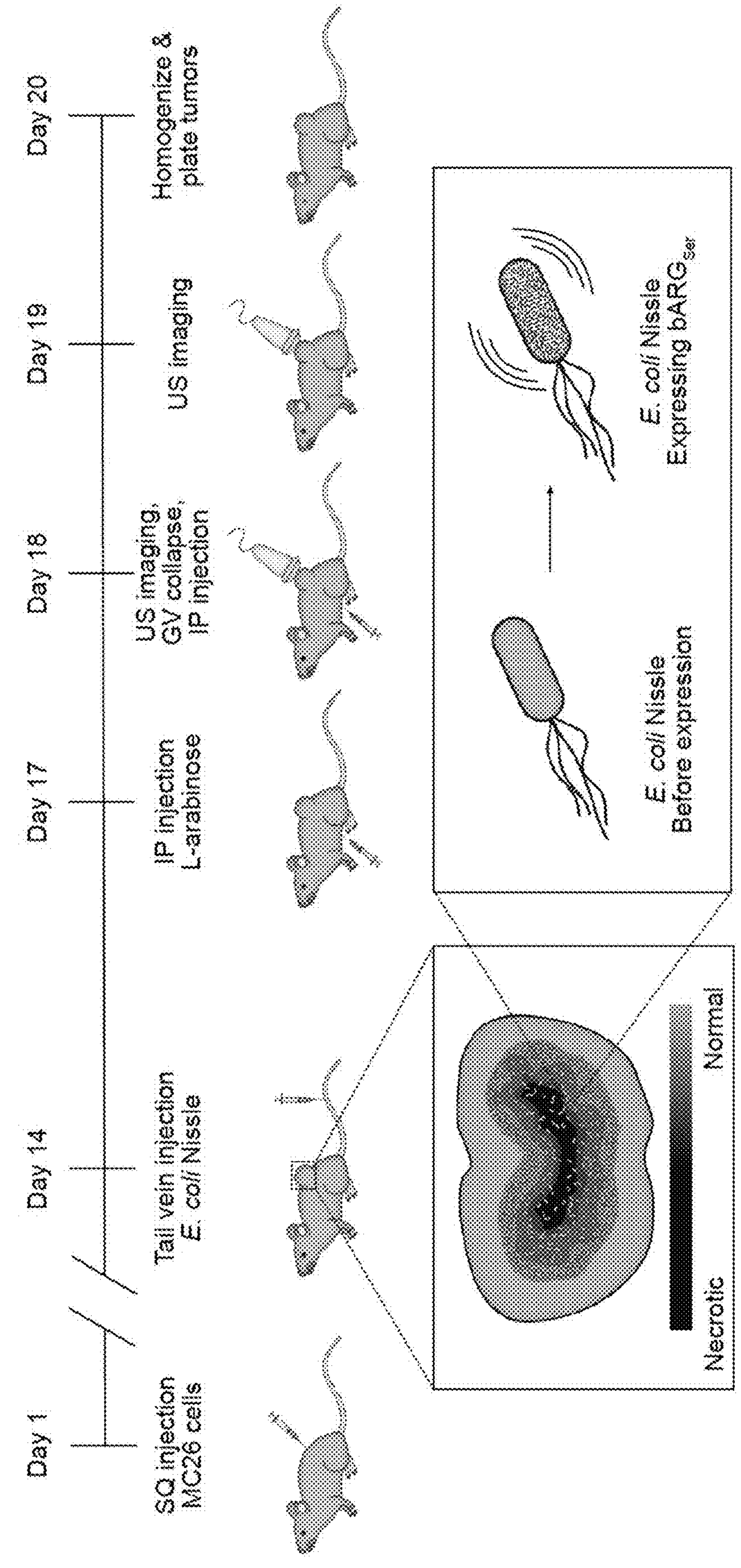
FIGS. 4A-4L depict non-limiting exemplary schematics and data related to in situ bARG$_{Ser}$ expression enabling ultrasound imaging of tumor colonization by EcN.
Figures 4B, 4C, 4D, 4E:
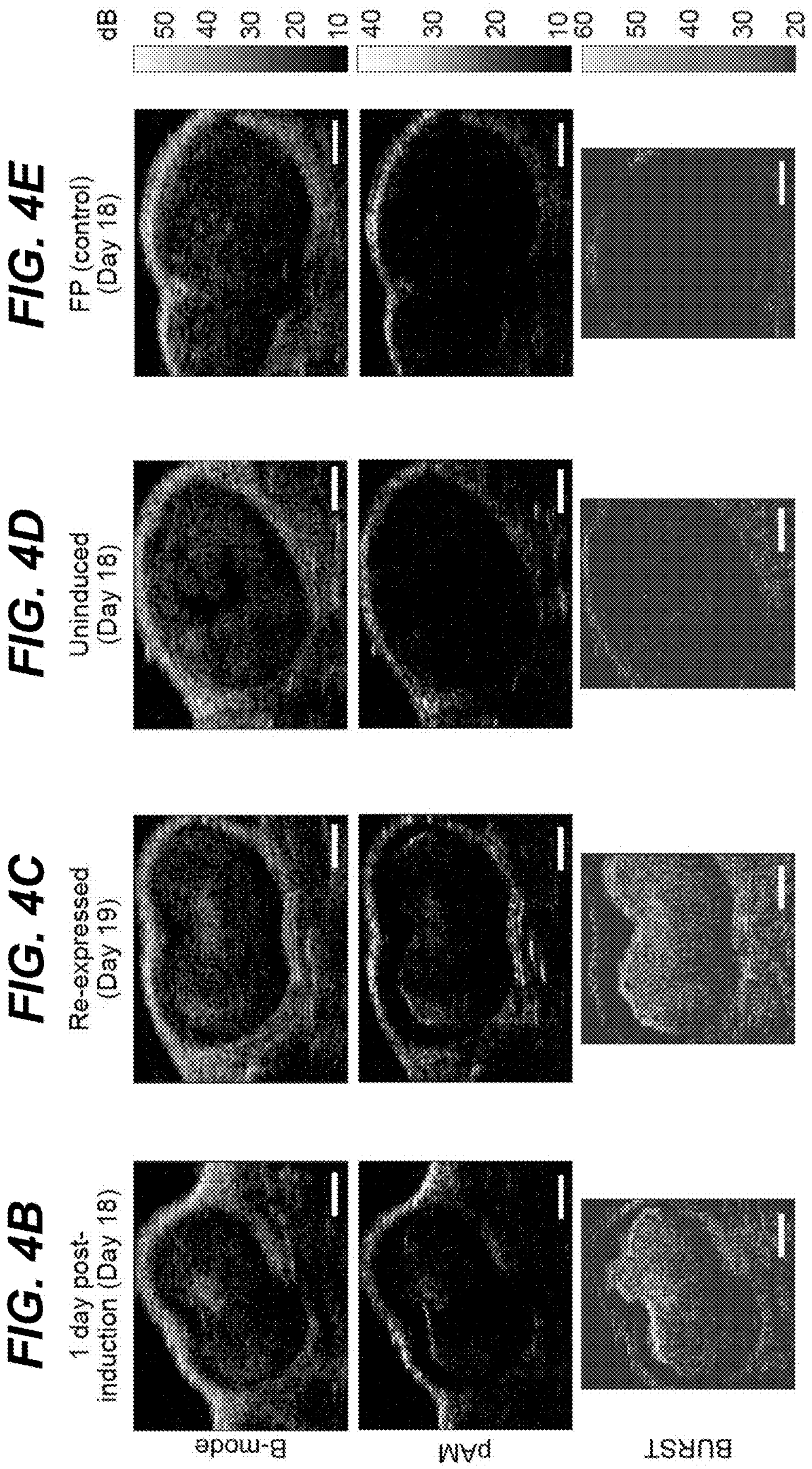
Figure 4I:
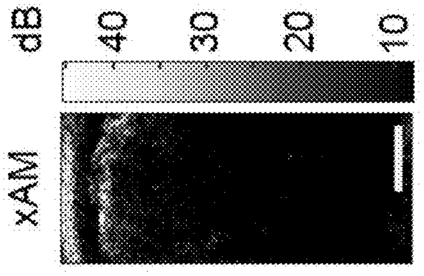
Figure 4H:
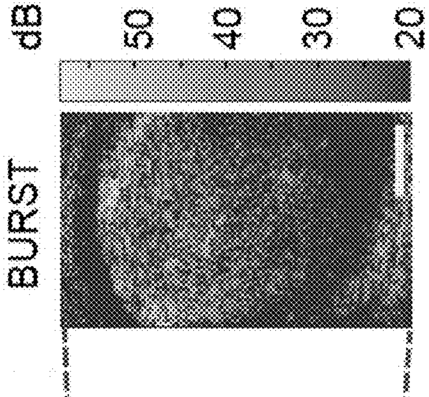
Figure 4G:
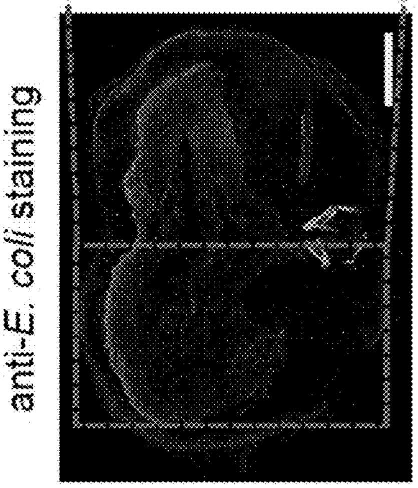
Figure 4F:
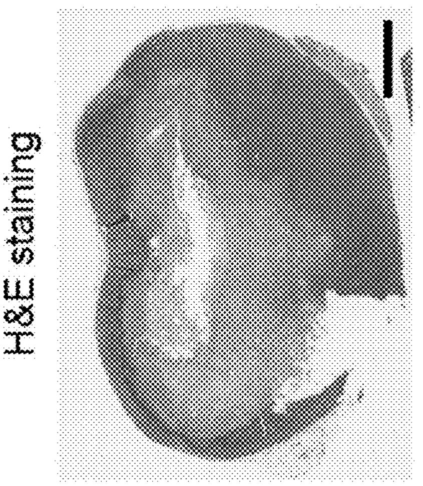
Figure 4J:
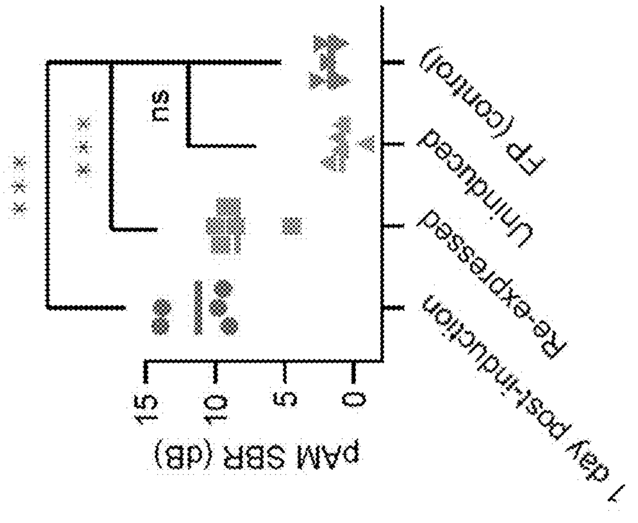
Figure 4K:
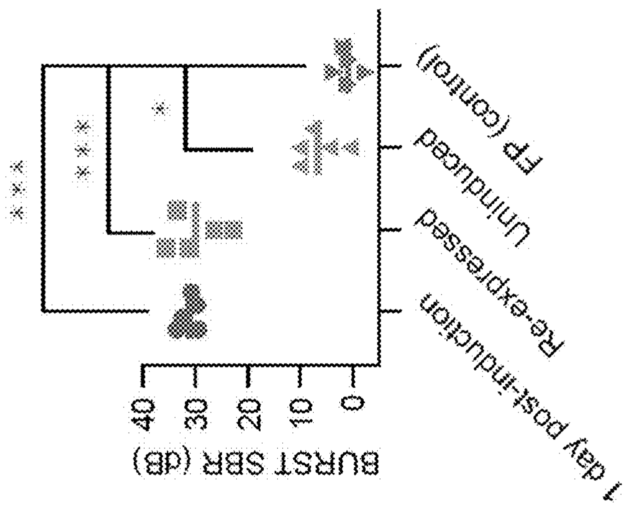
Figure 4L:
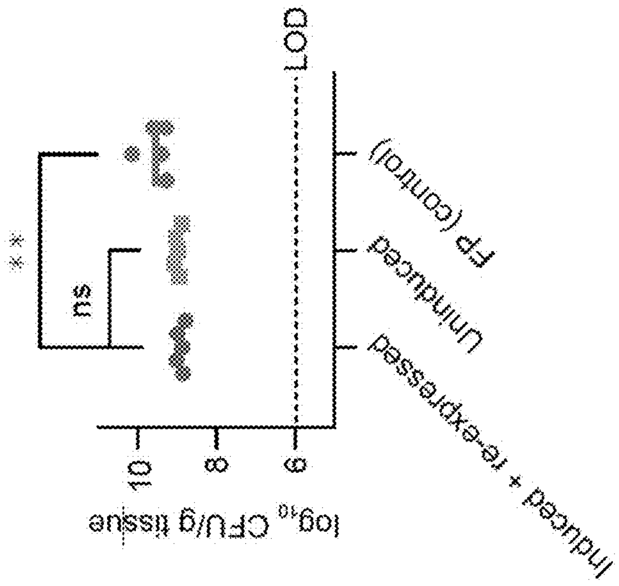

To test the ability of $bARG_{Ser}$ to overcome this limitation, subcutaneous MC26 tumors were formed in mice and, when the tumors reached a substantial size, intravenously injected EcN cells containing the pBAD-$bARG_{Ser}$-AxeTxe plasmid, giving the bacteria 3 days to home to and colonize the tumors. GV expression was then induced and imaged the tumors with ultrasound (FIG. 4A). In all tumors colonized by $bARG_{Ser}$-expressing EcN, pAM, BURST, and xAM ultrasound contrast were observed one day after induction with L-arabinose (FIG. 4B and FIG. 22A). The signals were localized to the core of the tumor and concentrated at the interface between live and necrotic tissue, where the EcN primarily colonized, as confirmed with subsequent tissue histology (FIGS. 4F-4I and FIG. 23). This biodistribution reflects the immune-privileged environment of the necrotic tumor core and has been observed previously only with post-mortem ex vivo optical methods.

Furthermore, after applying 3 MPa of acoustic pressure throughout the tumor to collapse all the GVs, re-injecting the mice with L-arabinose inducer, and allowing >24 hours for re-expression, similar ultrasound signals were observed in all tumors colonized by $bARG_{Ser}$-expressing EcN (FIG. 4C and FIG. 22B). This result shows that $bARG_{Ser}$ can be used to visualize dynamic gene expression at multiple timepoints. Absent L-arabinose induction, no xAM or pAM ultrasound signals were observed from $bARG_{Ser}$-containing EcN (FIG. 4D and FIG. 22C); likewise, no xAM or pAM ultrasound signals were seen in tumors colonized by FP-expressing EcN (FIG. 4E, FIG. 4J and FIGS. 22D-22E). Low levels of BURST signal were observed in uninduced animals (FIG. 4K), likely due to small amounts of L-arabinose present in the diet combined with BURST imaging's high sensitivity.

To quantify tumor colonization, at the end of the experiment (day 20 in FIG. 4A) all mice were euthanized and their tumors were homogenized and plated on selective media. Tumors from all groups of mice (n=5 for induced and re-expressed $bARG_{Ser}$, n=5 for uninduced $bARG_{Ser}$, and n=5 for FP) contained more than $7\times10^8$ CFU/g tissue (FIG. 4L), indicating that the EcN can persist at high levels in tumors for at least 6 days after IV injection regardless of $bARG_{Ser}$ expression, collapse, and re-expression. The somewhat higher density of FP-expressing EcN suggested that maintenance of the smaller pBAD-FP-AxeTxe plasmid (7.2 kb versus 23.2 kb for pBAD-$bARG_{Ser}$-AxeTxe), which would impose less burden on the cell, may be easier in this in vivo context where oxygen and other nutrients are limited. Negligible mutational silencing was observed in EcN plated from tumor samples (FIGS. 24A-24C).

Taken together, disclosed in vivo experiments with EcN demonstrate that $bARG_{Ser}$ expression enables stable, nondestructive acoustic visualization of the microscale distribution of these probiotic agents in a therapeutically relevant context.

Figure 5A:
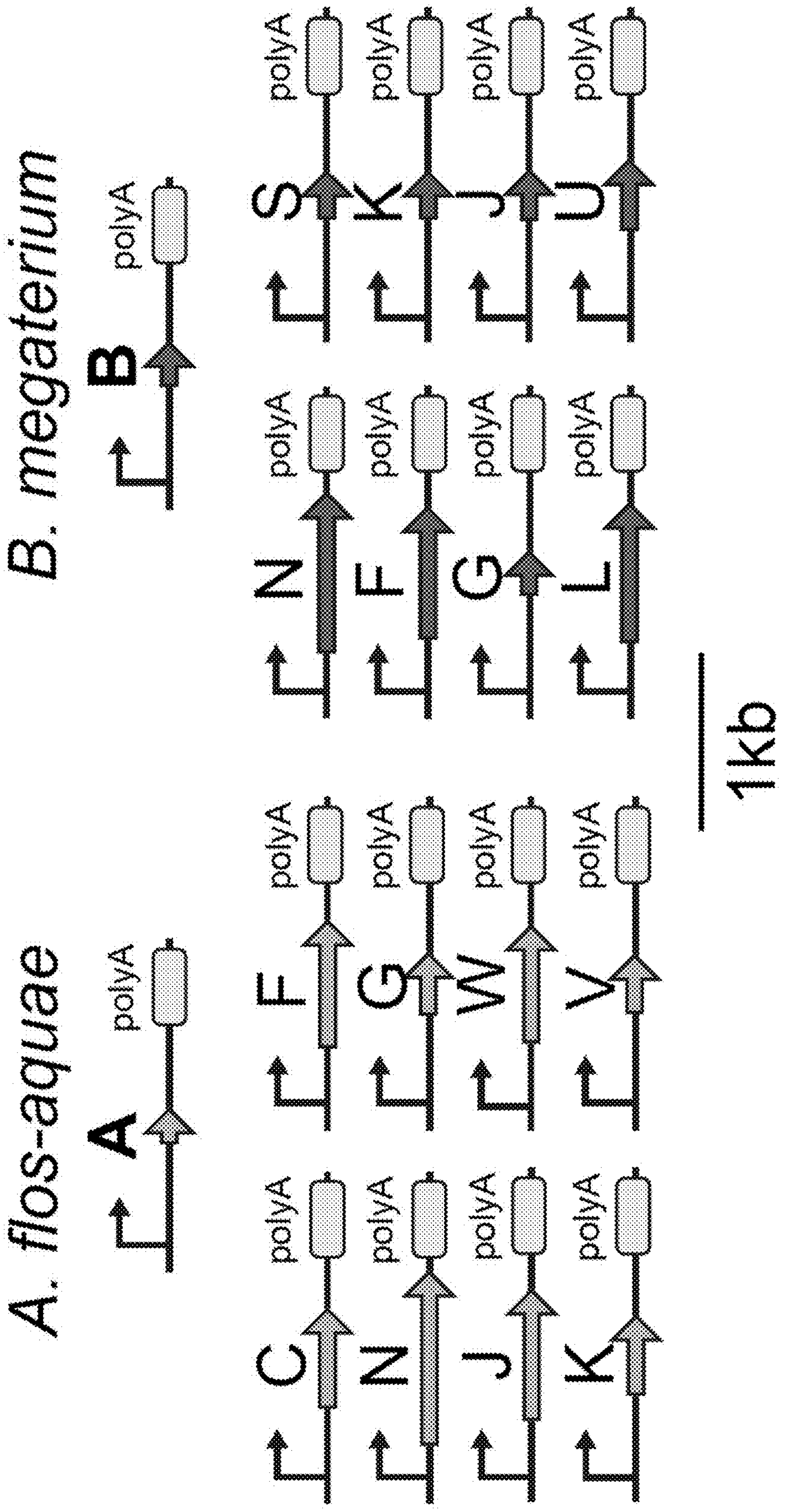
Figure 5B:
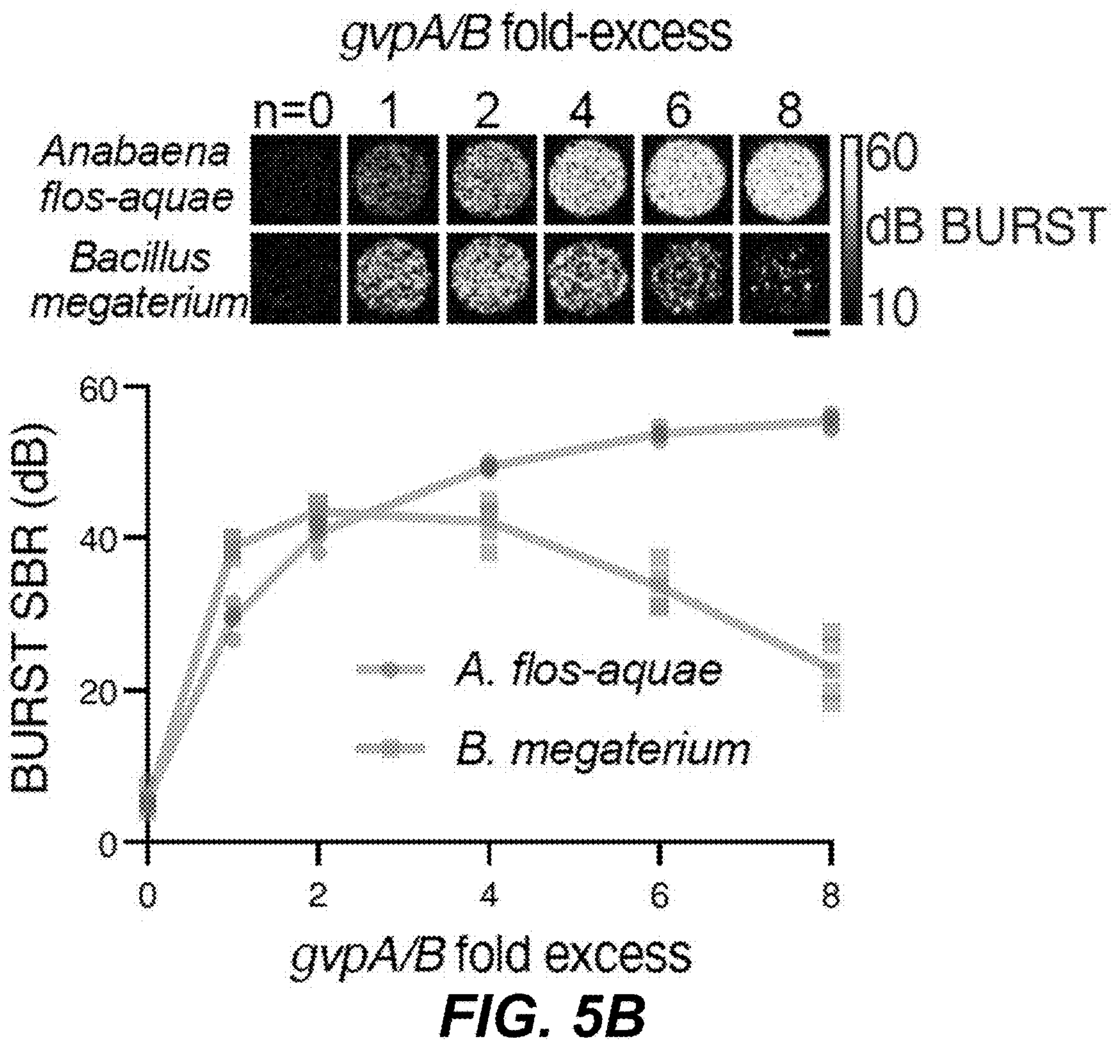

The *A. Flos-Aquae* GV Gene Cluster Produces Robust Nonlinear Ultrasound Contrast in Mammalian Cells Having developed second-generation ARGs for use in bacteria, the same was attempted for mammalian cells. The first-generation mammalian ARGs were based on the GV gene cluster from *B. megaterium* (referred to here as mAR- $G_{Mega}$). $mARG_{Mega}$ expression could only be detected with destructive collapse-based imaging due to a low level of GV expression and the lack of nonlinear contrast from the resulting GVs. Moreover, successful use of $mARG_{Mega}$ as a reporter gene required monoclonal selection of transduced cells and their treatment with a broadly-acting histone deacetylase inhibitor. Seeking mARGs that are expressed more robustly and produce nonlinear signal, mammalian versions of the genes contained in each of the three clusters that produced nonlinear signal in *E. coli* at 37° C. were cloned: *Serratia, A. flos-aquae*, and *A. fos-aquae/B. megaterium* (FIGS. 1D-1E). Equimolar transient cotransfections of the monocistronic genes derived from each gene cluster into HEK293T cells yielded detectable BURST signal only for the *A. flos-aquae* gene cluster and the positive control $mARG_{Mega}$ (FIGS. 5A-5B "1-fold excess").

Figure 25A:
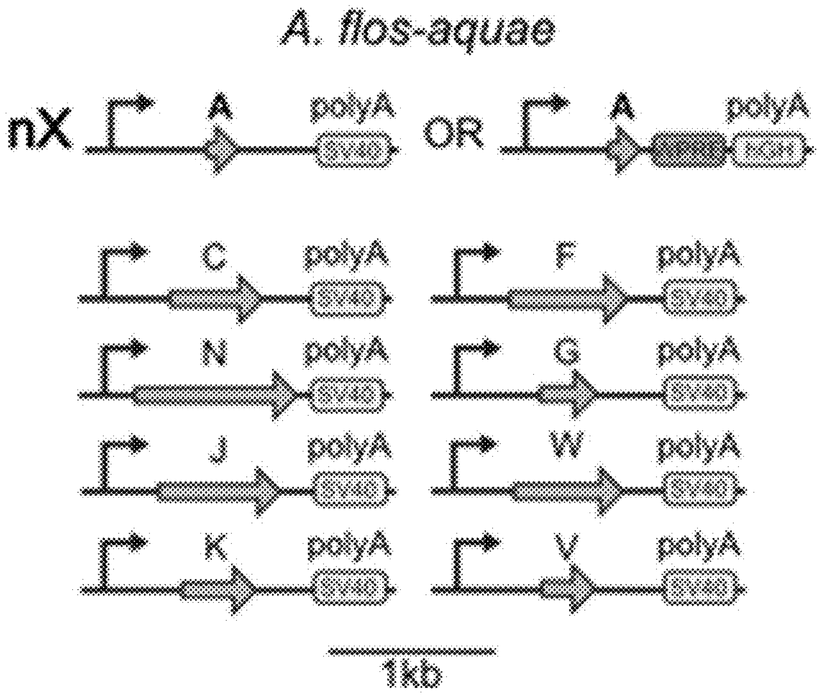
Figure 25B:
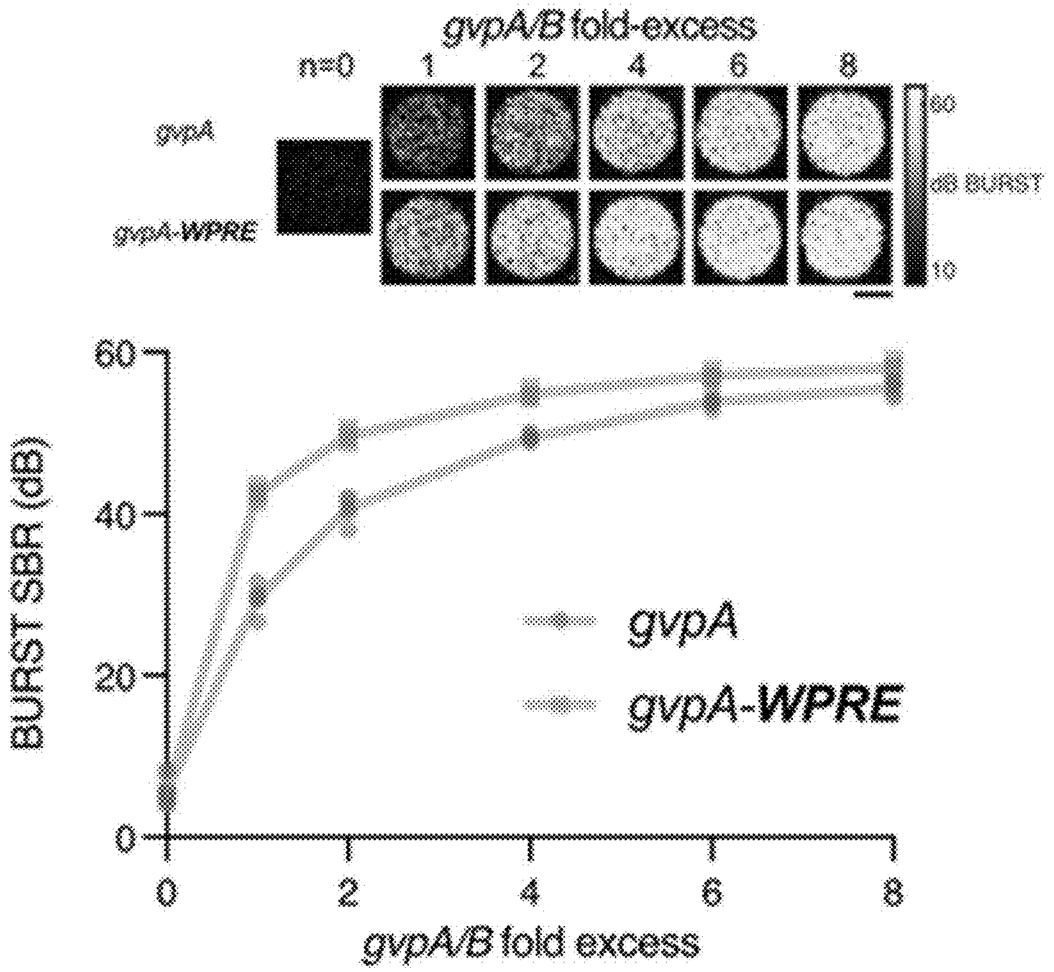

Given the multiple gvpA copies contained in the native *A. flos-aquae* GV operon, it was hypothesized that expressing the major structural protein GvpA at a higher stoichiometry relative to the other genes in this cluster could improve GV expression. To test this possibility, the amount of gvpA plasmid in the *A. flos-aquae* plasmid set was titrated, while keeping the DNA amount corresponding to other genes constant (the total DNA level was also kept constant with a padding vector). It was found that the BURST signal increased monotonically with increasing gvpA up to 8-fold gvpA excess (FIG. 5B). In contrast, the signal peaked at 2-fold excess of the homologous structural protein gvpB when expressing the *B. megaterium* cluster, possibly due to unincorporated or unchaperoned GvpB monomers, which may burden the cells. That this does not happen with the genes from *A. flos-aquae* within the range tested suggests that the assembly factors in this gene cluster may be more efficient at utilizing GvpA to form gas vesicles or that GvpA may pose less of a burden than GvpB. To further improve GvpA expression, the gvpA transcript was stabilized with WPRE-hGH poly(A) elements, which resulted in peak signal at lower gvpA:chaperone ratios (FIGS. 25A-25B).

Figure 5C:
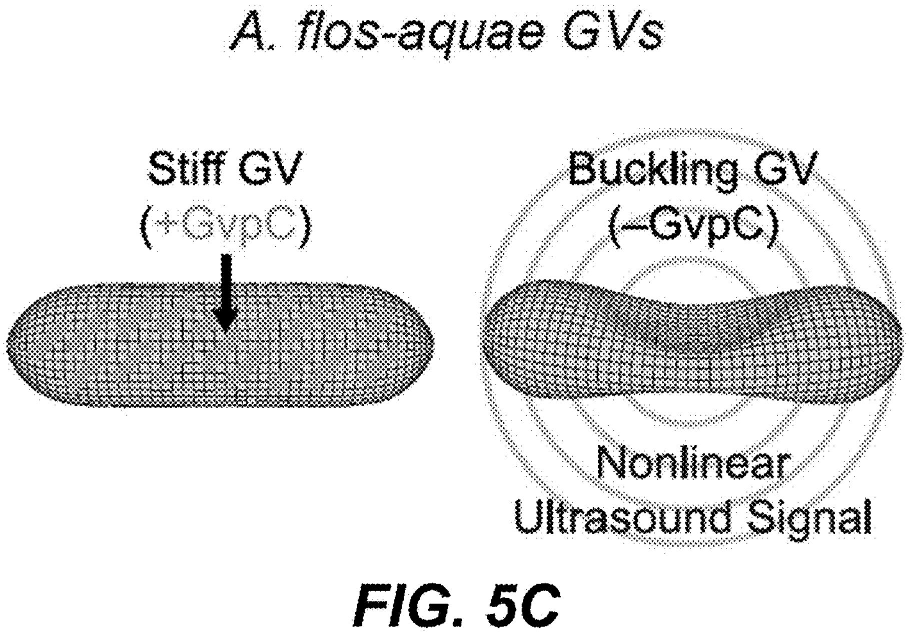
Figure 5D:
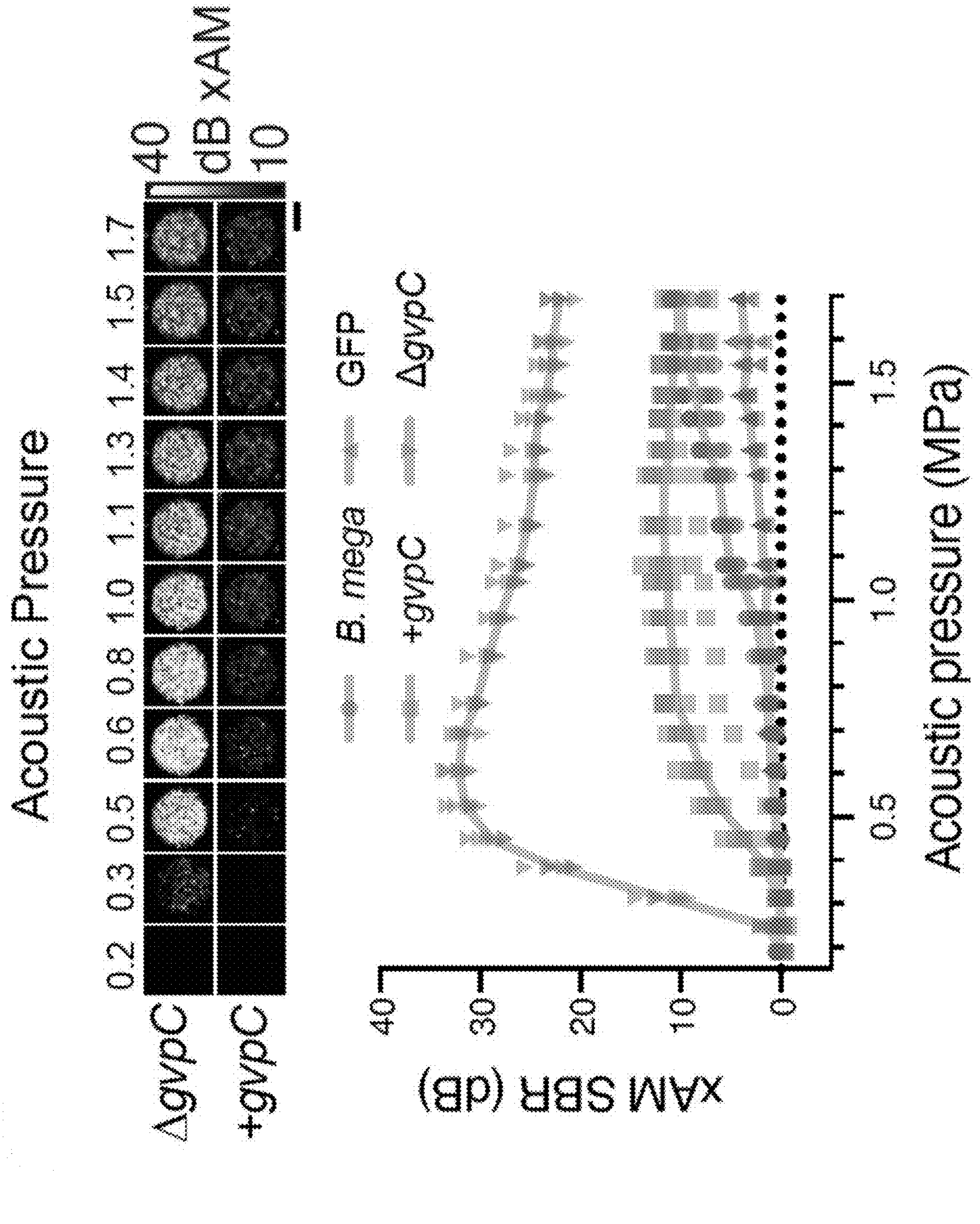
Figure 25C:
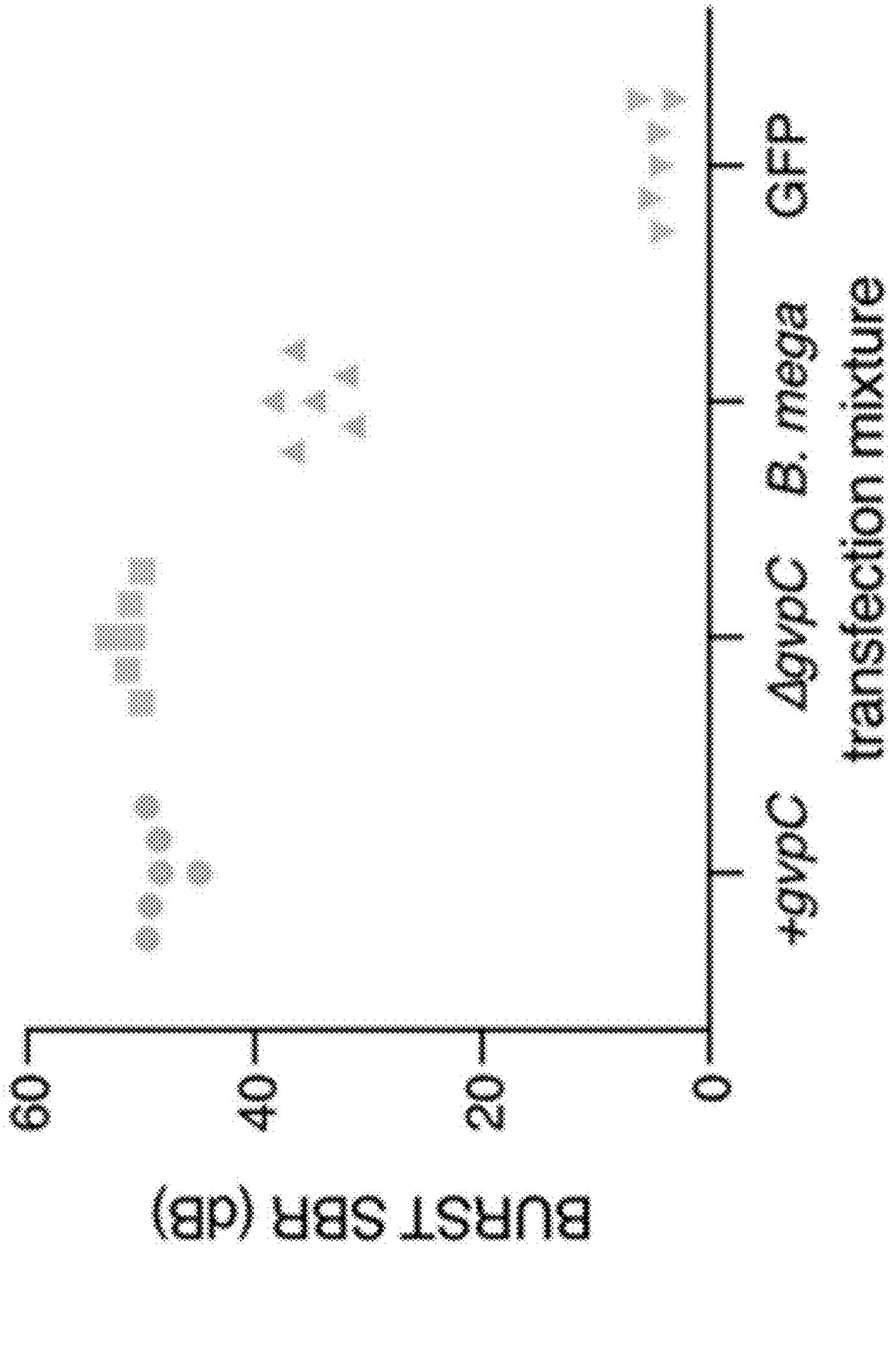

It was next examined if nonlinear ultrasound contrast could be observed from *A. flos-aquae* GVs to enable their discrimination from background. GvpC is a minor structural protein in *A. flos-aquae* GVs that binds to and mechanically reinforces the GV shell (FIG. 5C). Previously, in vitro chemical removal of GvpC from purified GVs was shown to enhance nonlinear ultrasound scattering by allowing the GVs to deform more strongly in response to acoustic pressure. When gvpC was omitted from the disclosed mammalian co-transfection mixture, a dramatic enhancement of nonlinear signal was observed in xAM imaging, with the peak signal achieved at around 0.6 MPa (FIG. 5D). By comparison, transfections including gvpC produced a much weaker xAM signal, while *B. megaterium* plasmids and GFP-expressing cells did not produce appreciable nonlinear contrast at any pressure. The omission of gvpC did not appreciably alter BURST contrast (FIG. 25C). These results indicate that the mammalian GVs derived from *A. flos-aquae* can provide strong, nondestructive, nonlinear ultrasound contrast.

Figure 5E:
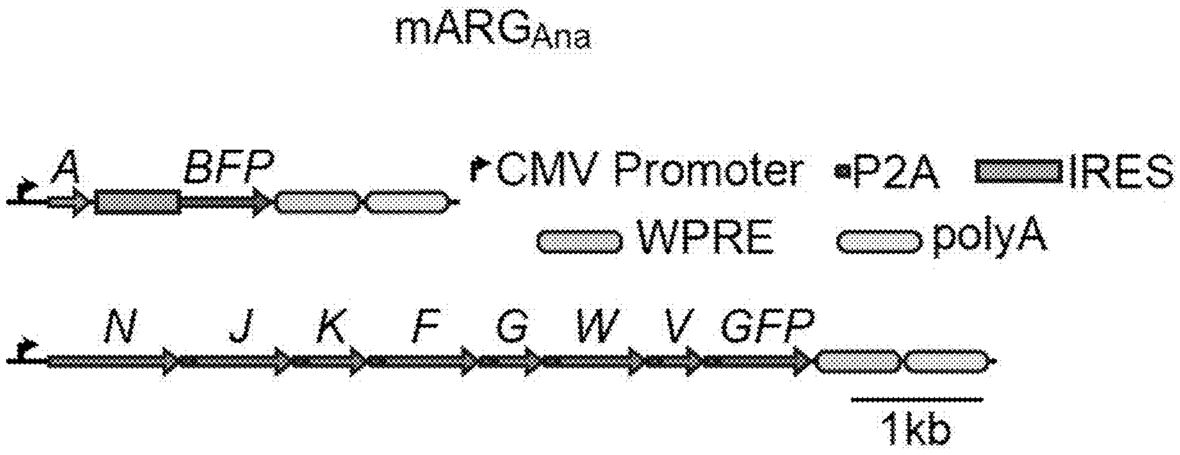
Figure 5F:
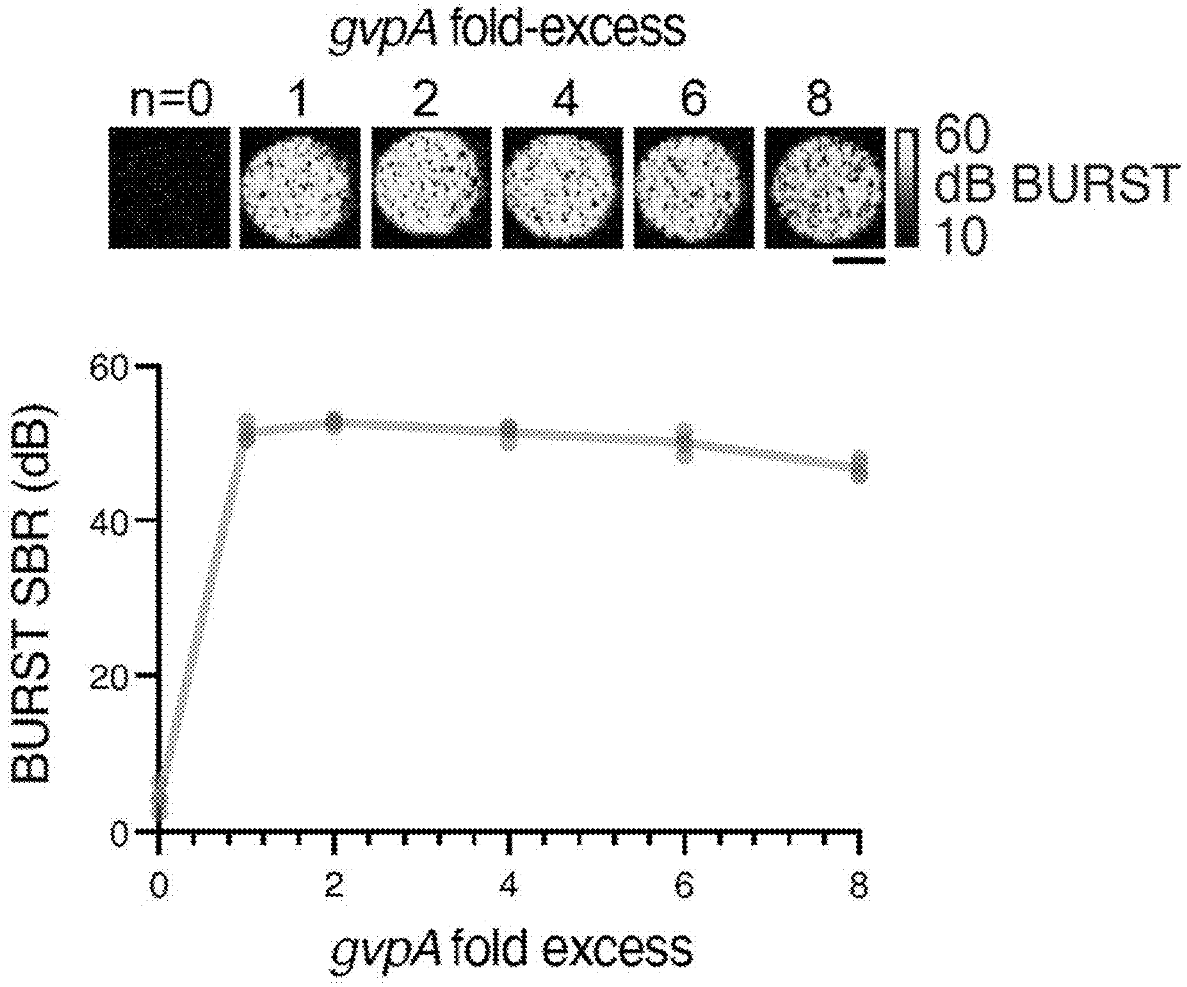

To create a convenient vector for mammalian expression of *A. flos-aquae* GVs, a polycistronic plasmid was constructed linking the assembly factor genes gvpNJKFGWV through P2A co-translational cleavage elements. gvpA was supplied on a separate plasmid to enable stoichiometric tuning. The gvpA and gvpNJKFGWV plasmids were labeled with IRES-BFP and P2A-GFP, respectively, to allow for fluorescent analysis and sorting. Both transcripts were driven by CMV promoters and stabilized by WPRE-hGH poly(A) elements. This pair of plasmids was termed $mARG_{Ana}$: mammalian ARGs adapted from *A. flos-aquae* (FIG. 5E). $mARG_{Ana}$ produced robust GV expression and ultrasound contrast in HEK293T cells transiently co-transfected with a 1- to 6-fold molar excess of gvpA (FIG. 5F).

Figure 5G:
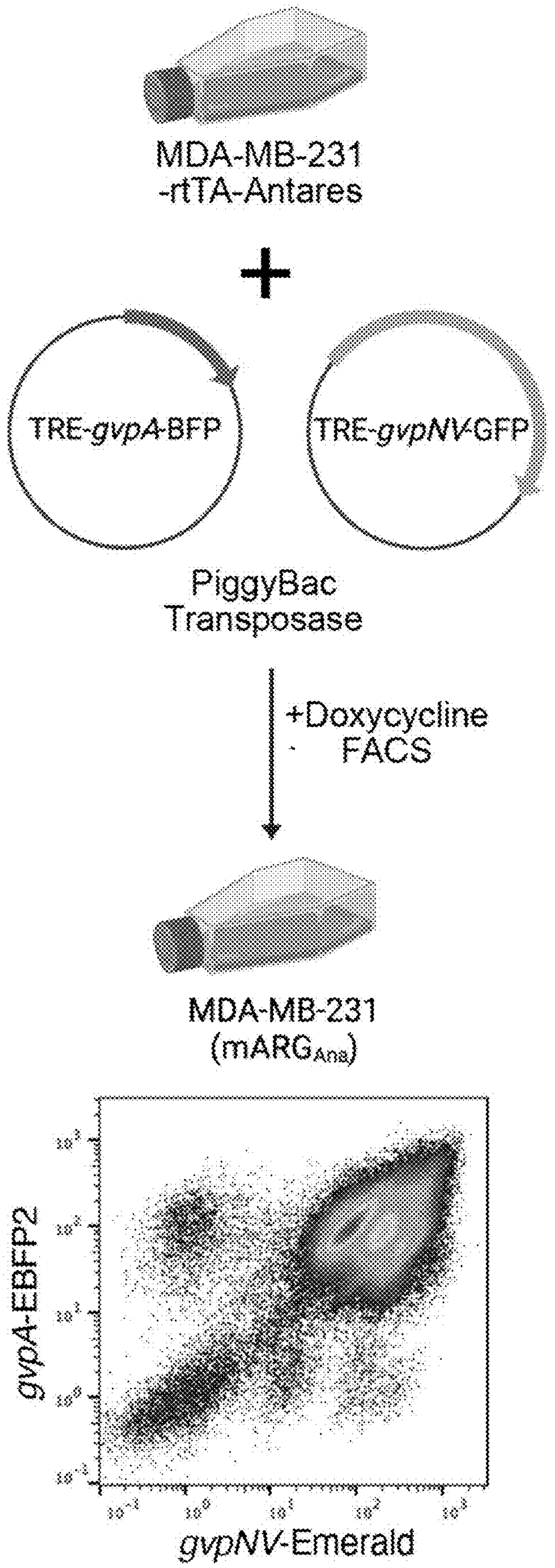
Figure 5I:
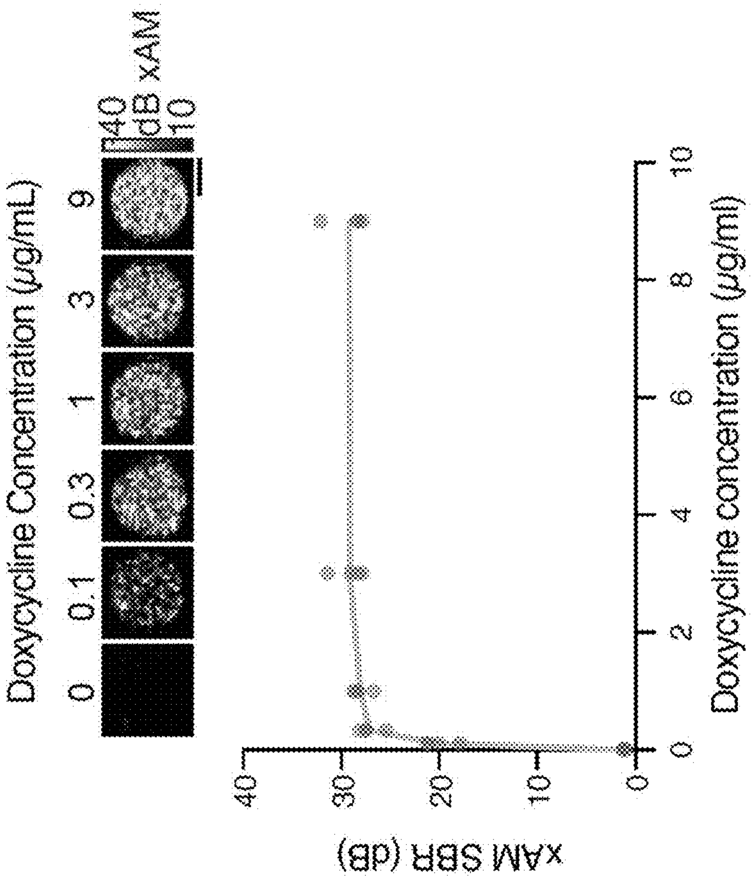
Figure 25D:
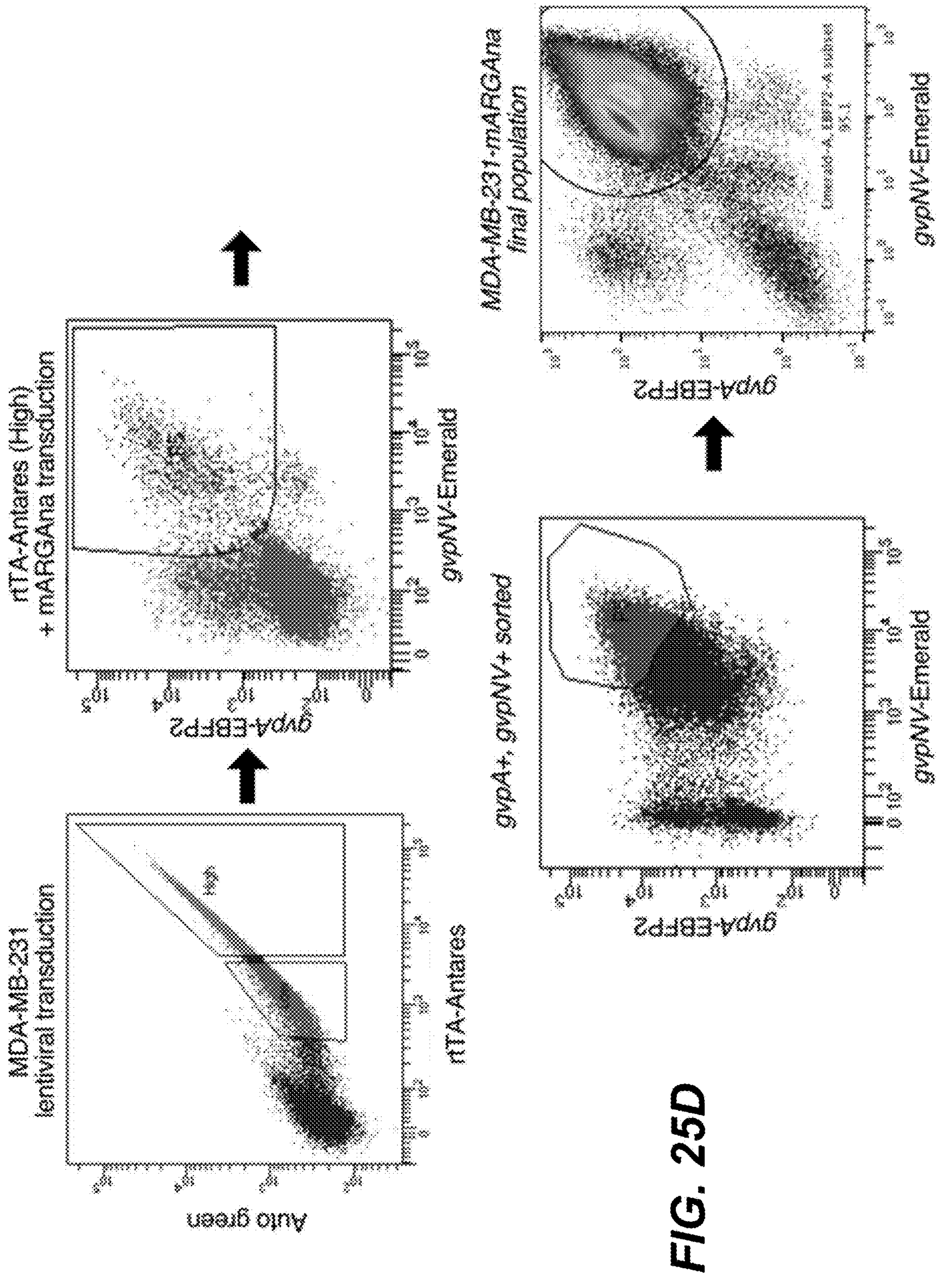

One of the most promising applications of mammalian reporter genes is the visualization of tumor growth in animal models of cancer, which are a critical platform for basic oncology research and the development of new therapeutics. To produce a stable cancer cell line expressing $mARG_{Ana}$, the disclosed polycistronic constructs were cloned into PiggyBac integration plasmids under a doxycycline-inducible TRE promoter. As a clinically relevant cancer model, the human breast cancer cell line MDA-MB-231 was chosen, which is widely used in tumor xenograft studies. These cells were engineered to constitutively co-express the rtTA transactivator and Antares optical reporter, then electrically transduced them with a mixture of $mARG_{Ana}$ and PiggyBac transposase plasmids at a 2:1 (gvpA:gvpNJKFGWV) molar ratio, and fluorescently sorted for co-expression of Antares, GFP and BFP (FIG. 5G and FIG. 25D).

Figure 5H:
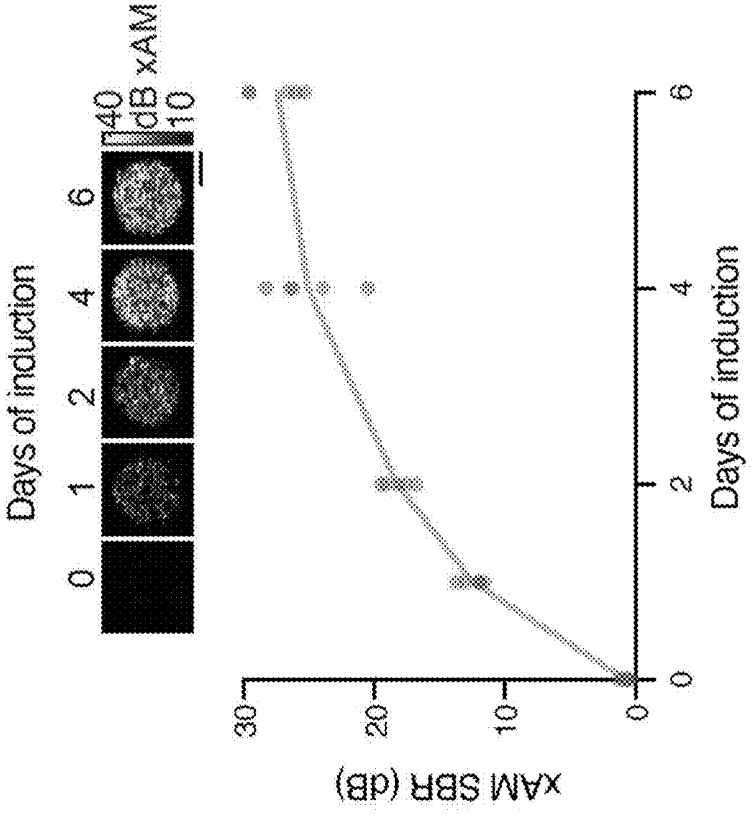
Figure 5K:
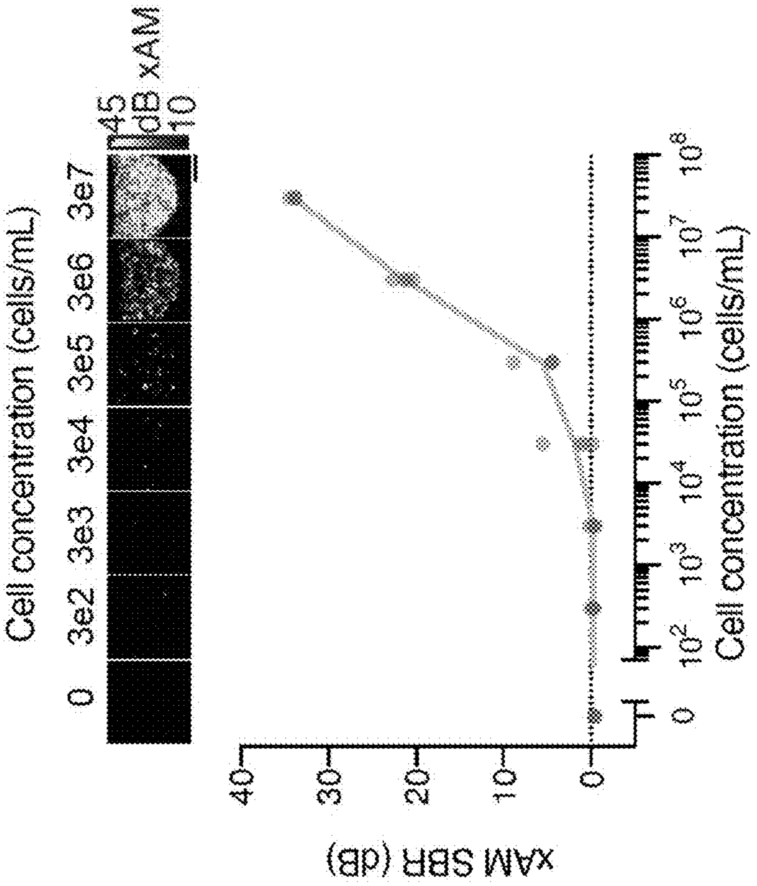
Figure 5J:
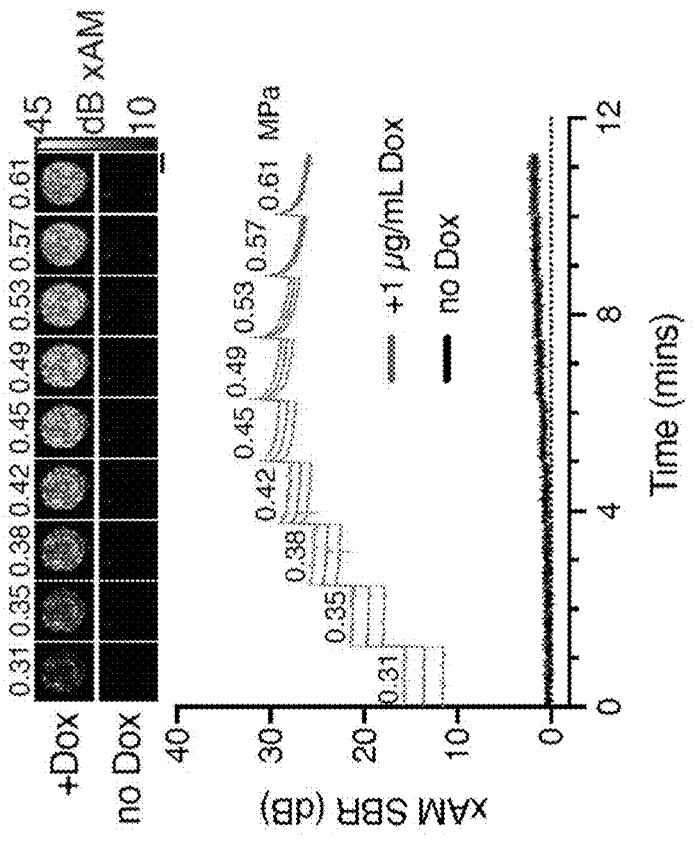
Figure 25E:
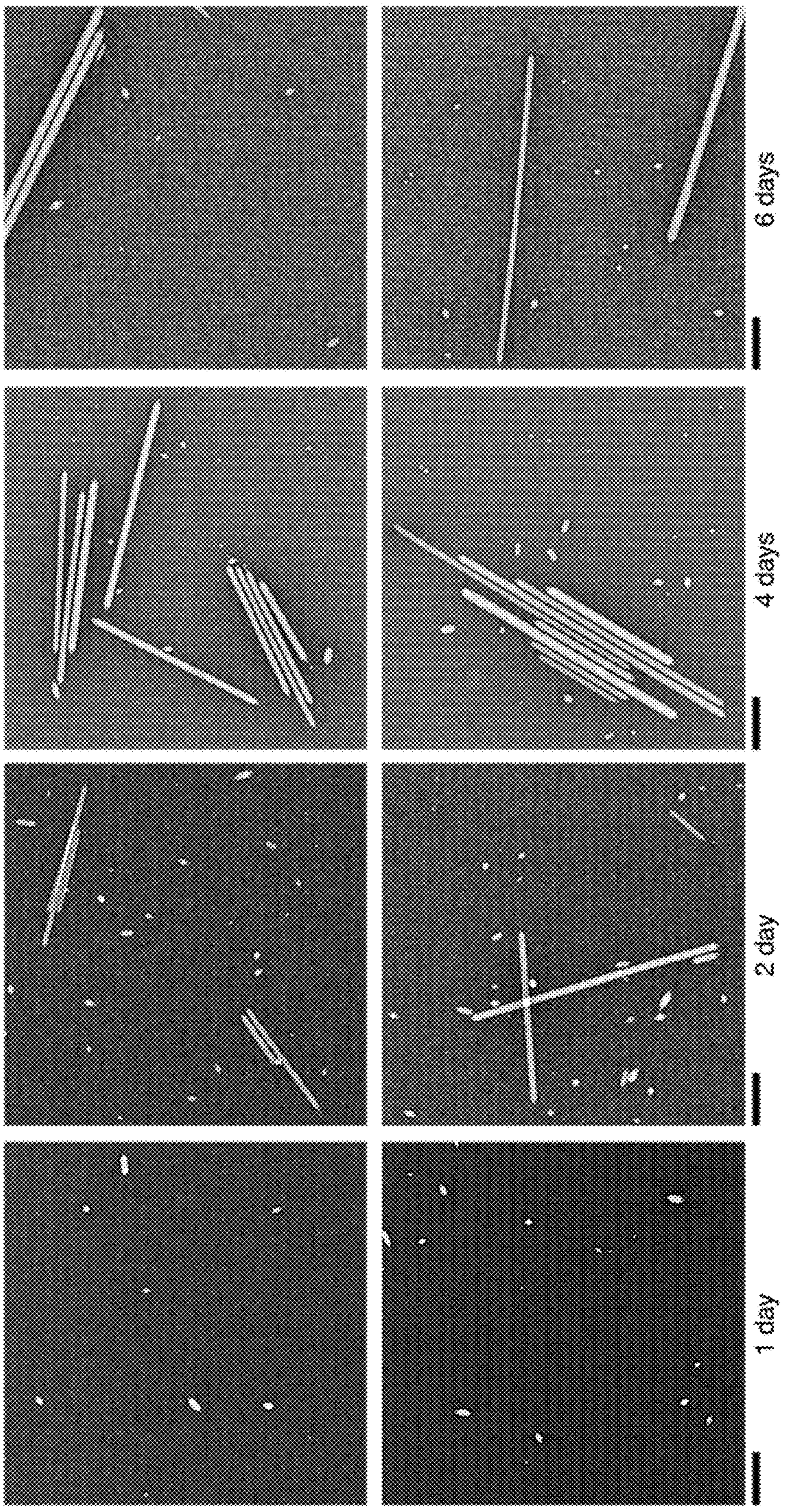

The resulting polyclonal MDA-MB-231-$mARG_{Ana}$ cells showed xAM contrast after a single day of doxycycline induction, which increased substantially through day 6 (FIG. 5H). The expression of GVs in these cells was confirmed by electron microscopy (FIG. 25E). The ultrasound signal increased steeply with increasing doxycycline doses up to 1 μg/mL, above which the signal saturated (FIG. 5I). xAM signal was detected from induced cells starting from an acoustic pressure of 0.31 MPa, whereas uninduced control cells did not produce signal at any pressure (FIG. 5J). At pressures above 0.42 kPa, the xAM signal gradually decreased over time, indicating the partial collapse of GVs. 0.42 MPa was chosen as the xAM imaging pressure for subsequent experiments, providing the optimal balance of signal stability and signal strength.

Figure 25G:
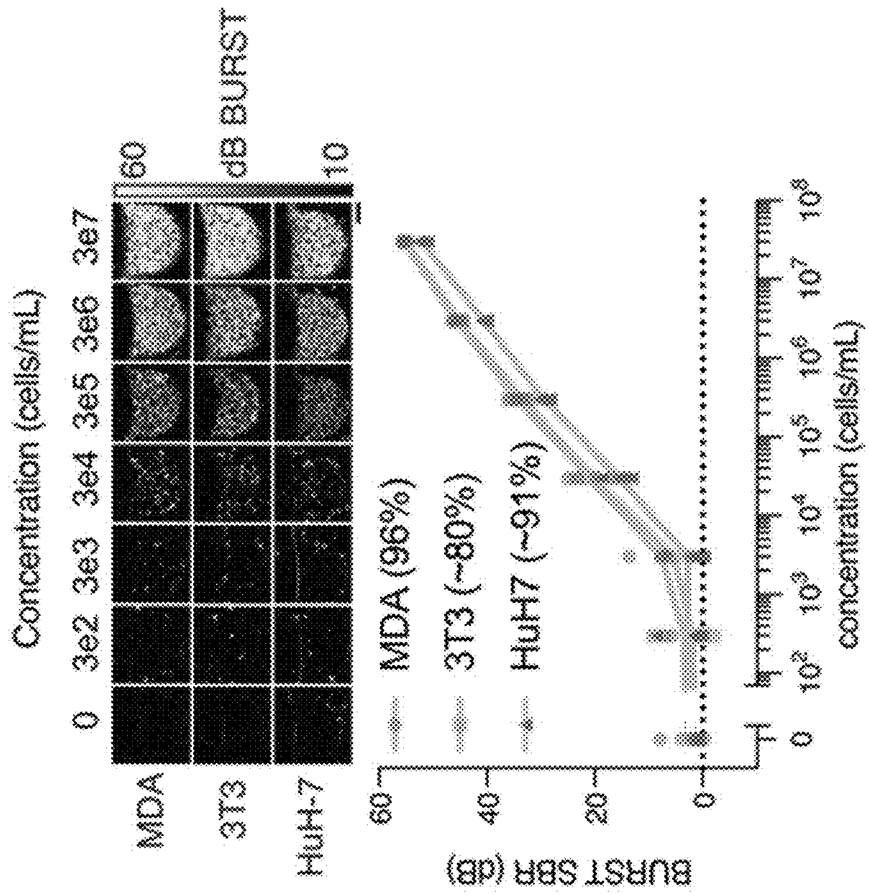
Figure 25F:
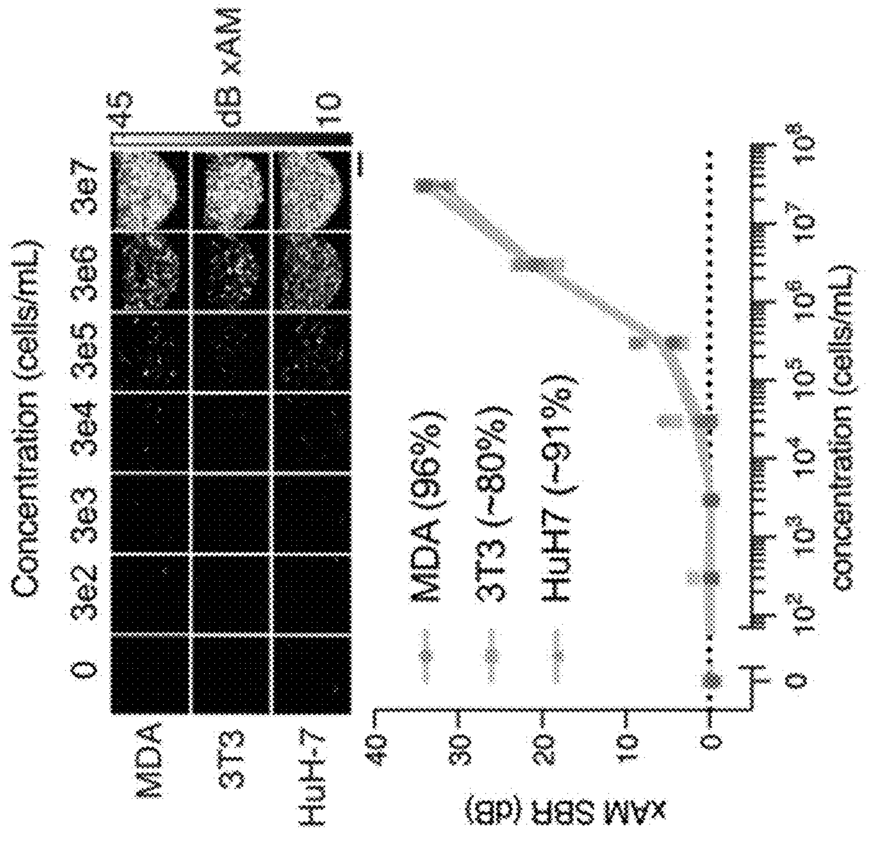

To test whether second-generation mammalian ARGs generalize beyond HEK293T and MDA-MB-231 cells, mouse 3T3 fibroblasts and human HuH7 hepatocytes were also engineered to express the $mARG_{Ana}$ operon. Both cell types showed excellent xAM contrast, providing a similar xAM detection sensitivity as MDA cells (FIG. 5K, FIG. 25F). At 300 k cells/mL for MDA-MB-231 and 3T3, and at 30 k cells/mL for HuH7, the detection limit surpassed the reported destructive imaging sensitivity of first-generation $mARG_{Mega}$ by one and two orders of magnitude respectively. With BURST imaging, $mARG_{Ana}$ cells could be detected still more sensitively, at concentrations down to 3,000 cells/mL for 3T3-$mARG_{Ana}$ and 30,000 cells/mL for MDA-MB-231-$mARG_{Ana}$ and HuH7-$mARG_{Ana}$ (FIG. 25G).

Figure 6E:
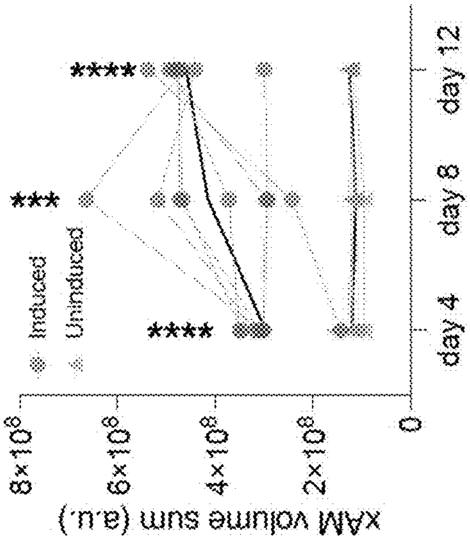
Figure 6D:
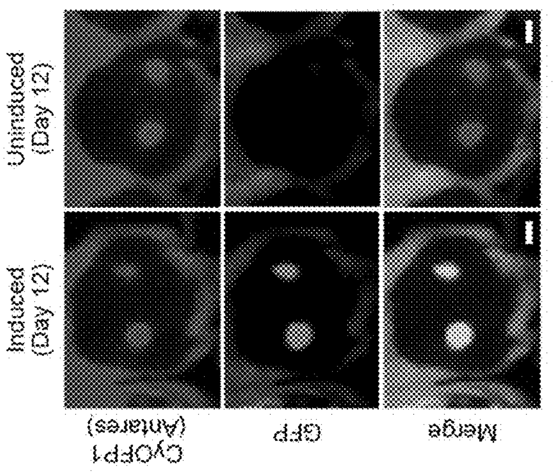
Figure 6C:
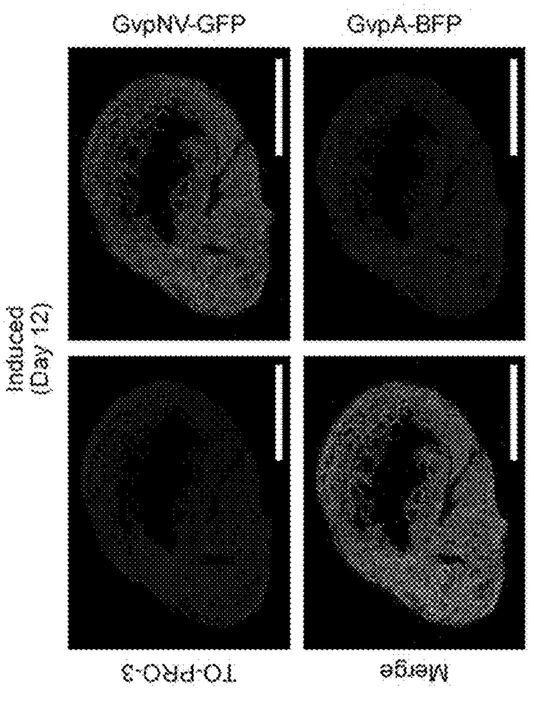

$mARG_{Ana}$ Expression Enables Visualization of In Vivo Gene Expression Patterns in an Orthotopic Tumor Model The ability of $mARG_{Ana}$ to reveal the spatial distribution of gene expression in tumor xenografts in living mice was next tested. Orthotopic tumors were formed by injecting MDA-MB-231-$mARG_{Ana}$ cells bilaterally in the fourth mammary fat pads of female immunocompromised mice. The mice were then split into doxycycline-induced and uninduced groups. Ultrasound images of the tumors were acquired as they grew, with 3 imaging sessions distributed over 12 days (FIG. 6A). All induced tumors produced bright and specific xAM contrast starting from the first timepoint (day 4), whereas the uninduced tumors did not (FIG. 6B). The acquisition of adjacent planes allowed 3D visualization of expression patterns (data not shown). The nonlinear xAM signal was highly specific to the viable tumor cells, being absent outside the anatomically visible tumor boundaries and within the cores of the larger tumors imaged at 8 and 12 days. The observed spatial pattern of gene expression in these tumors was corroborated by fluorescence microscopy of formalin-fixed tumor sections obtained from euthanized mice on day 12 (FIG. 6C, FIGS. 26A-26C), confirming the ability of $mARG_{Ana}$ to report microscale patterns of gene expression noninvasively in living animals. In contrast, in vivo fluorescence images of the mice lacked information about the spatial distribution of gene expression within the tumor (FIG. 6D). GV was quantified expression over time as a volumetric sum of xAM signal over all acquired image planes (FIG. 6E). The induced tumors had significantly higher total signal than the uninduced controls at all time points. These experiments demonstrate the ability of $mARG_{Ana}$ to serve as a highly effective reporter gene for the noninvasive monitoring of tumor growth and gene expression.

The primary advantage of ultrasound imaging over optical methods is deeper penetration. To ensure that $mARG_{Ana}$ expression can be detected in deep tissue beyond what can be easily shown in mice, MDA-MB-231-$mARG_{Ana}$ cells were imaged using xAM through a slab of beef liver thicker than 1 cm. As expected, the MDA-MB-231-$mARG_{Ana}$ cells were readily detectable (FIG. 26B). Moreover, this xAM signal was highly specific to MDA-MB-231-$mARG_{Ana}$ cells, and did not appear in the ARG-negative liver tissue (FIG. 26C).

Real-Time Nondestructive Ultrasound Imaging of $mARG_{Ana}$ Expression Enables Ultrasound-Guided Biopsy of Genetically Defined Cell Populations One of the most common uses of ultrasound in biological research and medicine is to spatially guide procedures such as biopsies. By enabling non-destructive imaging, second-generation mARGs create the possibility for such procedures to be targeted based on in vivo gene expression patterns. Notably, because real-time procedure guidance requires dynamic non-destructive imaging, such guidance was not possible with previous ARGs. To demonstrate this concept, ultrasound-guided biopsies were performed on chimeric tumors created by making adjacent subcutaneous injections of MDA-MB-231-$mARG_{Ana}$ cells and MDA-MB-231 cells expressing Antares (FIG. 7A). The chimeric composition of these tumors was visualized by obtaining 3D tomograms of the tumor mass (data not shown). Fine needle aspiration biopsies were then performed targeting either the xAM-positive or the xAM-negative regions of each tumor (FIG. 7B, data not shown). Flow cytometric analysis of dissociated biopsy samples showed a very high correlation between $mARG_{Ana}$-positive (GFP-positive) cells that were sampled from xAM-positive regions and vice versa (FIG. 7C, FIG. 27). These results demonstrate that $mARG_{Ana}$ expression enables genetically targeted in vivo procedures under ultrasound guidance.

DISCUSSION

These results establish two second-generation ARG constructs—$bARG_{Ser}$ and $mARG_{Ana}$—that provide unprecedented, real-time ultrasound detection sensitivity and specificity when expressed in bacteria and mammalian cells. These gene clusters, obtained through a systematic phylogenetic screen and optimized through genetic engineering, produce bright nonlinear ultrasound signal when expressed in situ in tumors, either by bacterial agents colonizing the necrotic core of a tumor, or by the tumor cells themselves. When imaged using a highly sensitive and specific nondestructive ultrasound imaging paradigm, this nonlinear signal enables real-time monitoring of the precise locations and transcriptional activities of these cells and is sufficiently stable to image cellular biodistribution and gene expression over multiple days. Furthermore, real-time nondestructive imaging of ARGs enables ultrasound-guided procedures such as biopsies to target genetically defined cells.

These results comprise a major advance over previous work on heterologous GV expression in bacterial and mammalian cells. Previous bARG constructs required the host bacteria to be cultured and pre-express GVs under ideal laboratory conditions before in vivo injection, while the previous mARG construct only produced ultrasound contrast when expressed in a sorted monoclonal cell line treated with a global epigenetic activator. In both cases, sensitive and specific detection of these cells relied on destructive imaging methods that produce one-time contrast, hindering their use in monitoring dynamic biological processes or guiding real-time interventions.

With these major improvements, it is anticipated that these new ARGs will be useful for many applications that demand the noninvasive imaging of cells deep inside the body. bARGs can be used to track therapeutic bacteria as they home to and proliferate in tumors or other target organs. The distribution of the bacteria in the tumor provides a critical readout of whether the therapy is working as designed or needs to be adjusted or re-administered (for example, when the tumor is only partially colonized). In addition, the spatial distribution is important in guiding focused energy procedures applied to the cells, such as focused ultrasound. Other applications provided herein include the study of the gastrointestinal (GI) microbiome and the tracking of probiotics designed to diagnose or treat GI conditions. In these applications, luminescence imaging would provide limited in vivo resolution due to light scattering, and would be difficult to scale to larger animals or human patients.

Second-generation mARGs provided herein can be used in biological research to visualize the growth and viability of tissues such as tumors and sample their contents with ultrasound-guided procedures. Similar approaches can be applied to study the immune system, the brain and organismal development, where the mARGs could be expressed constitutively or under phenotype-dependent promoters. In addition, mARG expression provided herein can enable the tracking of therapeutic mammalian cells, such as T-cells, stem cells and transplants analogously to the imaging of bacterial agents demonstrated in this study, and provide a means to target these therapeutic cells for biopsies and other image-guided interventions. Moreover, the fact that the new mARGs are based on *A. flos-aquae* GVs creates a connection between mammalian expression and molecular engineering, including the development of acoustic biosensors to monitor more dynamic cellular signals such as enzyme activity.

The envisioned applications of both bacterial and mammalian ARGs will benefit from the relative simplicity and low cost of ultrasound compared to other non-invasive techniques such as nuclear imaging and MRI, while providing in vivo resolution and potential for human translatability beyond what is currently possible with optical methods.

While these results represent an important step in the development of ARGs, additional improvements are provided herein which further expand their utility in biotechnology. First, in some embodiments, the expression kinetics of ARGs are slower than those of fluorescent proteins in bacteria and mammalian cells, and faster expression would facilitate the imaging of more dynamic genetic outputs. However, there are numerous scenarios in which expression kinetics on the order of one day are acceptable. For example, the processes of tumor growth and tumor infiltration by therapeutic cells are adequately captured, as shown in this study. Additional examples include inflammation, mammalian development, and stem cell expansion and migration. To enable a broader range of applications, the kinetics of ARG expression can be accelerated through further genetic engineering as described herein, for example by pre-expressing certain genes in the ARG cluster (e.g., the assembly factors) and conditionally expressing the remaining genes (e.g., the structural proteins). Second, the ability to multiplex different "colors" of ARGs nondestructively in vivo can enable discrimination between different strains of engineered bacteria in a consortium, between different mammalian cell types in a tissue, or between bacterial and mammalian cells in close proximity, such as in a bacterially-colonized tumor. Third, the *Serratia* GV gene cluster is relatively large, making it more challenging to clone and incorporate with other genetic elements. As provided herein, the engineering of a shorter cluster with similar acoustic properties would simplify these efforts. Similarly, the current $mARG_{Ana}$ cluster is delivered using two polycistronic plasmids; consolidating this cluster into a single plasmid, as described herein, can increase transfection efficiency, and shortening it could facilitate its viral packaging and delivery to endogenous cells in situ. Fourth, in some embodiments, the potentially burdensome effects of large plasmid size and ARG expression on cellular metabolism may be more pronounced in vivo than in vitro under ideal growth and expression conditions (FIGS. 2A-2I, FIGS. 511-5I, FIGS. 15A-15F, FIGS. 16A-16D, FIGS. 17A-17B, FIGS. 18A-18B). While the in vivo expression of both $bARG_{Ser}$ (FIGS. 4A-4L) and $mARG_{Ana}$ (FIGS. 6A-6E) yielded strong and specific ultrasound signals without obvious effects on cell migration and growth, strategies to reduce construct size and tightly regulate ARG expression are described herein and can become more important depending on the ARG application embodiment. The ability of second-generation ARGs, demonstrated here, to function in cells from two different mammalian species and two different bacterial species, is an encouraging sign for their broader utility.

The phylogenetic screening approach was successful in identifying $bARG_{Ser}$ and $mARG_{Ana}$ as greatly improved ARGs. However, out of practical necessity, this screen subsampled the available phylogenetic space, and testing additional GV-encoding gene clusters could reveal ARGs with new or further-improved properties. Improvements can also be made in the screening strategy. It is challenging to identify all the gvp genes in a given genome (see Methods), and there is considerable regulation of GV cluster transcription by factors inside or outside the clusters. Therefore, in a given cloned cluster, it is possible that either essential genes are missing or cryptic regulatory elements are included. These issues could be resolved by synthesizing multiple versions of each putative gene cluster and screening a larger number of them in higher throughput. Even with optimal genetic constructs, it is likely that gene clusters from some species will not successfully form GVs in a given heterologous host due to differences in growth temperature, turgor pressure or the presence or absence of specific host factors. The phylogenetic screening strategy used in this study could thus be adapted to find optimal ARGs for use in other species of interest.

Just as improvements to and adaptations of fluorescent proteins enabled a wide range of microscopy applications that were mere speculations when GFP was first harnessed as a biotechnology, the systematic development of next-generation ARGs will help bring to reality the promise of sensitive, high-resolution noninvasive imaging of cellular function inside intact mammals.

Materials and Methods

Genomic Mining of ARG Clusters

A literature search was conducted to find papers reporting the production of gas vesicles in any species. Search terms included "gas vesicle," "gas vacuole," "aerotope," and "aerotype." If the report did not include a strain name, then any available 16S rRNA gene sequence was used (as it was assumed that any other strain of the same species would fall in the same place on the phylogenetic tree), but no GV gene cluster sequence was used (even if it was available for one or more strains of that species) because it was found during the disclosed analysis that: 1) several reports describe species for which some strains produce GVs but others don't, and 2) comparison of GV gene cluster sequences of multiple strains of the same species almost always showed differences-often very significant ones. Further, even if a reference stating that a given organism produced GVs was not available, 16S rRNA gene sequences from all members of the following genera were included because GV production is a diacritical taxonomic feature for these genera: *Dolichospermum, Limnoraphis* and *Planktothrix.*

GV clusters were identified in genomes through a combination of annotations and sequence similarity to known gyp genes. However, there were two challenges in identifying all gvps in a given genome: 1) there is little to no annotation for many gvps, and 2) GV gene clusters are not always contiguous in genomes, and gvps can occasionally be found hundreds of kb away from the main cluster(s). It was attempted to only select "well-behaved" GV clusters for testing (i.e., ones in which all gvps identified in that genome were present in clusters, and these clusters contained a minimum of non-gyp genes, which could increase the metabolic burden of cluster expression without increasing GV yield), but it is possible that even for these clusters, some gvps were not cloned.

Of the list of 288 strains reported to form gas vesicles, 270 had 16S rRNA gene sequences available. These were downloaded from NCBI using a custom Python script, and a multiple sequence alignment was constructed using Clustal Omega. This alignment was used to generate a phylogenetic tree file using ClustalW2, which was rendered using EvolView. Only unique species are displayed in the phylogenetic trees in FIG. 1A and FIG. 8.

Bacterial Plasmid Construction and Molecular Biology

Organisms were obtained from commercial distributors as indicated in Table 1. If an organism was shipped as a liquid culture, the culture was centrifuged and the pellet resuspended in ddH2O, as it was found that even trace amounts of certain culture media could completely inhibit PCR. Fragments were amplified by PCR using Q5 polymerase and assembled into a pET28a(+) vector (Novagen) via Gibson Assembly using reagents from New England Biolabs (NEB). Sub-cloning and other modifications to plasmids were also performed with Gibson Assembly using reagents from NEB. Assemblies were transformed into NEB Stable *E. coli*. All constructs were verified by Sanger sequencing.

TABLE 1

| GENOMIC PRIMERS | | | |
|---|---|---|---|
| Organism Name | Source | NCBI Accession Number | Primer Sequence |
| *Anabaena flos-aquae* (*Dolichospermum flos-aquae*) | CCAP 1403/13F | CP051206.1 | SEQ ID NO: 4 (F1)<br>SEQ ID NO: 5 (R1) |
| *Bacillus megaterium* | ATCC 19213 | CP047699.1 | SEQ ID NO: 6 (F1)<br>SEQ ID NO: 7 (R1) |
| *Desulfobacterium vacuolatum* | DSM 3385 | FWXY01000008.1 | SEQ ID NO: 8 (F1)<br>SEQ ID NO: 9 (R1)<br>SEQ ID NO: 10 (F2)<br>SEQ ID NO: 11 (R2) |
| *Serratia* sp. | ATCC 39006 | CP025084.1 | SEQ ID NO: 12 (F1)<br>SEQ ID NO: 13 (R1)<br>SEQ ID NO: 14 (F2)<br>SEQ ID NO: 15 (R2) |

*Halobacterium salinarum* has two chromosomal GV gene clusters (plus additional plasmid-borne ones), which were cloned and tested separately. *Methanosarcina vacuolata* has only one cluster, but while its genome sequence in the NCBI database has two copies of GvpA1 and one copy of GvpA2, genomic PCR disclosed herein yielded a product with only one copy of GvpA1. In a second cloning step, a copy of GvpA2 was added to the cloned cluster. While we were able to PCR GvpA2 from the genome, it was not contiguous with the rest of the cluster. Therefore, and without being bound by any particular theory, it is possible that either there was an error in the assembly of the genome sequence (likely caused by the high sequence similarity of the GvpA genes), or that the genotype of the disclosed strain differs slightly from that of the strain sequenced.

In Vitro Bacterial Expression of ARGs

For initial testing, all constructs were expressed in BL21 (DE3) *E. coli* (NEB). Fifty pL of electrocompetent *E. coli* were transformed with 1.5 μL of purified plasmid DNA (Econospin 96-well filter plate, Epoch Life Science), and 1 mL of SOC medium (NEB) was added immediately after electroporation. These cultures were incubated at 37° C. for 2 hr, and 150 uL was inoculated into larger 1.5 mL LB cultures containing 100 μg/mL kanamycin and 1% (w/v) glucose (for catabolite repression of the BL21(DE3) PlacUV5 promoter) in a deep-well 96-well plate and grown overnight in a shaking incubator at 30° C. Square dual-layer LB agar plates were prepared as described previously, with varying concentrations of IPTG and 100 μg/mL kanamycin in the bottom layer, and 1% (w/v) glucose and 100 μg/mL kanamycin in the top layer. LB agar was incubated at 60° C. for 12-36 hr after dissolution to allow it to degas. After the agar solidified, plates were dried at 37° C. to remove all condensation on the top layer that would cause the bacterial patches to run together. A multichannel pipette was used to thoroughly mix overnight cultures and drop 1 μL of each culture onto the surface of the dual-layer plates, with care taken to avoid puncturing the agar which results in artifacts during ultrasound scans. Importantly, low-retention pipette tips were used, as it was found that the small volumes of culture would wet the outsides of standard pipette tips, resulting in inaccurate volume dispensing. Patches were allowed to dry completely before plates were flipped and incubated at 37° C. for 24 hr or 30° C. for 48 hr.

For in vitro expression experiments in EcN, the appropriate plasmids were first transformed via electroporation and the outgrowth was plated on LB (Miller)-agar plates with the appropriate antibiotic (25 μg/mL chloramphenicol or 50 μg/mL kanamycin) and 1% (w/v) glucose. The resulting colonies were used to inoculate 2 mL LB (Miller) medium with the appropriate antibiotic and 1% (w/v) glucose, and these cultures were incubated at 250 rpm and 37° C. overnight. Glycerol stocks were prepared by mixing the overnight cultures in a 1:1 volume ratio with 50% (v/v) glycerol and storing at −80° C. The night before expression experiments, glycerol stocks were used to inoculate overnight cultures (2 mL LB medium with the appropriate antibiotic and 1% (w/v) glucose) which were incubated at 37° C. and shaken at 250 rpm. For expression on solid media, 1 μL of overnight culture was dropped onto square dual-layer LB agar plates with 2× the final inducer (IPTG, aTc, or L-arabinose) concentration in the bottom layer, 1% (w/v) glucose in the top layer, and the appropriate antibiotic in both layers (50 μg/mL chloramphenicol or 100 μg/mL kanamycin). Plates were allowed to dry, and then inverted and incubated at 37° C. for 24 hours before imaging with ultrasound. For expression in liquid media, 500 μL of each overnight culture was used to inoculate 50 mL LB supplemented with 0.4% (w/v) glucose and 25 μg/mL chloramphenicol in 250 mL baffled flasks. Cultures were incubated at 37° C. and 250 rpm until reaching at $OD_{600}$ of 0.1-0.3. At this point, cultures were induced by addition of L-arabinose and placed back at 37° C. and 250 rpm. For time titration experiments, 0.1% (w/v) L-arabinose was used for induction and 0.5 mL of each culture was removed at 0, 1, 3, 5, 7, 9, 11, and 24 hours post-induction for $OD_{600}$ and ultrasound measurements. For L-arabinose titration experiments, L-arabinose concentrations ranging from 0 to 1% (w/v) were used for induction, and cultures were incubated for 24 hours at 37° C. and 250 rpm after addition of L-arabinose before ultrasound imaging. For cell concentration titration experiments, cultures were incubated for 24 hours at 37° C. and 250 rpm after addition of 0.1% (w/v) L-arabinose before ultrasound imaging. All cultures were stored at 4° C. or on ice until casting in phantoms and imaging with ultrasound. In all liquid culture experiments, cultures were prescreened for the presence of GVs by phase contrast microscopy before being imaged with ultrasound.

In vitro expression experiments in *S. typhimurium* were performed as described above for EcN, except plasmids were transformed into an attenuated version of *Salmonella enterica* serovar *typhimurium* strain SL1344, 2×YT medium was used instead of LB medium, and induction in liquid culture was performed by adding L-arabinose to the medium at the time of inoculation at an $OD_{600}$ of 0.05.

To assess plasmid stability of pBAD-bARG$_{Ser}$-AxeTxe in EcN, the glycerol stock of this strain was used to inoculate 2 mL LB (Miller) supplemented with 25 μg/mL chloramphenicol and 1% (w/v) glucose, and this culture was incubated at 37° C. and 250 rpm overnight. Twenty μL of the overnight culture was subcultured into 2 mL LB with 25 μg/mL chloramphenicol, 2 mL LB without antibiotics, and 2 mL LB without antibiotics and with 0.1% (w/v) L-arabinose, each in quadruplicate. Every 24 hours, 20 μL of each culture was sub-cultured into fresh media of the same conditions. All cultures were incubated at 37° C. and 250 rpm. On days 1-3, 5, and 7, serial dilutions of each culture were plated on LB-agar without antibiotics, LB-agar with 25 μg/mL chloramphenicol, and LB-agar with 25 μg/mL chloramphenicol+0.1% (w/v) L-arabinose+0.4% (w/v) glucose. Plates were incubated at 37° C. for at least 16 hours and colonies were counted and screened manually. Plasmid retention was assessed by taking the ratio of CFUs on LB-agar plates with chloramphenicol to CFUs on LB-agar plates without antibiotics. The presence of mutations that disrupt the ability to express functional $bARG_{Ser}$ was assessed by a loss of colony opacity on LB-agar plates with 25 μg/mL chloramphenicol+0.1% (w/v) L-arabinose+0.4% (w/v) glucose.

In Vitro Ultrasound Imaging of Bacteria Expressing ARGs on Solid Media

Ultrasound imaging of bacterial patches was performed using a Verasonics Vantage programmable ultrasound scanning system and an L10-4v 128-element linear array transducer (Verasonics) with a center frequency of 6 MHz and an element pitch of 300 μm. Image acquisition was performed using a custom imaging script with a 64-ray-lines protocol and a synthetic aperture of 65 elements. The transmit waveform was set to a voltage of 50 V and a frequency of 10 MHz, with 1 waveform cycle and 67% intra-pulse duty cycle. In xAM mode, a custom sequence detailed previously was used with an angle of 19.5°. RF data from 4 repeated acquisitions was coherently averaged prior to beamforming for each image plane.

Agar plates containing bacterial patches were coated with a thin layer of LB agar and immersed in PBS to allow acoustic coupling to the L10-4v transducer. The transducer was connected to a BiSlide computer-controlled 3D translatable stage (Velmex) and positioned above the plane of the plate at an angle of 15° from the vertical (to minimize specular reflection from the plastic dishes and agar) and a distance of 20 mm from the bacterial patches. The imaging sequence was applied sequentially to acquire image planes covering the full area of all plates. A custom script was used to automate the scan by controlling the motor stage in tandem with the ultrasound system, translating 0.5 mm in the azimuthal direction between rows and 19.5 mm in the lateral direction between columns. In the case of differential imaging scans, the full scan sequence was repeated after returning the motor stage to its origin and adjusting the voltage of the transducer.

For image processing and analysis, custom beamforming scripts were applied on-line to reconstruct image planes from the acquired RF data at each location. The intensity data for each plane was saved for off-line processing. All image planes were concatenated to form a 3D volume with all plates and colonies. A 2D image of the colonies was extracted from the 3D volume by taking the maximum intensity over a manually-defined depth range for all voxel columns. 2D differential images were obtained by subtracting the post-collapse 2D image from the pre-collapse 2D image. Bacterial patch intensities were then quantified from these 2D images. Sample ROIs were drawn around the center of each patch to avoid artefacts from the edges, and background ROIs were drawn around representative regions without patches. The signal-to-background ratio (SBR) was calculated as the mean pixel intensity of the sample ROI divided by the mean pixel intensity of the background. Conversion to decibels (dB) was calculated as 20*log 10(SBR). For display, images were normalized by dividing by the average background signal of all images being compared and setting the lower and upper limits of the colormaps to be the same, where the lower limit was equal to a constant A times the average background and the upper limit was equal to a constant B times the maximum pixel intensity out of all images being compared; images were then converted to dB. For xAM and differential xAM images of bacterial patches, A was set to 1 and B was set to 0.5.

In Vitro Ultrasound Imaging of Bacteria Expressing ARGs Suspended in Agarose Phantoms To create phantoms for ultrasound imaging of bacteria from liquid cultures or suspended in PBS from patches on solid media, wells were cast with a custom 3D-printed mold using 1% (w/v) agarose in PBS, which was degassed by incubating at 65° C. for at least 16 hours. Cultures or cell suspensions to be analyzed were diluted in ice-cold PBS to 2× the final desired cell concentration (calculated from the measured $OD_{600}$), incubated at 42° C. for one minute, and mixed 1:1 with 1% (w/v) agarose in PBS at 42° C. for a final concentration of 1×. This mixture was then loaded into the wells in duplicate and allowed to solidify. Care was taken not to introduce bubbles during this process. The phantoms were submerged in PBS, and ultrasound images were acquired using a Verasonics Vantage programmable ultrasound scanning system and an L22-14v 128-element linear array transducer with a center frequency of 18.5 MHz with 67%-6-dB bandwidth, an element pitch of 100 μm, an elevation focus of 8 mm, and an elevation aperture of 1.5 mm. The transducer was attached to a custom-made manual translation stage to move between samples. B-mode and xAM images were acquired using the same parameters as described previously: the frequency and transmit focus were set to 15.625 MHz and 5 mm, respectively, and each image was an average of 50 accumulations. B-mode imaging was performed with a conventional 128-ray-lines protocol, where each ray line was a single pulse transmitted with an aperture of 40 elements. xAM imaging was performed using a custom sequence detailed previously with an angle of 19.5° and an aperture of 65 elements. The transmitted pressure at the focus was calibrated using a Fibre-Optic Hydrophone (Precision Acoustics), and the peak positive pressure was used as the "acoustic pressure" in FIGS. 3A-3I. BURST images were acquired as a series of pAM images as described previously, except the focus was set to 6 mm, and the acoustic pressure was set to 0.15 MPa (1.6V) for the first 10 frames and 3.0 MPa (25V) for the last 46 frames.

To measure the xAM signal at varying acoustic pressures, an automated voltage ramp imaging script was used to acquire an xAM image at each voltage step (0.5 V increments from 2 to 25 V), immediately followed by a B-mode acquisition at a constant voltage of 1.6 V (0.15 MPa) before another xAM acquisition at the next voltage step; the voltage was held constant for 10 seconds at each step before the image was saved. To measure the xAM and B-mode signals over time at various acoustic pressures, another script was used to automatically save an xAM or B-mode image every second while the voltage was automatically increased by 2 V approximately every 70 seconds. Each frame consisted of 64 ray lines, which took 180 μs each to acquire, giving a pulse repetition rate of 86.8 Hz. Based on these results, all subsequent in vitro xAM images of $bARG_{Ser}$-expressing EcN were acquired at 18V (1.29 MPa).

For experiments in FIGS. 19A-19C and FIGS. 21A-21K, a different transducer, an L22-14vX transducer, was used which had a different pressure-to-voltage calibration. Consequently, for ultrasound imaging of *S. typhimurium*, xAM imaging was performed at 1.72 MPa (14V), unless otherwise noted, and BURST was performed using 0.16 MPa (1.6V) for the first 10 frames and 3.7 MPa (25V) for the final 46 frames.

xAM and B-mode image processing and analysis were performed as described above, except that custom beamforming scripts were applied off-line to reconstruct images from the saved RF data for each sample, no 3D reconstruction was performed as images captured at single locations, circular ROIs were drawn around sample and background regions (taking care to avoid bubbles) to calculate SBRs, and values of A=1.4 and B=0.5 were used to normalize images for display. BURST images were reconstructed using the signal template unmixing algorithm as described previously; as above, circular ROIs were then drawn around sample and background regions to calculate SBRs and values of A=3 and B=1 were used to normalize images for display.

Microscopy of Bacteria

For TEM imaging, cells expressing GVs were diluted to $OD_{600}$~1 in 10 mM HEPES (pH 7.5) or culture media. 3 μL of the sample was applied to a freshly glow-discharged (Pelco EasiGlow, 15 mA, 1 min) Formvar/carbon-coated, 200 mesh copper grid (Ted Pella) for 1 min before being reduced to a thin film by blotting. Grids with cells were washed three times in 10 mM HEPES (pH 7.5), blotted, air-dried, and imaged without the stain. Image acquisition was performed using a Tecnai T12 (FEI, now Thermo Fisher Scientific) electron microscope operated at 120 kV, equipped with a Gatan Ultrascan 2 k×2 k CCD.

For phase contrast microcopy (PCM) imaging, cells expressing GVs were scraped off from plates and re-suspended in PBS at an $OD_{600}$ of 1-2, or liquid cultures were used directly. Suspensions were transferred to glass slides and PCM images were acquired using a Zeiss Axiocam microscope with a 40×Ph2 objective.

In Vivo Bacterial ARG Expression and Ultrasound Imaging

All in vivo experiments were performed under a protocol approved by the Institutional Animal Care and Use of Committee (IACUC) of the California Institute of Technology. For experiments involving tumor colonization with EcN, MC26 cells were grown in DMEM media in T225 flasks. After trypsinization and resuspension in PBS+0.1 mg/mL DNAseI, $5\times10^6$ MC26 cells were injected subcutaneously into the right flank of 6-8-week-old female Balb/cJ mice. Tumors were allowed to grow for 14 days (reaching sizes of 200-300 $mm^3$) before injecting $10^8$ EcN cells suspended in PBS via the lateral tail vein. The day before injection of EcN, Ibuprofen was added to the drinking water at 0.2 mg/mL to ameliorate side effects of EcN injections. To prepare the EcN for injection, the appropriate glycerol stocks were used to inoculate 2 mL LB+1% (w/v) glucose+ 25 μg/mL chloramphenicol which was incubated at 37° C. and 250 rpm overnight. The overnight culture (500 L) was used to inoculate 50 mL LB+0.4% (w/v) glucose+25 μg/mL chloramphenicol in 250 mL baffled flasks, which was grown at 37° C. and 250 rpm until reaching an $OD_{600}$ of 0.3-0.6. This culture was pelleted, washed 4 times with PBS, resuspended in PBS at an $OD_{600}$ of 0.625, and used for injection. Three days after injection of EcN, mice were injected intraperitoneally with 120 mg L-arabinose to induce the EcN. Starting 24 hours after induction, ultrasound images of tumors were acquired as described below. After imaging, 3.0 MPa acoustic pressure was applied throughout the tumor to collapse GVs, and mice were injected again intraperitoneally with 120 mg L-arabinose. The next day, mice were imaged again with ultrasound for re-expression of GVs. The following day, all mice were euthanized and tumors were excised, homogenized, serially diluted, and plated on selective media (LB-agar+25 μg/mL chloramphenicol) as well as on induction plates (LB-agar+25 μg/mL chloramphenicol+ 0.4% (w/v) glucose+0.1% (w/v) L-arabinose). Colonies on plates with chloramphenicol were manually counted to quantify the levels of colonization, and colonies on induction plates were screened for a non-opaque mutant phenotype.

For ultrasound imaging, mice were anesthetized with 2% isoflurane and maintained at 37° C. using a heating pad. Images were acquired using the L22-14v transducer attached to a manual translation stage described above. Any hair on or around the tumors was removed with Nair, and Aquasonic 100 ultrasound transmission gel was used to couple the transducer to the skin. Parabolic B-mode and parabolic AM (pAM) images were first acquired using a custom 128 ray line script. Each image was formed from 96 focused beam ray lines, each with a 32-element aperture and 6 mm focus. The transmit waveform was set to a voltage of 1.6V in B-mode or 8V in pAM and a frequency of 15.625 MHz, with 1 waveform cycle and 67% intra-pulse duty. In B-mode, each ray line was a single transmit with all 32 elements, and in pAM each ray line consisted of one transmit with all 32 elements followed by 2 transmits in which first the odd and then the even-numbered elements are silenced. Subsequently, xAM images, additional B-mode images, and finally BURST images were acquired at the same location without moving the transducer using the same parameters as described above for the in vitro experiments (e.g. 18V for xAM, 1.6V for B-mode, and 1.6V to 25V for BURST). At least two separate locations spaced at least 2 mm apart in each tumor were imaged with B-mode, pAM, and xAM. Ultrasound images of tumors were quantified as described above where the sample ROIs were drawn around the necrotic cores in the tumors and the background ROIs were drawn around regions in the gel above the mouse. Images were normalized and plotted on a dB scale as described above except the scaling factors were A=2.5 and B=1 for xAM and pAM and the corresponding B-mode tumor images, and A=10 and B=0.5 for BURST images.

Histology of Tumors Colonized by Bacteria

Tumors were colonized with pBAD-$bARG_{Ser}$-AxeTxe EcN following the same protocol as described above. The day after inducing GV expression with IP injections of L-arabinose, BURST, xAM and B-mode images of tumors were acquired as described above. Shortly after imaging, mice were euthanized by sedation with isoflurane and cervical dislocation. Tumors were resected, placed in 10% buffered formalin for 48 hours, and then washed and stored in 70% ethanol. Tumors were then cut in half along the approximate plane of imaging, placed in tissue cassettes, and sent to the Translational Pathology Core Laboratory at UCLA, which embedded samples in paraffin and performed H&E staining, immunohistochemistry, and microscopy imaging. Immunohistochemistry was performed using Opal IHC kits (Akoya Biosciences) according to the manufacturer's instructions. Tissue sections were incubated with either polyclonal rabbit anti-*E. coli* antibody (Virostat; catalogue number 1001) or non-reactive rabbit IgG isotype control antibody as a negative control. All sections were then incubated with an Opal 520 polymer anti-rabbit HRP antibody (Akoya Biosciences) and counterstained with DAPI. Sections were imaged in the appropriate fluorescence or brightfield channels using a high throughput scanning system (Leica Aperio VERSA) with 40 μm resolution.

Mammalian Plasmid Construction

Monocistronic plasmids were constructed using standard cloning techniques including Gibson assembly and conventional restriction and ligation. Coding sequences for the *A. flos-aquae* GV genes were codon-optimized and synthesized by Integrated DNA Technologies, and subcloned into a pCMVSport backbone with a CMV promoter as described previously. gvpA-WPRE-hGH polyA was constructed by subcloning gvpA between PstI and MluI sites of pCMVSport vector with WPRE-hGH polyA.

Polycistronic $mARG_{Ana}$ assembly factor genes gvpNJKFGWV were synthesized by Twist Bioscience in a pTwist-CMV vector. Emerald GFP was subcloned in-frame downstream of the gvpNJKFGWV ORF via a P2A linker and the entire pNJKFGWV-GFP ORF was subcloned into a pCMVSport backbone with WPRE-hGH-poly(A) elements using NEBuilder HiFi DNA Assembly (NEB). gvpA-IRES-EBFP2-WPRE-hGH polyA was constructed by Gibson assembly of a PCR-amplified IRES-EBFP2 fragment into the XbaI site of gvpA-WPRE-hGH polyA plasmid.

PiggyBac transposon plasmids were constructed by PCR amplifying the region between the start codon of gvpNJKFGWV or gvpA and the end of the hGH poly(A) from the pCMVSport plasmids. The amplified regions were Gibson-assembled into the PiggyBac transposon backbone (System Biosciences) with a TRE3G promoter (Takara Bio) for doxycycline-inducible expression.

The lentiviral transfer plasmid with constitutively expressed tetracycline transactivator (pEF1α-rtTA-Antares-WPRE) was constructed as follows: pNCS-Antares was obtained from Addgene (#74279) and P2A was added to the N-terminus of Antares with a primer overhang during PCR. This fragment was subcloned into the lentiviral transfer plasmid pEF1α-rtTA-WPRE between rtTA and WPRE in-frame with the rtTA ORF using NEBuilder HiFi DNA Assembly.

HEK293T Cell Culture, Transient Transfection, In Vitro Ultrasound Imaging of Transient Expression of GVs Suspended in Agarose Phantoms HEK293T cells (ATCC, CLR-2316) were cultured in 24-well plates at 37° C., 5% CO2 in a humidified incubator in 0.5 ml DMEM (Corning, 10-013-CV) with 10% FBS (Gibco) and 1× penicillin/streptomycin until about 80% confluency before transfection as described previously. Briefly, transient transfection mixtures were created by mixing of around 600 ng of plasmid mixture with polyethyleneimine (PEI-MAX; Polysciences Inc.) at 2.58 pg polyethyleneimine per pg of DNA. The mixture was incubated for 12 minutes at room temperature and added drop-wise to HEK293T cells. Media was changed after 12-16 hours and daily thereafter. For gvpA titration experiments, pUC19 plasmid DNA was used to keep the total amount of DNA constant.

After three days of expression, cells were dissociated using Trypsin/EDTA, counted using disposable hemocytometers (Bulldog), and centrifuged at 300 g for 6 minutes at room temperature. Cells were resuspended with 1% low-melt agarose (GoldBio) in PBS at 40° C. at ~30 million cells/mL (FIG. 5B, FIG. 5F), ~15 million cells/mL (FIG. 5D), or ~7.5 million cells/mL (FIG. 25C) before loading into wells of preformed phantoms consisting of 1% agarose (Bio-Rad) in PBS.

Phantoms were imaged using L22-14v transducer (Verasonics) while submerged in PBS on top of an acoustic absorber pad. For BURST imaging, wells were centered around the 8 mm natural focus of the transducer and a BURST pulse sequence was applied in pAM acquisition mode as described above, except the focus was set to 8 mm, and the acoustic pressure was set to 0.26 MPa (1.6V) for the first 10 frames and 2.11 MPa (10V) for the remaining frames. The xAM voltage ramps and B-mode images were acquired concurrently using the same parameters as described above, except the transducer voltage was varied from 4 to 24V in steps of 0.5V for xAM, and 10 frames, each consisting of 15 accumulations, were acquired per voltage. The well depth and the B-mode transmit focus were set to 5 mm. All image quantification was performed as described above, where the sample ROIs were drawn inside the well and the background ROIs were drawn around an empty region in the agarose phantom for SBR calculation. All images were normalized and plotted on a dB scale as described above except the scaling factors were A=2 and B=0.5.

Genomic Integration and FACS

MDA-MB-231 (ATCC, HTB26), 3T3 (ATCC, CRL-1658) and HuH7 (JCRB0403) cells were cultured in DMEM (Corning, 10-013-CV) supplemented with 10% FBS (Gibco) and 1× penicillin/streptomycin at 37° C. and 5% CO2 in a humidified incubator unless noted otherwise. Cells were lentivirally transduced with pEF1α-rtTA-Antares-WPRE and sorted based on strong Antares fluorescence (Ex: 488 nm, Em: 610/20BP+595LP) using BD FACSAria II for MDA-MB-231 cells and MACSQuant Tyto (B2 channel) for 3T3 and HuH7 cells. MDA-MB-231-rtTA-Antares cells were then electroporated in 20 ul format using 4D-Nucleofector using CH-125 protocol in SF buffer (Lonza) with 1 pg PiggyBac transposon:transposase plasmid mixture (2:1 PB-gvpA:PB-gvpNV transposons, 285 ng PiggyBac transposase). 3T3-rtTA-Antares cells were transfected with the same PiggyBac plasmid mixture using PEI-MAX in a 12-well format and HuH7 cells were transfected using Lipofectamine 3000. Cells were expanded into surface-treated T75 flasks in TET-free media and were induced for 12 hours with 1 μg/mL doxycycline before sorting for triple positive cells (gated for Antares, then Emerald and EBFP2). The sorted cells were returned to DMEM with TET-free FBS (Takara). MDA-MB-231-$mARG_{Ana}$ was sorted twice. The first round of sorting was performed with permissive gates and the enriched population was ~50% double positive for Emerald and EBFP2 as analyzed with MACSQuant VYB (Miltenyi Biotec). This population was sorted again with stricter gates to ~95% purity. 3T3-$mARG_{Ana}$ cells were sorted for strong Emerald and EBFP2 fluorescence using MACSQuant Tyto only once, yielding a population that was ~80% double positive. HuH7 cells were sorted twice to ~91% purity using MACSQuant Tyto. Cells were expanded in TET-free media and frozen in Recovery Cell Culture Freezing Medium (Gibco) using Mr. Frosty cell freezing container (Nalgene) filled with isopropanol at −80° C., and then stored in liquid nitrogen vapor phase until use.

In Vitro Ultrasound Imaging of MDA-MB-231 $mARG_{Ana}$ Cells Suspended in Agarose Phantoms For all in vitro experiments, MDA-MB-231-$mARG_{Ana}$ cells were cultured in DMEM supplemented with 10% TET-free FBS and penicillin/streptomycin. For xAM imaging of MDA-MB-231-$mARG_{Ana}$ cells suspended in agarose phantoms, cells were cultured in 24-well plates in 0.5 mL media. For FIG. 5H, cells were seeded at 7,500 cells per well and induced with 1 μg/mL doxycycline after an overnight incubation and at subsequent days as indicated (5 replicates per condition), except for the uninduced control which was grown in a 10 cm dish without doxycycline. Media was changed daily thereafter until cell harvest. Cells were trypsinized with 100 pL Trypsin/EDTA for 6 minutes at 37° C., after which the trypsin was quenched by addition of 900 pL media. The cell number was equalized between different days of expression at 140,000 cells and pelleted at 300 g for 6 minutes. Cells were then resuspended in 20 μl 1% low-melt agarose (GoldBio) in PBS at 40° C. and loaded into the wells of preformed 1% agarose (Bio-Rad) phantoms in PBS. Ultrasound images were acquired with L22-14v 128-element linear array transducer (Verasonics). xAM voltage ramp and B-mode images were acquired concurrently using the same parameters as described above (the transducer voltage was varied from 4 to 24V in steps of 0.5V for xAM and 10 frames, each consisting of 15 accumulations, were acquired per voltage. The B-mode transmit focus was set to 5 mm). Images taken at the voltage that produced peak xAM signal (9V, 0.54 MPa) were chosen for quantification. For FIG. 5I and FIG. 5J, cells were seeded at 66,666 cells per well and induced with the indicated doxycycline concentrations after an overnight incubation in TET-free media (4 replicates per doxycycline concentration). Cells were incubated for 4 days with daily media/doxycycline changes. Cells were harvested as above, and ~420,000 cells from each condition were loaded per agarose phantom well. xAM and B-mode images were acquired concurrently using the same parameters as described above except the transducer voltage was varied from 6V to 10V in steps of 0.5V for xAM and 120 frames, each consisting of 15 accumulations, were acquired per voltage (~75 seconds/voltage). The B-mode transmit focus was set to 6 mm. Images taken at 7.5V (0.42 MPa) were chosen for display and quantification in FIG. 5I (doxycycline response). For FIG. 5K and FIGS. 25F-25G, cells were seeded in 10-cm dishes and induced as above for 4 days. Cells were harvested as above and resuspended at 60,000,000 cells/mL. 10-fold serial dilutions were performed with each cell line. Each cell dilution was mixed 1:1 with 2% low-melt agarose before loading into agarose phantom wells. Cells were imaged with an L22-14vX transducer at 5.5V (0.61 MPa) for xAM: the highest pressure that produced stable signal over a 30-second exposure and using 2V to 15V pAM BURST.

For imaging of MDA-MB-231 cells under thick liver tissue, cells were induced with doxycycline in T225 flasks for 4 days. Cells were harvested as above and resuspended at 30,000,000 cells/mL in 1% low-melt agarose in PBS prior to loading into agarose phantom wells. >1 cm beef liver section (99 Ranch Market) was overlaid on top of the agarose phantom and secured with needles. The phantom and liver were submerged in a PBS bath and the transducer was positioned 20 mm away from the interface between the liver and the agarose phantom. Ultrasound imaging was performed using a L10-4v linear array transducer (Verasonics) using the same parameters as above, except the xAM voltage was varied between 2V (0.078 MPa) and 30V (2.51 MPa). B-mode was acquired at 1.6V (0.25 MPa). Each voltage was held for 5 frames, each consisting of 15 accumulations.

All image quantification was performed as described above where the sample ROIs were drawn inside the well and the background ROIs were drawn around an empty region in the agarose phantom for SBR calculation. All Images were normalized and plotted on a dB scale as described above except the scaling factors were A=2 and B=0.5. The xAM/B-mode overlay was made with the B-mode image as background. A binary alpha mask was applied to the xAM image, giving pixel values lower than 2× the average background a value of 0 and all values above this threshold a value of 1.

TEA/Imaging of GVs Expressed in Mammalian Cells

For TEM, cells were cultured in 6-well plates in 2 mL media. 1 μg/mL doxycycline was added to the wells at indicated times with daily media plus doxycycline changes thereafter until harvest. Cells were lysed by adding 400 μL of Solulyse-M (Genlantis) supplemented with 25 units/mL Benzonase Nuclease (Novagen) directly to the 6-well plates and incubating for 1 hour at 4° C. with agitation. The lysates were then transferred to 1.5 mL microcentrifuge tubes. Eight hundred μL of 10 mM HEPES pH 7.5 was added to each tube, and lysates were centrifuged overnight at 300 g and 8° C. Thirty μL of the supernatant was collected from the surface from the side of the tube facing the center of the centrifuge rotor and transferred to a new tube. Three μL of each sample was loaded onto freshly glow-discharged (Pelco EasiGlow, 15 mA, 1 min) formvar/carbon 200 mesh grids (Ted Pella) and blotted after 1 minute then air-dried. The unstained grids were imaged on a FEI Tecnai T12 transmission electron microscope equipped with a Gatan Ultrascan CCD.

In Vivo Ultrasound Imaging of $mARG_{Ana}$ Expressing Orthotopic Tumors, Whole Animal Fluorescence Imaging and Tumor Fluorescence Microscopy Tumor xenograft experiments were conducted in NSG mice aged 12-weeks and 6 days (The Jackson Laboratory). To implement an orthotopic model of breast cancer, all the mice were female. MDA-MB-231-$mARG_{Ana}$ cells were grown in T225 flasks in DMEM supplemented with 10% TET-free FBS and penicillin/streptomycin until confluency as described above. Cells were harvested by trypsinization with 6 mL Trypsin/EDTA for 6 minutes and quenched with fresh media. Cells were washed once in DMEM without antibiotics or FBS before pelleting by centrifugation at 300 g. Cell pellets were resuspended in 1:1 mixture of ice-cold Matrigel (HC, GFR) (Corning 354263) and PBS ($Ca^{2+}$, $Mg^{2+}$-free) at 30 million cells/mL. Fifty pL Matrigel suspensions were injected bilaterally into the $4^{th}$ mammary fat pads at 1.5 million cells per tumor via subcutaneous injection. 12 hours after tumor injection and every 12 hours thereafter (except the mornings of ultrasound imaging sessions) test mice were intraperitoneally injected with 150 μL of saline containing 150 μg of doxycycline for induction of GV expression. Control mice were not injected with doxycycline.

For ultrasound imaging, mice were depilated around the $4^{th}$ mammary fat pads using Nair (Aloe Vera) for ultrasound coupling with Aquasonic 100 gel. Mice were anesthetized with 2.5% isoflurane and maintained at 37° C. in supine position on a heating pad. The first imaging session (day 4) consisted of 8 induced tumors from 4 mice and 7 uninduced tumors from 4 mice. One of the uninduced mice died during the first imaging session, which resulted in two fewer uninduced control tumors for the remaining imaging sessions.

Ultrasound images were acquired with an L22-14v 128-element linear array transducer. xAM and B-mode images were acquired concurrently using the same parameters as described in the in vitro section above except the transducer voltage was held at constant 7.5V (0.42 MPa) for xAM and 3 frames, each consisting of 15 accumulations, were acquired per section. A motor stage was programed to move 100 μm per section for a total of 150 sections per tumor. The B-mode transmit focus was set to 6 mm. Ultrasound images of tumors were quantified as described above where the sample ROIs were drawn around the tumors and the background ROIs were drawn around regions in the gel above the mouse. Images were normalized and plotted on a dB scale as described above except the scaling factors were A=2 and B=0.5 for both xAM and the corresponding B-mode tumor images. The xAM volume quantification was performed by summing all pixel values from all sections in each tomogram between 2 mm and 10 mm in depth.

On the last day of ultrasound imaging, mice were anesthetized with 100 mg/kg ketamine, and 10 mg/kg xylazine and whole-body imaged in supine position using ChemiDoc MP imaging system with Image Lab software (BIO-RAD). Fluorescence channels were set as follows: blue epi illumination with 530/28 filter for Emerald/GFP and 605/50 filter for Antares/CyOFP1. Images were processed and merged using the FIJI package of ImageJ.

After whole-body fluorescence imaging, mice were euthanized and tumors were resected and placed in 10% formalin solution for 24 hours at 4° C., after which they were transferred to PBS. Fixed tumors were embedded in 2% agarose in PBS and sectioned to 100 μm slices using a vibratome. Sections were stained with TO-PRO-3 nucleus stain, mounted using Prolong Glass (Invitrogen) and imaged using a Zeiss LSM 980 confocal microscope with ZEN Blue. Images were processed using the FIJI package of ImageJ. For micrographs of tumors from both induced and uninduced mice, the Emerald channel was capped between 0 and 25497, EBFP2 channel between 0 and 17233 and TO-PRO-3 channel between 5945 and 53136 for display.

In Vivo Ultrasound-Guided Biopsy of $mARG_{Ana}$-Expressing Chimeric Tumors

Chimeric tumor biopsy experiments were conducted in female NCG mice aged 8-weeks (Charles River Laboratories). MDA-MB-231-$mARG_{Ana}$ and MDA-MB-231-rtTA-Antares cells were grown and harvested as above. Cell pellets were resuspended in a 1:1 mixture of ice-cold Matrigel (HC, GFR) (Corning 354263) and PBS ($Ca^{2+}$- and $Mg^{2+}$-free) at 30 million cells/mL. 100 pL Matrigel suspensions of MDA-MB-231-$mARG_{Ana}$ were injected bilaterally into the 4$^{th}$ mammary fat pads at 3 million cells per tumor lobe via subcutaneous injection. After 1 hr, additional 100 pL Matrigel suspensions of MDA-MB-231-rtTA-Antares were injected close to the edge of the blisters created by the first injections to create dual-lobed chimeric tumors with heterogeneous gene expression patterns. Mice were intraperitoneally injected with 150 μL of saline containing 150 μg of doxycycline for induction of GV expression starting 12 hours after tumor injection and then every 12 hours thereafter for 5 days.

Mice were prepared for ultrasound imaging as above. Ultrasound images were acquired with an L22-14vX 128-element linear array transducer. xAM and B-mode imaging was performed as above except the transducer voltage was held at 5.5V (0.481 MPa) for xAM and 1.6V (0.161 MPa) for B-mode and the motor stage was programed to move either 200 μm per section for whole-tumor scans or was held stationary for biopsy video acquisition. Image normalization and scaling was performed as above. xAM/B-mode overlay was made as above.

To perform a fine-needle aspiration biopsy, a 23G needle was fitted to a 3 mL Luer-lock syringe prefilled with PBS. The syringe was mounted on a 3D-printed holder attached to a manual translation stage. Each biopsy attempt consisted of positioning the ultrasound probe over a tumor and moving the needle into the field of view. The needle was then inserted into either the xAM-positive or xAM-negative region of the tumor, guided by live xAM and B-mode imaging. The needle was wiggled back-and-forth a couple times before pulling the syringe plunger to aspirate cells. The tumor sample was then ejected into a tube with PBS. The biopsy was repeated for attempts that did not produce a visible cell pellet. Each sample was treated with Trypsin/EDTA for 6 minutes at 37° C., then quenched with fresh media.

Flow cytometry was performed with MACSQuant 10 (Miltenyi Biotec). GFP was measured with the B1 channel and Antares using B2. All biopsy attempts for a given tumor/sampling condition were analyzed separately, but their resulting FCS data files were concatenated. Data analysis was performed in FlowJo. For quantification of biopsy samples, each population was first gated for Antares-positive cells to exclude endogenous mouse cells. Antares-positive cells were then gated based on FSC/SSC and single cells were gated using FSC-A vs FSC-W. The resulting populations contained on average 6947 cells with a SD of 6960 cells and range between 72 and 21958 cells. % GFP-positive ($mARG_{Ana}$-positive) was assessed based on these resulting populations.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A mammalian cell, comprising: one or more promoters operably linked to one or more gas vesicles (GV) polynucleotides comprising: one or more gas vesicle assembly (GVA) gene(s) encoding one or more GVA protein(s); and one or more gas vesicle structural (GVS) gene(s) encoding one or more GVS protein(s), wherein the one or more GVA gene(s) and/or the one or more GVS gene(s) are derived from *Anabaena flos-aquae* and wherein each of the one or more GVA gene(s) and/or the one or more GVS gene(s) comprise gvpA, gvpC, gvpN, gvpJ, gvK, gypF, gvpG, gvpV, or gvpW, wherein the one or more GVA protein(s) and the one or more GVS protein(s) are capable of forming gas vesicles (GVs) upon expression in the mammalian cell, and wherein said GVs are capable of producing nonlinear ultrasound contrast.

2. The mammalian cell of claim 1, wherein the mammalian cell comprises a cancer cell, an immortalized cell line, an antigen-presenting cell, a dendritic cell, a macrophage, a neural cell, a brain cell, an astrocyte, a microglial cell, and a neuron, a spleen cell, a lymphoid cell, a lung cell, a lung epithelial cell, a skin cell, a keratinocyte, an endothelial cell, an alveolar cell, an alveolar macrophage, an alveolar pneumocyte, a vascular endothelial cell, a mesenchymal cell, an epithelial cell, a colonic epithelial cell, a hematopoietic cell, a bone marrow cell, a Claudius cell, Hensen cell, Merkel cell, Muller cell, Paneth cell, Purkinje cell, Schwann cell, Sertoli cell, acidophil cell, acinar cell, adipoblast, adipocyte, brown or white alpha cell, amacrine cell, beta cell, capsular cell, cementocyte, chief cell, chondroblast, chondrocyte, chromaffin cell, chromophobic cell, corticotroph, delta cell, Langerhans cell, follicular dendritic cell, enterochromaffin cell, ependymocyte, epithelial cell, basal cell, squamous cell, endothelial cell, transitional cell, erythroblast, erythrocyte, fibroblast, fibrocyte, follicular cell, germ cell, gamete, ovum, spermatozoon, oocyte, primary oocyte, secondary oocyte, spermatid, spermatocyte, primary spermatocyte, secondary spermatocyte, germinal epithelium, giant cell, glial cell, astroblast, astrocyte, oligodendroblast, oligodendrocyte, glioblast, goblet cell, gonadotroph, granulosa cell, haemocytoblast, hair cell, hepatoblast, hepatocyte, hyalocyte, interstitial cell, juxtaglomerular cell, keratinocyte, keratocyte, lemmal cell, leukocyte, granulocyte, basophil, eosinophil, neutrophil, lymphoblast, B-lymphoblast, T-lymphoblast, lymphocyte, B-lymphocyte, T-lymphocyte, helper induced T-lymphocyte, Th1 T-lymphocyte, Th2 T-lymphocyte, natural killer cell, thymocyte, macrophage, Kupffer cell, alveolar macrophage, foam cell, histiocyte, luteal cell, lymphocytic stem cell, lymphoid cell, lymphoid stem cell, macroglial cell, mammotroph, mast cell, medulloblast, megakaryoblast, megakaryocyte, melanoblast, melanocyte, mesangial cell, mesothelial cell, metamyelocyte, monoblast, monocyte, mucous neck cell, myoblast, myocyte, muscle cell, cardiac muscle cell, skeletal muscle cell, smooth muscle cell, myelocyte, myeloid cell, myeloid stem cell, myoblast, myoepithelial cell, myofibrobast, neuroblast, neuroepithelial cell, neuron, odontoblast, osteoblast, osteoclast, osteocyte, oxyntic cell, parafollicular cell, paraluteal cell, peptic cell, pericyte, peripheral blood mononuclear cell, phaeochromocyte, phalangeal cell, pinealocyte, pituicyte, plasma cell, platelet, podocyte, proerythroblast, promonocyte, promyeloblast, promyelocyte, pronormoblast, reticulocyte, retinal pigment epithelial cell, retinoblast, small cell, somatotroph, stem cell, sustentacular cell, teloglial cell, a zymogenic cell, or any combination thereof.

3. The mammalian cell of claim 1, wherein the mammalian cell is a reporting therapeutic cell, wherein the reporting therapeutic cell is autologous, allogenic, or xenogenic, and wherein the presence and/or functionality of the reporting therapeutic cell is capable of being monitored in vivo by application of ultrasound (US).

4. The method of claim 3, wherein the reporting therapeutic cell is a replacement for a cell that is absent, diseased, infected, and/or involved in maintaining, promoting, or causing a disease or condition in a subject in need.

5. The mammalian cell of claim 1, wherein the expression of the GVs within the mammalian cell is capable of being detected via dynamic non-destructive imaging, and wherein the dynamic non-destructive imaging comprises:

nonlinear ultrasound imaging;

cross-propagating amplitude modulation pulse sequence (xAM) imaging; and/or parabolic AM (pAM) imaging.

6. The mammalian cell of claim 1, wherein the mammalian cell comprises:

a first GV polynucleotide encoding GvpA, a second GV polynucleotide encoding GvpN, a third GV polynucleotide encoding GvpJ, a fourth GV polynucleotide encoding GvpK, a fifth GV polynucleotide encoding GvpF, a sixth GV polynucleotide encoding GvpG, a seventh GV polynucleotide encoding GvpW, and an eighth GV polynucleotide encoding GvpV, and wherein two or more of the GV polynucleotides are operably linked to a tandem gene expression element.

7. The mammalian cell of claim 1, wherein the mammalian cell comprises a DNA sequence that is at least 95%, 98%, 99%, or 100% identical to SEQ ID NO: 2 and/or SEQ ID NO: 3 comprising a promoter, a GVA gene, a GVS gene, a tandem gene expression element, a terminator, operators, or any combination thereof.

8. The mammalian cell of claim 1, wherein the mammalian cell is robust to mutations reducing or abrogating GV expression, and wherein the mammalian cell is robust to said mutations for at least 5 days, 10 days, 20 days, 40 days, 80 days, or 100 days, of continuous culture and/or within a subject.

9. A method of monitoring a cell-based therapy, comprising:

administering to a subject an effective amount of the reporting therapeutic cell(s) of claim 3, and applying ultrasound (US) to a target site of the subject, thereby monitoring the cell-based therapy.

* * * * *